United States Patent
Ding et al.

(10) Patent No.: US 9,981,944 B2
(45) Date of Patent: *May 29, 2018

(54) GDF-8 INHIBITORS

(71) Applicants: Rigel Pharmaceuticals, Inc., South San Francisco, CA (US); Bristol-Myers Squibb Company, Princeton, NJ (US)

(72) Inventors: Pingyu Ding, Foster City, CA (US); Marina Gelman, San Francisco, CA (US); Todd Kinsella, Redwood City, CA (US); Rajinder Singh, Belmont, CA (US); Somasekhar Bhamidipati, Foster City, CA (US); Upender Velaparthi, Cheshire, CT (US); Robert M. Borzilleri, New Hope, PA (US); Hasibur Rahaman, Bangalore (IN); Jayakumar Sankara Warrier, Bangalore (IN)

(73) Assignees: RIGEL PHARMACEUTICALS, INC, South San Francisco, CA (US); BRISTOL-MYERS SQUIBB COMPANY, Princeton, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/043,729

(22) Filed: Feb. 15, 2016

(65) Prior Publication Data

US 2016/0264553 A1   Sep. 15, 2016

Related U.S. Application Data

(60) Provisional application No. 62/119,052, filed on Feb. 20, 2015.

(51) Int. Cl.
| | | |
|---|---|---|
| *C07D 401/04* | (2006.01) |
| *C07D 471/04* | (2006.01) |
| *C07D 487/04* | (2006.01) |
| *C07B 59/00* | (2006.01) |
| *C07C 53/06* | (2006.01) |
| *C07C 53/18* | (2006.01) |
| *C07D 401/14* | (2006.01) |

(52) U.S. Cl.
CPC .......... *C07D 401/14* (2013.01); *C07B 59/002* (2013.01); *C07C 53/06* (2013.01); *C07C 53/18* (2013.01); *C07D 471/04* (2013.01); *C07D 487/04* (2013.01); *C07B 2200/05* (2013.01)

(58) Field of Classification Search
CPC .. C07D 401/14; C07D 471/04; C07D 487/04; C07C 53/06; C07C 53/18; C07B 2200/15; C07B 59/002
See application file for complete search history.

(56) References Cited

FOREIGN PATENT DOCUMENTS

| WO | WO 0125205 A1 * | 4/2001 | ........... C07D 213/22 |
|---|---|---|---|
| WO | WO-2012003912 A8 * | 3/2012 | ........... C07D 213/74 |
| WO | 2014/055955 | 4/2014 | |

* cited by examiner

*Primary Examiner* — Sarah Pihonak
(74) *Attorney, Agent, or Firm* — McDonnell Boehnen Hulbert & Berghoff LLP; Travis Young

(57) ABSTRACT

Disclosed are 2,2'-bipyridyl compounds, as well as pharmaceutical compositions and methods of use thereof. One embodiment is a compound having the structure

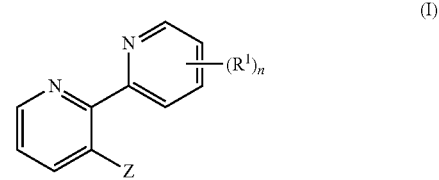

(I)

and pharmaceutically acceptable salts, prodrugs and N-oxides thereof (and solvates and hydrates thereof), wherein $R^1$, Z and n are as described herein. In certain embodiments, a compound disclosed herein inhibits GDF8, and can be used to treat disease by blocking GDF8 signaling.

19 Claims, No Drawings

GDF-8 INHIBITORS

BACKGROUND OF THE DISCLOSURE

Field of the Disclosure

This disclosure relates to pharmaceutically active compounds and methods for their use. In particular the disclosure relates to kinase inhibitors. In one aspect the compounds also inhibit the signaling of cytokines such as TGF-β1, Growth Differentiation Factor-8 (GDF-8) and other members of the TGF-βs, activins, inhibins, bone morphogenetic proteins and Mullerian-inhibiting substance, that signal through a family of transmembrane kinase receptors. The inhibitors are useful for treating inflammatory disorders, such as inflammatory or obstructive airway diseases, such as pulmonary hypertension, pulmonary fibrosis, liver fibrosis; and cancer. The inhibitors are particularly useful for diagnosing, preventing, or treating human or animal disorders in which an increase in muscle tissue would be therapeutically beneficial. Exemplary disorders include neuromuscular disorders (e.g., muscular dystrophy and muscle atrophy), congestive obstructive pulmonary disease, muscle wasting syndrome, sarcopenia, and cachexia; adipose tissue disorders (such as obesity); type 2 diabetes; and bone degenerative disease (such as osteoporosis).

Summary of the Related Art

Growth and Differentiation Factor-8 (GDF-8), also known as myostatin, and TGF-β are a members of the Transforming Growth Factor-beta (TGF-β) superfamily of structurally related growth factors, all of which possess physiologically important growth-regulatory and morphogenetic properties (Kingsley et al. (1994) Genes Dev., 8: 133-46; Hoodless et al. (1998) Curr. Topics Microbiol. Immunol., 228: 235-72). For example, activation of TGF-β1 signaling and expansion of extracellular matrix are early and persistent contributors to the development and progression of fibrotic disorders, such as involved in chronic renal disease and vascular disease. Border W. A., et al, N. Engl. J. Med., 1994; 331(19), 1286-92. GDF-8 is a negative regulator of skeletal muscle mass, and there is considerable interest in identifying factors which regulate its biological activity. For example, GDF-8 is highly expressed in the developing and adult skeletal muscle. The GDF-8 null mutation in transgenic mice is characterized by a marked hypertrophy and hyperplasia of the skeletal muscle (McPherron et al. (1997) Nature, 387: 83-90). Similar increases in skeletal muscle mass are evident in naturally occurring mutations of GDF-8 in cattle (Ashmore et al. (1974) Growth, 38: 501 507; Swatland and Kieffer (1994) J. Anim. Sci., 38: 752-757; McPherron and Lee (1997) Proc. Natl. Acad. Sci. USA, 94: 12457-12461; and Kambadur et al. (1997) Genome Res., 7: 910-915). Since GDF-8 is expressed in both developing and adult muscles, it is not clear whether it regulates muscle mass during development or in adults. Thus, the question of whether or not GDF-8 regulates muscle mass in adults is important from a scientific and therapeutic perspective. Recent studies have also shown that muscle wasting associated with HIV-infection in humans is accompanied by increases in GDF-8 protein expression (Gonzalez-Cadavid et al. (1998) PNAS, 95: 14938-43). In addition, GDF-8 can modulate the production of muscle-specific enzymes (e.g., creatine kinase) and modulate myoblast cell proliferation (WO 00/43781).

A number of human and animal disorders are associated with loss or functional impairment of muscle tissue, including muscular dystrophy, muscle atrophy, congestive obstructive pulmonary disease, muscle wasting syndrome, sarcopenia, and cachexia. To date, very few reliable or effective therapies exist for these disorders. However, the terrible symptoms associated with these disorders may be substantially reduced by employing therapies that increase the amount of muscle tissue in patients suffering from the disorders. While not curing the conditions, such therapies would significantly improve the quality of life for these patients and could ameliorate some of the effects of these diseases. Thus, there is a need in the art to identify new therapies that may contribute to an overall increase in muscle tissue in patients suffering from these disorders.

In addition to its growth-regulatory and morphogenetic properties in skeletal muscle, GDF-8 may also be involved in a number of other physiological processes, including glucose homeostasis in the development of type 2 diabetes and adipose tissue disorders, such as obesity. For example, GDF-8 modulates pre-adipocyte differentiation to adipocytes (Kim et al. (2001) BBRC, 281: 902-906).

There are also a number of conditions associated with a loss of bone, including osteoporosis, especially in the elderly and/or postmenopausal women. Currently available therapies for these conditions work by inhibiting bone resorption. A therapy that promotes new bone formation would be a desirable alternative to or addition to, these therapies.

Like TGF-β-1, -2, and -3, the GDF-8 protein is synthesized as a precursor protein consisting of an amino-terminal propeptide and a carboxy-terminal mature domain (McPherron and Lee, (1997) Proc. Natl. Acad. Sci. USA, 94: 12457-12461). Before cleavage, the precursor GDF-8 protein forms a homodimer. The amino-terminal propeptide is then cleaved from the mature domain. The cleaved propeptide may remain noncovalently bound to the mature domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). It is believed that two GDF-8 propeptides bind to the GDF-8 mature dimer (Thies et al. (2001) Growth Factors, 18: 251-259). Due to this inactivating property, the propeptide is known as the "latency-associated peptide" (LAP), and the complex of mature domain and propeptide is commonly referred to as the "small latent complex" (Gentry and Nash (1990) Biochemistry, 29: 6851-6857; Derynck et al. (1995) Nature, 316: 701-705; and Massague (1990) Ann. Rev. Cell Biol., 12: 597-641). Other proteins are also known to bind to GDF-8 or structurally related proteins and inhibit their biological activity. Such inhibitory proteins include follistatin, and potentially, follistatin-related proteins (Gamer et al. (1999) Dev. Biol., 208: 222-232). The mature domain is believed to be active as a homodimer when the propeptide is removed.

GDF-8 is highly conserved in sequence and in function across species. The amino acid sequence of murine and human GDF-8 is identical, as is the pattern of mRNA expression (McPherron et al. (1997) Nature 387: 83-90; Gonzalez-Cadavid et al. (1998) Proc. Natl. Acad. Sci. USA 95: 14938-14943). This conservation of sequence and function suggests that inhibition of GDF-8 in humans is likely to have a similar effect to inhibition of GDF-8 in mice.

GDF-8 is involved in the regulation of many critical biological processes. Due to its key function in these processes, GDF-8 may be a desirable target for therapeutic intervention.

For example, U.S. Pat. No. 7,320,789, shows that GDF-8 antibodies in mouse models can increase muscle strength (e.g., for treating sarcopenia). increase muscle mass and strength in dystrophic muscle (e.g., for treating Duchenne's muscular dystrophy), increase bone mass and bone density (e.g., for prevention and treatment of osteoporosis), augment bone healing (e.g., for treating an established muscle or bone degenerative disease (e.g., fracture repair and spine fusion, preventing the decline in bone mass, microarchitecture and strength associated with estrogen deficiency, increasing trabecular bone density), and are useful for treatment of metabolic disorders such as type 2 diabetes, impaired glucose tolerance, metabolic syndrome (e.g., syndrome X), insulin resistance induced by trauma (e.g., burns), and adipose tissue disorders (e.g., obesity).

In particular, therapeutic agents that inhibit the activity of GDF-8 may be used to treat human or animal disorders in which an increase in muscle tissue would be therapeutically beneficial, particularly muscle and adipose tissue disorders, bone degenerative diseases, neuromuscular disorders, and diabetes, as discussed above.

SUMMARY OF THE DISCLOSURE

In one aspect, the present disclosure relates to compounds of the formula (I),

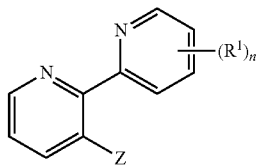

(I)

and pharmaceutically acceptable salts thereof, wherein n, $R^1$ and Z are defined herein.

In another aspect, disclosed are pharmaceutical compositions comprising a compound or pharmaceutically acceptable salt of a compound according to formula (I) and a pharmaceutically acceptable carrier, excipient, or diluent.

In another aspect, disclosed are methods for inhibiting GDF-8 in a cell comprising contacting the cell with an effective amount of a compound or pharmaceutically acceptable salt of a compound according to formula (I) or a pharmaceutical composition comprising a compound or pharmaceutically acceptable salt of a compound according to formula (I) and a pharmaceutically acceptable carrier, excipient, or diluent.

In another aspect, disclosed are methods for treating a patient suffering from a disease or disorder, wherein the patient would therapeutically benefit from an increase in mass or strength of muscle tissue, comprising administering to a patient a therapeutically effective amount of a compound or pharmaceutically acceptable salt of a compound according to formula (I) or a pharmaceutical composition comprising a compound or pharmaceutically acceptable salt of a compound according to formula (I) and a pharmaceutically acceptable carrier, excipient, or diluent.

In another aspect, disclosed are methods for increasing muscle mass in a mammal comprising administering a therapeutically effective amount of a compound or pharmaceutically acceptable salt of a compound according to formula (I) or a pharmaceutical composition comprising a compound or pharmaceutically acceptable salt of a compound according to formula (I) and a pharmaceutically acceptable carrier, excipient, or diluent.

In another aspect, disclosed are methods for increasing muscle strength in a mammal comprising administering a therapeutically effective amount of a compound or pharmaceutically acceptable salt according to formula (I) or a pharmaceutical composition comprising a compound or pharmaceutically acceptable salt according to formula (I) and a pharmaceutically acceptable carrier, excipient, or diluent.

In another aspect, disclosed are methods for increasing trabecular bone density in a patient in need thereof, comprising administering a therapeutically effective amount of a compound or pharmaceutically acceptable salt according to formula (I) or a pharmaceutical composition comprising a compound or pharmaceutically acceptable salt according to formula (I) and a pharmaceutically acceptable carrier, excipient, or diluent.

In another aspect, the compounds and compositions disclosed herein are useful for inhibiting a TGF-β superfamily cytokine, including without limitation, TGF-β, GDF-8, Activin-A, or combinations thereof in vitro, ex vitro, and in vivo for the purposes of studying the effects of GDF-8 inhibition on biological processes influenced by GDF-8 activity. Embodiments according to this aspect comprise contacting or administering (as appropriate) a compound or composition described herein under circumstances that facilitate contact between the compound or composition and GDF-8, thereby facilitating inhibition of GDF-8 by the compound or composition. Optionally, methods of inhibiting GDF-8 in vitro, ex vitro, and in vivo are followed by an appropriate assay for determining the effects of the inhibition. One embodiment of this aspect comprises a method of inhibiting GDF-8 in vivo comprising administering an effect GDF-8-inhibiting amount of a compound or composition disclosed herein to a mammal, such as a human.

DETAILED DESCRIPTION OF THE DISCLOSURE

In one aspect, the invention comprises compounds that inhibit one or more kinases, such as a TGF-β receptor superfamily kinase. As such and without limitation to any particular theory, the presently disclosed compounds inhibit signaling of TGF-β superfamily cytokines, such as TGF-β, Activin A, GDF-8 or combinations thereof.

In embodiment $I_0$ of this first aspect, the compounds have structural formula (P):

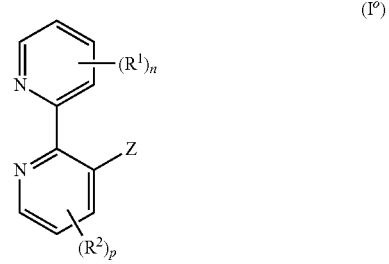

(I°)

or a pharmaceutically acceptable salt, prodrug, or N-oxide thereof, or a solvate or hydrate thereof,
wherein
n is 1, 2, 3 or 4;
$R^1$ is hydrogen, halogen, cyano, nitro, $C_{1-6}$alkyl, $C_{1-6}$haloalkyl, $C_{3-8}$cycloalkyl, $C_{3-8}$ cycloalkenyl, heterocyclyl, aryl, heteroaryl, —$R^a$, or —$C_{1-6}$ alkyl-$R^a$, wherein $R^a$ is —$OR^{S1}$, —$SR^{S1}$, —$NR^{S1}R^{S1}$, —$C(O)R^{S1}$, —$C(O)OR^{S1}$, —$C(O)NR^{S1}R^{S1}$, —$S(O)_2NR^{S1}R^{S1}$, —$OC(O)R^{S1}$, —N(R$^{S1}$)C(O)R$^{S1}$, —OC(O)OR$^{S1}$, —O(CH$_2$)$_m$C(O)NR$^{S1}$R$^{S1}$, —N(R$^{S1}$)C(O)OR$^{S1}$, —N(R)C(O)NR$^{S1}$R$^{S1}$, —N(R$^{S1}$)S(O)$_2$NR$^{S1}$R$^{S1}$, or —N(R$^{S1}$)S(O)$_2$R$^{S1}$;
  wherein m is 0, 1, 2 or 3; and
  wherein each R$^{S1}$ is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano;
  p is 1, 2, 3 or 4;
R$^2$ is hydrogen, halogen, cyano, nitro, C$_{1-6}$alkyl, C$_{1-6}$haloalkyl, C$_{3-8}$cycloalkyl, C$_{3-8}$cycloalkenyl, heterocyclyl, aryl, heteroaryl, —R$^b$, or —C$_{1-6}$alkyl-R$^b$, wherein R$^b$ is —OR$^{S4}$, —SR$^{S4}$, —NR$^{S4}$R$^{S4}$, —C(O)R$^{S4}$, —C(O)OR$^{S4}$, —C(O)NR$^{S4}$R$^{S4}$, —S(O)$_2$NR$^{S4}$R$^{S4}$, —OC(O)R$^{S4}$, —N(R$^{S4}$)C(O)R$^{S4}$, —OC(O)OR$^{S4}$, —O(CH$_2$)$_q$C(O)NR$^{S4}$R$^{S4}$, —N(R$^{S4}$)C(O)OR$^{S4}$, —N(R)C(O)NR$^{S4}$R$^{S4}$, —N(R$^{S4}$)S(O)$_2$NR$^{S4}$R$^{S4}$ or —N(R$^{S4}$)S(O)$_2$R$^{S4}$;
  wherein q is 0, 1, 2 or 3; and
  wherein each R$^{S4}$ is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano;
Z is
a fused bicyclic ring of the formula,

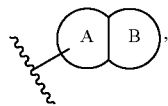

wherein
  ring A is Ar or 6-membered Het,
  ring B is 5- or 6-membered Het,
  wherein
    Z is optionally substituted by one or two —R$^Z$ groups that are each independently halogen, cyano, C$_{1-6}$alkyl, C$_{1-6}$haloalkyl, —C$_1$-C$_6$alkoxy, —OR$^{S2}$, —SR$^{S2}$, —NR$^{S2}$$_2$, —C(O)R$^{S2}$, —C(O)OR$^{S2}$, —C(O)NR$^{S2}$$_2$, —S(O)$_2$NR$^{S2}$$_2$, —S(O)$_2$R$^{S2}$, —OC(O)R$^{S2}$, —N(R$^{S2}$)C(O)R$^{S2}$, —OC(O)OR$^{S2}$, —OC(O)NR$^{S2}$$_2$, —N(R$^{S2}$)C(O)OR$^{S2}$, —N(R$^{S2}$)C(O)NR$^{S2}$$_2$, —N(R$^{S2}$)S(O)$_2$R$^{S2}$, —OP(O)(OR$^{S2}$)$_2$ or —CH$_2$—OP(O)(OR$^{S2}$), wherein each alkyl, haloalkyl and alkoxy is optionally substituted by one or two —R$^{Z2}$ groups;
    wherein each R$^{S2}$ is independently hydrogen, C$_1$-C$_6$alkyl, C$_1$-C$_6$haloalkyl, C$_1$-C$_6$alkyl-O—C$_1$-C$_6$alkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano; and
    each —R$^{Z2}$ is independently halogen, cyano, C$_{1-6}$alkyl, C$_{1-6}$haloalkyl, —C$_1$-C$_6$alkoxy, —OR$^{S3}$, —SR$^{S3}$, —NR$^{S3}$$_2$, —C(O)R$^{S3}$, —C(O)OR$^{S3}$, —C(O)NR$^{S3}$$_2$, —S(O)$_2$NR$^{S3}$$_2$, —S(O)$_2$R$^{S3}$, —OC(O)R$^{S3}$, —N(R$^{S3}$)C(O)R$^{S3}$, —OC(O)OR$^{S3}$, —OC(O)NR$^{S3}$$_2$, —N(R$^{S3}$)C(O)OR$^{S3}$, —N(R$^{S3}$)C(O)NR$^{S3}$$_2$, —N(R$^{S3}$)S(O)$_2$R$^{S3}$, —OP(O)(OR$^{S3}$)$_2$ or —CH$_2$—OP(O)(OR$^{S3}$); and
    wherein each R$^{S3}$ is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano.

In embodiment I$_1$ of this first aspect, the compounds have structural formula (I):

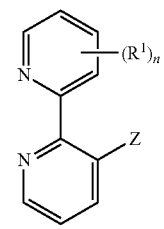

(I)

or a pharmaceutically acceptable salt, prodrug, or N-oxide thereof, or a solvate or hydrate thereof,
wherein
  n is 1, 2, 3 or 4;
  R$^1$ is hydrogen, halogen, cyano, nitro, C$_{1-6}$alkyl, C$_{1-6}$haloalkyl, C$_{3-8}$cycloalkyl, C$_{3-8}$cycloalkenyl, heterocyclyl, aryl, heteroaryl, —R$^a$, or —C$_{1-6}$ alkyl-R$^a$, wherein R$^a$ is —OR$^{S1}$, —SR$^{S1}$, —NR$^{S1}$R$^{S1}$, —C(O)R$^{S1}$, —C(O)OR$^{S1}$, —C(O)NR$^{S1}$R$^{S1}$, —S(O)$_2$NR$^{S1}$R$^{S1}$, —OC(O)R$^{S1}$, —N(R$^{S1}$)C(O)R$^{S1}$, —OC(O)OR$^{S1}$, —O(CH$_2$)$_m$C(O)NR$^{S1}$R$^{S1}$, —N(R$^{S1}$)C(O)OR$^{S1}$, —N(R)C(O)NR$^{S1}$R$^{S1}$, —N(R$^{S1}$)S(O)$_2$NR$^{S1}$R$^{S1}$, —N(R$^{S1}$)S(O)$_2$R$^{S1}$;
  wherein m is 0, 1, 2 or 3; and
  wherein each R$^{S1}$ is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano;
Z is
a fused bicyclic ring of the formula,

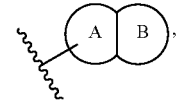

wherein
  ring A is Ar or 6-membered Het,
  ring B is 5- or 6-membered Het,
  wherein
    Z is optionally substituted by one or two —R$^Z$ groups that are each independently halogen, cyano, C$_{1-6}$alkyl, C$_{1-6}$haloalkyl, —C$_1$-C$_6$alkoxy, —OR$^{S2}$, —SR$^{S2}$, —NR$^{S2}$$_2$, —C(O)R$^{S2}$, —C(O)OR$^{S2}$, —C(O)NR$^{S2}$$_2$, —S(O)$_2$NR$^{S2}$$_2$, —S(O)$_2$R$^{S2}$, —OC(O)R$^{S2}$, —N(R$^{S2}$)C(O)R$^{S2}$, —OC(O)OR$^{S2}$, —OC(O)NR$^{S2}$$_2$, —N(R$^{S2}$)C(O)OR$^{S2}$, —N(R$^{S2}$)C(O)NR$^{S2}$$_2$, —N(R$^{S2}$)S(O)$_2$R$^{S2}$, —OP(O)(OR$^{S2}$)$_2$ or —CH$_2$—OP(O)(OR$^{S2}$), wherein each alkyl, haloalkyl and alkoxy is optionally substituted by one or two —R$^{Z2}$ groups;
    wherein each R$^{S2}$ is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano; and each —$R^{Z2}$ is independently halogen, cyano, $C_{1-6}$alkyl, $C_{1-6}$haloalkyl, —$C_1$-$C_6$alkoxy, —$OR^{S3}$, —$SR^{S3}$, —$NR^{S3}{}_2$, —$C(O)R^{S3}$, —$C(O)OR^{S3}$, —$C(O)NR^{S3}{}_2$, —$S(O)_2NR^{S3}{}_2$, —$S(O)_2R^{S3}$, —$OC(O)R^{S3}$, —$N(R^{S3})C(O)R^{S3}$, —$OC(O)OR^{S3}$, —$OC(O)NR^{S3}{}_2$, —$N(R^{S3})C(O)OR^{S3}$, —$N(R^{S3})C(O)NR^{S3}{}_2$, —$N(R^{S3})S(O)_2R^{S3}$, —$OP(O)(OR^{S3})_2$ or —$CH_2$—$OP(O)(OR^{S3})$; and wherein each $R^{S3}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

In embodiment I', the compounds are of embodiment $I_1$, provided that the compound is not any compound expressly recited in International Publication No. WO 2014/055955 A1.

In embodiment I'', the compounds are of embodiment $I_0$, provided that the compound is not any compound expressly recited in International Publication No. WO 2014/055955 A1.

In embodiment $I_2$, the compounds are of embodiment $I_1$, provided that the compound is not 5-(6'-methyl-[2,2'-bipyridin]-3-yl)-1H-indazole.

In embodiment $I_2$', the compounds are of embodiment $I_0$, provided that the compound is not 5-(6'-methyl-[2,2'-bipyridin]-3-yl)-1H-indazole.

In embodiment $I_3$, the compounds are of embodiment $I_1$, wherein
Z is
a fused bicyclic ring of the formula,

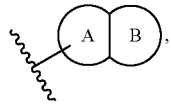

wherein
ring A is Ar or 6-membered Het,
ring B is 5- or 6-membered Het,
wherein
Z is optionally substituted by one or two —$R^Z$ groups that are each independently halogen, cyano, $C_{1-6}$alkyl, $C_{1-6}$haloalkyl, —$C_1$-$C_6$alkoxy, —$OR^{S2}$, —$SR^{S2}$, —$NR^{S2}{}_2$, —$C(O)R^{S2}$, —$C(O)OR^{S2}$, —$C(O)NR^{S2}{}_2$, —$S(O)_2NR^{S2}{}_2$, —$S(O)_2R^{S2}$, —$OC(O)R^{S2}$, —$N(R^{S2})C(O)R^{S2}$, —$OC(O)OR^{S2}$, —$OC(O)NR^{S2}{}_2$, —$N(R^{S2})C(O)OR^{S2}$, —$N(R^{S2})C(O)NR^{S2}{}_2$, —$N(R^{S2})S(O)_2R^{S2}$, —$OP(O)(OR^{S2})_2$ or —$CH_2$—$OP(O)(OR^{S2})$;

wherein each $R^{S2}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

In embodiment $I_4$, the compounds are of embodiment $I_1$, wherein
Z is
a fused bicyclic ring of the formula,

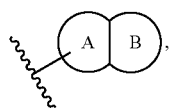

wherein
(1) ring A is Ar or 6-membered Het, and
ring B is a 6-membered Het; or
(2) ring A is 6-membered Het, and
ring B is a 5-membered Het;
wherein Z is optionally substituted by one or two —$R^Z$ groups.

In embodiment $I_4$, the compounds are of embodiment $I_1$, wherein n is 1 or 2 and each $R^1$ is independently halogen $C_{1-6}$alkyl, $C_{1-6}$haloalkyl or $C_{3-8}$cycloalkyl.

The invention further comprises subgenera of formula (I) in which structural formula (I), n, $R^1$ and Z are any group or combinations of groups as defined hereinbelow (e.g., wherein the compound is of structural formula (I) as defined in any of the above embodiments and Z is benzoimidizolyl optionally substituted with one $R^Z$ group, wherein $R^Z$ is halogen; or the compound is formula (Ib), Z is group (2g), $R^1$ is group (1d) and n is group (3e)):

Structural Formula (I) is One of Formulae (Ia)-(Im):

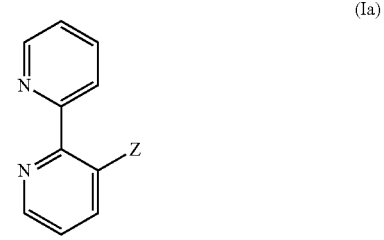

(Ia)

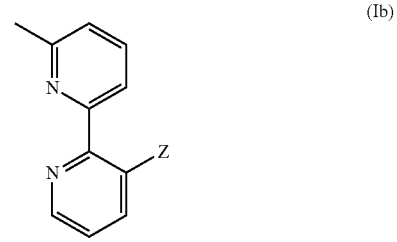

(Ib)

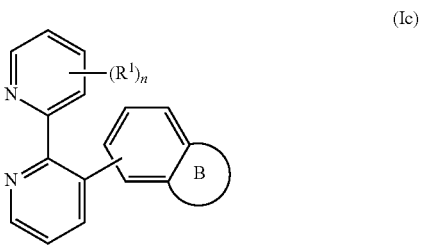

(Ic)

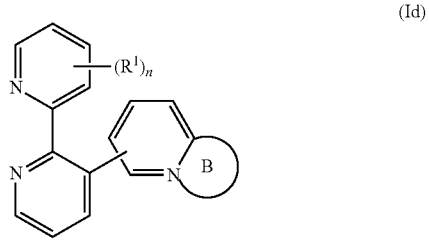

(Id)

-continued (Ie)
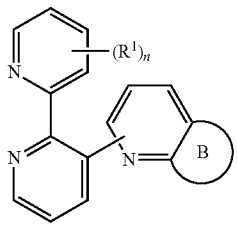

(If)
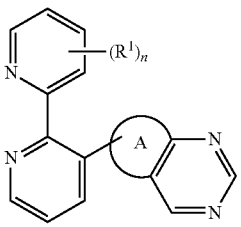

(Ig)
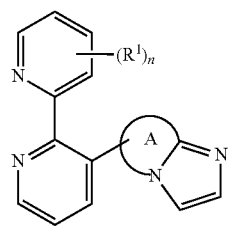

(Ih)
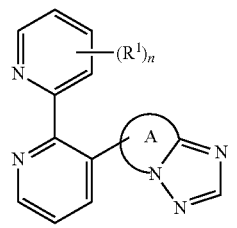

(Ii)
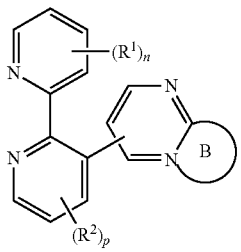

(Ij)
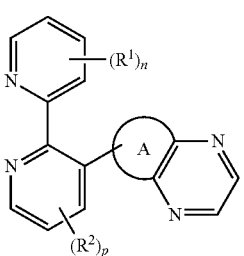

-continued (Ik)
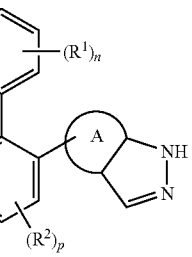

(Il)
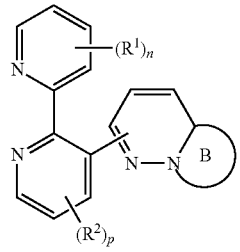

(Im)
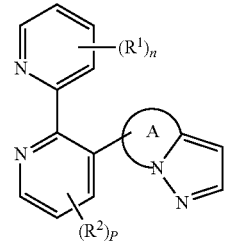

$R^1$ is Selected from One of the Following Groups (1a)-(1tt):

(1a) $R^1$ is hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —$R^a$, or —$C_{1-6}$alkyl-$R^a$, wherein $R^a$ is —$OR^{S1}$, —$SR^{S1}$, —$NR^{S1}R^{S1}$, —C(O)$R^{S1}$, —C(O)O$R^{S1}$, —C(O)N$R^{S1}R^{S1}$, —S(O)$_2$N$R^{S1}R^{S1}$, —OC(O)$R^{S1}$, —N($R^{S1}$)C(O)$R^{S1}$, —OC(O)O$R^{S1}$, —O(CH$_2$)$_m$C(O)N$R^{S1}R^{S1}$, —N($R^{S1}$)C(O)O$R^{S1}$, —N(R)C(O)N$R^{S1}R^{S1}$, —N($R^{S1}$)S(O)$_2$N$R^{S1}R^{S1}$ or —N($R^{S1}$)S(O)$_2R^{S1}$, wherein m is 0, 1, 2 or 3; and wherein each $R^{S1}$ is independently hydrogen, $C_1$-$C_6$alkyl, $C_1$-$C_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(1b) $R^1$ is as described in (1a), wherein $R^{S1}$ is independently hydrogen or $C_1$-$C_6$alkyl.

(1c) $R^1$ is hydrogen, —$R^a$, or —$C_{1-6}$alkyl-$R^a$, wherein $R^a$ is —$OR^{S1}$, —$SR^{S1}$, —$NR^{S1}R^{S1}$, —C(O)$R^{S1}$, —C(O)O$R^{S1}$, —C(O)N$R^{S1}R^{S1}$, —S(O)$_2$N$R^{S1}R^{S1}$, —OC(O)$R^{S1}$, —N($R^{S1}$)C(O)$R^{S1}$, —OC(O)O$R^{S1}$, —O(CH$_2$)$_m$C(O)N$R^{S1}R^{S1}$, —N($R^{S1}$)C(O)O$R^{S1}$, —N(R)C(O)N$R^{S1}R^{S1}$, —N($R^{S1}$)S(O)$_2$N$R^{S1}R^{S1}$, —N($R^{S1}$)S(O)$_2R^{S1}$, wherein m is 0, 1, 2 or 3; and wherein each $R^{S1}$ is independently hydrogen, $C_1$-$C_6$alkyl, $C_1$-$C_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(1d) $R^1$ is as described in (1c), wherein $R^{S1}$ is independently hydrogen or $C_1$-$C_6$alkyl.

(1e) $R^1$ is hydrogen, halogen, cyano, nitro, $C_{1-6}$alkyl, $C_{1-6}$haloalkyl, —$R^a$, or —$C_{1-6}$alkyl-$R^a$, wherein $R^a$ is —$OR^{S1}$, —$SR^{S1}$, —$NR^{S1}R^{S1}$, —$C(O)OR^{S1}$, —$C(O)NR^{S1}R^{S1}$, —$S(O)_2NR^{S1}R^{S1}$, —$OC(O)R^{S1}$, —$N(R^{S1})C(O)R^{S1}$, —$OC(O)OR^{S1}$, —$O(CH_2)_mC(O)NR^{S1}R^{S1}$, —$N(R^{S1})C(O)OR^{S1}$, —$N(R)C(O)NR^{S1}R^{S1}$; —$N(R^{S1})S(O)_2NR^{S1}R^{S1}$ or —$N(R^{S1})S(O)_2R^{S1}$, wherein m is 0, 1, 2 or 3; and wherein each $R^{S1}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(1f) $R^1$ is as described in (1e), wherein $R^{S1}$ is independently hydrogen or $C_1$-$C_6$alkyl.

(1g) $R^1$ is hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —$R^a$, or —$C_{1-6}$alkyl-$R^a$, wherein $R^a$ is —$OR^{S1}$, —$SR^{S1}$, —$NR^{S1}R^{S1}$, —$C(O)R^{S1}$, —$C(O)OR^{S1}$, —$C(O)NR^{S1}R^{S1}$, —$S(O)_2NR^{S1}R^{S1}$, —$OC(O)R^{S1}$, —$N(R^{S1})C(O)R^{S1}$, —$OC(O)OR^{S1}$, —$N(R^{S1})C(O)OR^{S1}$, —$N(R)C(O)NR^{S1}R^{S1}$, —$N(R^{S1})S(O)_2NR^{S1}R^{S1}$ or —$N(R^{S1})S(O)_2R^{S1}$, wherein each $R^{S1}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(1h) $R^1$ is as described in (1g), wherein $R^{S1}$ is independently hydrogen or $C_1$-$C_6$alkyl.

(1i) $R^1$ is hydrogen, halogen, cyano, nitro, $C_{1-6}$alkyl, $C_{1-6}$haloalkyl, —$R^a$, or —$C_{1-6}$alkyl-$R^a$, wherein $R^a$ is —$OR^{S1}$, —$SR^{S1}$, —$NR^{S1}R^{S1}$, —$C(O)OR^{S1}$, —$C(O)NR^{S1}R^{S1}$, —$S(O)_2NR^{S1}R^{S1}$, —$OC(O)R^{S1}$, —$N(R^{S1})C(O)R^{S1}$, —$OC(O)OR^{S1}$, —$N(R^{S1})C(O)OR^{S1}$;

wherein each $R^{S1}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(1j) $R^1$ is as described in (1i), wherein $R^{S1}$ is independently hydrogen or $C_1$-$C_6$alkyl.

(1k) $R^1$ is hydrogen, halogen, cyano, $C_{1-6}$alkyl, —$R^a$, or —$C_{1-6}$alkyl-$R^a$, wherein $R^a$ is —$OR^{S1}$, —$SR^{S1}$, —$NR^{S1}R^{S1}$, —$C(O)R^{S1}$, —$C(O)OR^{S1}$, —$C(O)NR^{S1}R^{S1}$, —$S(O)_2NR^{S1}R^{S1}$, —$OC(O)R^{S1}$, —$N(R^{S1})C(O)R^{S1}$, —$OC(O)OR^{S1}$, —$N(R^{S1})C(O)OR^{S1}$, wherein each $R^{S1}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(1l) $R^1$ is as described in (1k), wherein $R^{S1}$ is independently hydrogen or $C_1$-$C_6$alkyl.

(1m) $R^1$ is hydrogen, halogen, cyano, $C_{1-6}$alkyl or —$R^a$, wherein $R^a$ is —$OR^{S1}$, —$SR^{S1}$, —$NR^{S1}R^{S1}$, —$C(O)R^{S1}$, —$C(O)OR^{S1}$, —$C(O)NR^{S1}R^{S1}$, —$S(O)_2NR^{S1}R^{S1}$, —$OC(O)R^{S1}$, —$N(R^{S1})C(O)R^{S1}$, —$OC(O)OR^{S1}$, —$N(R^{S1})C(O)OR^{S1}$;

wherein each $R^{S1}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(1n) $R^1$ is as described in (1m), wherein $R^{S1}$ is independently hydrogen or $C_1$-$C_6$alkyl.

(1o) $R^1$ is hydrogen or —$R^a$, wherein $R^a$ is —$OR^{S1}$, —$SR^{S1}$, —$NR^{S1}R^{S1}$, —$C(O)R^{S1}$, —$C(O)OR^{S1}$, —$C(O)NR^{S1}R^{S1}$, —$S(O)_2NR^{S1}R^{S1}$, —$OC(O)R^{S1}$, —$N(R^{S1})C(O)R^{S1}$, —$OC(O)OR^{S1}$, —$N(R^{S1})C(O)OR^{S1}$;

wherein each $R^{S1}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(1p) $R^1$ is as described in (1o), wherein $R^{S1}$ is independently hydrogen or $C_1$-$C_6$alkyl.

(1q) $R^1$ is halogen, cyano, $C_{1-6}$alkyl or —$R^a$, wherein $R^a$ is —$OR^{S1}$, —$SR^{S1}$, —$NR^{S1}R^{S1}$, —$C(O)R^{S1}$, —$C(O)OR^{S1}$, —$C(O)NR^{S1}R^{S1}$, —$S(O)_2NR^{S1}R^{S1}$, —$OC(O)R^{S1}$, —$N(R^{S1})C(O)R^{S1}$, —$OC(O)OR^{S1}$, —$N(R^{S1})C(O)OR^{S1}$;

wherein each $R^{S1}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(1r) $R^1$ is as described in (1q), wherein $R^{S1}$ is independently hydrogen or $C_1$-$C_6$alkyl.

(1s) $R^1$ is hydrogen or —$R^a$, wherein $R^a$ is —$OR^{S1}$, —$SR^{S1}$, —$NR^{S1}R^{S1}$, —$C(O)R^{S1}$, —$C(O)OR^{S1}$, —$C(O)NR^{S1}R^{S1}$, —$S(O)_2NR^{S1}R^{S1}$, —$OC(O)R^{S1}$, —$N(R^{S1})C(O)R^{S1}$, —$OC(O)OR^{S1}$, —$N(R^{S1})C(O)OR^{S1}$;

wherein each $R^{S1}$ is independently hydrogen, $C_1$-$C_6$alkyl, $C_1$-$C_6$haloalkyl, —($C_0$-$C_6$alkyl)-Ar, —($C_0$-$C_6$alkyl)-Het, —($C_0$-$C_6$alkyl)-Cak, or —($C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(1t) $R^1$ is as described in (1s), wherein $R^{S1}$ is independently hydrogen or $C_1$-$C_6$alkyl.

(1u) $R^1$ is hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl or heteroaryl.

(1v) $R^1$ is hydrogen, $C_{3-8}$cycloalkyl, $C_{3-8}$cycloalkenyl, heterocyclyl, aryl or heteroaryl.

(1w) $R^1$ is hydrogen, halogen, cyano, nitro, $C_{1-6}$alkyl or $C_{1-6}$haloalkyl.

(1x) $R^1$ is halogen, cyano, nitro, $C_{1-6}$alkyl or $C_{1-6}$haloalkyl.

(1y) $R^1$ is hydrogen, halogen, cyano or nitro.

(1z) $R^1$ is hydrogen, halogen, nitro, $C_{1-6}$alkyl or $C_{1-6}$haloalkyl.

(1aa) $R^1$ is hydrogen, halogen, cyano, $C_{1-6}$alkyl or $C_{1-6}$haloalkyl.

(1bb) $R^1$ is hydrogen, halogen, cyano, nitro or $C_{1-6}$haloalkyl.

(1cc) $R^1$ is hydrogen, cyano, nitro, $C_{1-6}$alkyl or $C_{1-6}$haloalkyl.

(1dd) $R^1$ is hydrogen, cyano, $C_{1-6}$alkyl or $C_{1-6}$haloalkyl.

(1ee) $R^1$ is hydrogen, halogen, $C_{1-6}$alkyl or $C_{1-6}$haloalkyl.

(1ff) $R^1$ is hydrogen, halogen, or $C_{1-6}$alkyl.

(1gg) $R^1$ is hydrogen or $C_{1-6}$alkyl.

(1hh) $R^1$ is hydrogen or halogen.

(1ii) $R^1$ is halogen or $C_{1-6}$alkyl.
(1jj) $R^1$ is halogen or $C_{1-4}$alkyl.
(1kk) $R^1$ is halogen or $C_{1-4}$alkyl.
(1ll) $R^1$ is hydrogen, halogen or methyl.
(1 mm) $R^1$ is halogen or methyl.
(1nn) $R^1$ is hydrogen, fluoro or methyl.
(1oo) $R^1$ is fluoro or methyl.
(1pp) $R^1$ is hydrogen, fluoro.
(1qq) $R^1$ is fluoro.
(1rr) $R^1$ is hydrogen, methyl.
(1ss) $R^1$ is methyl.
(1tt) $R^1$ is hydrogen.

Z is Selected from One of the Following Groups (2a)-(2dddd):

(2a) Z is
a fused bicyclic ring of the formula,

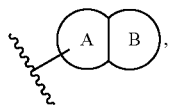

wherein
ring A is Ar or 6-membered Het,
ring B is 5- or 6-membered Het,
wherein
Z is optionally substituted by one or two —$R^Z$ groups that are each independently halogen, cyano, $C_{1-6}$alkyl, $C_{1-6}$haloalkyl, —$C_1$-$C_6$alkoxy, —$OR^{S2}$, —$SR^{S2}$, —$NR^{S2}{}_2$, —$C(O)R^{S2}$, —$C(O)OR^{S2}$, —$C(O)NR^{S2}{}_2$, —$S(O)_2NR^{S2}{}_2$, —$S(O)_2R^{S2}$, —$OC(O)R^{S2}$, —$N(R^{S2})C(O)R^{S2}$, —$OC(O)OR^{S2}$, —$OC(O)NR^{S2}{}_2$, —$N(R^{S2})C(O)OR^{S2}$, —$N(R^{S2})C(O)NR^{S2}{}_2$, —$N(R^{S2})S(O)_2R^{S2}$, —$OP(O)(OR^{S2})_2$ or —$CH_2$—$OP(O)(OR^{S2})$, wherein each alkyl, haloalkyl and alkoxy is optionally substituted by one or two —$R^{Z2}$ groups;
wherein each $R^{S2}$ is independently hydrogen, $C_1$-$C_6$alkyl, $C_1$-$C_6$haloalkyl, —$(C_0$-$C_6$alkyl)-Ar, —$(C_0$-$C_6$alkyl)-Het, —$(C_0$-$C_6$alkyl)-Cak, or —$(C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano; and
each —$R^{Z2}$ is independently halogen, cyano, $C_{1-6}$alkyl, $C_{1-6}$haloalkyl, —$C_1$-$C_6$alkoxy, —$OR^{S3}$, —$SR^{S3}$, —$NR^{S3}{}_2$, —$C(O)R^{S3}$, —$C(O)OR^{S3}$, —$C(O)NR^{S3}{}_2$, —$S(O)_2NR^{S3}{}_2$, —$S(O)_2R^{S3}$, —$OC(O)R^{S3}$, —$N(R^{S3})C(O)R^{S3}$, —$OC(O)OR^{S3}$, —$OC(O)NR^{S3}{}_2$, —$N(R^{S3})C(O)OR^{S3}$, —$N(R^{S3})C(O)NR^{S3}{}_2$, —$N(R^{S3})S(O)_2R^{S3}$, —$OP(O)(OR^{S3})_2$ or —$CH_2$—$OP(O)(OR^{S3})$; and
wherein each $R^{S3}$ is independently hydrogen, $C_1$-$C_6$alkyl, $C_1$-$C_6$haloalkyl, —$(C_0$-$C_6$alkyl)-Ar, —$(C_0$-$C_6$alkyl)-Het, —$(C_0$-$C_6$alkyl)-Cak, or —$(C_0$-$C_6$alkyl)-Hca, wherein Ar, Het, Cak, Hca, alkyl, and haloalkyl are optionally substituted with $C_1$-$C_6$alkyl, halogen, $C_1$-$C_6$haloalkyl or cyano.

(2b) Z is as described in (2a), provided that Z is not 5-(6'-methyl-[2,2'-bipyridin]-3-yl)-1H-indazole (2c) Z is as described in (2a), provided that Z is not

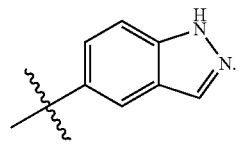 [SMILES: *c1ccc2[nH]ncc2c1]

(2d) Z is
a fused bicyclic ring of the formula,

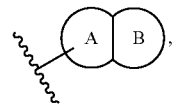

wherein
ring A is Ar or 6-membered Het,
ring B is 5- or 6-membered Het,
wherein
Z is optionally substituted by one or two —$R^Z$ groups that are each independently halogen, cyano, $C_{1-6}$alkyl, $C_{1-6}$haloalkyl, —$C_1$-$C_6$alkoxy, —$OR^{S2}$, —$SR^{S2}$, —$NR^{S2}{}_2$, —$C(O)R^{S2}$, —$C(O)OR^{S2}$, —$C(O)NR^{S2}{}_2$, —$S(O)_2NR^{S2}{}_2$, —$S(O)_2R^{S2}$, —$OC(O)R^{S2}$, —$N(R^{S2})C(O)R^{S2}$, —$OC(O)OR^{S2}$, —$OC(O)NR^{S2}{}_2$, —$N(R^{S2})C(O)OR^{S2}$, —$N(R^{S2})C(O)NR^{S2}{}_2$, —$N(R^{S2})S(O)_2R^{S2}$, —$OP(O)(OR^{S2})_2$ or —$CH_2$—$OP(O)(OR^{S2})$.

(2e) Z is as described in (2d), provided that Z is not 5-(6'-methyl-[2,2'-bipyridin]-3-yl)-1H-indazole (2f) Z is as described in (2d), provided that Z is not

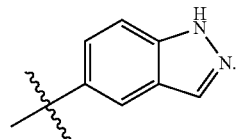 [SMILES: *c1ccc2[nH]ncc2c1]

(2g) Z is
a fused bicyclic ring of the formula,

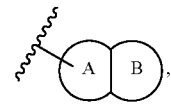

wherein
(1) ring A is Ar or 6-membered Het, and
ring B is a 6-membered Het; or
(2) ring A is 6-membered Het, and
ring B is a 5-membered Het;
optionally substituted as described in (2a) above.

(2h) Z is
a fused bicyclic ring of the formula,

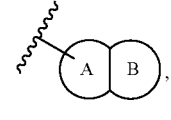

wherein
(1) ring A is Ar or 6-membered Het, and
ring B is a 6-membered Het; or
(2) ring A is 6-membered Het, and
ring B is a 5-membered Het;
optionally substituted as described in (2d) above.
(2i) Z is
a fused bicyclic ring of the formula,

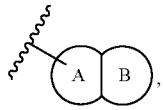

wherein
(1) ring A is Ar, and
ring B is a 6-membered Het; or
(2) ring A is 6-membered Het, and
ring B is a 5-membered Het;
optionally substituted as described in (2a) above.
(2j) Z is
a fused bicyclic ring of the formula,

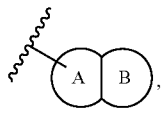

wherein
(1) ring A is Ar, and
ring B is a 6-membered Het; or
(2) ring A is 6-membered Het, and
ring B is a 5-membered Het;
optionally substituted as described in (2d) above.
(2k) Z is
a fused bicyclic ring of the formula,

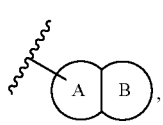

wherein
(1) ring A is 6-membered Het, and
ring B is a 6-membered Het; or
(2) ring A is 6-membered Het, and
ring B is a 5-membered Het;
optionally substituted as described in (2a) above.
(2l) Z is
a fused bicyclic ring of the formula,

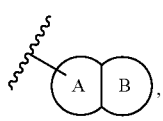

wherein
(1) ring A is 6-membered Het, and
ring B is a 6-membered Het; or
(2) ring A is 6-membered Het, and
ring B is a 5-membered Het;
optionally substituted as described in (2d) above.

(2m) Z is
a fused bicyclic ring of the formula,

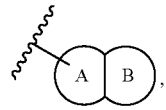

wherein
ring A is Ar or 6-membered Het, and
ring B is a 6-membered Het; or
optionally substituted as described in (2a) above.
(2n) Z is
a fused bicyclic ring of the formula,

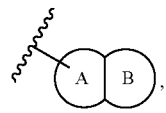

wherein
ring A is Ar or 6-membered Het, and
ring B is a 6-membered Het; or
optionally substituted as described in (2d) above.
(2o) Z is
a fused bicyclic ring of the formula,

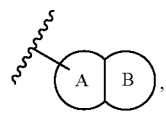

wherein
ring A is Ar, and
ring B is a 6-membered Het; or
optionally substituted as described in (2a) above.
(2p) Z is
a fused bicyclic ring of the formula,

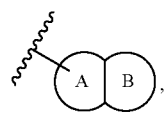

wherein
ring A is Ar, and
ring B is a 6-membered Het; or
optionally substituted as described in (2d) above.
(2q) Z is
a fused bicyclic ring of the formula,

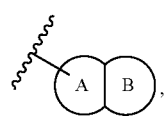

wherein
ring A is 6-membered Het, and
ring B is a 6-membered Het; or
optionally substituted as described in (2a) above.

(2r) Z is
a fused bicyclic ring of the formula,

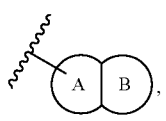

wherein
ring A is 6-membered Het, and
ring B is a 6-membered Het; or
optionally substituted as described in (2d) above.
(2s) Z is
a fused bicyclic ring of the formula,

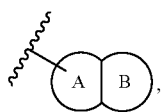

wherein
ring A is 6-membered Het, and
ring B is a 5-membered Het;
optionally substituted as described in (2a) above.
(2t) Z is
a fused bicyclic ring of the formula,

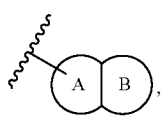

wherein
ring A is 6-membered Het, and
ring B is a 5-membered Het;
optionally substituted as described in (2d) above.
(2u) Z is

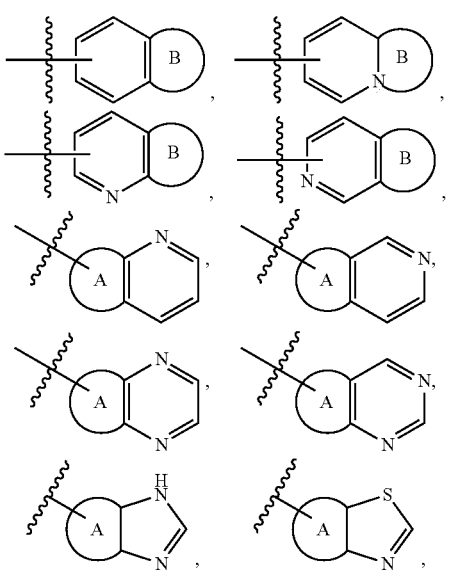

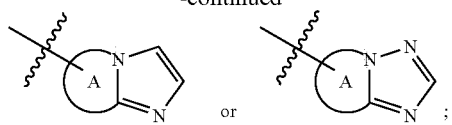

or optionally substituted as described in (2a) above.
(2v) Z is

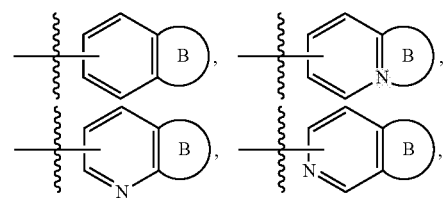

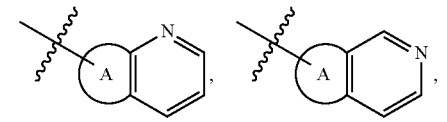

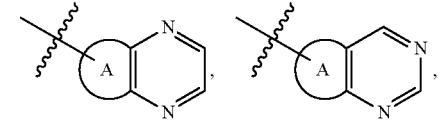

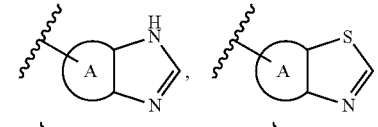

or optionally substituted as described in (2d) above.
(2w) Z is

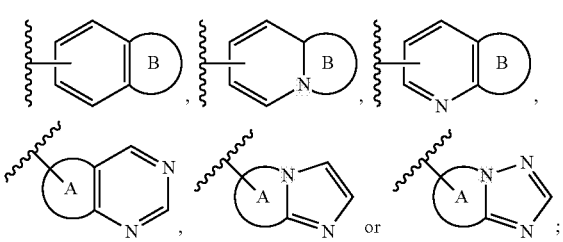

or optionally substituted as described in (2a) above.
(2x) Z is

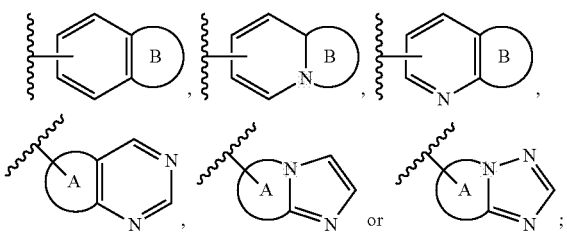

or optionally substituted as described in (2d) above.

(2y) Z is

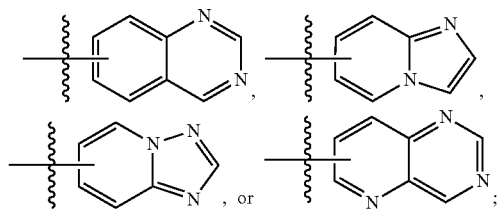

optionally substituted as described in (2a) above.
(2z) Z is

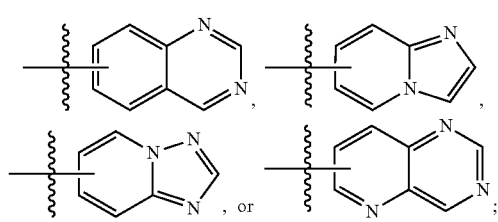

optionally substituted as described in (2d) above.
(2aa) Z is

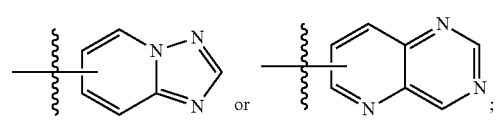

optionally substituted as described in (2a) above.
(2bb) Z is

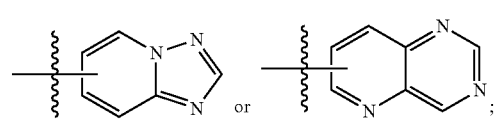

optionally substituted as described in (2d) above.
(2cc) Z is

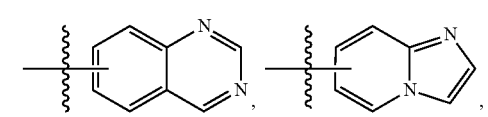

optionally substituted as described in (2a) above.
(2dd) Z is

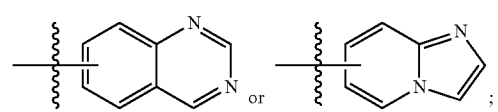

optionally substituted as described in (2d) above.

(2ee) Z is,

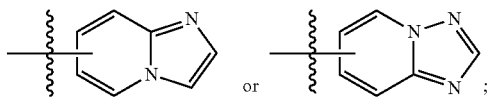

optionally substituted as described in (2a) above.
(2ff) Z is,

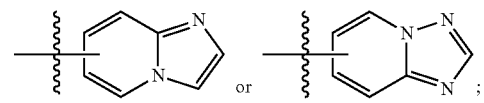

optionally substituted as described in (2d) above.
(2gg) Z is

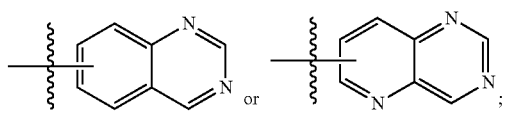

optionally substituted as described in (2a) above.
(2hh) Z is

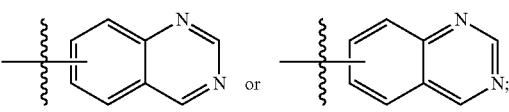

optionally substituted as described in (2d) above.
(2ii) Z is

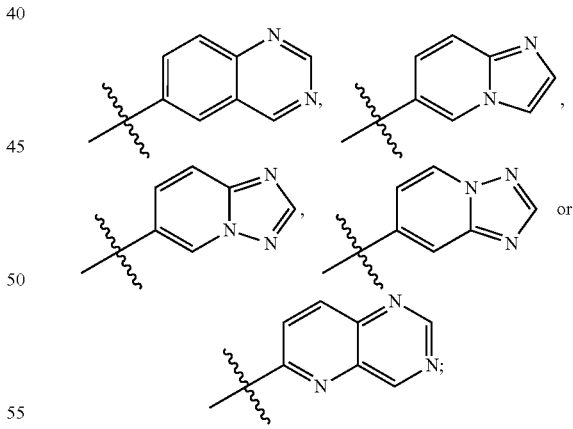

optionally substituted as described in (2a) above.
(2jj) Z is

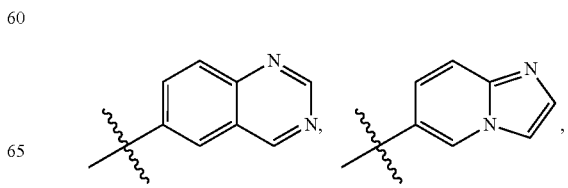

-continued

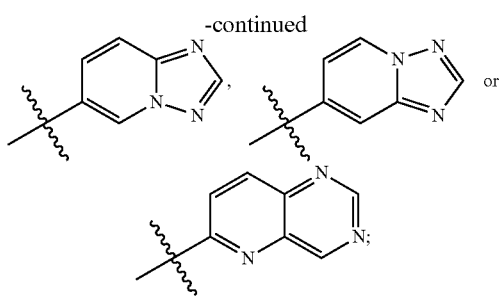

optionally substituted as described in (2d) above.
(2kk) Z is

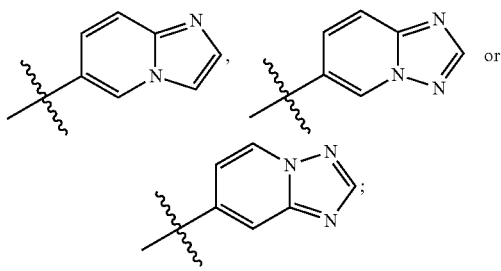

optionally substituted as described in (2d) above.
(2ll) Z is

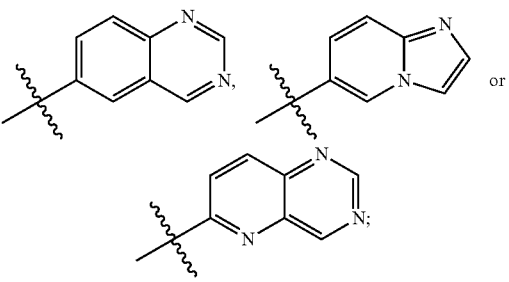

optionally substituted as described in (2d) above.
(2 mm) Z is

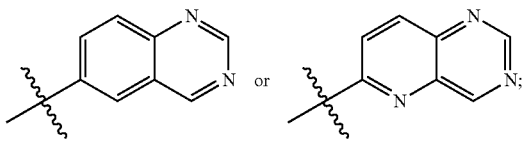 [SMILES: *c1ccc2ncncc2c1 ; *c1ccc2ncncc2n1]

optionally substituted as described in (2d) above.
(2nn) Z is

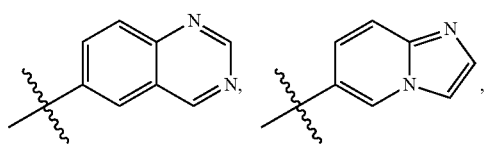

-continued

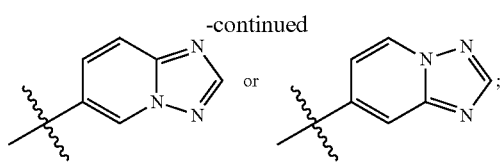

optionally substituted as described in (2d) above.
(2oo) Z is

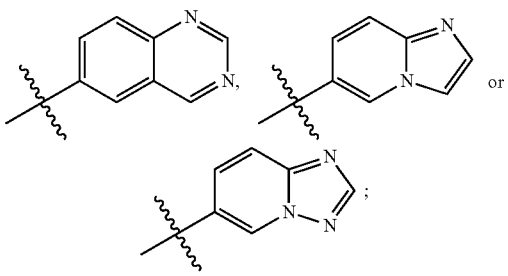

optionally substituted as described in (2d) above.
(2pp) Z is

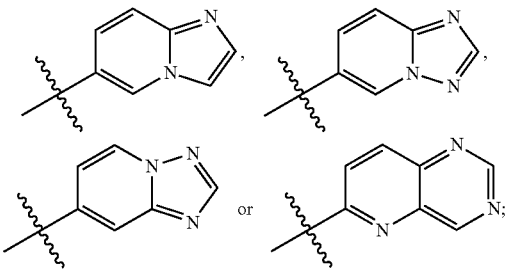

optionally substituted as described in (2d) above.
(2qq) Z is

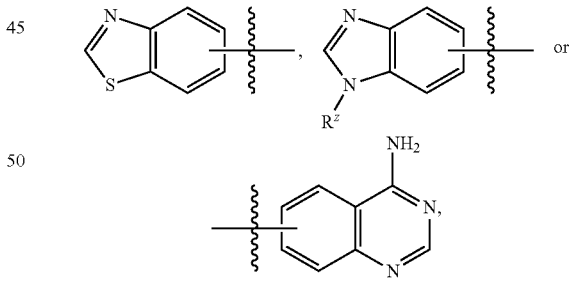

optionally substituted as described in (2a) above, and wherein $R^z$ is as described in (2a) above.
(2rr) Z is

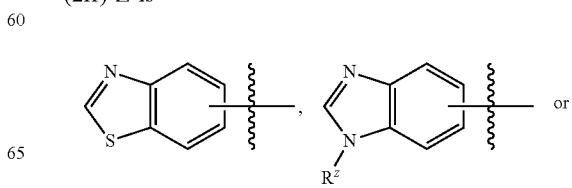

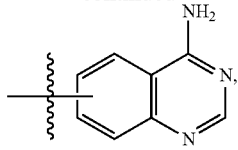
wherein $R^Z$ is as described in (2a) above.
(2ss) Z is
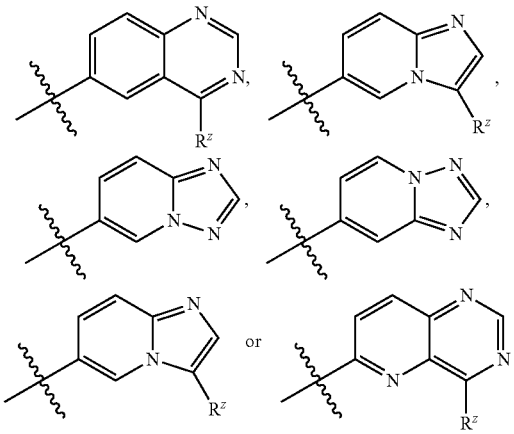
wherein $R^Z$ is as described in (2a).
(2tt) Z is
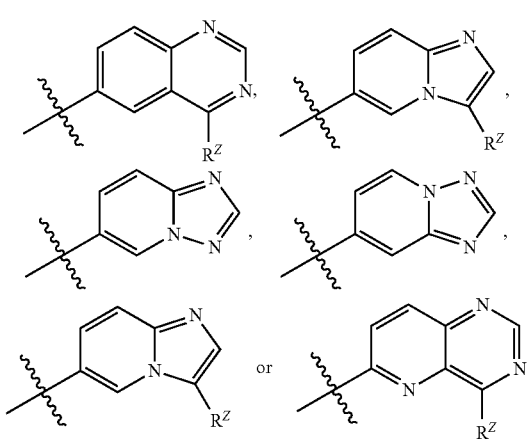
wherein $R^Z$ is as described in (2d).
(2uu) Z is
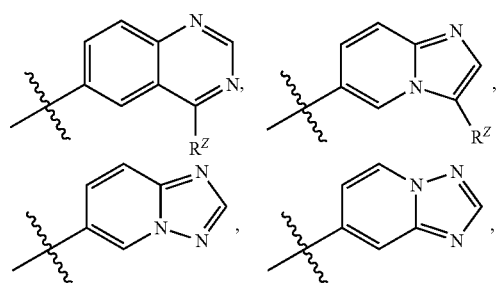
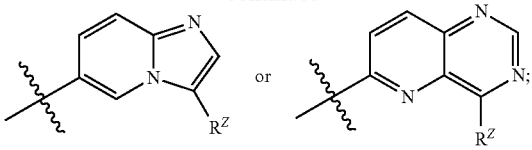
wherein $R^Z$ is —NH$_2$, -cyano or —C(O)NH$_2$.
(2vv) Z is
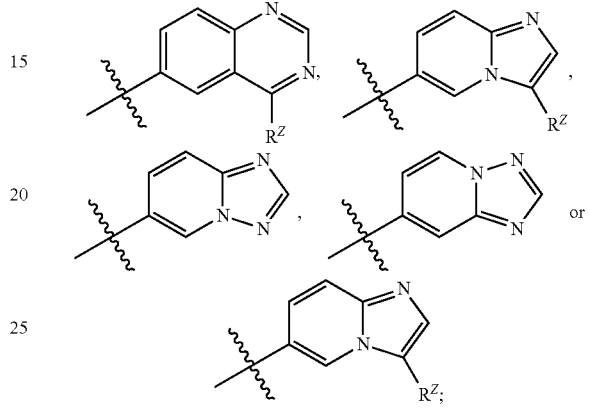
wherein $R^Z$ is as described in (2d).
(2ww) Z is
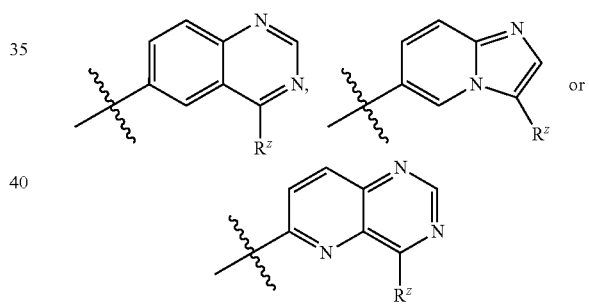
wherein $R^Z$ is as described in (2d).
(2xx) Z is
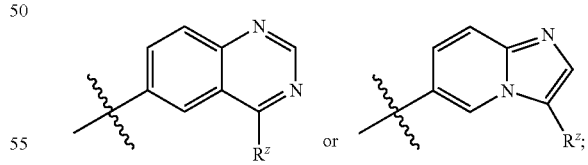
wherein $R^Z$ is as described in (2d).
(2yy) Z is
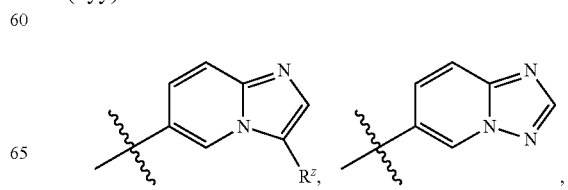

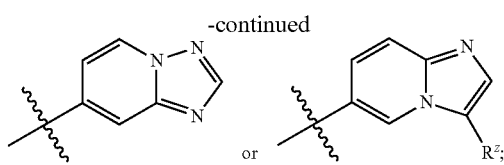
wherein $R^z$ is as described in (2d).
(2zz) Z is
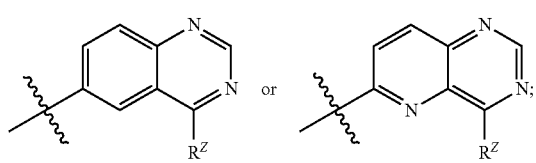
wherein $R^z$ is as described in (2d).
(2aaa) Z is
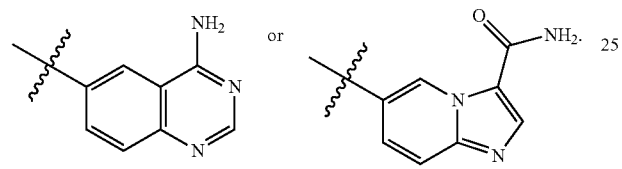
(2bbb) Z is
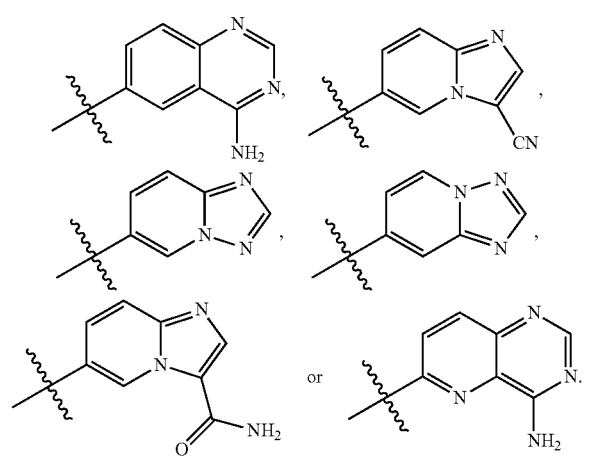
(2ccc) Z is
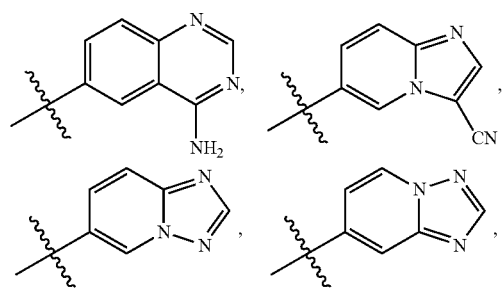
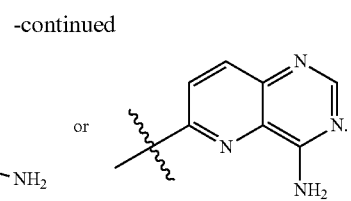
(2ddd) Z is
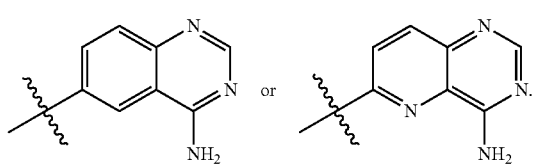 [SMILES: *c1ccc2ncnc(N)c2c1 ; "or" ; *c1ccc2ncnc(N)c2n1]
(2eee) Z is
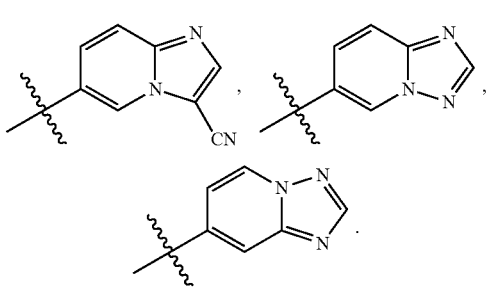
(2fff) Z is
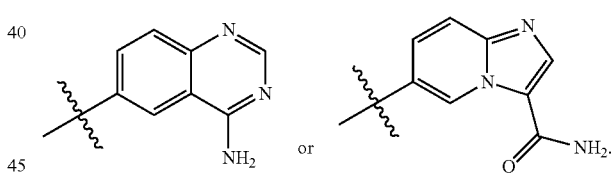
(2ggg) Z is
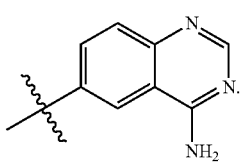 [SMILES: *c1ccc2ncnc(N)c2c1]
(2hhh) Z is
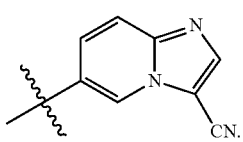 [SMILES: *c1ccc2ncc(C#N)n2c1]

(2iii) Z is
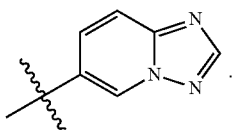
(2jjj) Z is
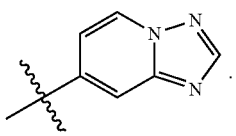
(2kkk) Z is
(2lll) Z is
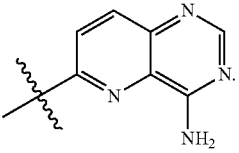 [SMILES: *c1ccc2ncnc(N)c2n1]
(2mmm) Z is
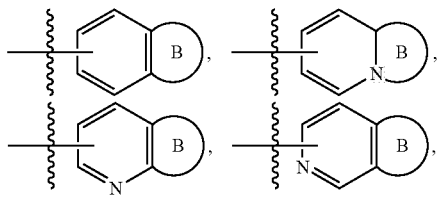
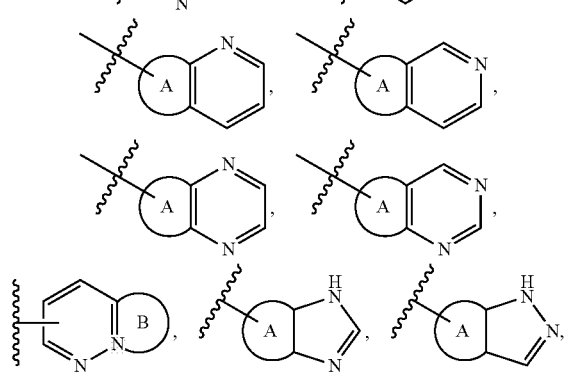
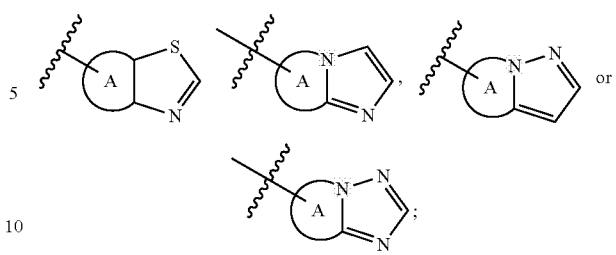
optionally substituted as described in (2a) above.
(2nnn) Z is
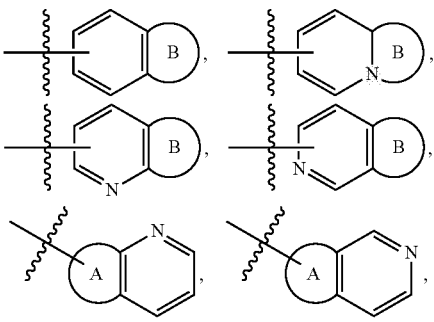
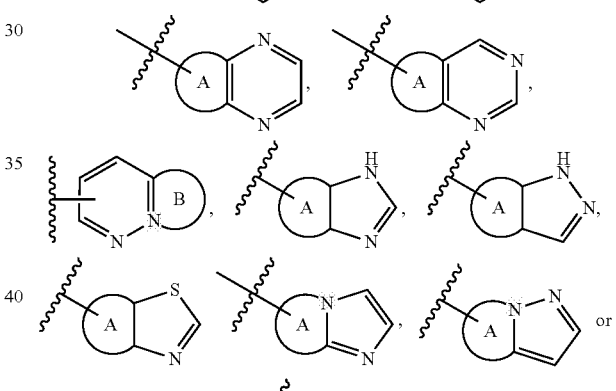
optionally substituted as described in (2d) above.
(2ooo) Z is
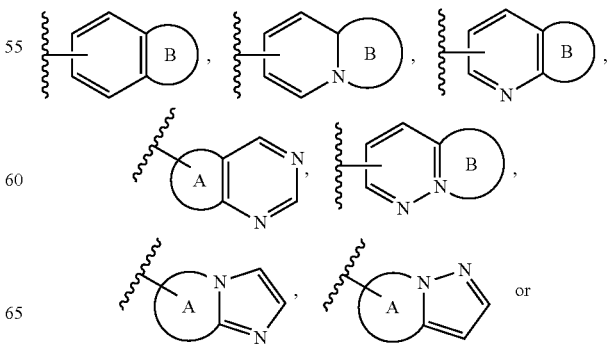

-continued

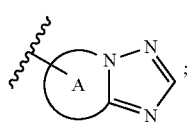

optionally substituted as described in (2a) above.

(2ppp) Z is

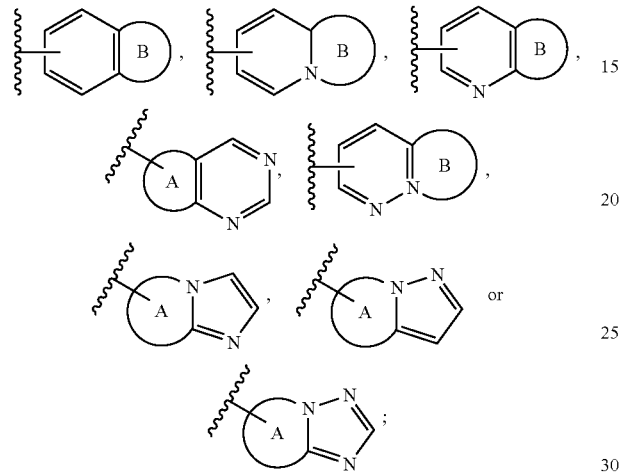

optionally substituted as described in (2d) above.

(2qqq) Z is

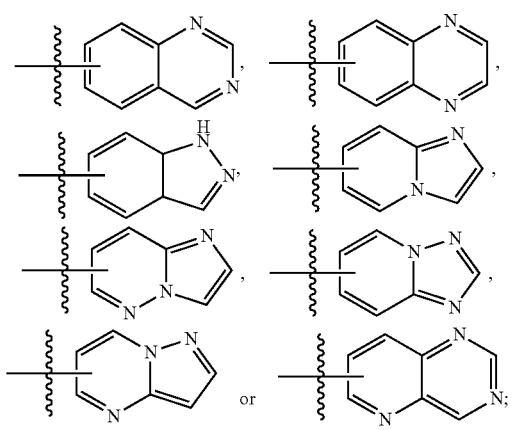

optionally substituted as described in (2a) above.

(2rrr) Z is

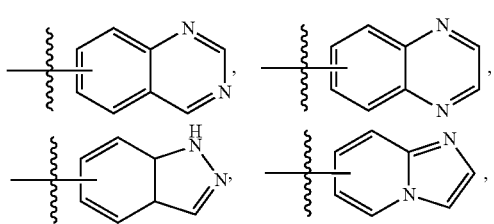

-continued

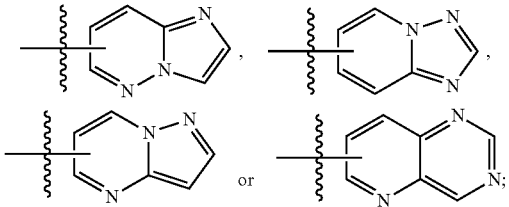

optionally substituted as described in (2d) above.

(2sss) Z is

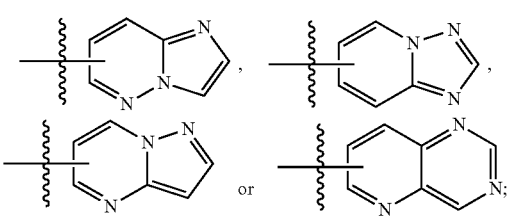

optionally substituted as described in (2a) above.

(2ttt) Z is

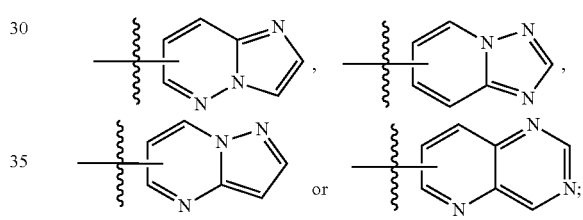

optionally substituted as described in (2d) above.

(2uuu) Z is

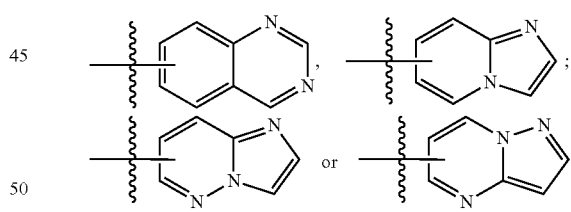

optionally substituted as described in (2a) above.

(2vvv) Z is

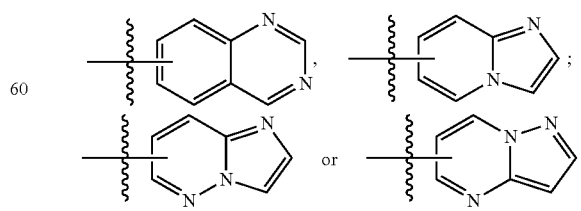

optionally substituted as described in (2d) above.

(2www) Z is
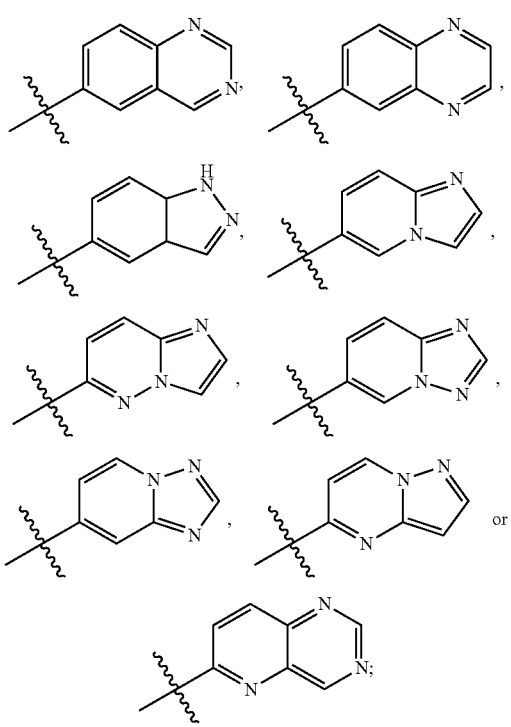
optionally substituted as described in (2a) above.
(2xxx) Z is
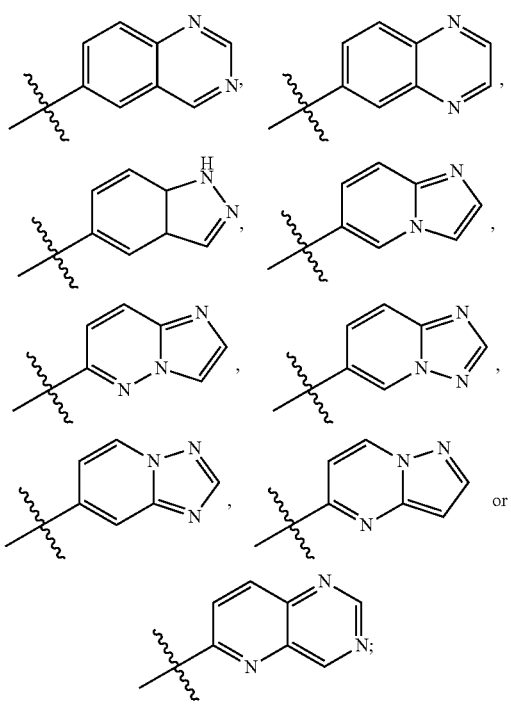
optionally substituted as described in (2d) above.
(2yyy) Z is
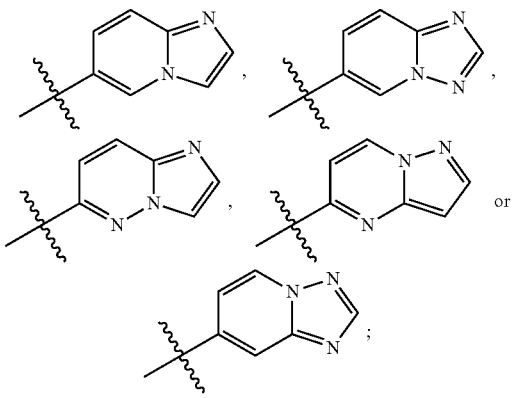
optionally substituted as described in (2d) above.
(2zzz) Z is
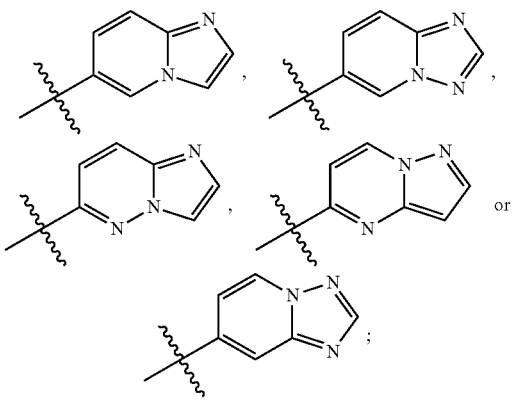
optionally substituted as described in (2d) above.
(2aaaa) Z is
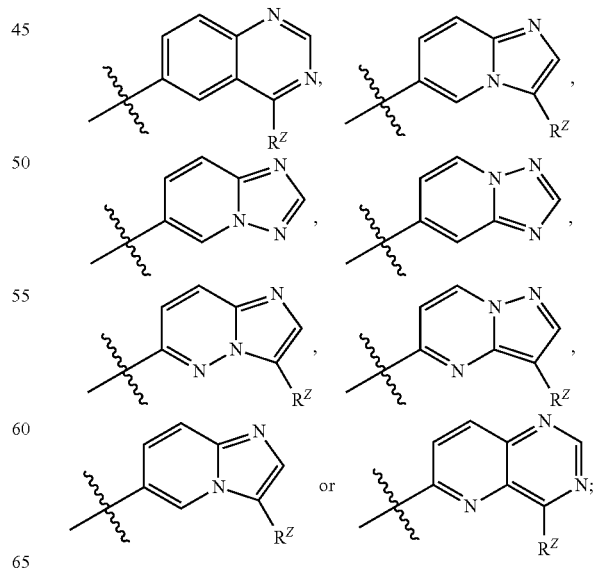
wherein $R^Z$ is as described in (2a).

(2bbbb) Z is

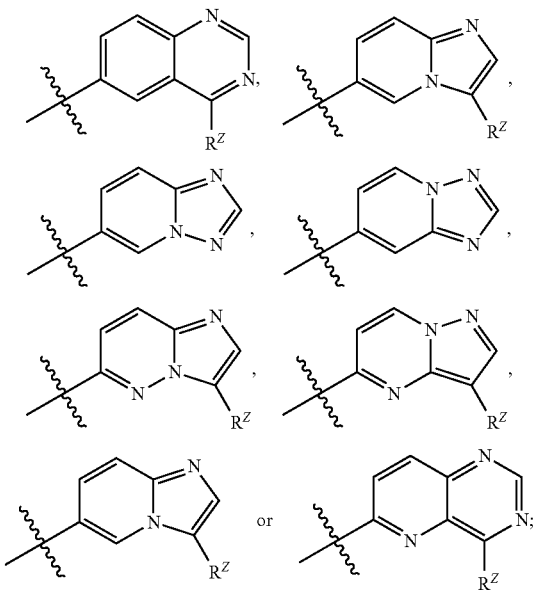

wherein $R^Z$ is as described in (2d).

(2cccc) Z is

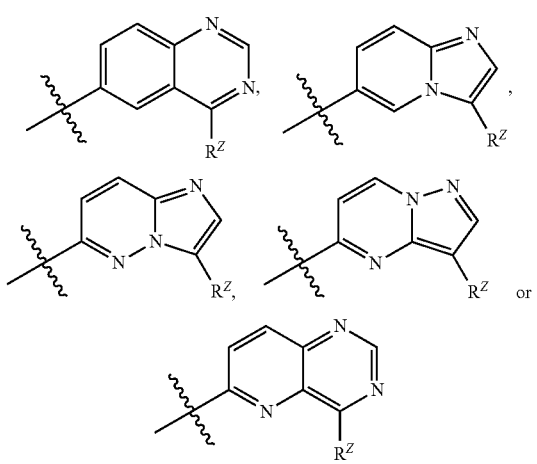

wherein $R^Z$ is as described in (2d).

(2dddd) Z is

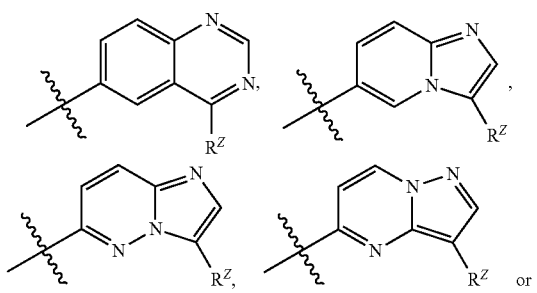

wherein $R^Z$ is as described in (2d).

n is Selected from One of the Following Groups (3a)-(3i):
(3a) n is 0, 1, 2, 3 or 4.
(3b) n is 0, 1, 2 or 3.
(3c) n is 0, 1 or 2.
(3d) n is 0 or 1.
(3e) n is 0.
(3f) n is 1.
(3g) n is 2.
(3h) n is 3.
(3i) n is 4.

Particular embodiments of this aspect of the invention comprise compounds of any one of the formulae (I), (I') and (Ia)-(Im), each as defined in each of the following rows (or a pharmaceutically acceptable salt, prodrug, or N-oxide thereof, or a solvate or hydrate thereof), wherein each entry is a group number as defined above (e.g., (3i) refers to n is 4 and a dash "-" indicates that the variable is as defined in embodiment $I_1$ or defined according to any one of the applicable variable definitions (1a)-(3i) [e.g., when $R^1$ is a dash, it can be either as defined in any of embodiments $I_1$-$I_8$ or any one of definitions (1a)-(1tt)]:

|         | (I)   | $R^1$  | Z      | n    |
|---------|-------|--------|--------|------|
| (1)-1   | (Ia)  | X      | (2a)   | X    |
| (1)-2   | (Ib)  | X      | (2b)   | X    |
| (1)-3   | (Ic)  | X      | (2d)   | (3d) |
| (1)-4   | (Id)  | (1aa)  | (2q)   | (3e) |
| (1)-5   | (Ie)  | (1ff)  | X      | (3f) |
| (1)-6   | (If)  | (1m)   | X      | (3g) |
| (1)-7   | (Ig)  | (1s)   | X      | (3a) |
| (1)-8   | (Ih)  | (1rr)  | X      | (3c) |
| (1)-9   | (Ib)  | X      | (2p)   | (3d) |
| (1)-10  | (Ic)  | X      | (2r)   | (3e) |
| (1)-11  | (Id)  | (1a)   | (2k)   | (3f) |
| (1)-12  | (Id)  | (1q)   | (2r)   | (3g) |
| (1)-13  | (Ia)  | X      | (2w)   | X    |
| (1)-14  | (Ib)  | X      | (2x)   | X    |
| (1)-15  | (Ic)  | X      | (2bb)  | (3a) |
| (1)-16  | (Id)  | (1aa)  | (2k)   | (3c) |
| (1)-17  | (Ie)  | (1ff)  | X      | (3d) |
| (1)-18  | (If)  | (1m)   | X      | (3e) |
| (1)-19  | (Ig)  | (1s)   | X      | (3f) |
| (1)-20  | (Ih)  | (1rr)  | X      | (3g) |
| (1)-21  | (Ia)  | X      | (2bbb) | X    |
| (1)-22  | (Ib)  | X      | (2d)   | X    |
| (1)-23  | (Ic)  | X      | (2x)   | (3a) |
| (1)-24  | (Id)  | (1q)   | (2r)   | (3c) |
| (1)-25  | (Ie)  | (1u)   | X      | (3d) |
| (1)-26  | (If)  | (1aa)  | X      | (3e) |
| (1)-27  | (Ig)  | (1ff)  | X      | (3f) |
| (1)-28  | (Ih)  | (1m)   | X      | (3g) |
| (1)-29  | (Ib)  | X      | (2r)   | —    |
| (1)-30  | (Ic)  | X      | (2t)   | (3d) |
| (1)-31  | (Id)  | (1ss)  | (2k)   | —    |
| (1)-32  | (Ia)  | X      | (2w)   | X    |
| (1)-33  | (Ib)  | X      | (2x)   | X    |
| (1)-34  | (Ic)  | X      | (2bb)  | —    |
| (1)-35  | (Id)  | (1rr)  | (2s)   | (3a) |
| (1)-36  | (Ie)  | (1rr)  | X      | (3c) |
| (1)-37  | (If)  | (2s)   | X      | (3d) |
| (1)-38  | (Ig)  | (2j)   | X      | (3e) |
| (1)-39  | (Ih)  | (2o)   | X      | —    |
| (1)-40  | (Ie)  | (2p)   | X      | (3a) |

-continued

| | (I) | R¹ | Z | n |
|---|---|---|---|---|
| (1)-41 | (If) | (1ff) | X | (3c) |
| (1)-42 | (Ig) | (1m) | X | (3d) |
| (1)-43 | (Ih) | (1s) | X | (3e) |
| (1)-44 | (Ib) | X | (2p) | X |
| (1)-45 | (Ic) | X | (2r) | — |
| (1)-46 | (Id) | (2j) | (2q) | (3d) |
| (1)-47 | (Ig) | (2o) | X | — |
| (1)-48 | (Ih) | (2p) | X | (3d) |
| (1)-49 | (Ib) | X | (2x) | X |
| (1)-50 | (Ic) | X | (2bb) | (3a) |
| (1)-51 | (Id) | (1aa) | (2r) | (3c) |
| (1)-52 | (Ie) | (1ff) | X | (3d) |
| (1)-53 | (If) | (1m) | X | (3e) |
| (1)-54 | (Ig) | (1s) | X | (3f) |
| (1)-55 | (Ih) | (1rr) | X | (3g) |
| (1)-56 | (Ib) | X | (2bbb) | — |
| (1)-57 | (Ic) | X | (2x) | (3d) |
| (1)-58 | (Id) | (1a) | (2k) | — |
| (1)-59 | (Ib) | X | (2ii) | X |
| (1)-60 | (Ic) | X | (2jj) | — |
| (1)-61 | (Id) | (1rr) | (2s) | (3a) |
| (1)-62 | (Ie) | (2s) | X | (3c) |
| (1)-63 | (If) | (2j) | X | (3d) |
| (1)-64 | (Ig) | (2o) | X | (3e) |
| (1)-65 | (Ih) | (2p) | X | (3f) |
| (1)-66 | (Ib) | X | (2i) | X |
| (1)-67 | (Ic) | X | (2j) | (3a) |
| (1)-68 | (Id) | (2s) | (2q) | (3c) |
| (1)-69 | (Ic) | X | (2p) | (3d) |
| (1)-70 | (Id) | (2o) | (2k) | (3e) |
| (1)-71 | (Ie) | (2p) | X | (3f) |
| (1)-72 | (If) | (1rr) | X | (3g) |
| (1)-73 | (Ig) | (1ff) | X | — |
| (1)-74 | (Ih) | (1m) | X | — |
| (1)-75 | (Ic) | X | (2bb) | (3a) |
| (1)-76 | (Id) | (1rr) | (2q) | (3c) |
| (1)-77 | (Ie) | (2s) | X | (3d) |
| (1)-78 | (If) | (2j) | X | (3e) |
| (1)-79 | (Ig) | (2o) | X | (3f) |
| (1)-80 | (Ih) | (2p) | X | (3g) |
| (1)-81 | (Ib) | X | (2bbb) | X |
| (1)-82 | (Ic) | X | (2jj) | — |
| (1)-83 | (Id) | (1ff) | (2r) | (3a) |
| (1)-84 | (Ic) | X | (2ww) | (3c) |
| (1)-85 | (Id) | (1s) | (2s) | (3d) |
| (1)-86 | (Ie) | (1rr) | X | (3e) |
| (1)-87 | (If) | (1rr) | X | (3f) |
| (1)-88 | (Ig) | (1rr) | X | (3g) |
| (1)-89 | (Ih) | (1rr) | X | — |
| (1)-90 | (Ib) | X | (2h) | X |
| (1)-91 | (Ic) | X | (2i) | — |
| (1)-92 | (Id) | (1rr) | (2k) | — |
| (1)-93 | (Ia) | X | (2o) | X |
| (1)-94 | (Ib) | X | (2p) | X |
| (1)-95 | (Ic) | X | (2r) | (3a) |
| (1)-96 | (Ig) | (1m) | X | (3c) |
| (1)-97 | (Ih) | (1s) | X | (3d) |
| (1)-98 | (Ic) | X | (2ww) | (3e) |
| (1)-99 | (Id) | (1rr) | (2q) | (3f) |
| (1)-100 | (Ia) | X | (2bbb) | X |
| (1)-101 | (Ib) | X | (2g) | X |
| (1)-102 | (Ic) | X | (2h) | (3a) |
| (1)-103 | (Id) | (1ff) | (2k) | (3c) |
| (1)-104 | (Ie) | (1m) | X | (3d) |
| (1)-105 | (If) | (1s) | X | (3e) |
| (1)-106 | (Ig) | (1rr) | X | (3f) |
| (1)-107 | (Ih) | (1rr) | X | (3g) |
| (1)-108 | (Ia) | X | (2t) | X |
| (1)-109 | (Ib) | X | (2u) | X |
| (1)-110 | (Ic) | X | (2w) | — |
| (1)-111 | (Id) | (1rr) | (2r) | (3d) |
| (1)-112 | (Ib) | X | (2bb) | X |
| (1)-113 | (Ic) | X | (2ii) | — |
| (1)-114 | (Id) | (1aa) | (2q) | (3d) |
| (1)-115 | (Ie) | (1ff) | X | (3a) |
| (1)-116 | (If) | (1m) | X | (3c) |
| (1)-117 | (Ig) | (1s) | X | (3d) |
| (1)-118 | (Ih) | (1rr) | X | (3e) |
| (1)-119 | (Ib) | X | (2qq) | (3f) |
| (1)-120 | (Ic) | X | (2ww) | (3g) |
| (1)-121 | (Id) | (1a) | (2q) | — |
| (1)-122 | (Ia) | X | (2bbb) | X |
| (1)-123 | (Ib) | X | (2b) | — |
| (1)-124 | (Ic) | X | (2d) | (3d) |
| (1)-125 | (Id) | (1s) | (2r) | — |
| (1)-126 | (Ia) | X | (2h) | X |
| (1)-127 | (Ib) | X | (2i) | X |
| (1)-128 | (Ic) | X | (2j) | — |
| (1)-129 | (Id) | — | (2s) | (3a) |
| (1)-130 | (Ie) | (2s) | X | (3c) |
| (1)-131 | (If) | (2j) | X | (3d) |
| (1)-132 | (Ig) | (2o) | X | (3e) |
| (1)-133 | (Ih) | (2p) | X | (3f) |
| (1)-134 | (Ia) | X | (2w) | X |
| (1)-135 | (Ib) | X | (2x) | X |
| (1)-136 | (Ic) | X | (2bb) | (3a) |
| (1)-137 | (Id) | (2s) | (2s) | (3c) |
| (1)-138 | (Ie) | (2j) | X | (3d) |
| (1)-139 | (If) | (2o) | X | (3e) |
| (1)-140 | (Ig) | (2p) | X | (3f) |
| (1)-141 | (Ih) | (2p) | X | (3g) |
| (1)-142 | (Ia) | (1rr) | (2bbb) | — |
| (1)-143 | (Ib) | X | (2qq) | X |
| (1)-144 | (Ic) | X | (2ww) | (3d) |
| (1)-145 | (Id) | (1m) | (2s) | — |
| (1)-146 | (Ie) | (1s) | X | (3a) |
| (1)-147 | (If) | (1rr) | X | (3c) |
| (1)-148 | (Ig) | (1rr) | X | (3d) |
| (1)-149 | (Ih) | (1rr) | X | (3e) |
| (1)-150 | (Ib) | X | (2i) | (3f) |
| (1)-151 | (Ic) | X | (2j) | (3g) |
| (1)-152 | (Id) | (1s) | (2q) | — |
| (1)-153 | (Ia) | X | (2p) | X |
| (1)-154 | (Ib) | X | (2r) | X |
| (1)-155 | (Ic) | — | (2t) | — |
| (1)-156 | (Ib) | X | (2u) | X |
| (1)-157 | (Ic) | X | (2w) | (3a) |
| (1)-158 | (Id) | (1aa) | (2k) | (3c) |
| (1)-159 | (Ie) | (1ff) | X | (3d) |
| (1)-160 | (If) | (1m) | X | (3e) |
| (1)-161 | (Ig) | (1s) | X | (3f) |
| (1)-162 | (Ih) | (1rr) | X | (3g) |
| (1)-163 | (Ie) | (1ss) | X | (3d) |
| (1)-164 | (If) | (1tt) | X | — |
| (1)-165 | (Ig) | (1a) | X | (3d) |
| (1)-166 | (Ih) | (1q) | X | — |
| (1)-167 | (Ia) | X | (2qq) | X |
| (1)-168 | (Ib) | X | (2qq) | X |
| (1)-169 | (Ic) | X | (2jj) | (3a) |
| (1)-170 | (Id) | (1ff) | (2q) | (3c) |
| (1)-171 | (Ie) | (1m) | X | (3a) |
| (1)-172 | (If) | (1s) | X | (3c) |
| (1)-173 | (Ig) | (1rr) | X | (3d) |
| (1)-174 | (Ih) | — | X | (3e) |
| (1)-175 | (Ic) | — | (2h) | (3a) |
| (1)-176 | (Id) | (2s) | (2k) | (3c) |
| (1)-177 | (Ie) | (2j) | X | (3d) |
| (1)-178 | (If) | (2o) | X | (3e) |
| (1)-179 | (Ig) | (2p) | X | (3f) |
| (1)-180 | (Ih) | — | X | (3g) |
| (1)-181 | (Ib) | X | (2t) | X |
| (1)-182 | (Ic) | X | (2u) | — |
| (1)-183 | (Id) | (1rr) | (2r) | (3d) |
| (1)-184 | (Ia) | X | (2x) | X |
| (1)-185 | (Ib) | X | (2bb) | X |
| (1)-186 | (Ic) | X | (2ii) | — |
| (1)-187 | (Id) | (1m) | (2s) | (3a) |
| (1)-188 | (Ie) | (1s) | X | (3c) |
| (1)-189 | (If) | (1rr) | X | (3d) |
| (1)-190 | (Ig) | (2s) | X | (3e) |
| (1)-191 | (Ih) | (2j) | X | (3f) |
| (1)-192 | (Ie) | (2o) | X | (3g) |
| (1)-193 | (If) | (2p) | X | — |
| (1)-194 | (Ig) | (1rr) | X | (3d) |

| (I)-  | (I)  | R¹    | Z      | n    |
|-------|------|-------|--------|------|
| (1)-195 | (Ia) | X | (2o) | X |
| (1)-196 | (Ib) | X | (2p) | X |
| (1)-197 | (Ic) | X | (2r) | — |
| (1)-198 | (Ia) | X | (2t) | X |
| (1)-199 | (Ib) | X | (2u) | X |
| (1)-200 | (Ic) | X | (2w) | — |
| (1)-201 | (Ib) | X | (2x) | X |
| (1)-202 | (Ic) | X | (2bb) | (3a) |
| (1)-203 | (Id) | (1ff) | (2r) | (3c) |
| (1)-204 | (Ie) | (1m) | X | (3d) |
| (1)-205 | (If) | (1s) | X | (3e) |
| (1)-206 | (Ig) | (1rr) | X | (3f) |
| (1)-207 | (Ih) | — | X | (3g) |
| (1)-208 | (Ib) | X | (2bbb) | X |
| (1)-209 | (Ic) | X | (2jj) | — |
| (1)-210 | (Id) | (1aa) | (2s) | (3d) |
| (1)-211 | (Ic) | X | (2ww) | — |
| (1)-212 | (Id) | (1m) | (2r) | (3a) |
| (1)-213 | (Ie) | (1s) | X | (3c) |
| (1)-214 | (If) | (1rr) | X | (3d) |
| (1)-215 | (Ig) | (1ss) | X | (3e) |
| (1)-216 | (Ih) | (1tt) | X | (3f) |
| (1)-217 | (Ie) | (1a) | X | (3g) |
| (1)-218 | (If) | (1q) | X | — |
| (1)-219 | (Ig) | (1rr) | X | — |
| (1)-220 | (Ia) | X | (2i) | X |
| (1)-221 | (Ib) | X | (2j) | X |
| (1)-222 | (Ic) | X | (2o) | — |
| (1)-223 | (Ih) | — | (2s) | — |
| (1)-224 | (Ia) | X | (2r) | X |
| (1)-225 | (Ib) | X | (2t) | X |
| (1)-226 | (Ic) | X | (2u) | (3a) |
| (1)-227 | (Id) | (1m) | (2k) | (3c) |
| (1)-228 | (Ie) | (1s) | X | (3d) |
| (1)-229 | (If) | (1rr) | X | (3e) |
| (1)-230 | (Ig) | (2j) | X | (3f) |
| (1)-231 | (Ih) | (2o) | X | (3g) |
| (1)-232 | (Ie) | (2p) | X | — |
| (1)-233 | (If) | (1rr) | X | (3d) |
| (1)-234 | (Ig) | (1rr) | X | — |
| (1)-235 | (Ib) | X | (2bbb) | X |
| (1)-236 | (Ic) | X | (2t) | — |
| (1)-237 | (Id) | (2j) | (2s) | — |
| (1)-238 | (Ie) | (2o) | X | (3a) |
| (1)-239 | (If) | (2p) | X | (3c) |
| (1)-240 | (Ig) | (1ff) | X | (3d) |
| (1)-241 | (Ih) | (1m) | X | (3e) |
| (1)-242 | (Ie) | (1s) | X | (3f) |
| (1)-243 | (If) | (1rr) | X | (3g) |
| (1)-244 | (Ig) | — | X | — |
| (1)-245 | (Ia) | X | (2aaa) | X |
| (1)-246 | (Ib) | X | (2bbb) | X |
| (1)-247 | (Ic) | X | (2x) | — |
| (1)-248 | (Id) | (2j) | (2k) | (3d) |
| (1)-249 | (Ie) | (2o) | X | — |
| (1)-250 | (If) | (2p) | X | — |
| (1)-251 | (Ig) | (1aa) | X | (3a) |
| (1)-252 | (Ih) | (1ff) | X | (3c) |
| (1)-253 | (Id) | (1m) | (2r) | (3d) |
| (1)-254 | (Ie) | (1s) | X | (3e) |
| (1)-255 | (If) | (1rr) | X | (3f) |
| (1)-256 | (Ig) | (1ss) | X | (3g) |
| (1)-257 | (Ih) | (1u) | X | (3a) |
| (1)-258 | (Ie) | (1aa) | X | (3c) |
| (1)-259 | (If) | (1ff) | X | (3d) |
| (1)-260 | (Ig) | (1m) | X | (3a) |
| (1)-261 | (If) | (1s) | X | (3c) |
| (1)-262 | (Ig) | (1rr) | (2t) | (3d) |
| (1)-263 | (Ih) | (1ss) | X | (3e) |
| (1)-264 | (If) | (1tt) | X | (3f) |
| (1)-265 | (Ig) | (1a) | X | (3g) |
| (1)-266 | (Ih) | (1q) | X | — |
| (1)-267 | (Ia) | X | (2j) | X |
| (1)-268 | (Ib) | X | (2o) | X |
| (1)-269 | (Ic) | X | (2p) | (3a) |
| (1)-270 | (Id) | (2j) | (2r) | (3c) |
| (1)-271 | (Ie) | (2o) | X | (3d) |
| (1)-272 | (If) | (2p) | X | (3e) |
| (1)-273 | (Ig) | — | X | (3f) |
| (1)-274 | (Ih) | — | X | (3g) |
| (1)-275 | (Ia) | X | (2bb) | X |
| (1)-276 | (Ib) | X | (2ii) | X |
| (1)-277 | (Ic) | X | (2jj) | — |
| (1)-278 | (Id) | (1aa) | (2q) | (3a) |
| (1)-279 | (Ie) | (1ff) | X | (3c) |
| (1)-280 | (If) | (1m) | X | (3d) |
| (1)-281 | (Ig) | (1s) | X | (3e) |
| (1)-282 | (Ih) | (1rr) | X | (3f) |
| (1)-283 | (Ie) | (1ss) | X | (3g) |
| (1)-284 | (If) | (1tt) | X | (3e) |
| (1)-285 | (Ig) | (1a) | X | (3f) |
| (1)-286 | (Ih) | (1q) | X | (3g) |
| (1)-287 | (If) | (2s) | X | (3d) |
| (1)-288 | (Ig) | (2j) | (2t) | — |
| (1)-289 | (Ih) | (2o) | (2t) | — |
| (1)-290 | (Ia) | X | (2bb) | X |
| (1)-291 | (Ib) | X | (2ii) | X |
| (1)-292 | (Ic) | X | (2jj) | — |
| (1)-293 | (Id) | (1aa) | (2q) | (3d) |
| (1)-294 | (Ie) | (1ff) | X | (3a) |
| (1)-295 | (If) | (1m) | X | (3c) |
| (1)-296 | (Ig) | (1s) | X | (3d) |
| (1)-297 | (Ih) | (1rr) | X | (3e) |
| (1)-298 | (Ie) | (1ss) | X | (3f) |
| (1)-299 | (If) | (1tt) | X | (3g) |
| (1)-300 | (Ig) | (1a) | X | — |
| (1)-301 | (Ih) | (1u) | (2mmm) | (3a) |
| (1)-302 | (Ii) | (1aa) | (2nnn) | (3c) |
| (1)-303 | (Ij) | (1ff) | (2ppp) | (3d) |
| (1)-304 | (Ik) | (1m) | (2qqq) | (3e) |
| (1)-305 | (Il) | (1s) | (2cccc) | (3f) |
| (1)-306 | (Im) | (1rr) | (2dddd) | (3g) |
| (1)-307 | (Ih) | (1ss) | (2xxx) | (3a) |
| (1)-308 | (Ii) | (1tt) | (2yyy) | (3c) |
| (1)-309 | (Ij) | (1a) | (2aaaa) | (3d) |
| (1)-310 | (Ik) | (1q) | (2bbbb) | (3e) |
| (1)-311 | (Il) | (1u) | (2ppp) | (3f) |
| (1)-312 | (Im) | (1aa) | (2ppp) | (3g) |
| (1)-313 | (Ih) | (1ff) | (2qqq) | (3d) |
| (1)-314 | (Ii) | (1m) | (2cccc) | (3e) |
| (1)-315 | (Ij) | (1s) | (2ppp) | (3d) |
| (1)-316 | (Ik) | (1rr) | (2qqq) | (3e) |
| (1)-317 | (Il) | (1ss) | (2cccc) | (3f) |
| (1)-318 | (Im) | (1tt) | (2nnn) | (3g) |
| (1)-319 | (Ih) | (1a) | (2ppp) | (3c) |
| (1)-320 | (Ii) | (1q) | (2qqq) | (3d) |
| (1)-321 | (Ij) | (1m) | (2cccc) | (3e) |
| (1)-322 | (Ik) | (1s) | (2dddd) | (3f) |
| (1)-323 | (Il) | (1rr) | (2xxx) | (3g) |
| (1)-324 | (Im) | (1ss) | (2yyy) | (3d) |
| (1)-325 | (Ih) | (1tt) | (2aaaa) | (3e) |
| (1)-326 | (Ii) | (1a) | (2bbbb) | (3d) |
| (1)-327 | (Ij) | (1q) | (2mmm) | (3e) |
| (1)-328 | (Ik) | (1aa) | (2nnn) | (3f) |
| (1)-329 | (Il) | (1u) | (2ppp) | (3g) |
| (1)-330 | (Im) | (1aa) | (2qqq) | (3a) |
| (1)-331 | (Ih) | (1ff) | (2cccc) | (3c) |
| (1)-332 | (Ii) | (1m) | (2dddd) | (3d) |
| (1)-333 | (Ij) | (1s) | (2xxx) | (3d) |
| (1)-334 | (Ik) | (1rr) | (2yyy) | (3e) |
| (1)-335 | (Il) | (1ss) | (2aaaa) | (3f) |
| (1)-336 | (Im) | (1tt) | (2bbbb) | (3g) |

In some embodiments, the compound of formulae (I), (Ia)-(Im), (II) or (IIa)-(III) is one of the following compounds (or a pharmaceutically acceptable salt, prodrug, or N-oxide thereof, or a solvate or hydrate thereof):

| No. | Structure | Name |
|---|---|---|
| 1 | 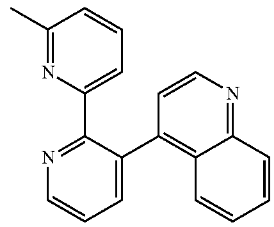 [SMILES: Cc1cccc(-c2ncccc2-c2ccnc3ccccc23)n1] | 4-(6'-methyl-[2,2'-bipyridin]-3-yl)quinoline |
| 2 | 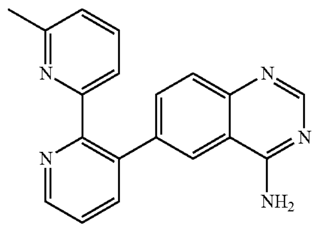 [SMILES: Cc1cccc(-c2ncccc2-c2ccc3ncnc(N)c3c2)n1] | 6-(6'-methyl-[2,2'-bipyridin]-3-yl)quinazolin-4-amine |
| 2A | 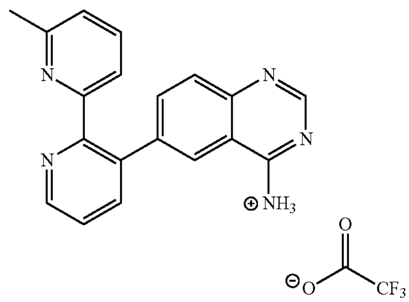 [SMILES: Cc1cccc(-c2ncccc2-c2ccc3ncnc([NH3+])c3c2)n1 ; O=C([O-])C(F)(F)F] | 6-(6'-methyl-[2,2'-bipyridin]-3-yl)quinazolin-4-aminium 2,2,2-trifluoroacetate |
| 2B | 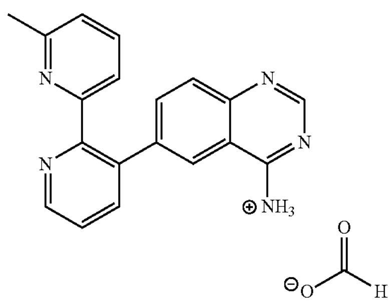 | 6-(6'-methyl-[2,2'-bipyridin]-3-yl)quinazolin-4-aminium formate |
| 3 | 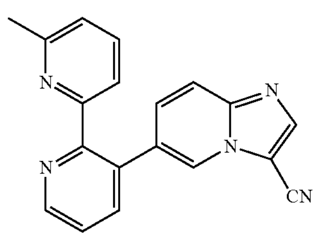 [SMILES: Cc1cccc(-c2ncccc2-c2ccc3ncc(C#N)n3c2)n1] | 6-(6'-Methyl-[2,2'-bipyridin]-3-yl)imidazo[1,2-a]pyridine-3-carbonitrile |
| 4 | 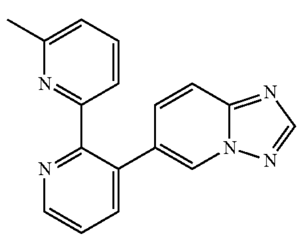 [SMILES: Cc1cccc(-c2ncccc2-c2ccc3ncnn3c2)n1] | 6-(6'-Methyl-[2,2'-bipyridin]-3-yl)-[1,2,4]triazolo[1,5-a]pyridine |

| No. | Structure | Name |
| --- | --- | --- |
| 5 | 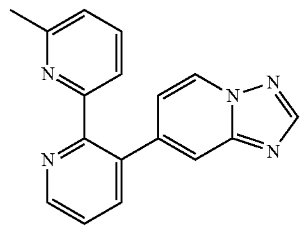 [SMILES: Cc1cccc(-c2ncccc2-c2ccn3ncnc3c2)n1] | 7-(6'-Methyl-[2,2'-bipyridin]-3-yl)-[1,2,4]triazolo[1,5-a]pyridine |
| 6 | 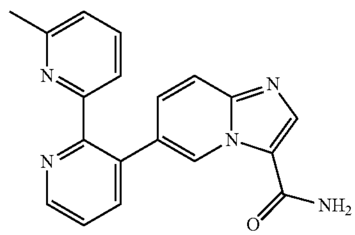 [SMILES: Cc1cccc(-c2ncccc2-c2ccc3ncc(C(N)=O)n3c2)n1] | 6-(6'-Methyl-[2,2'-bipyridin]-3-yl)imidazo[1,2-a]pyridine-3-carboxamide |
| 7 | 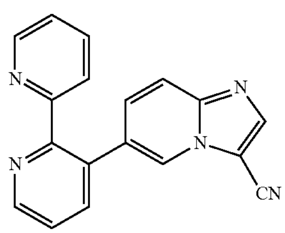 [SMILES: N#Cc1cnc2ccc(-c3cccnc3-c3ccccn3)cn12] | 6-([2,2'-Bipyridin]-3-yl)imidazo[1,2-a]pyridine-3-carbonitrile |
| 8 | 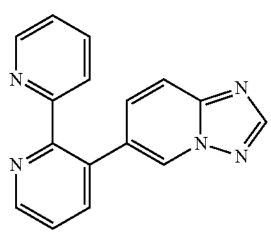 [SMILES: c1ccc(-c2ncccc2-c2ccc3ncnn3c2)nc1] | 6-([2,2'-Bipyridin]-3-yl)-[1,2,4]triazolo[1,5-a]pyridine |
| 9 | 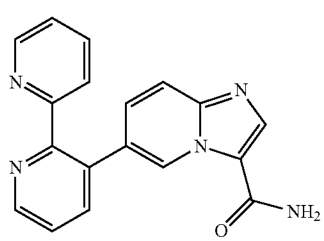 [SMILES: NC(=O)c1cnc2ccc(-c3cccnc3-c3ccccn3)cn12] | 6-([2,2'-Bipyridin]-3-yl)imidazo[1,2-a]pyridine-3-carboxamide |
| 10 | 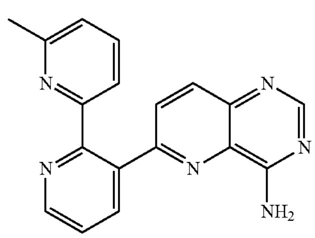 [SMILES: Cc1cccc(-c2ncccc2-c2ccc3ncnc(N)c3n2)n1] | 6-(6'-methyl-[2,2'-bipyridin]-3-yl)pyrido[3,2-d]pyrimidin-4-amine |

-continued

| No. | Structure | Name |
|---|---|---|
| 11 | 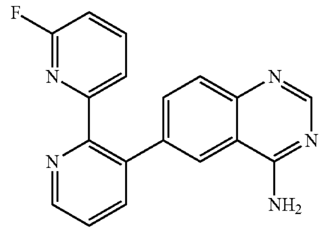 [SMILES: Nc1ncnc2ccc(-c3cccnc3-c3cccc(F)n3)cc12] | 6-(6'-fluoro-[2,2'-bipyridin]-3-yl)quinazolin-4-amine |
| 11A | 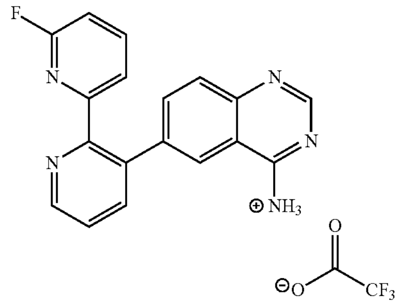 [SMILES: [NH3+]c1ncnc2ccc(-c3cccnc3-c3cccc(F)n3)cc12 ; O=C([O-])C(F)(F)F] | 6-(6'-fluoro-[2,2'-bipyridin]-3-yl)quinazolin-4-aminium 2,2,2-trifluoroacetate |
| 12 | 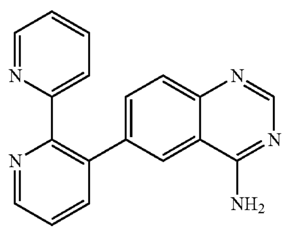 [SMILES: Nc1ncnc2ccc(-c3cccnc3-c3ccccn3)cc12] | 6-([2,2'-bipyridin]-3-yl)quinazolin-4-amine |
| 12A | 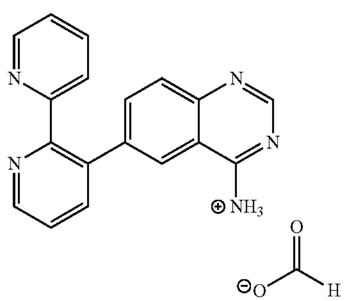 | 6-([2,2'-bipyridin]-3-yl)quinazolin-4-aminium formate |
| 13 | 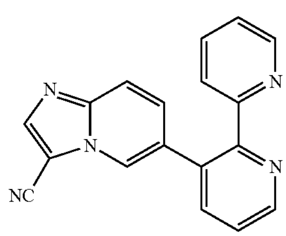 [SMILES: N#Cc1cnc2ccc(-c3cccnc3-c3ccccn3)cn12] | 6-([2,2'-bipyridin]-3-yl)imidazo[1,2-a]pyridine-3-carbonitrile |
| 14 | 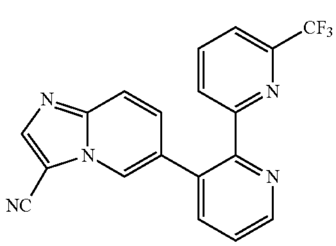 [SMILES: N#Cc1cnc2ccc(-c3cccnc3-c3cccc(C(F)(F)F)n3)cn12] | 6-(6'-(trifluoromethyl)-[2,2'-bipyridin]-3-yl)imidazo[1,2-a]pyridine-3-carbonitrile |

-continued

| No. | Structure | Name |
|---|---|---|
| 15 | 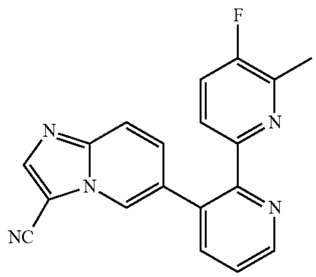 | 6-(5'-fluoro-6'-methyl-[2,2'-bipyridin]-3-yl)imidazo[1,2-a]pyridine-3-carbonitrile |
| 16 | 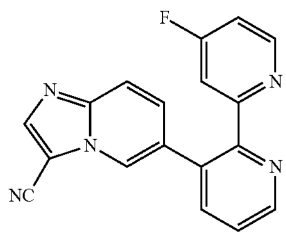 | 6-(4'-fluoro-[2,2'-bipyridin]-3-yl)imidazo[1,2-a]pyridine-3-carbonitrile |
| 17 | 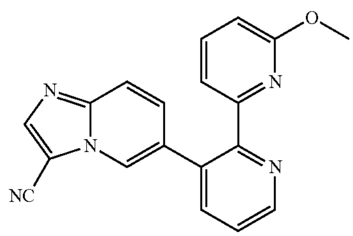 [SMILES: COc1cccc(-c2ncccc2-c2ccc3ncc(C#N)n3c2)n1] | 6-(6'-methoxy-[2,2'-bipyridin]-3-yl)imidazo[1,2-a]pyridine-3-carbonitrile |
| 18 | 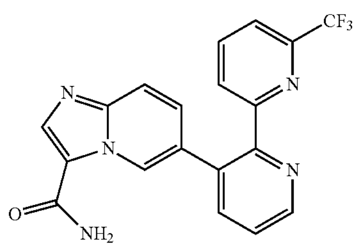 [SMILES: NC(=O)c1cnc2ccc(-c3cccnc3-c3cccc(C(F)(F)F)n3)cn12] | 6-(6'-(trifluoromethyl)-[2,2'-bipyridin]-3-yl)imidazo[1,2-a]pyridine-3-carboxamide |
| 19 | 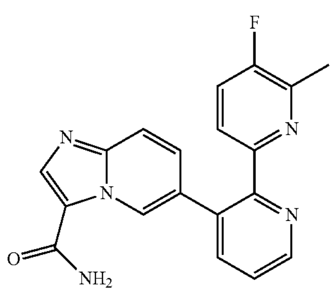 | 6-(5'-fluoro-6'-methyl-[2,2'-bipyridin]-3-yl)imidazo[1,2-a]pyridine-3-carboxamide |
| 20 | 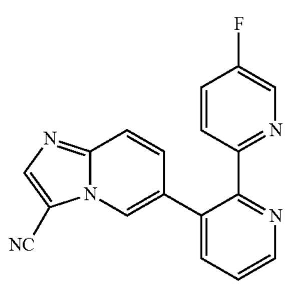 [SMILES: N#Cc1cnc2ccc(-c3cccnc3-c3ccc(F)cn3)cn12] | 6-(5'-fluoro-[2,2'-bipyridin]-3-yl)imidazo[1,2-a]pyridine-3-carbonitrile |

-continued

| No. | Structure | Name |
|---|---|---|
| 21 | 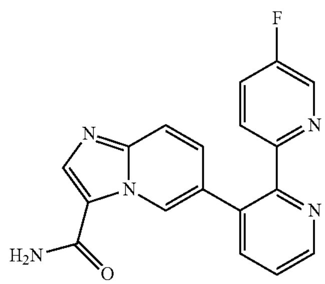 [SMILES: NC(=O)c1cnc2ccc(-c3cccnc3-c3ccc(F)cn3)cn12] | 6-(5'-fluoro-[2,2'-bipyridin]-3-yl)imidazo[1,2-a]pyridine-3-carboxamide |
| 22 | 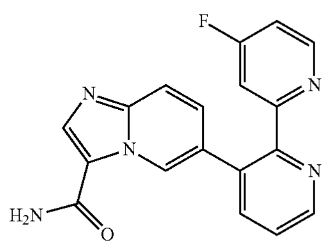 [SMILES: NC(=O)c1cnc2ccc(-c3cccnc3-c3cc(F)ccn3)cn12] | 6-(4'-fluoro-[2,2'-bipyridin]-3-yl)imidazo[1,2-a]pyridine-3-carboxamide |
| 23 | 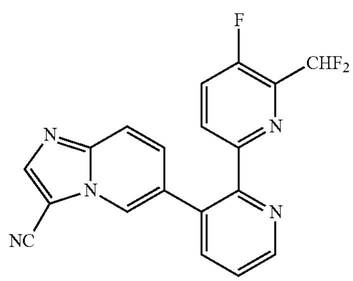 [SMILES: N#Cc1cnc2ccc(-c3cccnc3-c3ccc(F)c(C(F)F)n3)cn12] | 6-(6'-(difluoromethyl)-5'-fluoro-[2,2'-bipyridin]-3-yl)imidazo[1,2-a]pyridine-3-carbonitrile |
| 24 | 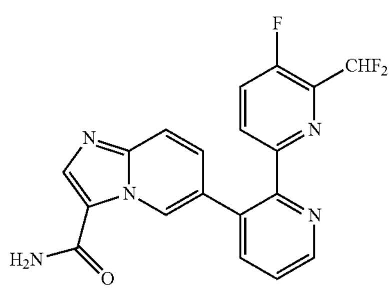 [SMILES: NC(=O)c1cnc2ccc(-c3cccnc3-c3ccc(F)c(C(F)F)n3)cn12] | 6-(6'-(difluoromethyl)-5'-fluoro-[2,2'-bipyridin]-3-yl)imidazo[1,2-a]pyridine-3-carboxamide |
| 25 | 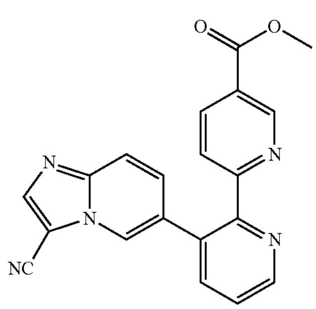 [SMILES: COC(=O)c1ccc(-c2ncccc2-c2ccc3ncc(C#N)n3c2)nc1] | methyl 3'-(3-cyanoimidazo[1,2-a]pyridin-6-yl)-[2,2'-bipyridine]-5-carboxylate |

-continued

| No. | Structure | Name |
|---|---|---|
| 26 | 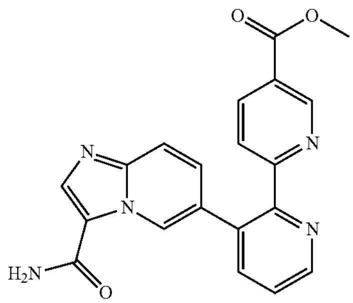 [SMILES: COC(=O)c1ccc(-c2ncccc2-c2ccc3ncc(C(N)=O)n3c2)nc1] | methyl 3'-(3-carbamoylimidazo[1,2-a]pyridin-6-yl)-[2,2'-bipyridine]-5-carboxylate |
| 27 | 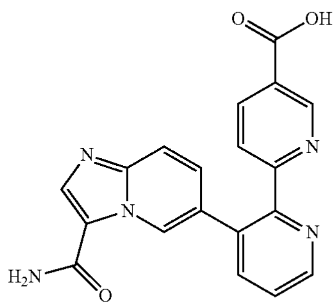 [SMILES: NC(=O)c1cnc2ccc(-c3cccnc3-c3ccc(C(=O)O)cn3)cn12] | 3'-(3-carbamoylimidazo[1,2-a]pyridin-6-yl)-[2,2'-bipyridine]-5-carboxylic acid |
| 28 | 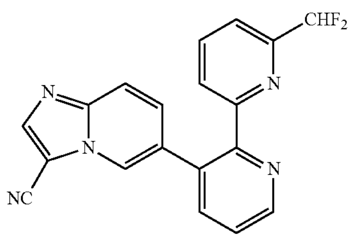 [SMILES: N#Cc1cnc2ccc(-c3cccnc3-c3cccc(C(F)F)n3)cn12] | 6-(6'-(difluoromethyl)-[2,2'-bipyridin]-3-yl)imidazo[1,2-a]pyridine-3-carbonitrile |
| 29 | 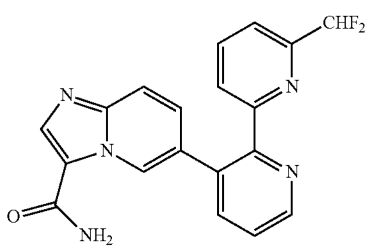 | 6-(6'-(difluoromethyl)-[2,2'-bipyridin]-3-yl)imidazo[1,2-a]pyridine-3-carboxamide |
| 30 | 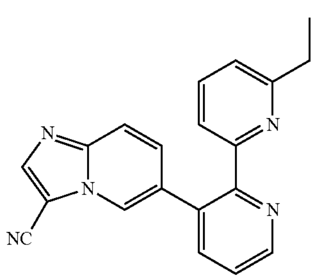 [SMILES: CCc1cccc(-c2ncccc2-c2ccc3ncc(C#N)n3c2)n1] | 6-(6'-ethyl-[2,2'-bipyridin]-3-yl)imidazo[1,2-a]pyridine-3-carbonitrile |

-continued

| No. | Structure | Name |
|---|---|---|
| 31 | 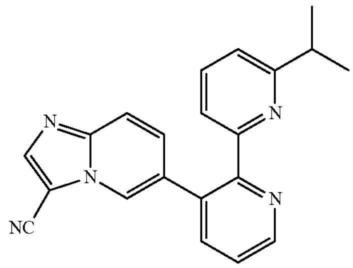 | 6-(6'-isopropyl-[2,2'-bipyridin]-3-yl)imidazo[1,2-a]pyridine-3-carbonitrile |
| 32 | 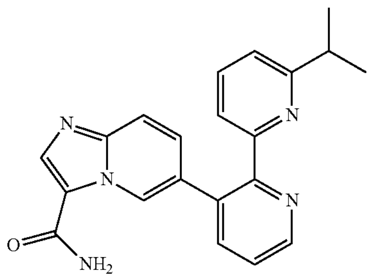 | 6-(6'-isopropyl-[2,2'-bipyridin]-3-yl)imidazo[1,2-a]pyridine-3-carboxamide |
| 33 | 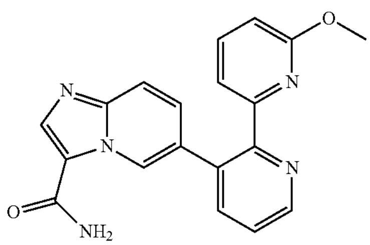 [SMILES: COc1cccc(-c2ncccc2-c2ccc3ncc(C(N)=O)n3c2)n1] | 6-(6'-methoxy-[2,2'-bipyridin]-3-yl)imidazo[1,2-a]pyridine-3-carboxamide |
| 34 | 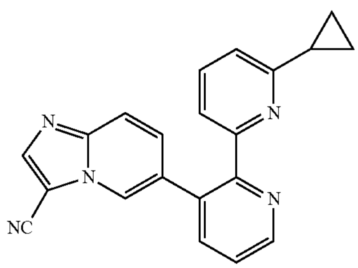 [SMILES: N#Cc1cnc2ccc(-c3cccnc3-c3cccc(C4CC4)n3)cn12] | 6-(6'-cyclopropyl-[2,2'-bipyridin]-3-yl)imidazo[1,2-a]pyridine-3-carbonitrile |
| 35 | 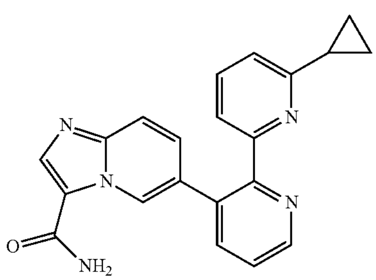 [SMILES: NC(=O)c1cnc2ccc(-c3cccnc3-c3cccc(C4CC4)n3)cn12] | 6-(6'-cyclopropyl-[2,2'-bipyridin]-3-yl)imidazo[1,2-a]pyridine-3-carboxamide |
| 36 | 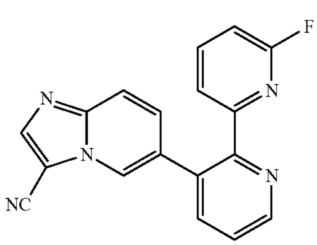 [SMILES: N#Cc1cnc2ccc(-c3cccnc3-c3cccc(F)n3)cn12] | 6-(6'-fluoro-[2,2'-bipyridin]-3-yl)imidazo[1,2-a]pyridine-3-carbonitrile |

-continued

| No. | Structure | Name |
|---|---|---|
| 37 | 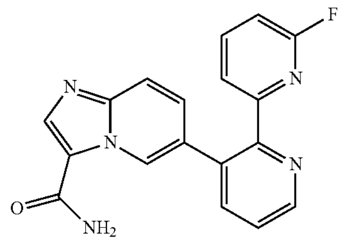 [SMILES: NC(=O)c1cnc2ccc(-c3cccnc3-c3cccc(F)n3)cn12] | 6-(6'-fluoro-[2,2'-bipyridin]-3-yl)imidazo[1,2-a]pyridine-3-carboxamide |
| 38 | 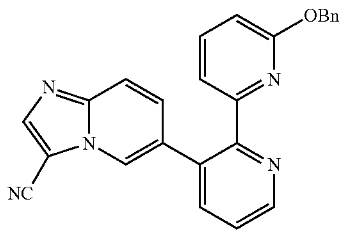 [SMILES: N#Cc1cnc2ccc(-c3cccnc3-c3cccc(OCc4ccccc4)n3)cn12] | 6-(6'-(benzyloxy)-[2,2'-bipyridin]-3-yl)imidazo[1,2-a]pyridine-3-carbonitrile |
| 39 | 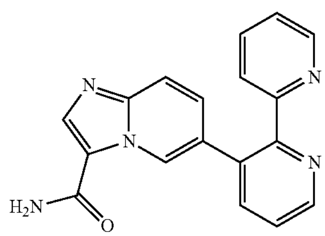 [SMILES: NC(=O)c1cnc2ccc(-c3cccnc3-c3ccccn3)cn12] | 6-([2,2'-bipyridin]-3-yl)imidazo[1,2-a]pyridine-3-carboxamide |
| 40 | 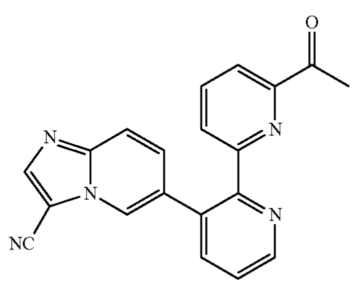 [SMILES: CC(=O)c1cccc(-c2ncccc2-c2ccc3ncc(C#N)n3c2)n1] | 6-(6'-acetyl-[2,2'-bipyridin]-3-yl)imidazo[1,2-a]pyridine-3-carbonitrile |
| 41 | 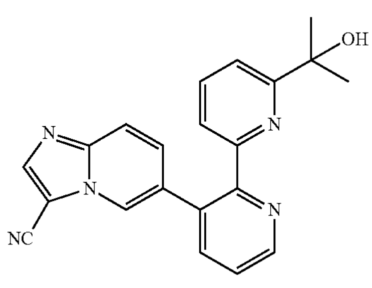 [SMILES: CC(C)(O)c1cccc(-c2ncccc2-c2ccc3ncc(C#N)n3c2)n1] | 6-(6'-6-(6'-(2-hydroxypropan-2-yl)-[2,2'-bipyridin]-3-yl)imidazo[1,2-a]pyridine-3-carbonitrile |
| 42 | 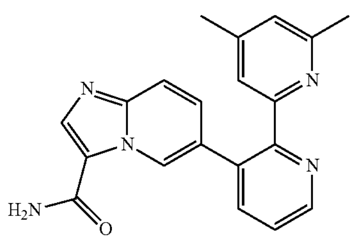 [SMILES: Cc1cc(C)nc(-c2ncccc2-c2ccc3ncc(C(N)=O)n3c2)c1] | 6-(4',6'-dimethyl-[2,2'-bipyridin]-3-yl)imidazo[1,2-a]pyridine-3-carboxamide |

-continued

| No. | Structure | Name |
|---|---|---|
| 43 | 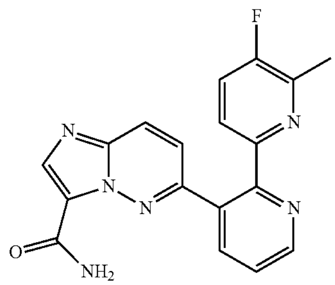 [SMILES: Cc1nc(-c2ncccc2-c2ccc3ncc(C(N)=O)n3n2)ccc1F] | 6-(5'-fluoro-6'-methyl-[2,2'-bipyridin]-3-yl)imidazo[1,2-b]pyridazine-3-carboxamide |
| 44 | 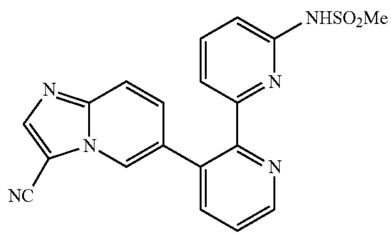 | N-(3'-(3-cyanoimidazo[1,2-a]pyridin-6-yl)-[2,2'-bipyridin]-6-yl)methanesulfonamide |
| 45 | 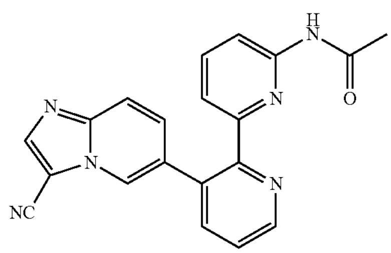 [SMILES: CC(=O)Nc1cccc(-c2ncccc2-c2ccc3ncc(C#N)n3c2)n1] | N-(3'-(3-cyanoimidazo[1,2-a]pyridin-6-yl)-[2,2'-bipyridin]-6-yl)acetamide |
| 46 | 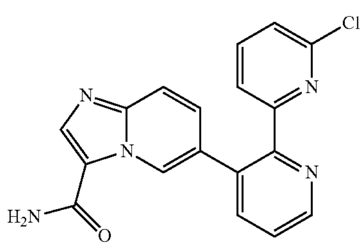 [SMILES: NC(=O)c1cnc2ccc(-c3cccnc3-c3cccc(Cl)n3)cn12] | 6-(6'-chloro-[2,2'-bipyridin]-3-yl)imidazo[1,2-a]pyridine-3-carboxamide |
| 47 | 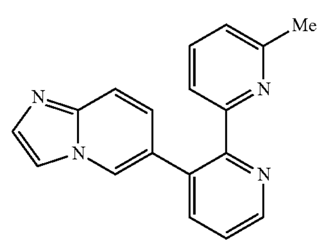 [SMILES: Cc1cccc(-c2ncccc2-c2ccc3nccn3c2)n1] | 6-(6'-methyl-[2,2'-bipyridin]-3-yl)imidazo[1,2-a]pyridine |
| 48 | 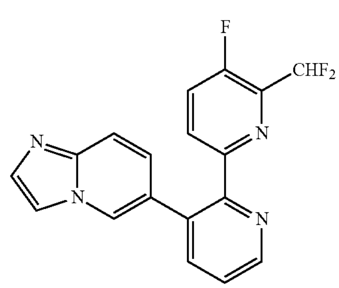 [SMILES: Fc1ccc(-c2ncccc2-c2ccc3nccn3c2)nc1C(F)F] | 6-(6'-(difluoromethyl)-5'-fluoro-[2,2'-bipyridin]-3-yl)imidazo[1,2-a]pyridine |

| No. | Structure | Name |
|---|---|---|
| 49 | 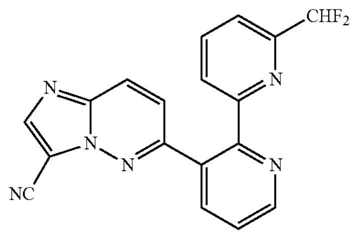 | 6-(6'-(difluoromethyl)-[2,2'-bipyridin]-3-yl)imidazo[1,2-b]pyridazine-3-carbonitrile |
| 50 | 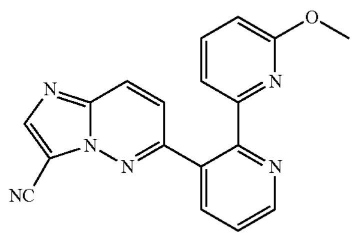 [SMILES: COc1cccc(-c2ncccc2-c2ccc3ncc(C#N)n3n2)n1] | 6-(6'-methoxy-[2,2'-bipyridin]-3-yl)imidazo[1,2-b]pyridazine-3-carbonitrile |
| 51 | 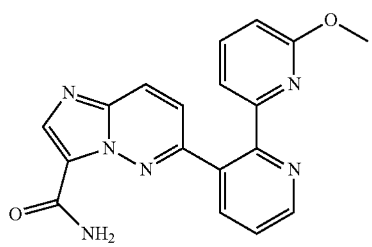 [SMILES: COc1cccc(-c2ncccc2-c2ccc3ncc(C(N)=O)n3n2)n1] | 6-(6'-methoxy-[2,2'-bipyridin]-3-yl)imidazo[1,2-b]pyridazine-3-carboxamide |
| 52 | 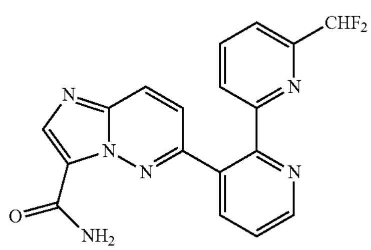 [SMILES: NC(=O)c1cnc2ccc(-c3cccnc3-c3cccc(C(F)F)n3)nn12] | 6-(6'-(difluoromethyl)-[2,2'-bipyridin]-3-yl)imidazo[1,2-b]pyridazine-3-carboxamide |
| 53 | 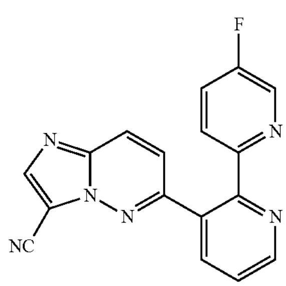 | 6-(5'-fluoro-[2,2'-bipyridin]-3-yl)imidazo[1,2-b]pyridazine-3-carbonitrile |
| 54 | 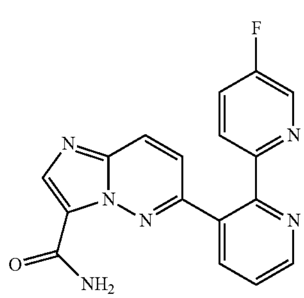 [SMILES: NC(=O)c1cnc2ccc(-c3cccnc3-c3ccc(F)cn3)nn12] | 6-(5'-fluoro-[2,2'-bipyridin]-3-yl)imidazo[1,2-b]pyridazine-3-carboxamide |

-continued

| No. | Structure | Name |
|---|---|---|
| 55 | 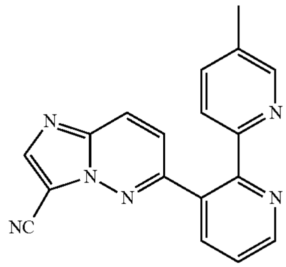 [SMILES: Cc1ccc(-c2ncccc2-c2ccc3ncc(C#N)n3n2)nc1] | 6-(5'-methyl-[2,2'-bipyridin]-3-yl)imidazo[1,2-b]pyridazine-3-carbonitrile |
| 56 | 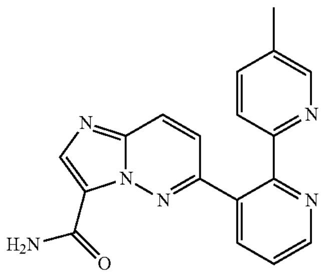 [SMILES: Cc1ccc(-c2ncccc2-c2ccc3ncc(C(N)=O)n3n2)nc1] | 6-(5'-methyl-[2,2'-bipyridin]-3-yl)imidazo[1,2-b]pyridazine-3-carboxamide |
| 57 | 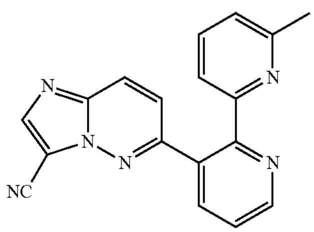 [SMILES: Cc1cccc(-c2ncccc2-c2ccc3ncc(C#N)n3n2)n1] | 6-(6'-methyl-[2,2'-bipyridin]-3-yl)imidazo[1,2-b]pyridazine-3-carbonitrile |
| 58 | 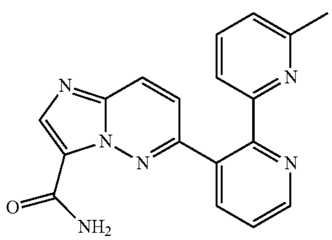 [SMILES: Cc1cccc(-c2ncccc2-c2ccc3ncc(C(N)=O)n3n2)n1] | 6-(6'-methyl-[2,2'-bipyridin]-3-yl)imidazo[1,2-b]pyridazine-3-carboxamide |
| 59 | 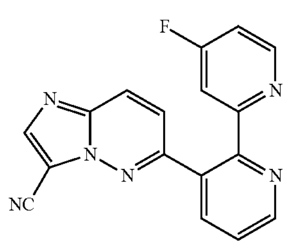 [SMILES: N#Cc1cnc2ccc(-c3cccnc3-c3cc(F)ccn3)nn12] | 6-(4'-fluoro-[2,2'-bipyridin]-3-yl)imidazo[1,2-b]pyridazine-3-carbonitrile |
| 60 | 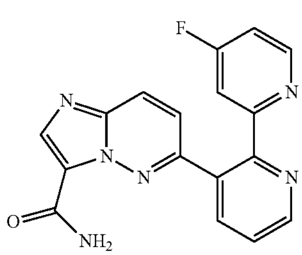 [SMILES: NC(=O)c1cnc2ccc(-c3cccnc3-c3cc(F)ccn3)nn12] | 6-(4'-fluoro-[2,2'-bipyridin]-3-yl)imidazo[1,2-b]pyridazine-3-carboxamide |

-continued

| No. | Structure | Name |
|---|---|---|
| 61 | 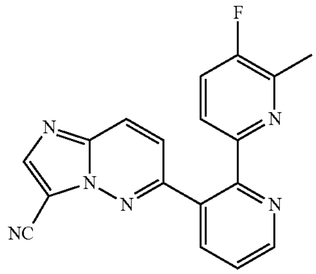 [SMILES: Cc1nc(-c2ncccc2-c2ccc3ncc(C#N)n3n2)ccc1F] | 6-(5'-fluoro-6'-methyl-[2,2'-bipyridin]-3-yl)imidazo[1,2-b]pyridazine-3-carbonitrile |
| 63 | 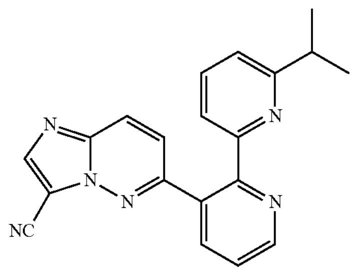 [SMILES: CC(C)c1cccc(-c2ncccc2-c2ccc3ncc(C#N)n3n2)n1] | 6-(6'-isopropyl-[2,2'-bipyridin]-3-yl)imidazo[1,2-b]pyridazine-3-carbonitrile |
| 64 | 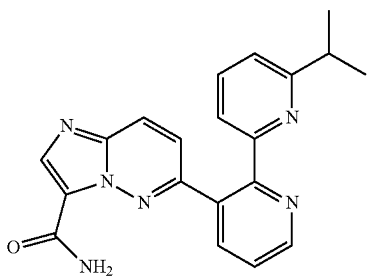 [SMILES: CC(C)c1cccc(-c2ncccc2-c2ccc3ncc(C(N)=O)n3n2)n1] | 6-(6'-isopropyl-[2,2'-bipyridin]-3-yl)imidazo[1,2-b]pyridazine-3-carboxamide |
| 65 | 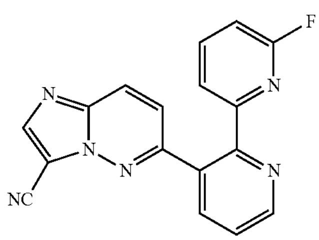 | 6-(6'-fluoro-[2,2'-bipyridin]-3-yl)imidazo[1,2-b]pyridazine-3-carbonitrile |
| 66 | 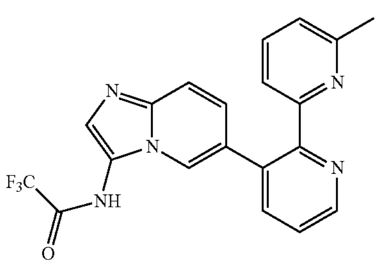 [SMILES: Cc1cccc(-c2ncccc2-c2ccc3ncc(NC(=O)C(F)(F)F)n3c2)n1] | 2,2,2-trifluoro-N-(6-(6'-methyl-[2,2'-bipyridin]-3-yl)imidazo[1,2-a]pyridin-3-yl)acetamide |
| 67 | 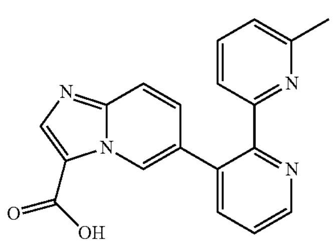 [SMILES: Cc1cccc(-c2ncccc2-c2ccc3ncc(C(=O)O)n3c2)n1] | 6-(6'-methyl-[2,2'-bipyridin]-3-yl)imidazo[1,2-a]pyridine-3-carboxylic acid |

| No. | Structure | Name |
|---|---|---|
| 68 | 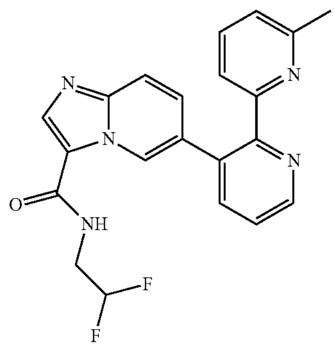 [SMILES: Cc1cccc(-c2ncccc2-c2ccc3ncc(C(=O)NCC(F)F)n3c2)n1] | N-(2,2-difluoroethyl)-6-(6'-methyl-[2,2'-bipyridin]-3-yl)imidazo[1,2-a]pyridine-3-carboxamide |
| 69 | 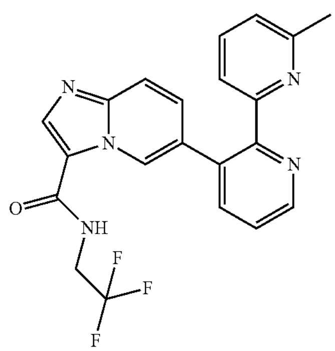 [SMILES: Cc1cccc(-c2ncccc2-c2ccc3ncc(C(=O)NCC(F)(F)F)n3c2)n1] | 6-(6'-methyl-[2,2'-bipyridin]-3-yl)-N-(2,2,2-trifluoroethyl)imidazo[1,2-a]pyridine-3-carboxamide |
| 70 | 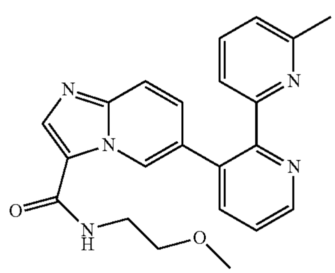 [SMILES: COCCNC(=O)c1cnc2ccc(-c3cccnc3-c3cccc(C)n3)cn12] | N-(2-methoxyethyl)-6-(6'-methyl-[2,2'-bipyridin]-3-yl)imidazo[1,2-a]pyridine-3-carboxamide |
| 71 | 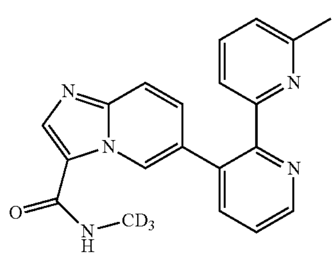 [SMILES: [2H]C([2H])([2H])NC(=O)c1cnc2ccc(-c3cccnc3-c3cccc(C)n3)cn12] | N-($^2$H$_3$)methyl-6-[2-(6-methylpyridin-2-yl)pyridin-3-yl]imidazo[1,2-a]pyridine-3-carboxamide |
| 72 | 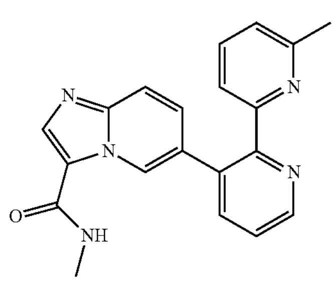 [SMILES: CNC(=O)c1cnc2ccc(-c3cccnc3-c3cccc(C)n3)cn12] | methyl-6-(6'-methyl-[2,2'-bipyridin]-3-yl)imidazo[1,2-a]pyridine-3-carboxamide |

-continued

| No. | Structure | Name |
| --- | --- | --- |
| 73 | 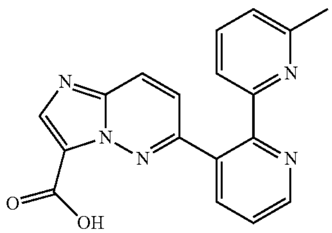 [SMILES: Cc1cccc(-c2ncccc2-c2ccc3ncc(C(=O)O)n3n2)n1] | 6-(6'-methyl-[2,2'-bipyridin]-3-yl)imidazo[1,2-b]pyridazine-3-carboxylic acid |
| 74 | 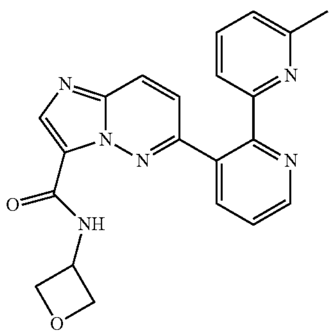 [SMILES: Cc1cccc(-c2ncccc2-c2ccc3ncc(C(=O)NC4COC4)n3n2)n1] | 6-(6'-methyl-[2,2'-bipyridin]-3-yl)-N-(oxetan-3-yl)imidazo[1,2-b]pyridazine-3-carboxamide |
| 75 | 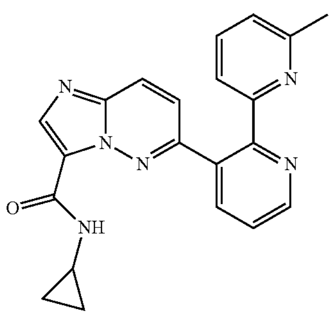 [SMILES: Cc1cccc(-c2ncccc2-c2ccc3ncc(C(=O)NC4CC4)n3n2)n1] | N-cyclopropyl-6-(6'-methyl-[2,2'-bipyridin]-3-yl)imidazo[1,2-b]pyridazine-3-carboxamide |
| 76 | 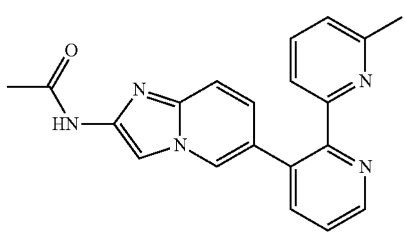 [SMILES: CC(=O)Nc1cn2cc(-c3cccnc3-c3cccc(C)n3)ccc2n1] | N-(6-(6'-methyl-[2,2'-bipyridin]-3-yl)imidazo[1,2-a]pyridin-2-yl)acetamide |
| 77 | 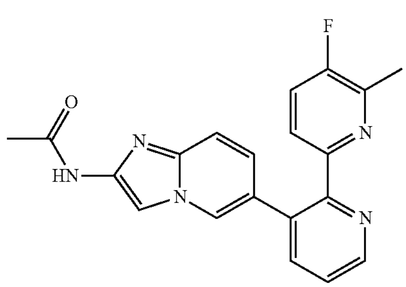 [SMILES: CC(=O)Nc1cn2cc(-c3cccnc3-c3ccc(F)c(C)n3)ccc2n1] | N-(6-(5'-fluoro-6'-methyl-[2,2'-bipyridin]-3-yl)imidazo[1,2-a]pyridin-2-yl)acetamide |

-continued

| No. | Structure | Name |
|---|---|---|
| 78 | 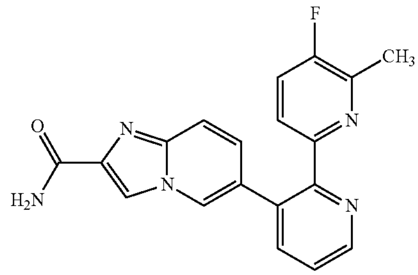 [SMILES: Cc1nc(-c2ncccc2-c2ccc3nc(C(N)=O)cn3c2)ccc1F] | 6-(5'-fluoro-6'-methyl-[2,2'-bipyridin]-3-yl)imidazo[1,2-a]pyridine-2-carboxamide |
| 79 | 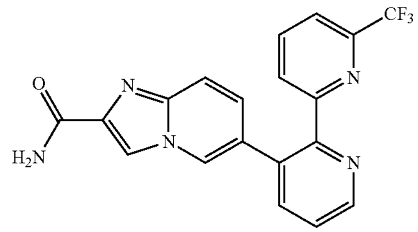 [SMILES: NC(=O)c1cn2cc(-c3cccnc3-c3cccc(C(F)(F)F)n3)ccc2n1] | 6-(6'-(trifluoromethyl)-[2,2'-bipyridin]-3-yl)imidazo[1,2-a]pyridine-2-carboxamide |
| 80 | 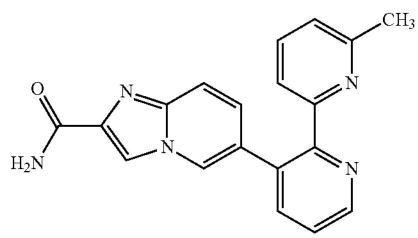 [SMILES: Cc1cccc(-c2ncccc2-c2ccc3nc(C(N)=O)cn3c2)n1] | 6-(6'-methyl-[2,2'-bipyridin]-3-yl)imidazo[1,2-a]pyridine-2-carboxamide |
| 81 | 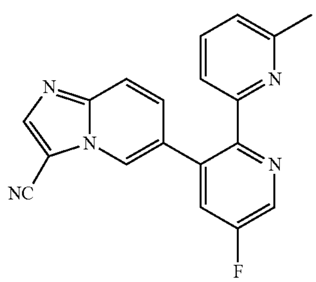 [SMILES: Cc1cccc(-c2ncc(F)cc2-c2ccc3ncc(C#N)n3c2)n1] | 6-(5-fluoro-6'-methyl-[2,2'-bipyridin]-3-yl)imidazo[1,2-a]pyridine-3-carbonitrile |
| 82 | 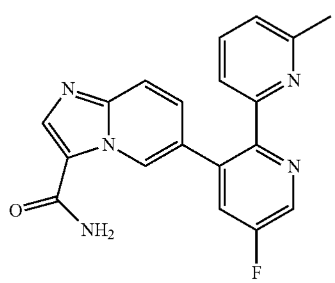 [SMILES: Cc1cccc(-c2ncc(F)cc2-c2ccc3ncc(C(N)=O)n3c2)n1] | 6-(5-fluoro-6'-methyl-[2,2'-bipyridin]-3-yl)imidazo[1,2-a]pyridine-3-carboxamide |
| 83 | 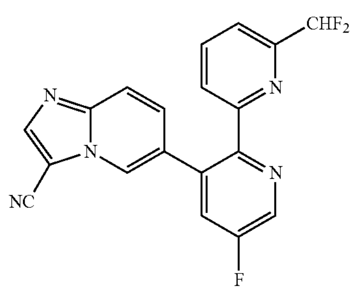 [SMILES: N#Cc1cnc2ccc(-c3cc(F)cnc3-c3cccc(C(F)F)n3)cn12] | 6-(6'-(difluoromethyl)-5-fluoro-[2,2'-bipyridin]-3-yl)imidazo[1,2-a]pyridine-3-carbonitrile |

| No. | Structure | Name |
|---|---|---|
| 84 | 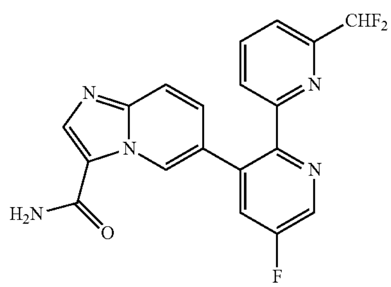 [SMILES: NC(=O)c1cnc2ccc(-c3cc(F)cnc3-c3cccc(C(F)F)n3)cn12] | 6-(6'-(difluoromethyl)-5-fluoro-[2,2'-bipyridin]-3-yl)imidazo[1,2-a]pyridine-3-carboxamide |
| 85 | 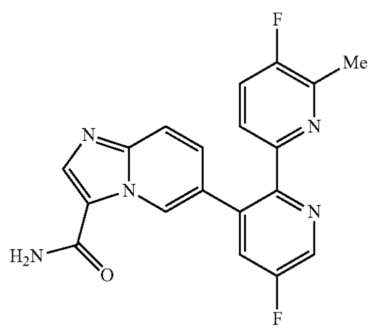 [SMILES: Cc1nc(-c2ncc(F)cc2-c2ccc3ncc(C(N)=O)n3c2)ccc1F] | 6-(5,5'-difluoro-6'-methyl-[2,2'-bipyridin]-3-yl)imidazo[1,2-a]pyridine-3-carboxamide |
| 86 | 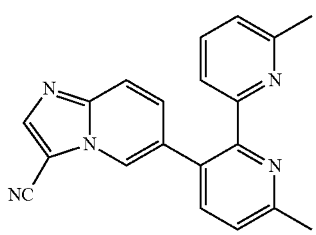 [SMILES: Cc1cccc(-c2nc(C)ccc2-c2ccc3ncc(C#N)n3c2)n1] | 6-(6,6'-dimethyl-[2,2'-bipyridin]-3-yl)imidazo[1,2-a]pyridine-3-carbonitrile |
| 87 | 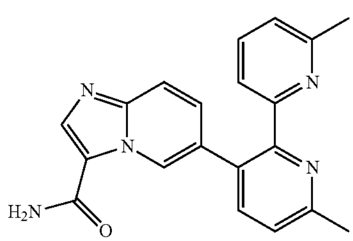 [SMILES: Cc1cccc(-c2nc(C)ccc2-c2ccc3ncc(C(N)=O)n3c2)n1] | 6-(6,6'-dimethyl-[2,2'-bipyridin]-3-yl)imidazo[1,2-a]pyridine-3-carbonitrile |
| 88 | 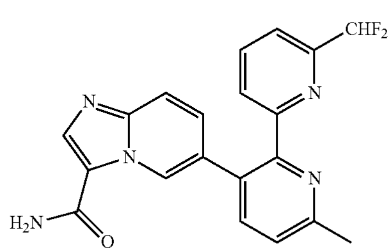 [SMILES: Cc1ccc(-c2ccc3ncc(C(N)=O)n3c2)c(-c2cccc(C(F)F)n2)n1] | 6-(6'-(difluoromethyl)-6-methyl-[2,2'-bipyridin]-3-yl)imidazo[1,2-a]pyridine-3-carboxamide |
| 89 | 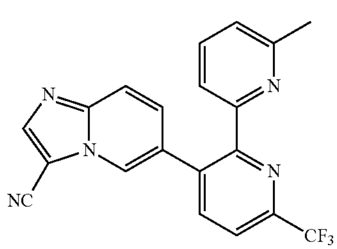 [SMILES: Cc1cccc(-c2nc(C(F)(F)F)ccc2-c2ccc3ncc(C#N)n3c2)n1] | 6-(6'-methyl-6-(trifluoromethyl)-[2,2'-bipyridin]-3-yl)imidazo[1,2-a]pyridine-3-carbonitrile |

-continued

| No. | Structure | Name |
|---|---|---|
| 90 | 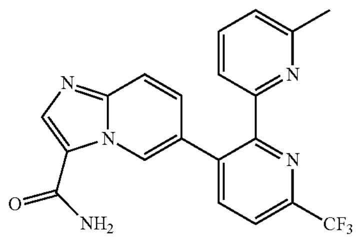 [SMILES: Cc1cccc(-c2nc(C(F)(F)F)ccc2-c2ccc3ncc(C(N)=O)n3c2)n1] | 6-(6'-methyl-6-(trifluoromethyl)-[2,2'-bipyridin]-3-yl)imidazo[1,2-a]pyridine-3-carboxamide |
| 91 | 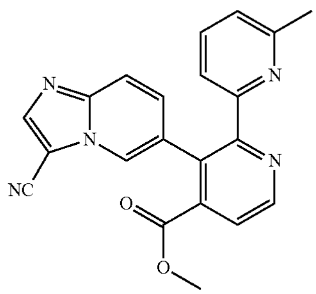 [SMILES: COC(=O)c1ccnc(-c2cccc(C)n2)c1-c1ccc2ncc(C#N)n2c1] | methyl 3-(3-cyanoimidazo[1,2-a]pyridin-6-yl)-6'-methyl-[2,2'-bipyridine]-4-carboxylate |
| 92 | 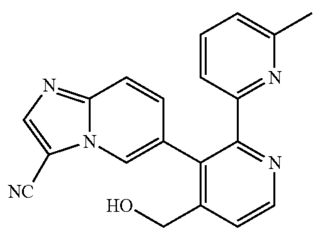 [SMILES: Cc1cccc(-c2nccc(CO)c2-c2ccc3ncc(C#N)n3c2)n1] | 6-(4-(hydroxymethyl)-6'-methyl-[2,2'-bipyridin]-3-yl)imidazo[1,2-a]pyridine-3-carbonitrile |
| 93 | 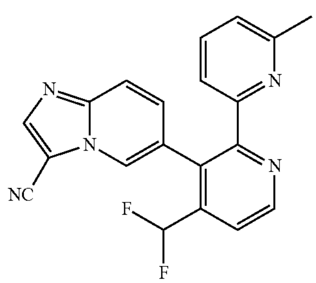 [SMILES: Cc1cccc(-c2nccc(C(F)F)c2-c2ccc3ncc(C#N)n3c2)n1] | 6-(4-(difluoromethyl)-6'-methyl-[2,2'-bipyridin]-3-yl)imidazo[1,2-a]pyridine-3-carbonitrile |
| 94 | 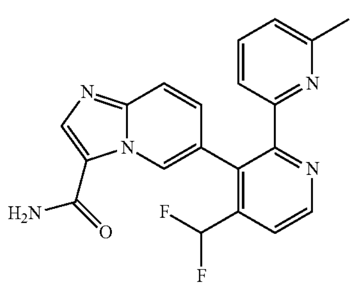 [SMILES: Cc1cccc(-c2nccc(C(F)F)c2-c2ccc3ncc(C(N)=O)n3c2)n1] | 6-(4-(difluoromethyl)-6'-methyl-[2,2'-bipyridin]-3-yl)imidazo[1,2-a]pyridine-3-carboxamide |
| 95 | 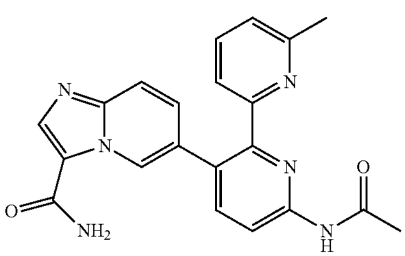 [SMILES: CC(=O)Nc1ccc(-c2ccc3ncc(C(N)=O)n3c2)c(-c2cccc(C)n2)n1] | 6-(6-acetamido-6'-methyl-[2,2'-bipyridin]-3-yl)imidazo[1,2-a]pyridine-3-carboxamide |

| No. | Structure | Name |
|---|---|---|
| 96 | 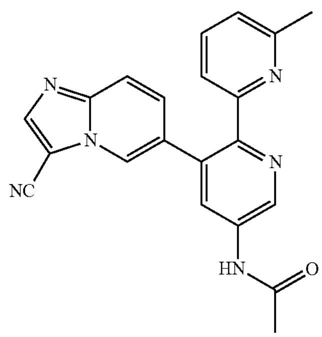 [SMILES: CC(=O)Nc1cnc(-c2cccc(C)n2)c(-c2ccc3ncc(C#N)n3c2)c1] | N-(3-(3-cyanoimidazo[1,2-a]pyridin-6-yl)-6'-methyl-[2,2'-bipyridin]-5-yl)acetamide |
| 97 | 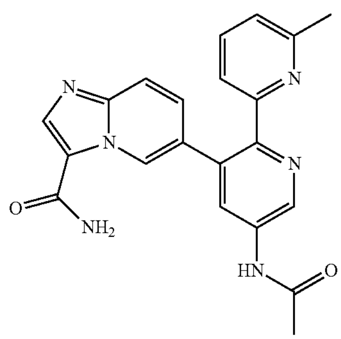 [SMILES: CC(=O)Nc1cnc(-c2cccc(C)n2)c(-c2ccc3ncc(C(N)=O)n3c2)c1] | 6-(5-acetamido-6'-methyl-[2,2'-bipyridin]-3-yl)imidazo[1,2-a]pyridine-3-carboxamide |
| 98 | 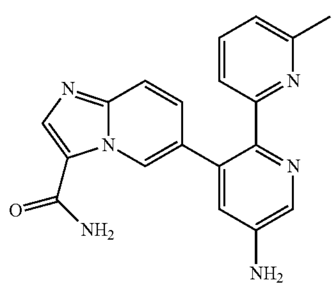 [SMILES: Cc1cccc(-c2ncc(N)cc2-c2ccc3ncc(C(N)=O)n3c2)n1] | 6-(5-amino-6'-methyl-[2,2'-bipyridin]-3-yl)imidazo[1,2-a]pyridine-3-carboxamide |
| 99 | 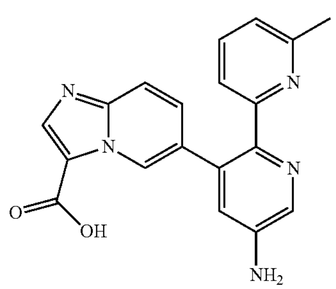 [SMILES: Cc1cccc(-c2ncc(N)cc2-c2ccc3ncc(C(=O)O)n3c2)n1] | 6-(5-amino-6'-methyl-[2,2'-bipyridin]-3-yl)imidazo[1,2-a]pyridine-3-carboxylic acid |
| 100 | 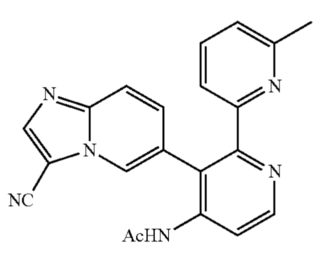 [SMILES: CC(=O)Nc1ccnc(-c2cccc(C)n2)c1-c1ccc2ncc(C#N)n2c1] | N-(3-(3-cyanoimidazo[1,2-a]pyridin-6-yl)-6'-methyl-[2,2'-bipyridin]-4-yl)acetamide |

-continued

| No. | Structure | Name |
|---|---|---|
| 101 | 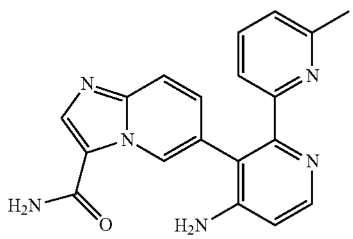 [SMILES: Cc1cccc(-c2nccc(N)c2-c2ccc3ncc(C(N)=O)n3c2)n1] | 6-(4-amino-6'-methyl-[2,2'-bipyridin]-3-yl)imidazo[1,2-a]pyridine-3-carboxamide |
| 102 | 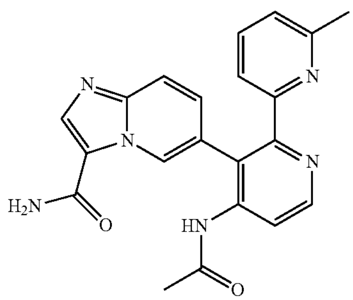 [SMILES: CC(=O)Nc1ccnc(-c2cccc(C)n2)c1-c1ccc2ncc(C(N)=O)n2c1] | 6-(4-acetamido-6'-methyl-[2,2'-bipyridin]-3-yl)imidazo[1,2-a]pyridine-3-carboxamide |
| 103 | 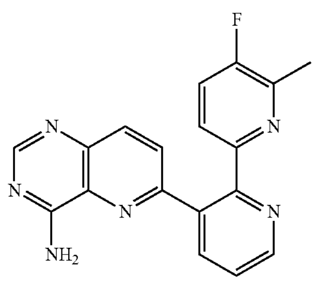 [SMILES: Cc1nc(-c2ncccc2-c2ccc3ncnc(N)c3n2)ccc1F] | 6-(5'-fluoro-6'-methyl-[2,2'-bipyridin]-3-yl)pyrido[3,2-d]pyrimidin-4-amine |
| 104 | 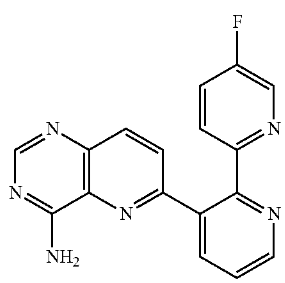 [SMILES: Nc1ncnc2ccc(-c3cccnc3-c3ccc(F)cn3)nc12] | 6-(5'-fluoro-[2,2'-bipyridin]-3-yl)pyrido[3,2-d]pyrimidin-4-amine |
| 105 | 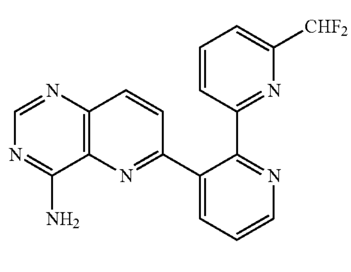 [SMILES: Nc1ncnc2ccc(-c3cccnc3-c3cccc(C(F)F)n3)nc12] | 6-(6'-(difluoromethyl)-[2,2'-bipyridin]-3-yl)pyrido[3,2-d]pyrimidin-4-amine |

-continued
| No. | Structure | Name |
|---|---|---|
| 106 | 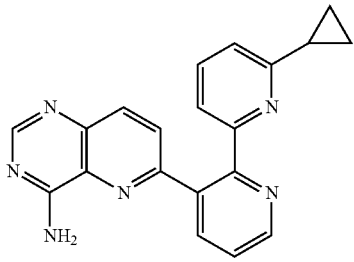 [SMILES: Nc1ncnc2ccc(-c3cccnc3-c3cccc(C4CC4)n3)nc12] | 6-(6'-cyclopropyl-[2,2'-bipyridin]-3-yl)pyrido[3,2-d]pyrimidin-4-amine |
| 107 | 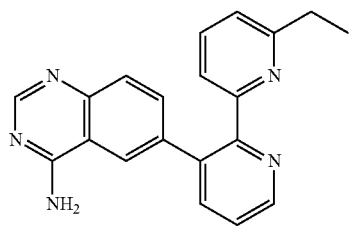 [SMILES: CCc1cccc(-c2ncccc2-c2ccc3ncnc(N)c3c2)n1] | 6-(6'-ethyl-[2,2'-bipyridin]-3-yl)quinazolin-4-amine |
| 108 | 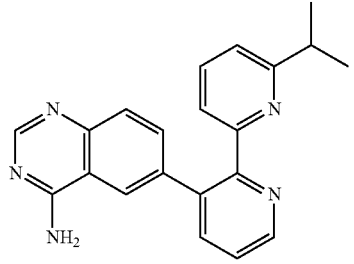 [SMILES: CC(C)c1cccc(-c2ncccc2-c2ccc3ncnc(N)c3c2)n1] | 6-(6'-isopropyl-[2,2'-bipyridin]-3-yl)quinazolin-4-amine |
| 109 | 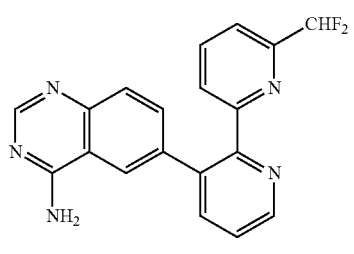 [SMILES: Nc1ncnc2ccc(-c3cccnc3-c3cccc(C(F)F)n3)cc12] | 6-(6'-(difluoromethyl)-[2,2'-bipyridin]-3-yl)quinazolin-4-amine |
| 110 | 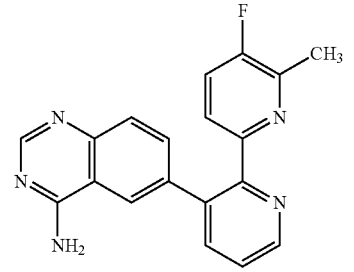 [SMILES: Cc1nc(-c2ncccc2-c2ccc3ncnc(N)c3c2)ccc1F] | 6-(5'-fluoro-6'-methyl-[2,2'-bipyridin]-3-yl)imidazo[1,2-a]pyridine-2-carboxamide |
| 111 | 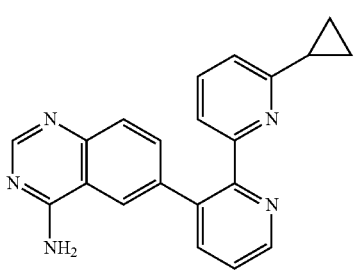 [SMILES: Nc1ncnc2ccc(-c3cccnc3-c3cccc(C4CC4)n3)cc12] | 6-(6'-isopropyl-[2,2'-bipyridin]-3-yl)quinazolin-4-amine |

-continued

| No. | Structure | Name |
|---|---|---|
| 112 | 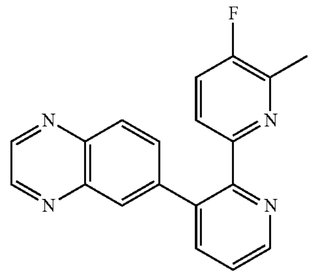 [SMILES: Cc1nc(-c2ncccc2-c2ccc3nccnc3c2)ccc1F] | 6-(5'-fluoro-6'-methyl-[2,2'-bipyridin]-3-yl)quinoxaline |
| 113 | 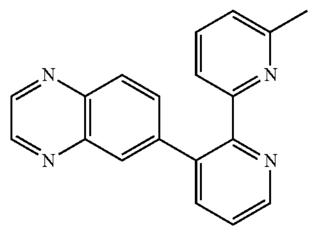 [SMILES: Cc1cccc(-c2ncccc2-c2ccc3nccnc3c2)n1] | 6-(6'-methyl-[2,2'-bipyridin]-3-yl)quinoxaline |
| 114 | 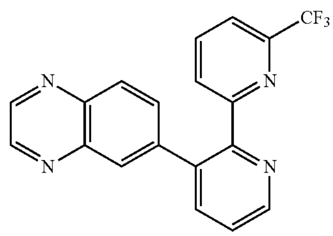 [SMILES: FC(F)(F)c1cccc(-c2ncccc2-c2ccc3nccnc3c2)n1] | 6-(6'-(trifluoromethyl)-[2,2'-bipyridin]-3-yl)quinoxaline |
| 115 | 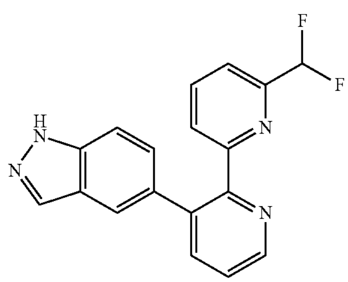 [SMILES: FC(F)c1cccc(-c2ncccc2-c2ccc3[nH]ncc3c2)n1] | 5-(6'-(difluoromethyl)-[2,2'-bipyridin]-3-yl)-1H-indazole |
| 116 | 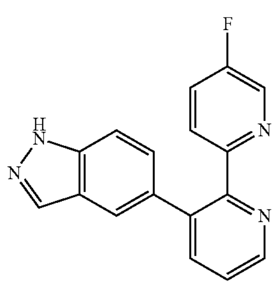 [SMILES: Fc1ccc(-c2ncccc2-c2ccc3[nH]ncc3c2)nc1] | 5-(5'-fluoro-[2,2'-bipyridin]-3-yl)-1H-indazole |
| 117 | 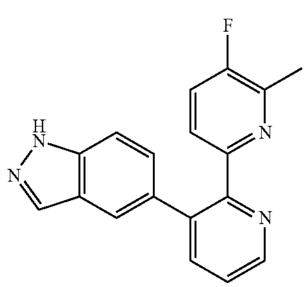 [SMILES: Cc1nc(-c2ncccc2-c2ccc3[nH]ncc3c2)ccc1F] | 5-(5'-fluoro-6'-methyl-[2,2'-bipyridin]-3-yl)-1H-indazole |

| No. | Structure | Name |
|---|---|---|
| 118 | 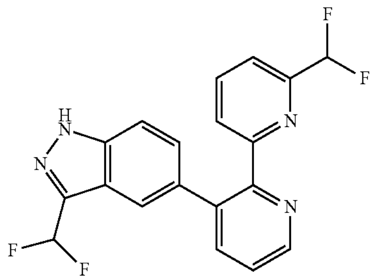 [SMILES: FC(F)c1cccc(-c2ncccc2-c2ccc3[nH]nc(C(F)F)c3c2)n1] | 3-(difluoromethyl)-5-(6'-(difluoromethyl)-[2,2'-bipyridin]-3-yl)-1H-indazole |
| 119 | 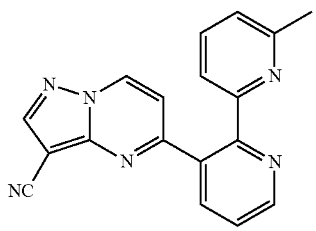 [SMILES: Cc1cccc(-c2ncccc2-c2ccn3ncc(C#N)c3n2)n1] | 5-(6'-methyl-[2,2'-bipyridin]-3-yl)pyrazolo[1,5-a]pyrimidine-3-carbonitrile |
| 120 | 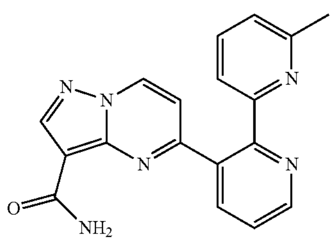 [SMILES: Cc1cccc(-c2ncccc2-c2ccn3ncc(C(N)=O)c3n2)n1] | 5-(6'-methyl-[2,2'-bipyridin]-3-yl)pyrazolo[1,5-a]pyrimidine-3-carboxamide |
| 121 | 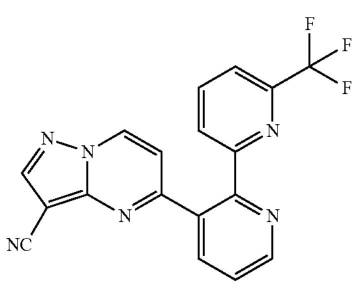 [SMILES: N#Cc1cnn2ccc(-c3cccnc3-c3cccc(C(F)(F)F)n3)nc12] | 5-(6'-(trifluoromethyl)-[2,2'-bipyridin]-3-yl)pyrazolo[1,5-a]pyrimidine-3-carbonitrile |
| 122 | 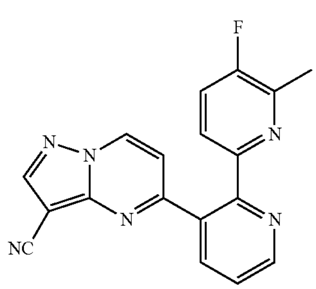 [SMILES: Cc1nc(-c2ncccc2-c2ccn3ncc(C#N)c3n2)ccc1F] | 5-(5'-fluoro-6'-methyl-[2,2'-bipyridin]-3-yl)pyrazolo[1,5-a]pyrimidine-3-carbonitrile |

-continued

| No. | Structure | Name |
|---|---|---|
| 123 | 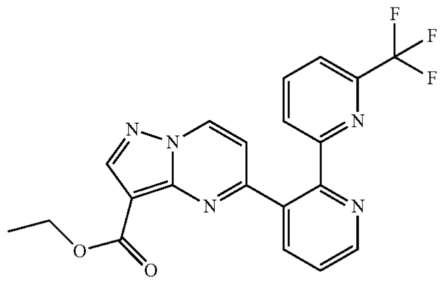 [SMILES: CCOC(=O)c1cnn2ccc(-c3cccnc3-c3cccc(C(F)(F)F)n3)nc12] | ethyl 5-(6'-(trifluoromethyl)-[2,2'-bipyridin]-3-yl)pyrazolo[1,5-a]pyrimidine-3-carboxylate |
| 124 | 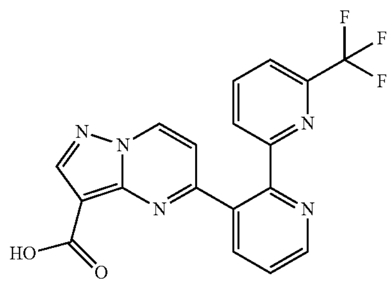 [SMILES: O=C(O)c1cnn2ccc(-c3cccnc3-c3cccc(C(F)(F)F)n3)nc12] | 5-(6'-(trifluoromethyl)-[2,2'-bipyridin]-3-yl)pyrazolo[1,5-a]pyrimidine-3-carboxylic acid |
| 125 | 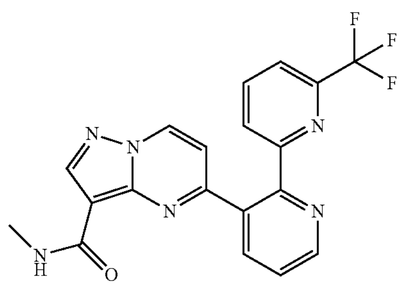 [SMILES: CNC(=O)c1cnn2ccc(-c3cccnc3-c3cccc(C(F)(F)F)n3)nc12] | N-methyl-5-(6'-(trifluoromethyl)-[2,2'-bipyridin]-3-yl)pyrazolo[1,5-a]pyrimidine-3-carboxamide |
| 126 | 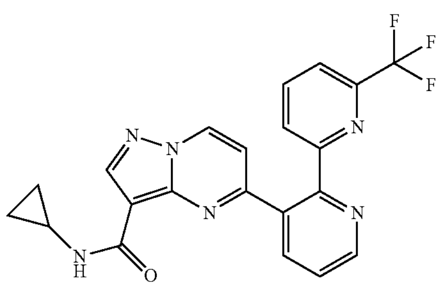 [SMILES: O=C(NC1CC1)c1cnn2ccc(-c3cccnc3-c3cccc(C(F)(F)F)n3)nc12] | N-cyclopropyl-5-(6'-(trifluoromethyl)-[2,2'-bipyridin]-3-yl)pyrazolo[1,5-a]pyrimidine-3-carboxamide |
| 127 | 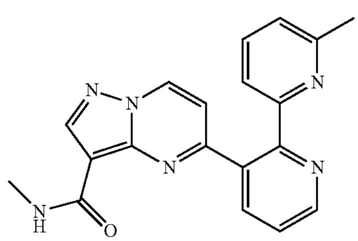 | N-methyl-5-(6'-methyl-[2,2'-bipyridin]-3-yl)pyrazolo[1,5-a]pyrimidine-3-carboxamide |
| 128 | 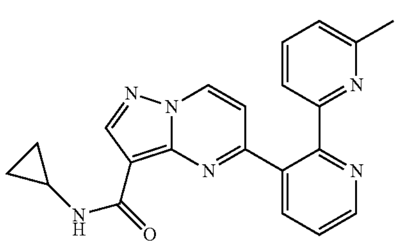 [SMILES: Cc1cccc(-c2ncccc2-c2ccn3ncc(C(=O)NC4CC4)c3n2)n1] | N-cyclopropyl-5-(6'-methyl-[2,2'-bipyridin]-3-yl)pyrazolo[1,5-a]pyrimidine-3-carboxamide |

| No. | Structure | Name |
| --- | --- | --- |
| 129 | 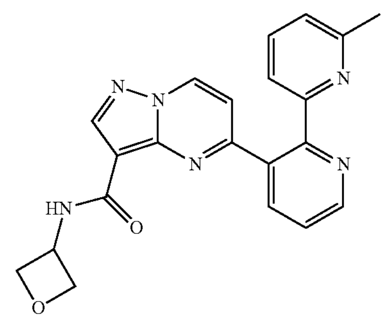 [SMILES: Cc1cccc(-c2ncccc2-c2ccn3ncc(C(=O)NC4COC4)c3n2)n1] | 5-(6'-methyl-[2,2'-bipyridin]-3-yl)-N-(oxetan-3-yl)pyrazolo[1,5-a]pyrimidine-3-carboxamide |
| 130 | 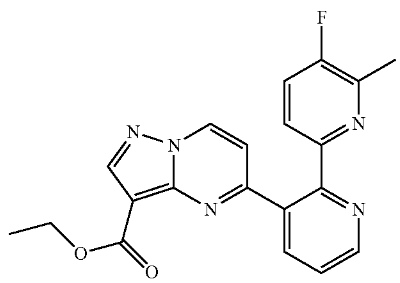 [SMILES: CCOC(=O)c1cnn2ccc(-c3cccnc3-c3ccc(F)c(C)n3)nc12] | ethyl 5-(5'-fluoro-6'-methyl-[2,2'-bipyridin]-3-yl)pyrazolo[1,5-a]pyrimidine-3-carboxylate |
| 131 | 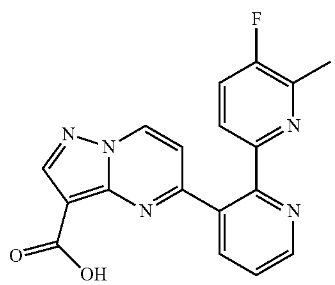 [SMILES: Cc1nc(-c2ncccc2-c2ccn3ncc(C(=O)O)c3n2)ccc1F] | 5-(5'-fluoro-6'-methyl-[2,2'-bipyridin]-3-yl)pyrazolo[1,5-a]pyrimidine-3-carboxylic acid |
| 132 | 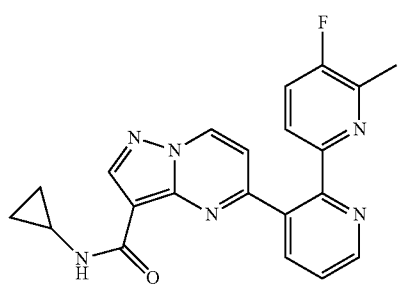 [SMILES: Cc1nc(-c2ncccc2-c2ccn3ncc(C(=O)NC4CC4)c3n2)ccc1F] | N-cyclopropyl-5-(5'-fluoro-6'-methyl-[2,2'-bipyridin]-3-yl)pyrazolo[1,5-a]pyrimidine-3-carboxamide |
| 133 | 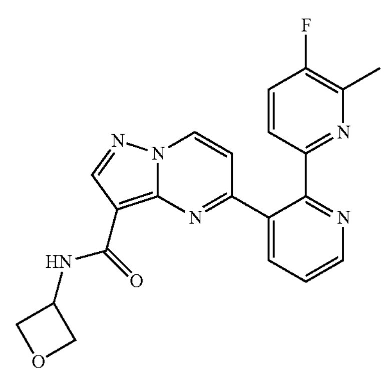 [SMILES: Cc1nc(-c2ncccc2-c2ccn3ncc(C(=O)NC4COC4)c3n2)ccc1F] | 5-(5'-fluoro-6'-methyl-[2,2'-bipyridin]-3-yl)-N-(oxetan-3-yl)pyrazolo[1,5-a]pyrimidine-3-carboxamide |

-continued

| No. | Structure | Name |
|---|---|---|
| 134 | 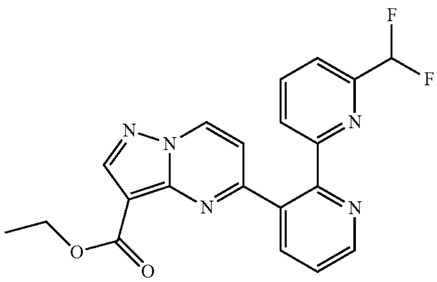 [SMILES: CCOC(=O)c1cnn2ccc(-c3cccnc3-c3cccc(C(F)F)n3)nc12] | ethyl 5-(6'-(difluoromethyl)-[2,2'-bipyridin]-3-yl)pyrazolo[1,5-a]pyrimidine-3-carboxylate |
| 135 | 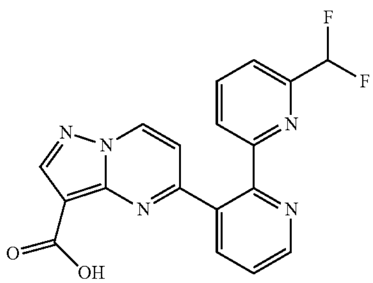 [SMILES: O=C(O)c1cnn2ccc(-c3cccnc3-c3cccc(C(F)F)n3)nc12] | 5-(6'-(difluoromethyl)-[2,2'-bipyridin]-3-yl)pyrazolo[1,5-a]pyrimidine-3-carboxylic acid |
| 136 | 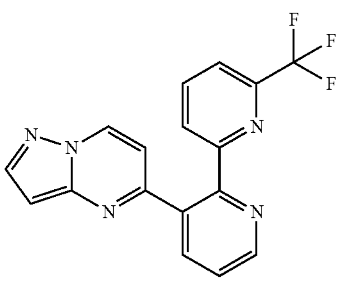 [SMILES: FC(F)(F)c1cccc(-c2ncccc2-c2ccn3nccc3n2)n1] | 5-(6'-(trifluoromethyl)-[2,2'-bipyridin]-3-yl)pyrazolo[1,5-a]pyrimidine |
| 137 | 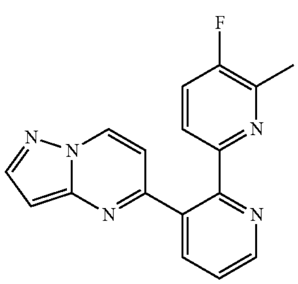 [SMILES: Cc1nc(-c2ncccc2-c2ccn3nccc3n2)ccc1F] | 5-(5'-fluoro-6'-methyl-[2,2'-bipyridin]-3-yl)pyrazolo[1,5-a]pyrimidine |
| 138 | 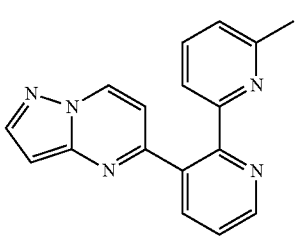 [SMILES: Cc1cccc(-c2ncccc2-c2ccn3nccc3n2)n1] | 5-(6'-methyl-[2,2'-bipyridin]-3-yl)pyrazolo[1,5-a]pyrimidine |

In embodiment II$_1$ of this aspect, the invention comprises compounds having the structure of formula (II):

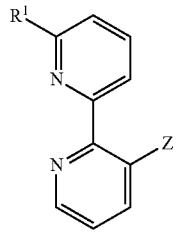
(II)

or a pharmaceutically acceptable salt, prodrug or N-oxide thereof, or solvate or hydrate thereof,
wherein
R$^1$ is hydrogen, halogen, cyano, nitro, C$_{1-6}$alkyl or C$_{1-6}$haloalkyl;
Z is
a fused bicyclic ring of the formula,

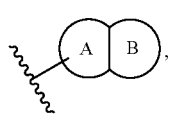

wherein
ring A is Ar or 6-membered Het,
ring B is 5- or 6-membered Het,
wherein
Z is optionally substituted by one or two —R$^Z$ groups that are each independently halogen, cyano, C$_{1-6}$alkyl, C$_{1-6}$haloalkyl, —C$_1$-C$_6$alkoxy, —OR$^{S2}$, —SR$^{S2}$, —NR$^{S2}$$_2$, —C(O)R$^{S2}$, —C(O)OR$^{S2}$, —C(O)NR$^{S2}$$_2$, —S(O)$_2$NR$^{S2}$$_2$, —S(O)$_2$R$^{S2}$, —OC(O)R$^{S2}$, —N(R$^{S2}$)C(O)R$^{S2}$, —OC(O)OR$^{S2}$, —OC(O)NR$^{S2}$$_2$, —N(R$^{S2}$)C(O)OR$^{S2}$, —N(R$^{S2}$)C(O)NR$^{S2}$$_2$, —NR$^{S2}$)S(O)$_2$R$^{S2}$, —OP(O)(OR$^{S2}$)$_2$ or —CH$_2$—OP(O)(OR$^{S2}$);
wherein each R$^{S2}$ is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano.
In embodiment II$_2$, the compounds are of embodiment II$_1$, provided that the compound is not 5-(6'-methyl-[2,2'-bipyridin]-3-yl)-1H-indazole.
In embodiment II$_3$, the compounds are of embodiment II$_1$, wherein
Z is
a fused bicyclic ring of the formula,

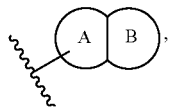

wherein
(1) ring A is Ar or 6-membered Het, and
   ring B is a 6-membered Het; or
(2) ring A is 6-membered Het, and
   ring B is a 5-membered Het;

wherein Z is optionally substituted by one or two —R$^Z$ groups.

In embodiment II$_4$, the compounds are of embodiment II$_1$, wherein
Z is

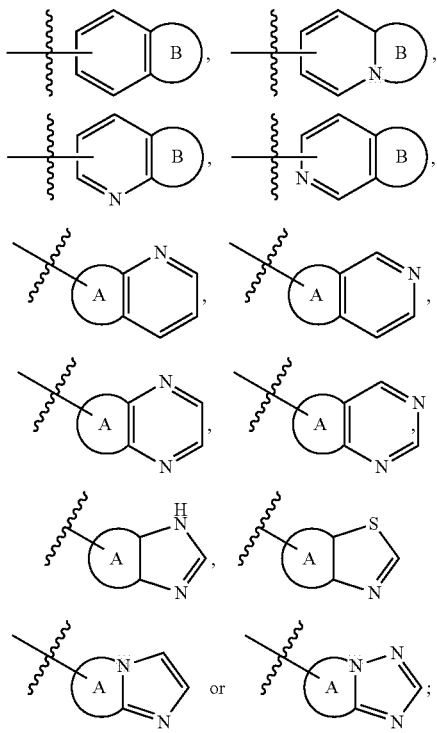

wherein Z is optionally substituted by one or two —R$^Z$ groups.

In embodiment II$_5$, the compounds are of embodiment II$_1$, wherein
Z is

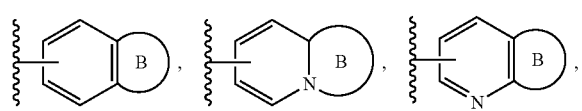

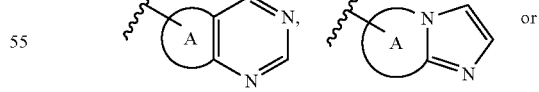

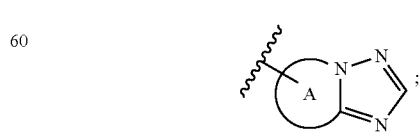

wherein Z is optionally substituted by one or two —R$^Z$ groups.

In embodiment II₆, the compounds are of embodiment II₁, wherein

Z is

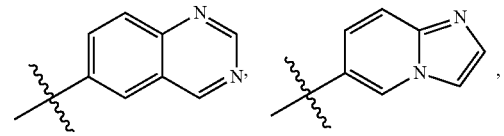

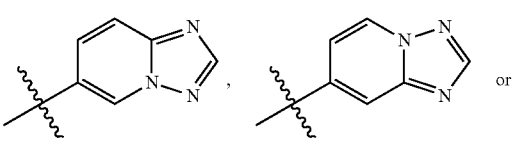, or

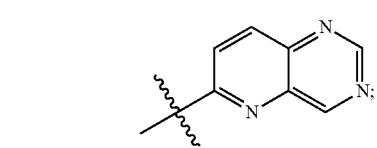

wherein Z is optionally substituted by one or two —R$^Z$ groups.

In embodiment II₇, the compounds are of any of embodiments II₁-II₆, wherein Z is unsubstituted.

In embodiment II₈, the compounds are of any of embodiments II₁-II₇, wherein R¹ is hydrogen or methyl.

In embodiment II₉, the compounds of the invention are one of formulae (IIa)-(III), wherein R¹ and Z are as defined in embodiments II₁-II₈ above:

Structural Formula (II) is One of Formulae (IIa)-(III):

(IIa)

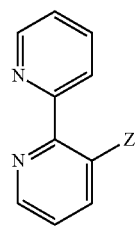

(IIb)

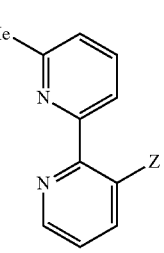

(IIc)

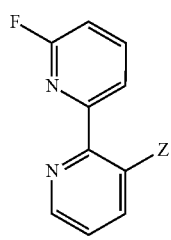

-continued (IId)

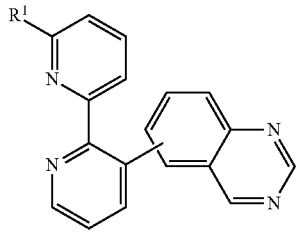

(IIe)

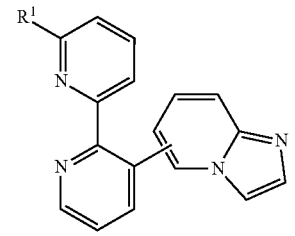

(IIf)

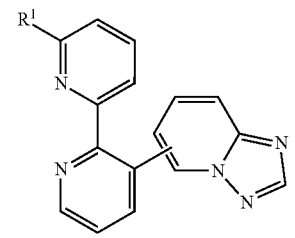

(IIg)

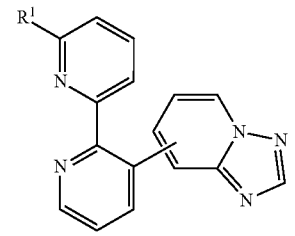

(IIh)

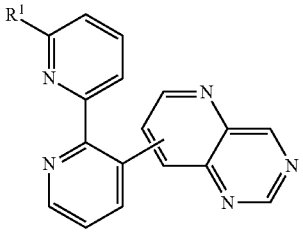

(IIi)

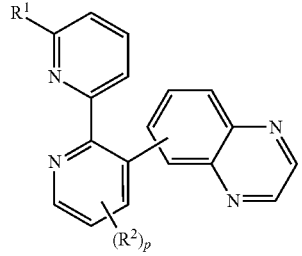

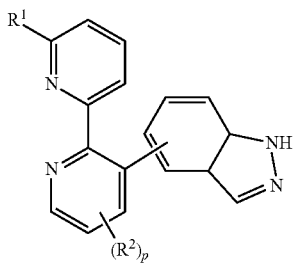

(IIj)

(IIk)

(III)

Particular embodiments of this aspect of the invention comprise compounds of any one of the formulae (II), and (IIa)-(IIg), each as defined in each of the following rows (or a pharmaceutically acceptable salt, prodrug, or N-oxide thereof, or a solvate or hydrate thereof), wherein each entry is a group number as defined above (e.g., (1ss) refers to $R^1$ is methyl, and a dash "-" indicates that the variable is as defined in embodiment $I_1$ or defined according to any one of the applicable variable definitions (1a)-(1tt) and (2a)-(2dddd) [e.g., when $R^1$ is a dash, it can be either as defined in any of embodiments $II_1$-$II_8$ or any one of the applicable definitions (1a)-(1tt)]:

|         | (II)  | $R^1$ | Z      |
|---------|-------|-------|--------|
| (2)-1   | (IIa) | X     | (2a)   |
| (2)-2   | (IIb) | X     | (2b)   |
| (2)-3   | (IIc) | X     | (2d)   |
| (2)-4   | (IId) | (1aa) | (2q)   |
| (2)-5   | (IIe) | (1ff) | (2s)   |
| (2)-6   | (IIf) | (1m)  | (2m)   |
| (2)-7   | (IIg) | (1s)  | (2s)   |
| (2)-8   | (IIh) | (1rr) | (2t)   |
| (2)-9   | (IIh) | (1ss) | (2p)   |
| (2)-10  | (IIf) | (1tt) | (2r)   |
| (2)-11  | (IIb) | (1a)  | (2k)   |
| (2)-12  | (IIc) | (1q)  | (2r)   |
| (2)-13  | (IId) | X     | (2w)   |
| (2)-14  | (IIf) | X     | (2x)   |
| (2)-15  | (IIb) | (1u)  | (2bb)  |
| (2)-16  | (IIc) | (1aa) | (2k)   |
| (2)-17  | (IId) | (1ff) | (2q)   |
| (2)-18  | (IIc) | (1m)  | (2q)   |
| (2)-19  | (IId) | (1s)  | (2t)   |
| (2)-20  | (IIe) | (1rr) | (2t)   |
| (2)-21  | (IIf) | X     | (2bbb) |
| (2)-22  | (IIg) | X     | (2d)   |
| (2)-23  | (IIh) | (1a)  | (2x)   |
| (2)-24  | (IIh) | (1q)  | (2r)   |
| (2)-25  | (IIf) | (1u)  | (2q)   |
| (2)-26  | (IIb) | (1aa) | (2n)   |
| (2)-27  | (IIc) | (1ff) | (2s)   |
| (2)-28  | (IId) | (1m)  | (2s)   |
| (2)-29  | (IIc) | (1s)  | (2r)   |
| (2)-30  | (IId) | (1rr) | (2t)   |
| (2)-31  | (IIb) | (1ss) | (2k)   |
| (2)-32  | (IIc) | X     | (2w)   |
| (2)-33  | (IId) | X     | (2x)   |
| (2)-34  | (IIe) | (1q)  | (2bb)  |
| (2)-35  | (IIf) | (1rr) | (2s)   |
| (2)-36  | (IIg) | (1rr) | (2l)   |
| (2)-37  | (IIh) | (2s)  | (2p)   |
| (2)-38  | (IIh) | (2j)  | (2t)   |
| (2)-39  | (IIc) | (2o)  | (2s)   |
| (2)-40  | (IId) | (2p)  | (2l)   |
| (2)-41  | (IIb) | (1ff) | (2m)   |
| (2)-42  | (IIc) | (1m)  | (2s)   |
| (2)-43  | (IId) | (1s)  | (2t)   |
| (2)-44  | (IIc) | X     | (2p)   |
| (2)-45  | (IId) | (2s)  | (2r)   |
| (2)-46  | (IIb) | (2j)  | (2q)   |
| (2)-47  | (IIc) | (2o)  | (2t)   |
| (2)-48  | (IId) | (2p)  | (2s)   |
| (2)-49  | (IIe) | X     | (2x)   |
| (2)-50  | (IIf) | (1u)  | (2bb)  |
| (2)-51  | (IIg) | (1aa) | (2r)   |
| (2)-52  | (IIh) | (1ff) | (2l)   |
| (2)-53  | (IIe) | (1m)  | (2o)   |
| (2)-54  | (IIf) | (1s)  | (2t)   |
| (2)-55  | (IIb) | (1rr) | (2t)   |
| (2)-56  | (IIc) | (1ss) | (2bbb) |
| (2)-57  | (IId) | (1tt) | (2x)   |
| (2)-58  | (IIc) | (1a)  | (2k)   |
| (2)-59  | (IId) | X     | (2ii)  |
| (2)-60  | (IIb) | (1rr) | (2jj)  |
| (2)-61  | (IIc) | (1rr) | (2s)   |
| (2)-62  | (IId) | (2s)  | (2r)   |
| (2)-63  | (IIe) | (2j)  | (2p)   |
| (2)-64  | (IIf) | (2o)  | (2s)   |
| (2)-65  | (IIg) | (2p)  | (2s)   |
| (2)-66  | (IIh) | X     | (2i)   |
| (2)-67  | (IId) | (1rr) | (2j)   |
| (2)-68  | (IIf) | (2s)  | (2q)   |
| (2)-69  | (IIb) | (2j)  | (2p)   |
| (2)-70  | (IIc) | (2o)  | (2k)   |
| (2)-71  | (IId) | (2p)  | (2l)   |
| (2)-72  | (IIg) | (1rr) | (2q)   |
| (2)-73  | (IIh) | (1ff) | (2t)   |
| (2)-74  | (IIc) | (1m)  | (2s)   |
| (2)-75  | (IIc) | (1s)  | (2bb)  |
| (2)-76  | (IId) | (1rr) | (2q)   |
| (2)-77  | (IIe) | (2s)  | (2q)   |
| (2)-78  | (IIf) | (2j)  | (2q)   |
| (2)-79  | (IIg) | (2o)  | (2s)   |
| (2)-80  | (IIh) | (2p)  | (2t)   |
| (2)-81  | (IIf) | X     | (2bbb) |
| (2)-82  | (IIf) | (1rr) | (2jj)  |
| (2)-83  | (IIb) | (1ff) | (2r)   |
| (2)-84  | (IIc) | (1m)  | (2ww)  |
| (2)-85  | (IId) | (1s)  | (2s)   |
| (2)-86  | (IIf) | (1rr) | (2r)   |
| (2)-87  | (IIb) | (1rr) | (2m)   |
| (2)-88  | (IIc) | (1rr) | (2t)   |
| (2)-89  | (IId) | (1rr) | (2t)   |
| (2)-90  | (IId) | X     | (2h)   |
| (2)-91  | (IIe) | (1rr) | (2i)   |
| (2)-92  | (IIf) | (1rr) | (2k)   |
| (2)-93  | (IIg) | X     | (2o)   |
| (2)-94  | (IIh) | X     | (2p)   |
| (2)-95  | (IIa) | X     | (2r)   |
| (2)-96  | (IIf) | (1m)  | (2t)   |
| (2)-97  | (IIb) | (1s)  | (2t)   |

-continued

| | (II) | R¹ | Z |
|---|---|---|---|
| (2)-98 | (IIc) | (1rr) | (2ww) |
| (2)-99 | (IId) | (1rr) | (2q) |
| (2)-100 | (IIf) | X | (2bbb) |
| (2)-101 | (IIb) | X | (2g) |
| (2)-102 | (IIc) | (1rr) | (2h) |
| (2)-103 | (IId) | (1ff) | (2k) |
| (2)-104 | (IId) | (1m) | (2q) |
| (2)-105 | (IIe) | (1s) | (2r) |
| (2)-106 | (IIf) | (1rr) | (2t) |
| (2)-107 | (IIg) | (1rr) | (2s) |
| (2)-108 | (IIh) | X | (2t) |
| (2)-109 | (IIg) | X | (2u) |
| (2)-110 | (IId) | (1rr) | (2w) |
| (2)-111 | (IIf) | (1rr) | (2r) |
| (2)-112 | (IIb) | X | (2bb) |
| (2)-113 | (IIc) | (1u) | (2ii) |
| (2)-114 | (IId) | (1aa) | (2q) |
| (2)-115 | (IId) | (1ff) | (2k) |
| (2)-116 | (IIe) | (1m) | (2n) |
| (2)-117 | (IIf) | (1s) | (2t) |
| (2)-118 | (IIg) | (1rr) | (2t) |
| (2)-119 | (IIh) | (1ss) | (2qq) |
| (2)-120 | (IId) | (1tt) | (2ww) |
| (2)-121 | (IIf) | (1a) | (2q) |
| (2)-122 | (IIb) | X | (2bbb) |
| (2)-123 | (IIc) | (1ff) | (2b) |
| (2)-124 | (IId) | (1m) | (2d) |
| (2)-125 | (IIb) | (1s) | (2r) |
| (2)-126 | (IIc) | X | (2h) |
| (2)-127 | (IId) | X | (2i) |
| (2)-128 | (IIe) | — | (2j) |
| (2)-129 | (IIf) | — | (2s) |
| (2)-130 | (IIg) | (2s) | (2k) |
| (2)-131 | (IIh) | (2j) | (2p) |
| (2)-132 | (IIb) | (2o) | (2t) |
| (2)-133 | (IIf) | (2p) | (2t) |
| (2)-134 | (IIb) | X | (2w) |
| (2)-135 | (IIc) | X | (2x) |
| (2)-136 | (IId) | — | (2bb) |
| (2)-137 | (IIf) | (2s) | (2s) |
| (2)-138 | (IIb) | (2j) | (2l) |
| (2)-139 | (IIc) | (2o) | (2q) |
| (2)-140 | (IId) | (2p) | (2s) |
| (2)-141 | (IId) | | (2t) |
| (2)-142 | (IIe) | (1rr) | (2bbb) |
| (2)-143 | (IIf) | X | (2qq) |
| (2)-144 | (IIg) | (1ff) | (2ww) |
| (2)-145 | (IIh) | (1m) | (2s) |
| (2)-146 | (IIa) | X | (2k) |
| (2)-147 | (IIf) | (1rr) | (2o) |
| (2)-148 | (IIb) | (1rr) | (2s) |
| (2)-149 | (IIc) | (1rr) | (2s) |
| (2)-150 | (IId) | (1ff) | (2i) |
| (2)-151 | (IIb) | (1m) | (2j) |
| (2)-152 | (IIc) | (1s) | (2q) |
| (2)-153 | (IId) | X | (2p) |
| (2)-154 | (IIe) | X | (2r) |
| (2)-155 | (IIf) | — | (2t) |
| (2)-156 | (IIg) | X | (2u) |
| (2)-157 | (IIh) | (1u) | (2w) |
| (2)-158 | (IIf) | (1aa) | (2k) |
| (2)-159 | (IId) | (1ff) | (2q) |
| (2)-160 | (IIe) | (1m) | (2n) |
| (2)-161 | (IIf) | (1s) | (2s) |
| (2)-162 | (IIg) | (1rr) | (2t) |
| (2)-163 | (IIh) | (1ss) | (2r) |
| (2)-164 | (IIb) | (1tt) | (2r) |
| (2)-165 | (IIf) | (1a) | (2t) |
| (2)-166 | (IIb) | (1q) | (2s) |
| (2)-167 | (IIc) | X | (2qq) |
| (2)-168 | (IId) | X | (2qq) |
| (2)-169 | (IIb) | — | (2jj) |
| (2)-170 | (IIc) | (1ff) | (2q) |
| (2)-171 | (IId) | (1m) | (2r) |
| (2)-172 | (IIe) | (1s) | (2o) |
| (2)-173 | (IIf) | (1rr) | (2s) |
| (2)-174 | (IIg) | — | (2s) |
| (2)-175 | (IIh) | — | (2h) |
| (2)-176 | (IIa) | X | (2k) |
| (2)-177 | (IId) | (2j) | (2k) |
| (2)-178 | (IIe) | (2o) | (2o) |
| (2)-179 | (IIf) | (2p) | (2t) |
| (2)-180 | (IIb) | — | (2t) |
| (2)-181 | (IIc) | X | (2t) |
| (2)-182 | (IId) | (1rr) | (2u) |
| (2)-183 | (IIe) | (1rr) | (2r) |
| (2)-184 | (IIf) | X | (2x) |
| (2)-185 | (IIg) | X | (2bb) |
| (2)-186 | (IIh) | (1ff) | (2ii) |
| (2)-187 | (IIa) | (1m) | (2s) |
| (2)-188 | (IIf) | (1s) | (2l) |
| (2)-189 | (IIb) | (1rr) | (2n) |
| (2)-190 | (IIc) | (2s) | (2t) |
| (2)-191 | (IId) | (2j) | (2t) |
| (2)-192 | (IIg) | (2o) | (2q) |
| (2)-193 | (IIh) | (2p) | (2o) |
| (2)-194 | (IId) | (1rr) | (2s) |
| (2)-195 | (IIb) | X | (2o) |
| (2)-196 | (IIc) | X | (2p) |
| (2)-197 | (IId) | — | (2r) |
| (2)-198 | (IIe) | X | (2t) |
| (2)-199 | (IIf) | X | (2u) |
| (2)-200 | (IIg) | — | (2w) |
| (2)-201 | (IIh) | X | (2x) |
| (2)-202 | (IIb) | — | (2bb) |
| (2)-203 | (IId) | (1ff) | (2r) |
| (2)-204 | (IIe) | (1m) | (2q) |
| (2)-205 | (IIf) | (1s) | (2q) |
| (2)-206 | (IIb) | (1rr) | (2t) |
| (2)-207 | (IIc) | — | (2s) |
| (2)-208 | (IId) | X | (2bbb) |
| (2)-209 | (IIe) | (1u) | (2jj) |
| (2)-210 | (IIf) | (1aa) | (2s) |
| (2)-211 | (IIg) | (1ff) | (2ww) |
| (2)-212 | (IIh) | (1m) | (2r) |
| (2)-213 | (IIf) | (1s) | (2q) |
| (2)-214 | (IId) | (1rr) | (2m) |
| (2)-215 | (IIe) | (1ss) | (2s) |
| (2)-216 | (IIf) | (1tt) | (2s) |
| (2)-217 | (IIa) | X | (2r) |
| (2)-218 | (IIb) | (1q) | (2p) |
| (2)-219 | (IIc) | (1rr) | (2t) |
| (2)-220 | (IId) | X | (2i) |
| (2)-221 | (IIa) | X | (2j) |
| (2)-222 | (IIb) | — | (2o) |
| (2)-223 | (IIc) | — | (2s) |
| (2)-224 | (IId) | X | (2r) |
| (2)-225 | (IIe) | X | (2t) |
| (2)-226 | (IIf) | (1ff) | (2u) |
| (2)-227 | (IIg) | (1m) | (2k) |
| (2)-228 | (IIh) | (1s) | (2q) |
| (2)-229 | (IIa) | X | (2q) |
| (2)-230 | (IIg) | (2j) | (2s) |
| (2)-231 | (IIh) | (2o) | (2t) |
| (2)-232 | (IIg) | (2p) | (2r) |
| (2)-233 | (IIf) | (1rr) | (2o) |
| (2)-234 | (IIa) | X | (2t) |
| (2)-235 | (IIb) | X | (2bbb) |
| (2)-236 | (IIc) | (2s) | (2t) |
| (2)-237 | (IId) | (2j) | (2s) |
| (2)-238 | (IIe) | (2o) | (2r) |
| (2)-239 | (IIf) | (2p) | (2n) |
| (2)-240 | (IIg) | (1ff) | (2t) |
| (2)-241 | (IIg) | (1m) | (2s) |
| (2)-242 | (IIh) | (1s) | (2l) |
| (2)-243 | (IIb) | (1rr) | (2r) |
| (2)-244 | (IId) | — | (2s) |
| (2)-245 | (IIe) | X | (2aaa) |
| (2)-246 | (IIf) | X | (2bbb) |
| (2)-247 | (IIg) | (2s) | (2x) |
| (2)-248 | (IIh) | (2j) | (2k) |
| (2)-249 | (IIe) | (2o) | (2q) |
| (2)-250 | (IIg) | (2p) | (2jj) |
| (2)-251 | (IIh) | (1aa) | (2t) |

|  | (II) | R¹ | Z |
|---|---|---|---|
| (2)-252 | (IIe) | (1ff) | (2t) |
| (2)-253 | (IId) | (1m) | (2r) |
| (2)-254 | (IIe) | (1s) | (2k) |
| (2)-255 | (IIf) | (1rr) | (2r) |
| (2)-256 | (IId) | (1ss) | (2t) |
| (2)-257 | (IIe) | (1u) | (2s) |
| (2)-258 | (IIf) | (1aa) | (2q) |
| (2)-259 | X | (1ff) | (2p) |
| (2)-260 | (IIb) | (1m) | (2s) |
| (2)-261 | (IIc) | (1s) | (2q) |
| (2)-262 | (IId) | (1rr) | (2t) |
| (2)-263 | (IIe) | (1ss) | (2t) |
| (2)-264 | (IIf) | (1tt) | (2m) |
| (2)-265 | (IIg) | (1a) | (2s) |
| (2)-266 | (IIh) | (1q) | (2s) |
| (2)-267 | (IIc) | X | (2j) |
| (2)-268 | (IId) | X | (2o) |
| (2)-269 | (IIe) | (2s) | (2p) |
| (2)-270 | (IIf) | (2j) | (2r) |
| (2)-271 | (IIe) | (2o) | (2k) |
| (2)-272 | (IIf) | (2p) | (2o) |
| (2)-273 | (IIg) | — | (2t) |
| (2)-274 | (IIh) | — | (2t) |
| (2)-275 | (IId) | X | (2bb) |
| (2)-276 | (IIe) | X | (2ii) |
| (2)-277 | (IIf) | (1u) | (2jj) |
| (2)-278 | (IIg) | (1aa) | (2q) |
| (2)-279 | (IIh) | (1ff) | (2q) |
| (2)-280 | (IIb) | (1m) | (2q) |
| (2)-281 | (IIe) | (1s) | (2t) |
| (2)-282 | (IIf) | (1rr) | (2t) |
| (2)-283 | (IIb) | (1ss) | (2r) |
| (2)-284 | (IIc) | (1tt) | (2p) |
| (2)-285 | (IId) | (1a) | (2t) |
| (2)-286 | (IIe) | (1q) | (2t) |
| (2)-287 | (IIf) | (2s) | (2p) |
| (2)-288 | (IIg) | (2j) | (2t) |
| (2)-289 | (IIh) | (2o) | (2t) |
| (2)-290 | (IIe) | X | (2bb) |
| (2)-291 | (IIc) | X | (2ii) |
| (2)-292 | (IId) | (1u) | (2jj) |
| (2)-293 | (IIe) | (1aa) | (2q) |
| (2)-294 | (IIf) | (1ff) | (2k) |
| (2)-295 | (IIg) | (1m) | (2n) |
| (2)-296 | (IIh) | (1s) | (2s) |
| (2)-297 | (IIa) | X | (2s) |
| (2)-298 | (IId) | (1ss) | (2r) |
| (2)-299 | (IIe) | (1tt) | (2n) |
| (2)-300 | (IIf) | (1a) | (2s) |
| (2)-301 | (IIh) | (1u) | (2mmm) |
| (2)-302 | (IIi) | (1aa) | (2nnn) |
| (2)-303 | (IIj) | (1ff) | (2ppp) |
| (2)-304 | (IIk) | (1m) | (2qqq) |
| (2)-305 | (IIl) | (1s) | (2cccc) |
| (2)-306 | (IIh) | (1rr) | (2dddd) |
| (2)-307 | (IIi) | (1ss) | (2xxx) |
| (2)-308 | (IIj) | (1tt) | (2yyy) |
| (2)-309 | (IIk) | (1a) | (2aaaa) |
| (2)-310 | (IIl) | (1q) | (2bbbb) |
| (2)-311 | (IIh) | (1u) | (2ppp) |
| (2)-312 | (IIi) | (1aa) | (2ppp) |
| (2)-313 | (IIj) | (1ff) | (2qqq) |
| (2)-314 | (IIk) | (1m) | (2cccc) |
| (2)-315 | (IIl) | (1s) | (2ppp) |
| (2)-316 | (IIh) | (1rr) | (2qqq) |
| (2)-317 | (IIi) | (1ss) | (2cccc) |
| (2)-318 | (IIj) | (1tt) | (2nnn) |
| (2)-319 | (IIk) | (1a) | (2ppp) |
| (2)-320 | (IIh) | (1q) | (2qqq) |
| (2)-321 | (IIi) | (1m) | (2cccc) |
| (2)-322 | (IIj) | (1s) | (2dddd) |
| (2)-323 | (IIk) | (1rr) | (2xxx) |
| (2)-324 | (IIh) | (1ss) | (2yyy) |
| (2)-325 | (IIi) | (1tt) | (2aaaa) |
| (2)-326 | (IIj) | (1a) | (2bbbb) |
| (2)-327 | (IIk) | (1q) | (2mmm) |
| (2)-328 | (IIh) | (1aa) | (2nnn) |
| (2)-329 | (IIi) | (1u) | (2ppp) |
| (2)-330 | (IIj) | (1aa) | (2qqq) |
| (2)-331 | (IIk) | (1ff) | (2cccc) |
| (2)-332 | (IIh) | (1m) | (2dddd) |
| (2)-333 | (IIi) | (1s) | (2xxx) |
| (2)-334 | (IIj) | (1rr) | (2yyy) |
| (2)-335 | (IIk) | (1ss) | (2aaaa) |
| (2)-336 | (IIh) | (1tt) | (2bbbb) |

In some embodiments, the compound of formulae (II) or (IIa)-(IIg) is one of the following compounds (or a pharmaceutically acceptable salt, prodrug, or N-oxide thereof, or a solvate or hydrate thereof): 2, 2A, 3, 4, 5, 6, 9, 11, 11A, 12 and 12A.

In other embodiments, the compound of formulae (II) or (IIa)-(IIg) is compound 2 (or a pharmaceutically acceptable salt, prodrug, or N-oxide thereof, or a solvate or hydrate thereof).

In other embodiments, the compound of formulae (II) or (IIa)-(IIg) is compound 2A (or a pharmaceutically acceptable salt, prodrug, or N-oxide thereof, or a solvate or hydrate thereof).

In other embodiments, the compound of formulae (II) or (IIa)-(IIg) is compound 3 (or a pharmaceutically acceptable salt, prodrug, or N-oxide thereof, or a solvate or hydrate thereof).

In other embodiments, the compound of formulae (II) or (IIa)-(IIg) is compound 4 (or a pharmaceutically acceptable salt, prodrug, or N-oxide thereof, or a solvate or hydrate thereof).

In other embodiments, the compound of formulae (II) or (IIa)-(IIg) is compound 5 (or a pharmaceutically acceptable salt, prodrug, or N-oxide thereof, or a solvate or hydrate thereof).

In other embodiments, the compound of formulae (II) or (IIa)-(IIg) is compound 6 (or a pharmaceutically acceptable salt, prodrug, or N-oxide thereof, or a solvate or hydrate thereof).

In other embodiments, the compound of formulae (II) or (IIa)-(IIg) is compound 9 (or a pharmaceutically acceptable salt, prodrug, or N-oxide thereof, or a solvate or hydrate thereof).

In other embodiments, the compound of formulae (II) or (IIa)-(IIg) is compound 11 (or a pharmaceutically acceptable salt, prodrug, or N-oxide thereof, or a solvate or hydrate thereof).

In other embodiments, the compound of formulae (II) or (IIa)-(IIg) is compound 11A (or a pharmaceutically acceptable salt, prodrug, or N-oxide thereof, or a solvate or hydrate thereof).

In other embodiments, the compound of formulae (II) or (IIa)-(IIg) is compound 12 (or a pharmaceutically acceptable salt, prodrug, or N-oxide thereof, or a solvate or hydrate thereof).

In other embodiments, the compound of formulae (II) or (IIa)-(IIg) is compound 12A (or a pharmaceutically acceptable salt, prodrug, or N-oxide thereof, or a solvate or hydrate thereof).

In another aspect, the present invention comprises pharmaceutical compositions comprising a compound according to any one of the preceding aspects of the invention or any embodiment thereof, together with a pharmaceutically acceptable excipient, diluent, or carrier.

In another aspect, the invention comprises the use of a compound described by any one of the preceding aspects of the invention or any embodiment thereof, for the preparation of a medicament for the treatment of medical diseases or conditions that benefit from the inhibition of cytokine signaling. Medical conditions contemplated in this aspect include all diseases and conditions described herein.

The compounds of formulae (I°), (I), (I'), (Ia)-(Im), (II) and (IIa)-(III) described above are useful as kinase inhibitors and/or inhibitors of cytokine signaling. Exemplary kinases inhibited by the presently disclosed compounds include, without limitation, ACVR1; ACVR1B (ALK-4); ACVR1C; ACVR2A; ACVR2B; ACVRL1; BMPR1A; BMPR1B; BMPR2; TGFBR1 (ALK-5), PI3K and MAP4K4 (HGK). Exemplary cytokines, the signaling of which is inhibited by the present compounds include, without limitation, TGF-β superfamily, including Activin, Nodal, TGF-β1, and GDF-8. In one aspect the present compounds are selective for one or more kinase and/or cytokine signaling pathway. For example, exemplary compounds inhibit TGF-β1 signaling, GDF-8 signaling, or both. In one aspect the present compounds inhibit GDF-8 signaling preferentially to TGF-β1 signaling, such that GDF8 signaling is inhibited at least about 1.5-fold more potently or from about 1.1-fold to about 25-fold more potently. In one embodiment certain compounds inhibit GDF8 signaling at least about 5-fold more potently, such as from about 8-fold to about 50-fold, or at least about 10-fold more potently, such as from about 15-fold to about 300-fold more potently.

In particular, the present compounds can be use to treat disorders, such as pulmonary hypertension, chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, atherosclerosis, peritoneal and sub-dermal adhesion, kidney fibrosis, lung fibrosis, including idiopathic pulmonary fibrosis, and liver fibrosis, hepatitis B, hepatitis C, alcohol-induced hepatitis, cancer, haemochromatosis, primary biliary cirrhosis, restenosis, retroperitoneal fibrosis, mesenteric fibrosis, endometriosis, keloids, cancer, abnormal bone function, inflammatory disorders, scarring and photoaging of the skin.

Particular proliferative diseases that can be treated with the present compounds include those selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, melanoma, psoriasis, prostate hyperplasia, a neoplasia, a neoplasia of epithelial character, leukemias and lymphomas, a mammary carcinoma or a leukemia.

The compounds described herein also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, $^{18}$F etc. Thus, the disclosed compounds may be enriched in one or more of these isotopes relative to the natural abundance of such isotope. As is known to those of skill in the art, such isotopically enriched compounds are useful for a variety of purposes. For example, substitution with heavier isotopes such as deuterium ($^2$H) may afford certain therapeutic advantages that result from greater metabolic stability. Substitution with positron emitting isotopes, such as 18F can be useful in Positron Emission Tomography (PET) studies. By way of example, deuterium ($^2$H) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

In another aspect, the invention comprises combination therapies for the treatment of cancer, including both pre-malignant and malignant neoplasms. In this aspect, the invention comprises a method of treating cancer comprising administering to a subject a compound disclosed herein in conjunction with a therapeutic treatment of cancer. In some embodiments of the invention, the compounds disclosed herein are used in combination of standard of care anti-proliferative treatments of cancer. The amount of a compound disclosed herein for use in the combination therapy is an amount sufficient to inhibit signaling by members of the TGF-β superfamily, such as Nodal and Activin, which promote the survival and/or differentiation of cancer stem cells and thereby enhance the efficacy of the therapeutic treatment. Treatment with the present compounds thus blocks the ability of cancer stem cells to recapitulate a tumor destroyed by treatment with standard of care. Efficacy of treatment can be determined by any art recognized method generally employed for the particular cancer being treated and includes, for example, retardation, inhibition, or regression of tumor growth.

Reference to "combination therapy" and treatment with a compound disclosed herein "in conjunction with" another therapeutic treatment means that the compound and other therapeutic treatment can be administered simultaneously or sequentially such that the resultant treatment is more efficacious than either treatment alone.

One embodiment of treating cancer in a subject comprises administering to a subject in need thereof an amount described above of a compound disclosed herein in combination with the administration of a therapeutically effective amount of one or more chemotherapeutic agents, wherein the one or more chemotherapeutic agents is selected from the group consisting of antimetabolites, alkylating agents, coordination compounds, platinum complexes, DNA cross-linking compounds, inhibitors of transcription enzymes, tyrosine kinase inhibitors, protein kinase inhibitors, topoisomerase inhibitors, DNA minor-groove binding compounds, vinca alkaloids, taxanes, antitumor antibiotics, hormones, aromatase inhibitors, enzymes, growth factor receptors antibodies, cytokines, cell surface markers antibodies, HDAC inhibitors, HSP 90 inhibitors, BCL-2 inhibitors, B-raf inhibitors, MEK inhibitors, mTOR inhibitors, proteasome inhibitors and monoclonal antibodies.

Among the BCL-2 inhibitors useful in the invention is ABT-199.

Another embodiment of methods for treating a subject comprises administering to the subject an amount (as described above) of a compound disclosed herein in combination with the administration of a therapeutically effective amount of one or more chemotherapeutic agents, the one or more chemotherapeutic agents being independently selected from the group consisting of mechlorothamine, cyclophosphamide, ifosfamide, melphalan, chlorambucil, ethyleneimines, methylmelamines, procarbazine, dacarbazine, temozolomide, busulfan, carmustine, lomustine, methotrexate, fluorouracil, capecitabine, cytarabine, gemcitabine, cytosine arabinoside, mecaptopurine, fludarabine, cladribine, thioguanine, azathioprine, vinblastine, vincristine, paclitaxel, docetaxel, colchicine, actinomycin D, daunorubicin, bleomycin, L-asparaginase, cisplatin, carboplatin, oxaliplatin, prednisone, dexamethasone, amino glutethimide, formestane, anastrozole, hydroxyprogesterone caproate, medroxyprogesterone, tamoxifen, amsacrine, mitoxantrone, topotecan, irinotecan, camptothecin, afatinib, axitinib, bosutinib, bortezomib, carfilzomib, cabozantinib, cediranib, crizotinib, dasatinib, dabrafenib, evorolimus, ibrutinib, LDK378, LGX818, MEK162, regorafenib, ruxolitinib, selumetinib, sorafenib, trametinib, vemurafenib, erlotinib, gefitinib, imatinib, lapatinib, lestaurtinib, nilotinib, palbociclib, pazopanib, pomatinib, semaxanib, sirolimus, sunitinib, temsirolimus, vatalanib, vandetanib, anti Her2 antibodies, interferon-α, interferon-γ, interleukin 2, GM CSF, anti CTLA 4 antibodies, rituximab, anti CD33 antibodies, MGCD0103, vorinostat, 17-AAG, thalidomide, lenalidomide, rapamycin, CCI-779, doxorubicine, gemcitabine, melphalan, NPI052, gemtuzumab, alemtuzumab, cetuximab, ibritumomab tiuxaetan, tositumomab, iodine-131 tositumomab, trastuzumab, ado-trastuzumab emtansine, obinutuzumab, bevacizumab, rituximab, and anti-TRAIL death receptor antibodies.

Among the CTLA 4 antibodies that can be used in the present invention is ipilimumab, marketed as YERVOY® by Bristol-Myers Squibb.

Other chemotherapeutic agents include checkpoint pathway inhibitors, e.g., PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed TGF-β signalling inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The following table displays exemplary cancers treatable in the combination therapies of the invention and the therapeutic drug and/or other treatment for use with the compounds disclosed herein:

| Cancer | Drug or Treatment |
| --- | --- |
| Glioma | lomustine, temozolide and/or radiation |
| hepatocellular carcinoma | sorafenib, regorafenib |
| myelodysplastic syndromes | decitabine or azacytidine |
| pancreatic cancer | Gemcitabine |
| ovarian cancer, such as epithelial ovarian carcinoma | carboplatin, cisplatin, doxorubicin, gemcitabine, paclitaxel |
| breast cancer | Trastuzumab |
| basal and squamous skin carcinomas | 5-fluorouracil, imiquimod, photodynamic therapy (e.g. with 5-aminolevulinic acid), |
| head and neck carcinoma | bleomycin, cisplatin, cetuximab, docetaxel, fluorouracil, methotrexate |
| triple negative breast cancer | Paclitaxel |
| Prostate | abiraterone, enzalutamide |

In another aspect, the invention comprises a method of determining and measuring the ability of the compounds disclosed herein to inhibit signaling by members of the TGF-β superfamily, such as Nodal and Activin, in order to identify cancers and, more specifically, tumors. In one embodiment, neoplasms susceptible to such combination therapy can be identified by testing for Nodal and Activin signaling activity using techniques known to those skilled in the art, including, for example, assays described in Lonardo, E. et al. (2011) Cell Stem Cell 9, 433-446 (which is hereby incorporated by reference in its entirety). Optionally in this embodiment, where the tested compound is found to inhibit signalling of a member of the TGF-β superfamily, such as Nodal and Activin, in the tested neoplasm, the compound is subsequently used in a combination therapy for treatment of the neoplasm, as described herein.

Definitions

Terms used herein may be preceded and/or followed by a single dash, "—", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, arylalkyl, arylalkyl-, and alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, such as 1 to 6 carbons (i.e., inclusive of 1 and 6), 1 to 6 carbons, 1 to 3 carbons, or 1, 2, 3, 4, 5 or 6. The term "$C_m$-$C_n$alkyl" means an alkyl group having from m to n carbon atoms (i.e., inclusive of m and n). The term "$C_m$-$C_n$alkyl" means an alkyl group having from m to n carbon atoms. For example, "$C_1$-$C_6$alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$alkyl"), the group is simply a single covalent bond if it is a divalent radical or is a hydrogen atom if it is a monovalent radical. For example, the moiety "—($C_0$-$C_6$alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 6 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" or "Ar" represents an aromatic ring system having a single ring (e.g., phenyl) which is optionally fused to other aromatic hydrocarbon rings or non-aromatic hydrocarbon rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" or "Het" refers to an aromatic ring system containing at least one heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic ring, for example, cycloalkyl or heterocycloalkyl rings, wherein the cycloalkyl (Cak) and heterocycloalkyl (Hca) rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" or "Hca" refers to a non-aromatic ring or ring system containing at least one heteroatom that is preferably selected from nitrogen, oxygen and sulfur, wherein said heteroatom is in a non-aromatic ring. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" or "Cak" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused and/or bridged polycycles.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo (e.g., fluoro, chloro, bromo, and iodo), cyano, —($C_1$-$C_4$ fluoroalkyl), —O—($C_1$-$C_4$ fluoroalkyl), —C(O)—($C_0$-$C_4$alkyl), —C(O)O—($C_0$-$C_4$alkyl), —C(O)N($C_0$-$C_4$alkyl)($C_0$-$C_4$alkyl), —S(O)$_2$O—($C_0$-$C_4$alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below, unless specified otherwise.

Substituent groups for substituting for hydrogens on saturated carbon atoms in the specified group or radical are, unless otherwise specified, —$R^{60}$, halo, —$O^-M^+$, =O, —$OR^{70}$, —$SR^{70}$, —$S^-M^+$, =S, —$NR^{80}R^{80}$, =$NR^{70}$, =N—$OR^{70}$, trihalomethyl, —$CF_3$, —CN, —OCN, —SCN, —NO, —NO$_2$, =N$_2$, —N$_3$, —SO$_2R^{70}$, —SO$_2O^-M^+$, —SO$_2OR^{70}$, —OSO$_2R^{70}$, —OSO$_2O^-M^+$, —OSO$_2OR^{70}$, —P(O)(O$^-$)$_2$(M$^+$)$_2$, —P(O)(OR$^{70}$)O$^-M^+$, —P(O)(OR$^{70}$)$_2$, —C(O)R$^{70}$, —C(S)R$^{70}$, —C(NR$^{70}$)R$^{70}$, —C(O)O$^-$ M$^+$, —C(O)OR$^{70}$, —C(S)OR$^{70}$, —C(O)NR$^{80}R^{80}$, —C(NR$^{70}$)NR$^{80}R^{80}$, —OC(O)R$^{70}$, —OC(S)R$^{70}$, —OC(O)O$^-$ M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-M^+$, —NR$^{70}$CO$_2R^{70}$, —NR$^{70}$C(S)OR$^{70}$, —NR$^{70}$C(O)NR$^{80}R^{80}$, —NR$^{70}$C(NR$^{70}$)R$^{70}$ and —NR$^{70}$C(NR$^{70}$)NR$^{80}R^{80}$. Each R$^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{71}$, —SR$^{71}$, —S$^-$M$^+$, =S, —NR$^{81}R^{81}$, =NR$^{71}$, =N—OR$^{71}$, trihalomethyl, —CF$_3$, —CN, —OCN, —SCN, —NO, —NO$_2$, =N$_2$, —N$_3$, —SO$_2R^{71}$, —SO$_2O^-M^+$, —SO$_2OR^{71}$, —OSO$_2R^{71}$, —OSO$_2O^-M^+$, —OSO$_2OR^{71}$, —P(O)(O$^-$)$_2$(M$^+$)$_2$, —P(O)(OR$^{71}$)O$^-M^+$, —P(O)(OR$^{71}$)$_2$, —C(O)R$^{71}$, —C(S)R$^{71}$, —C(NR$^{71}$)R$^{71}$, —C(O)O$^-$M$^+$, —C(O)OR$^{71}$, —C(S)OR$^{71}$, —C(O)NR$^{81}R^{81}$, —C(NR$^{71}$)NR$^{81}R^{81}$, —OC(O)R$^{71}$, —OC(S)R$^{71}$, —OC(O)O$^-$M$^+$, —OC(O)OR$^{71}$, —OC(S)OR$^{71}$, —NR$^{71}$C(O)R$^{71}$, —NR$^{71}$C(S)R$^{71}$, —NR$^{71}$CO$_2^-M^+$, —NR$^{71}$CO$_2R^{71}$, —NR$^{71}$C(S)R$^{71}$, —NR$^{71}$C(O)NR$^{81}R^{81}$, —NR$^{71}$C(NR$^{71}$)R$^{71}$ and —NR$^{71}$C(NR$^{71}$)NR$^{81}R^{81}$. Each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$alkyl substitution; and each M$^+$ is a counter ion with a net single positive charge. Each R$^{71}$ is independently hydrogen or R$^{61}$, in which R$^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{72}$, —SR$^{72}$, —S$^-$ M$^+$, =S, —NR$^{82}R^{82}$, =NR$^{72}$, =N—OR$^{72}$, trihalomethyl, —CF$_3$, —CN, —OCN, —SCN, —NO, —NO$_2$, =N$_2$, —N$_3$, —SO$_2R^{71}$, —SO$_2O^-M^+$, —SO$_2OR^{72}$, —OSO$_2R^{72}$, —OSO$_2O^-M^+$, —OSO$_2OR^{72}$, —P(O)(O$^-$)$_2$(M$^+$)$_2$, —P(O)(OR$^{72}$)O$^-M^+$, —P(O)(OR$^{72}$)$_2$, —C(O)R$^{72}$, —C(S)R$^{72}$, —C(NR$^{72}$)R$^{72}$, —C(O)O$^-$M$^+$, —C(O)OR$^{72}$, —C(S)OR$^{72}$, —C(O)NR$^{82}R^{82}$, —C(NR$^{72}$)NR$^{82}R^{82}$, —OC(O)R$^{72}$, —OC(S)R$^{72}$, —OC(O)O$^-M^+$, —OC(O)OR$^{72}$, —OC(S)OR$^{72}$, —NR$^{72}$C(O)R$^{72}$, —NR$^{72}$C(S)R$^{72}$, —NR$^{72}$CO$_2^-M^+$, —NR$^{72}$CO$_2R^{72}$, —NR$^{72}$C(S)OR$^{72}$, —NR$^{72}$C(O)NR$^{82}R^{82}$, —NR$^{72}$C(NR$^{72}$)R$^{72}$ and —NR$^{72}$C(NR$^{72}$)NR$^{82}R^{82}$; and each R$^{81}$ is independently R$^{71}$ or alternatively, two R$^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution. Each R$^{72}$ is independently hydrogen, ($C_1$-$C_6$alkyl) or ($C_1$-$C_6$fluoroalkyl); each R$^{82}$ is independently R$^{72}$ or alternatively, two R$^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or $C_1$-$C_3$alkyl substitution. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}R^{80}$, trihalomethyl, —CF$_3$, —CN, —OCN, —SCN, —NO, —NO$_2$, —N$_3$, —SO$_2R^{70}$, —SO$_3^-M^+$, —SO$_3R^{70}$, —OSO$_2R^{70}$, —OSO$_3^-M^+$, —OSO$_3R^{70}$, —PO$_3^{-2}$(M$^+$)$_2$, —P(O)(OR$^{70}$)O$^-M^+$, —P(O)(OR$^{70}$)$_2$, —C(O)R$^{70}$, —C(S)R$^{70}$, —C(NR$^{70}$)R$^{70}$, —CO$_2^-M^+$, —CO$_2R^{70}$, —C(S)OR$^{70}$, —C(O)NR$^{80}R^{80}$, —C(NR$^{70}$)NR$^{80}R^{80}$, —OC(O)R$^{70}$, —OC(S)R$^{70}$, —OCO$_2^-$M$^+$, —OCO$_2R^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

Substituent groups for hydrogens on nitrogen atoms in "substituted" heteroalkyl and heterocycloalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)—R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

In certain embodiments, substituent groups on "substituted" alkyl, cycloalkyl, heterocycloalkyl, aryl and heteroaryl groups are -halo, —OH, —O—(C$_1$-C$_4$alkyl), —O—(C$_1$-C$_4$haloalkyl), —N(C$_0$-C$_4$alkyl)(C$_0$-C$_4$alkyl), —SH, —S(O)$_{0-2}$—(C$_1$-C$_4$alkyl), —(C$_1$-C$_4$alkyl), —(C$_1$-C$_4$haloalkyl), —C(O)—(C$_0$-C$_4$alkyl), —C(O)N(C$_0$-C$_4$alkyl)(C$_0$-C$_4$alkyl), —N(C$_0$-C$_4$alkyl)C(O)(C$_0$-C$_4$alkyl)(C$_0$-C$_4$alkyl), —C(O)O—(C$_0$-C$_4$alkyl), —OC(O)—(C$_0$-C$_4$alkyl), S(O)$_2$—O(C$_0$-C$_4$alkyl), and —NO$_2$, in which no alkyl is further substituted.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl) tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxoglutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}$F. Similarly, compounds may be enriched in the heavy isotopes of hydrogen: deuterium and tritium; and similarly can be enriched in a radioactive isotope of carbon, such as $^{13}$C. Such isotopic variant compounds undergo different metabolic pathways and can be useful, for example, in studying one or more kinase and/or cytokine signaling pathway and its role in disease.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" an enzyme with a compound includes the administration of a compound described herein to an individual or patient, such as a human, as well as, for example, introducing a compound into a sample containing a cellular or purified preparation containing the enzyme.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed or otherwise susceptible to the disease, condition or disorder but does not yet experience or display the pathology or symptomotology of the disease;

(2) inhibiting the disease; for example, inhibiting a disease, condition or disorder in an individual who is experiencing or displaying the pathology or symptomotology of the disease, condition or disorder; or (3) ameliorating the disease (including a symptom thereof); for example, ameliorating a disease, condition or disorder in an individual who is experiencing or displaying the pathology or symptomotology of the disease, condition or disorder (i.e., reversing the pathology and/or symptomotology) such as decreasing the severity of disease.

As used here, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomotology of the disease, condition or disorder (i.e., reversing or improving the pathology and/or symptomotology) such as decreasing the severity of disease or symptom thereof; or (ii) eliciting the referenced biological effect (e.g., modulation or inhibition of GDF-8 or TGF-β1).

Manifestation of amelioration of a disease condition by inhibiting GDF-8 or TGF-β1 may require the concomitant or sequential administration of additional therapeutic agents, such as antineoplastic agents in the case of cancer, or antiretroviral agents in the case of viral diseases. For example, administration of GDF-8 and TGF-β1 inhibitors for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical Formulations and Dosage Forms

The compounds of structural formulae (I)-(II) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(II).

In the pharmaceutical compositions disclosed herein, one or more compounds of structural formulae (I)-(II) may be present in association with one or more pharmaceutically acceptable carriers, diluents or excipients, and, if desired, other active ingredients. The pharmaceutical compositions containing compounds of structural formulae (I)-(II) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositions comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(II) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(II) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

EXAMPLES

General Synthetic Methodologies

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of any one of structural formula (V), (I) or (II) can be prepared according to the Schemes herein, or analogous synthetic schemes.

One of skill in the art can adapt the reaction sequences of the Schemes herein to fit the desired target molecule. Of course, in certain situations one of skill in the art will use different reagents to affect one or more of the individual steps or to use protected versions of certain of the substituents. Additionally, one skilled in the art would recognize that a compound or pharmaceutically acceptable salt of structural formulae (I), (II), or (I°) can be synthesized using different routes altogether.

Compounds suitable for use in the presently disclosed pharmaceutical compositions include compounds of disclosed, above. These compounds can be made according to the general schemes described above, for example using a procedure similar to that described below in the Examples.

The following examples are intended to further illustrate certain embodiments and are not intended to limit the scope of the presently disclosed compounds.

Methods of Treating Disease

The compounds of the present disclosure are useful to prevent, diagnose, and treat various medical disorders in humans or animals. The compounds are used to inhibit or reduce one or more activities associated with the GDF protein, relative to a GDF protein not bound by the same compounds. Optionally, the compounds inhibit or reduce one or more of the activities of mature GDF-8 (regardless of whether in monomeric form, active dimeric form, or complexed in a GDF-8 latent complex) relative to a mature GDF-8 protein that is not bound by the same compounds. In an embodiment, the activity of the mature GDF-8 protein, when bound by one or more of the presently disclosed compounds, is inhibited at least 50%, optionally at least 60, 62, 64, 66, 68, 70, 72, 72, 76, 78, 80, 82, 84, 86, or 88%, optionally at least 90, 91, 92, 93, or 94%, and optionally at least 95% to 100% relative to a mature GDF-8 protein that is not bound by one or more of the presently disclosed compounds.

The medical disorder being diagnosed, treated, or prevented by the presently disclosed compounds is optionally a muscle and neuromuscular disorder; an adipose tissue disorder such as obesity; type 2 diabetes, impaired glucose tolerance, metabolic syndromes (e.g., syndrome X), insulin resistance induced by trauma such as burns; or bone degenerative disease such as osteoporosis. The medical condition is optionally a muscle or neuromuscular disorder, such as muscular dystrophy, muscle atrophy, congestive obstructive pulmonary disease, muscle wasting syndrome, sarcopenia, or cachexia and disorders associated with a loss of bone, which include osteoporosis, especially in the elderly and/or postmenopausal women, glucocorticoid-induced osteoporosis, osteopenia, and osteoporosis-related fractures. Other target metabolic bone diseases and disorders amendable to treatment with GDF-8 inhibitors of the disclosure include low bone mass due to chronic glucocorticoid therapy, premature gonadal failure, androgen suppression, vitamin D deficiency, secondary hyperparathyroidism, nutritional deficiencies, and anorexia nervosa. The antibodies are optionally used to prevent, diagnose, or treat such medical disorders in mammals, optionally in humans.

The compounds or compositions of the present disclosure are administered in therapeutically effective amounts. As used herein, an "effective amount" of the antibody is a dosage which is sufficient to reduce the activity of GDF proteins to achieve a desired biological outcome (e.g., increasing muscle mass or strength). Generally, a therapeutically effective amount may vary with the subject's age, condition, and sex, as well as the severity of the medical condition in the subject. The dosage may be determined by a physician and adjusted, as necessary, to suit observed effects of the treatment. Generally, the compositions are administered so that compounds are given at a dose between 1 μg/kg and 20 mg/kg. Optionally, the compounds are given as a bolus dose, to maximize the circulating levels of compounds for the greatest length of time after the dose. Continuous infusion may also be used after the bolus dose.

The methods of treating, diagnosing, or preventing the above medical conditions with the presently disclosed compounds can also be used on other proteins in the TGF-β superfamily. Many of these proteins, e.g., BMP-11, are related in structure to GDF-8. Accordingly, in another embodiment, the disclosure comprises methods of treating the aforementioned disorders by administering to a subject a compound capable of inhibiting BMP-11 or activin, either alone or in combination with other TGF-β inhibitors, such as a neutralizing antibody against GDF-8.

Accordingly, in one aspect, the disclosure. In provides methods for inhibiting GDF-8 in a cell comprising contacting the cell with an effective amount of a compound or pharmaceutically acceptable salt of formula (I), (II), or (I°) or any embodiment thereof, or a pharmaceutical composition comprising the same. In another aspect, the disclosure comprises methods for treating a patient suffering from a disease or disorder, wherein the patient would therapeutically benefit from an increase in mass or strength of muscle tissue, comprising administering to a patient a therapeutically effective amount of a compound or pharmaceutically acceptable salt of formula (I), (II), or (I°) or any embodiment thereof, or a pharmaceutical composition comprising the same. The disease or disorder can be a muscular disorder, adipose tissue disorder, neuromuscular disorders, metabolic disorder, diabetes, or bone degenerative disorder. In certain embodiments, the disease or disorder is a muscular disorder, such as, but not limited to, muscular dystrophy, muscle atrophy, congestive obstructive pulmonary disease, muscle wasting syndrome, sarcopenia, or cachexia. In certain other embodiments, the disease or disorder is muscular dystrophy. In other embodiments, the disease or disorder is obesity, type 2 diabetes, impaired glucose tolerance, syndrome X, insulin resistance induced by trauma, or osteoporosis. In particular embodiments, the disease or disorder is osteoporosis.

In yet other embodiments, the disease or disorder is low bone mass due to chronic glucocorticoid therapy, premature gonadal failure, androgen suppression, vitamin D deficiency, secondary hyperparathyroidism, nutritional deficiencies, and anorexia nervosa.

In another aspect, the disclosure comprises methods for increasing muscle mass in a mammal comprising administering a therapeutically effective amount of a compound or pharmaceutically acceptable salt of formula (I), (II), or (I°) or any embodiment thereof, or a pharmaceutical composition comprising the same. In another aspect, the disclosure comprises methods for increasing muscle strength in a mammal comprising administering a therapeutically effective amount of a compound or pharmaceutically acceptable salt of formula (I), (II), or (I°) or any embodiment thereof, or a pharmaceutical composition comprising the same. In another aspect, the disclosure comprises methods for increasing trabecular bone density in a patient in need thereof, comprising administering a therapeutically effective amount of a compound or pharmaceutically acceptable salt of formula (I), (II), or (I°) or any embodiment thereof, or a pharmaceutical composition comprising the same. In any of the preceding methods and embodiments, thereof, the subject can be a mammal. As used herein, the terms "individual" or "patient" or "subject" are used interchangeably, and refers to any animal, including mammals, preferably mice, rats, other rodents, rabbits, dogs, cats, swine, cattle, sheep, horses, or primates, and most preferably humans.

The following examples are intended to further illustrate certain embodiments and are not intended to limit the scope of the presently disclosed compounds.

EXAMPLES

Example 1: Synthesis and Characterization

Scheme 1: General scheme for the preparation of 3-heteroaryl-2,2'-bipyridines from 2-pyridylzinc bromide

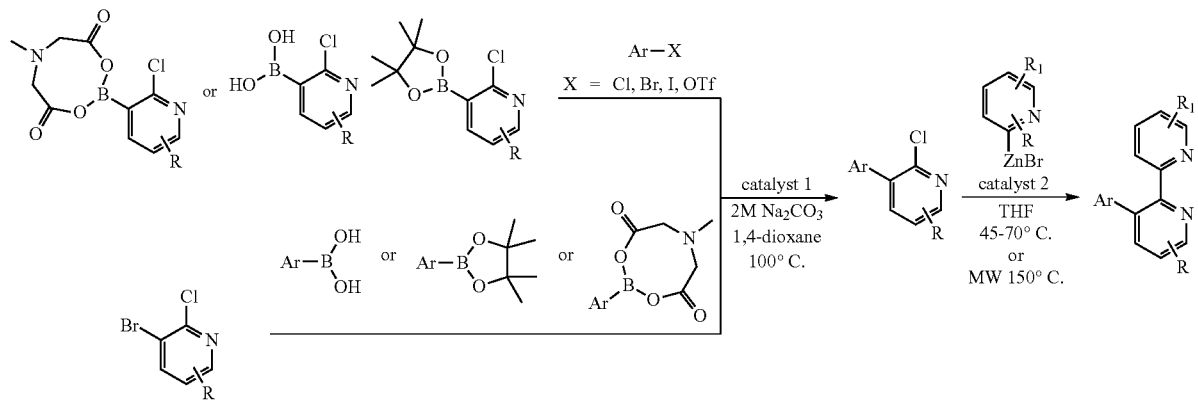

Catalyst 1:

Pd(PPh$_3$)$_4$ or Pd$_2$(dba)$_3$/2-dicyclohexylphosphino-2',6'-dimethoxybiphenyl (SPhos) or Pd(OAc)$_2$/2-dicyclohexylphosphino-2',6'-dimethoxybiphenyl (SPhos) or Pd$_2$(dba)$_3$/2-dicyclohexylphosphino-2',6'-dimethoxybiphenyl (Xphos), Pd(OAc)$_2$/2-dicyclohexylphosphino-2',6'-dimethoxybiphenyl (Xphos) or Chloro(2-dicyclohexylphosphino-2',6'-dimethoxy-1,1'-biphenyl)[2-(2'-amino-1,1'-biphenyl)]palladium(II)-(SPhos-Pd-G2) or Chloro(2-dicyclohexylphosphino-2',4'-6'-triisopropyl-1,1'-biphenyl)[2-2'-amino-1,1'-biphenyl)]palladium(II)-(XPhos-Pd-G2) or Pd$_2$(dba)$_3$/sodium 2'-dicyclohexylphosphino-2,6-dimethoxy-1,1'-biphenyl-3-sulfonate hydrate or Pd(OAc)$_2$/sodium 2'-dicyclohexylphosphino-2,6-dimethoxy-1,1'-biphenyl-3-sulfonate hydrate Catalyst 2:

Pd(PPh$_3$)$_4$ or Pd$_2$(dba)$_3$/2-dicyclohexylphosphino-2',6'-dimethoxybiphenyl (SPhos) or Pd(OAc)$_2$/2-dicyclohexylphosphino-2',6'-dimethoxybiphenyl (SPhos) or Pd$_2$(dba)$_3$/2-dicyclohexylphosphino-2',6'-dimethoxybiphenyl (Xphos), Pd(OAc)$_2$/2-dicyclohexylphosphino-2',6'-dimethoxybiphenyl (Xphos) or Chloro(2-dicyclohexylphosphino-2',6'-dimethoxy-1,1'-biphenyl)[2-(2'-amino-1,1'-biphenyl)]palladium(II)-(SPhos-Pd-G2) or Chloro(2-dicyclohexylphosphino-2',4'-6'-triisopropyl-1,1'-biphenyl)[2-2'-amino-1,1'-biphenyl)]palladium(II)-(XPhos-Pd-G2)

Scheme 2: General scheme for the preparation of 3-heteroaryl-2,2'-bipyridines from 2-pyridylboronic species

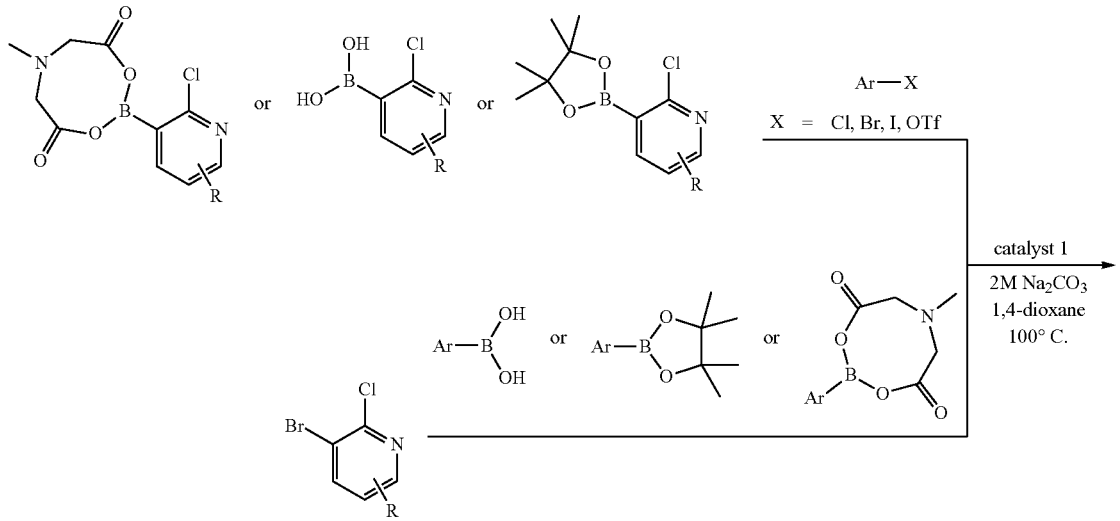

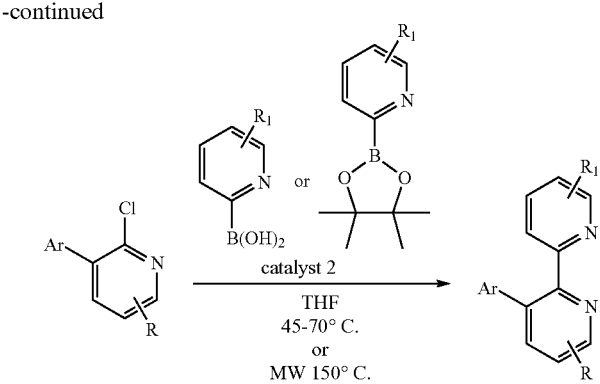

Scheme 3: Prophetic scheme for the preparation of 3-heteroaryl-2,2'-bipyridines

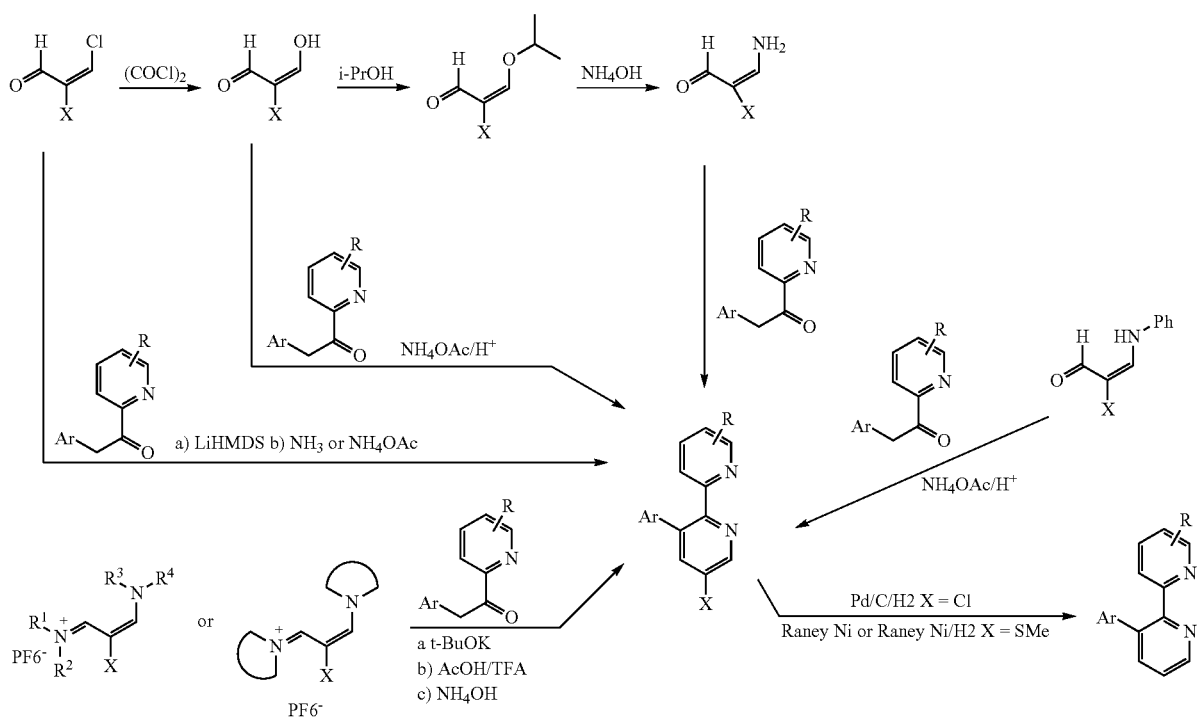

LC/MS: rt (Method A or Method B), rt=Peak Retention Time

Method A: Column: Luna 5 μm C8 (100×4.6 mm), Flow rate 1.0 mL/min, Mobile phase: A: H₂O 0.05% TFA, B: CH₃CN 0.05% TFA Method B: Column: Gemini 5 μm C18 (100×4.6 mm), Flow rate 1.5 mL/min, Mobile phase: A: H₂O 0.05% HCOOH, B: CH₃CN 0.05% HCOOH Compound 1: 4-(6'-Methyl-[2,2'-bipyridin]-3-yl)quinolone

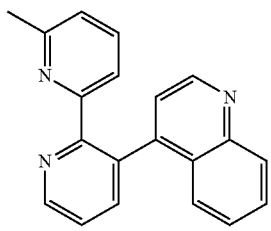 [SMILES: Cc1cccc(-c2ncccc2-c2ccnc3ccccc23)n1]

4-(2-Chloropyridin-3-yl)quinolone (200 mg, 0.83 mmol), Pd₂(dba)₃ (30 mg, 0.03 mmol) and 2-dicyclohexylphosphino-2',4',6'-triisopropylbiphenyl (XPHOS, 62 mg, 0.13 mmol) were transferred to a microwave vial (20 mL) containing a stir bar under argon atmosphere. Subsequently the vial was sealed and air was evacuated by vacuum. 6-Methyl-2-pyridylzinc bromide (0.5 M in THF, 4.0 mL, 2.0 mmol) was added to above reactants and degassed under vacuum followed by introducing argon via balloon. After three degas cycles, the reaction mixture was heated in a microwave (150° C.) for 40 min. The reaction mixture was diluted with saturated aqueous solution of Rochelle salt (5 mL) and concentrated to remove volatiles under reduced pressure. The crude concentrate was diluted with EtOAc (30 mL) and separated the organic layer. Aqueous layer was further extracted with EtOAc (30 mL). Combined organic layers were washed with aq. NaCl (10 mL), stirred over MgSO₄, filtered through a pad of Fluorosil®/Celite®, concentrated and purified by revere phase preparative HPLC. Product fractions were concentrated, diluted with water and neutralized with aq. NaHCO₃. The resultant solid was collected by filtration and dried to provide 4-(6'-methyl-[2,2'-bipyridin]-3-yl)quinolone (78 mg, 31%) as a white solid. ¹H NMR (300

MHz, DMSO-$d_6$) δ 8.84 (dd, J=4.7, 1.7 Hz, 1H), 8.81 (d, J=4.3 Hz, 1H), 7.99 (dt, J=8.4, 0.9 Hz, 1H), 7.89 (dd, J=7.7, 1.7 Hz, 1H), 7.78 (d, J=8.0 Hz, 1H), 7.70-7.52 (m, 3H), 7.34 (dd, J=4.4, 0.9 Hz, 2H), 7.26 (d, J=4.4 Hz, 1H), 6.90 (d, J=7.6 Hz, 1H), 1.59 (s, 3H).

Compound 3: 6-(6'-Methyl-[2,2'-bipyridin]-3-yl)imidazo[1,2-a]pyridine-3-carbonitrile

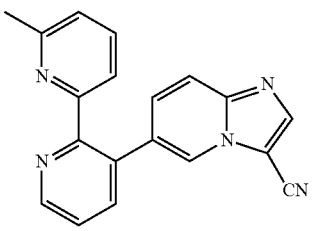 [SMILES: Cc1cccc(-c2ncccc2-c2ccc3ncc(C#N)n3c2)n1]

6-(2-Chloropyridin-3-yl)imidazo[1,2-a]pyridine-3-carbonitrile (175 mg, 0.69 mmol), chloro(2-dicyclohexylphosphino-2',6'-dimethoxy-1,1'-biphenyl)[2-(2'-amino-1,1'-biphenyl)]palladium(II)-(SPhos-Pd-G2, 35 mg, 0.05 mmol), dry THF (10 mL) and stir bar were transferred to a screw cap vial and sealed with a peaceable teflon cap. The stirring contents in the vial were degassed by application of vacuum and argon introduction in three degas cycles. Subsequently, degassed heterogeneous slurry was treated with 6-methyl-2-pyridylzinc bromide (0.5 M in THF, 2.77 mL, 1.38 mmol) under argon over a period of 3 min. The brown clear homogeneous reaction mixture was degassed again and heated to stir at 70° C. for 24 h. Multiple peaks were noticed along with 90% consumption of 6-(2-chloropyridin-3-yl)imidazo[1,2-a]pyridine-3-carbonitrile upon analyzing cooled reaction mixture to room temperature by LC/MS. At this stage, brown homogeneous reaction mixture was concentrated under reduced pressure and quenched with saturated aq. $Na_2CO_3$ solution (10 mL). The heterogeneous slurry was diluted with $CH_2Cl_2$ (50 mL), stirred and separated organic layer from semi-separable heterogenous mixture. Remaining aqueous layer was extracted with $CH_2Cl_2$ (2×50 mL). Combined organic layers were stirred over $MgSO_4$/Celite®, filtered and concentrated. The resultant crude was purified by Combiflash® on a Redifsep® 24G silica gel column and eluted with 100% $CH_2Cl_2$-1% 7N $NH_3$ MeOH/$CH_2Cl_2$. Fractions containing product and MH+ 185 impurity (MH+ 185) were concentrated under reduced pressure. The resulting pale yellow solid (100 mg) was stirred in EtOAc (4 mL), filtered and suction dried to provide 6-(6'-methyl-[2,2'-bipyridin]-3-yl)imidazo[1,2-a]pyridine-3-carbonitrile (68 mg, 31%) as off-white solid. $^1$H NMR (300 MHz, DMSO-$d_6$) δ 8.74 (dd, J=4.7, 1.6 Hz, 1H), 8.55 (dd, J=1.6, 1.0 Hz, 1H), 8.44 (d, J=0.4 Hz, 1H), 8.05 (dd, J=7.8, 1.6 Hz, 1H), 7.77-7.63 (m, 3H), 7.59 (dd, J=7.8, 4.7 Hz, 1H), 7.21 (dd, J=9.3, 1.7 Hz, 1H), 7.15 (d, J=7.5 Hz, 1H), 2.08 (s, 3H). LCMS: rt 3.80 min (A), purity 96%, MS (m/e) 312 (MH+).

Compound 4: 6-(6'-Methyl-[2,2'-bipyridin]-3-yl)-[1,2,4]triazolo[1,5-a]pyridine

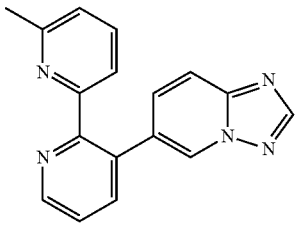 [SMILES: Cc1cccc(-c2ncccc2-c2ccc3ncnn3c2)n1]

A two necked round bottom flask containing a stir bar was fitted with reflux condenser to one of the necks and rubber septa to other neck. A three way stopcock was attached to reflux condenser and remaining two inlets were connected to argon balloon and vacuum pump hose. 6-(2-Chloropyridin-3-yl)-[1,2,4]triazolo[1,5-a]pyridine (1.0 g, 4.34 mmol), and Pd(PPh$_3$)$_4$ (0.15 g, 0.13 mmol) were transferred into reaction flask, introduced dry THF (20 mL) under vacuum and degassed by vacuum application followed by introduction of argon in three cycles. Subsequently, degassed heterogenous slurry was treated with 6-methyl-2-pyridylzinc bromide (0.5 M in THF, 17 mL, 8.5 mmol) under argon over a period of 3 min. The resulting dark heterogeneous suspension was degassed again and stirred at 70° C. overnight. Multiple peaks were noticed with 77% consumption of 6-(2-chloropyridin-3-yl)-[1,2,4]triazolo[1,5-a]pyridine upon analyzing cooled reaction mixture to room temperature by LC/MS. At this stage, brown reaction mixture was concentrated under reduced pressure and quenched with saturated aq. $Na_2CO_3$ (35 mL)/$CH_2Cl_2$ (130 mL) and stirred for 20 min. Organic layer from heterogeneous slurry was separated and extracted aqueous layer with $CH_2Cl_2$ (2×75 mL). Combined organic layers were stirred over $MgSO_4$/Celite®, filtered and concentrated. The resultant crude mixture was adsorbed on silica gel and purified by Combiflash® on a RediSep® 40G silica gel column and eluted with 100% $CH_2Cl_2$-2% 7N $NH_3$ MeOH/$CH_2Cl_2$. Product fractions containing MH+ 185 impurity were concentrated under reduced pressure. Thus obtained off-white solid (370 mg) was stirred in EtOAc (25 mL) for 5 min at 70° C., filtered hot mixture and suction dried to provide 6-(6'-methyl-[2,2'-bipyridin]-3-yl)-[1,2,4]triazolo[1,5-a]pyridine (315 mg, 25%). $^1$H NMR (300 MHz, DMSO-$d_6$) δ 8.90 (dd, J=1.7, 0.9 Hz, 1H), 8.74 (dd, J=4.7, 1.6 Hz, 1H), 8.47 (s, 1H), 8.01 (dd, J=7.8, 1.7 Hz, 1H), 7.79-7.69 (m, 2H), 7.66 (dd, J=9.2, 0.8 Hz, 1H), 7.58 (dd, J=7.8, 4.8 Hz, 1H), 7.26 (dd, J=9.2, 1.8 Hz, 1H), 7.13 (dd, J=7.2, 1.4 Hz, 1H), 2.02 (s, 3H). LCMS: rt 3.06 min (A), purity 97%, MS (m/e) 288 (MH+).

Compound 5: 7-(6'-Methyl-[2,2'-bipyridin]-3-yl)-[1,2,4]triazolo[1,5-a]pyridine

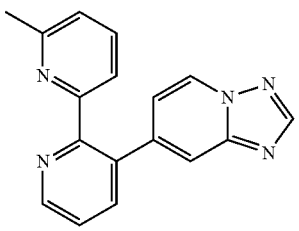

7-(6'-Methyl-[2,2'-bipyridin]-3-yl)-[1,2,4]triazolo[1,5-a]pyridine was prepared and isolated (229 mg, 18%) in an analogous manner to the preparation of 6-(6'-methyl-[2,2'-bipyridin]-3-yl)-[1,2,4]triazolo[1,5-a]pyridine by the reaction of 7-(2-chloropyridin-3-yl)-[1,2,4]triazolo[1,5-a]pyridine (1.0 g, 4.34 mmol) and 6-methyl-2-pyridylzinc bromide (0.5 M in THF, 17 mL, 8.5 mmol) in the presence of Pd(PPh$_3$)$_4$ (0.15 g, 0.13 mmol). White solid. $^1$H NMR (300 MHz, DMSO-d$_6$) δ 8.77 (dd, J=7.1, 0.8 Hz, 1H), 8.74 (dd, J=4.8, 1.6 Hz, 1H), 8.46 (s, 1H), 8.00 (dd, J=7.8, 1.6 Hz, 1H), 7.78-7.66 (m, 3H), 7.59 (dd, J=7.8, 4.7 Hz, 1H), 7.14 (dd, J=7.3, 1.3 Hz, 1H), 6.78 (dd, J=7.1, 1.9 Hz, 1H), 2.01 (s, 3H). LCMS: rt 3.08 min (A), purity 99%, MS (m/e) 288 (MH$^+$).

Compound 6: 6-(6'-Methyl-[2,2'-bipyridin]-3-yl)imidazo[1,2-a]pyridine-3-carboxamide

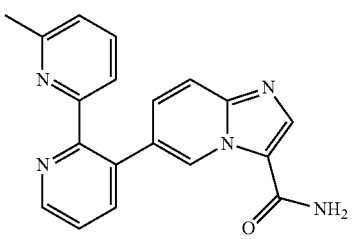 [SMILES: Cc1cccc(-c2ncccc2-c2ccc3ncc(C(N)=O)n3c2)n1]

Conc. H$_2$SO$_4$ (0.2 mL) was added to stirring TFA (0.8 mL) in a microwave vial (20 mL) for 3 min at room temperature and stirred pale brown homogeneous acidic mixture for additional period of 5 min. Solid 6-(6'-methyl-[2,2'-bipyridin]-3-yl)imidazo[1,2-a]pyridine-3-carbonitrile (125 mg, 0.40 mmol) was added in portions to above acidic solution at room temperature for 5 min and stirred heterogeneous mixture for 10 min. Subsequently, the mixture was heated at 85° C. Reaction mixture was analyzed by LC/MS after 2 h which indicated complete consumption of 6-(6'-methyl-[2,2'-bipyridin]-3-yl)imidazo[1,2-a]pyridine-3-carbonitrile. Reaction mixture was cooled to room temperature and poured onto ice-water. Subsequently, aqueous acidic homogenous solution was basified (pH>9) with 50% aq. NaOH and stirred at room temperature for 2 h. The resulting off-white precipitous solid was collected by suction filtration, washed with water, dried and purified by Combiflash® on a RediSep® 12G silica gel column and eluted with 100% CH$_2$Cl$_2$ followed by 7% 7N NH$_3$ MeOH/CH$_2$Cl$_2$. A white solid (60 mg, 45%) of 6-(6'-methyl-[2,2'-bipyridin]-3-yl)imidazo[1,2-a]pyridine-3-carboxamide was isolated upon drying the solid obtained after concentrating product fractions. $^1$H NMR (300 MHz, DMSO-d$_6$) δ 9.37 (d, J=1.5 Hz, 1H), 8.73 (dd, J=4.7, 1.6 Hz, 1H), 8.30 (s, 1H), 8.02-7.85 (overlapped br s, 1H), 7.96 (dd, J=7.8, 1.6 Hz, 1H), 7.69 (t, J=7.7 Hz, 1H), 7.60 (app s, 1H), 7.59-7.55 (m, 1H), 7.53 (d, J=9.8 Hz, 1H), 7.45-7.28 (br s, 1H), 7.11 (d, J=8.1 Hz, 1H), 7.08 (dd, J=9.3, 1.9 Hz, 1H), 2.08 (s, 3H). LCMS: rt 1.88 min (A), purity 96%, MS (m/e) 330 (MH$^+$).

Compound 7: 6-([2,2'-Bipyridin]-3-yl)imidazo[1,2-a]pyridine-3-carbonitrile

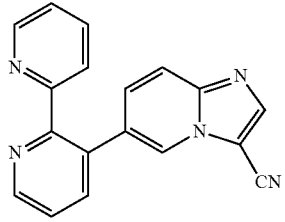

6-([2,2'-bipyridin]-3-yl)imidazo[1,2-a]pyridine-3-carbonitrile was prepared and isolated in an analogous manner to the preparation of 6-(6'-methyl-[2,2'-bipyridin]-3-yl)-[1,2,4]triazolo[1,5-a]pyridine by the reaction of -(2-chloropyridin-3-yl)imidazo[1,2-a]pyridine-3-carbonitrile (1.0 g, 3.93 mmol) and 2-pyridylzinc bromide (0.5 M in THF, 13 mL, 6.5 mmol) in the presence of Pd(PPh$_3$)$_4$ (0.14 g, 0.12 mmol). Off-White solid (435 mg, 37%). $^1$H NMR (300 MHz, DMSO-d$_6$) δ 8.75 (dd, J=4.7, 1.6 Hz, 1H), 8.56 (dd, J=1.7, 1.0 Hz, 1H), 8.43 (s, 1H), 8.28 (dt, J=4.8, 1.4 Hz, 1H), 8.09 (dd, J=7.8, 1.6 Hz, 1H), 7.89 (app d, J=1.4 Hz, 1H), 7.88 (app d, J=1.2 Hz, 1H), 7.64 (dd, J=9.2, 0.8 Hz, 1H), 7.61 (app dd, J=7.8, 4.8 Hz, 1H), 7.29 (app dd, J=9.2, 4.8 Hz, 1H), 7.14 (dd, J=9.3, 1.7 Hz, 1H). LCMS: rt 3.85 min (A), purity 95%, MS (m/e) 330 (MH$^+$).

Compound 8: 6-([2,2'-Bipyridin]-3-yl)-[1,2,4]triazolo[1,5-a]pyridine

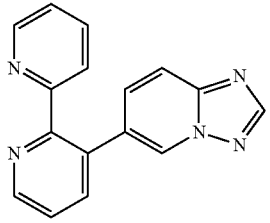 [SMILES: c1ccc(-c2ncccc2-c2ccc3ncnn3c2)nc1]

6-([2,2'-Bipyridin]-3-yl)-[1,2,4]triazolo[1,5-a]pyridine was prepared and isolated (395 mg, 31%) in an analogous manner to the preparation of 6-(6'-methyl-[2,2'-bipyridin]-3-yl)-[1,2,4]triazolo[1,5-a]pyridine by the reaction of 6-(2-chloropyridin-3-yl)-[1,2,4]triazolo[1,5-a]pyridine (1.0 g, 4.34 mmol) and 2-pyridylzinc bromide (0.5 M in THF, 17 mL, 8.5 mmol) in the presence of Pd(PPh$_3$)$_4$ (0.15 g, 0.13 mmol). Off-white solid. $^1$H NMR (300 MHz, DMSO-d$_6$) δ 8.93 (dd, J=1.8, 0.9 Hz, 1H), 8.74 (dd, J=4.8, 1.6 Hz, 1H), 8.47 (s, 1H), 8.25 (dt, J=4.8, 1.5 Hz, 1H), 8.04 (dd, J=7.8, 1.6 Hz, 1H), 7.90 (d, J=1.3 Hz, 1H), 7.88 (app d, J=1.2 Hz, 1H), 7.64 (dd, J=9.2, 0.8 Hz, 1H), 7.60 (app dd, J=7.8, 4.8 Hz, 1H), 7.29 (app dd, J=9.2, 4.8 Hz, 1H), 7.21 (dd, J=9.2, 1.8 Hz, 1H). LCMS: rt 3.11 min (A), purity 96%, MS (m/e) 274 (MH$^+$).

Compound 9: 6-([2,2'-Bipyridin]-3-yl)imidazo[1,2-a]pyridine-3-carboxamide

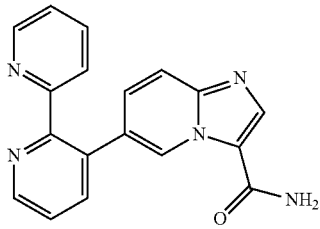 [SMILES: NC(=O)c1cnc2ccc(-c3cccnc3-c3ccccn3)cn12]

6-([2,2'-Bipyridin]-3-yl)imidazo[1,2-a]pyridine-3-carboxamide was prepared and isolated in an analogous manner to the preparation of 6-(6'-methyl-[2,2'-bipyridin]-3-yl)imidazo[1,2-a]pyridine-3-carboxamide from 6-([2,2'-bipyridin]-3-yl)imidazo[1,2-a]pyridine-3-carbonitrile (200 mg, 0.67 mmol). White solid (98 mg, 46%). $^1$H NMR (300 MHz, DMSO-$d_6$) δ 9.39 (dd, J=1.8, 0.9 Hz, 1H), 8.74 (dd, J=4.7, 1.6 Hz, 1H), 8.31 (s, 1H), 8.26 (dt, J=4.8, 1.4 Hz, 1H), 8.00-7.92 (overlapped br s, 1H), 7.99 (dd, J=7.8, 1.6 Hz, 1H), 7.87 (dd, J=7.9, 1.7 Hz, 1H), 7.85-7.79 (m, 1H), 7.59 (dd, J=7.8, 4.8 Hz, 1H), 7.51 (dd, J=9.3, 0.9 Hz, 1H), 7.37 (br s, 1H), 7.28 (ddd, J=6.7, 4.8, 2.1 Hz, 1H), 7.02 (dd, J=9.3, 1.9 Hz, 1H). LCMS: rt 1.88 min (A), purity 97%, MS (m/e) 316 (MH$^+$).

Compound 10: 6-(6'-methyl-[2,2'-bipyridin]-3-yl)pyrido[3,2-d]pyrimidin-4-amine

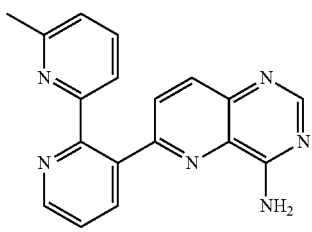 [SMILES: Cc1cccc(-c2ncccc2-c2ccc3ncnc(N)c3n2)n1]

6-(6'-Methyl-[2,2'-bipyridin]-3-yl)pyrido[3,2-d]pyrimidin-4-amine was prepared as depicted in the following Scheme:

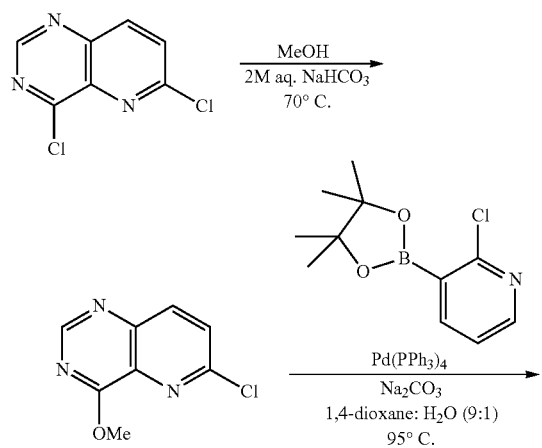

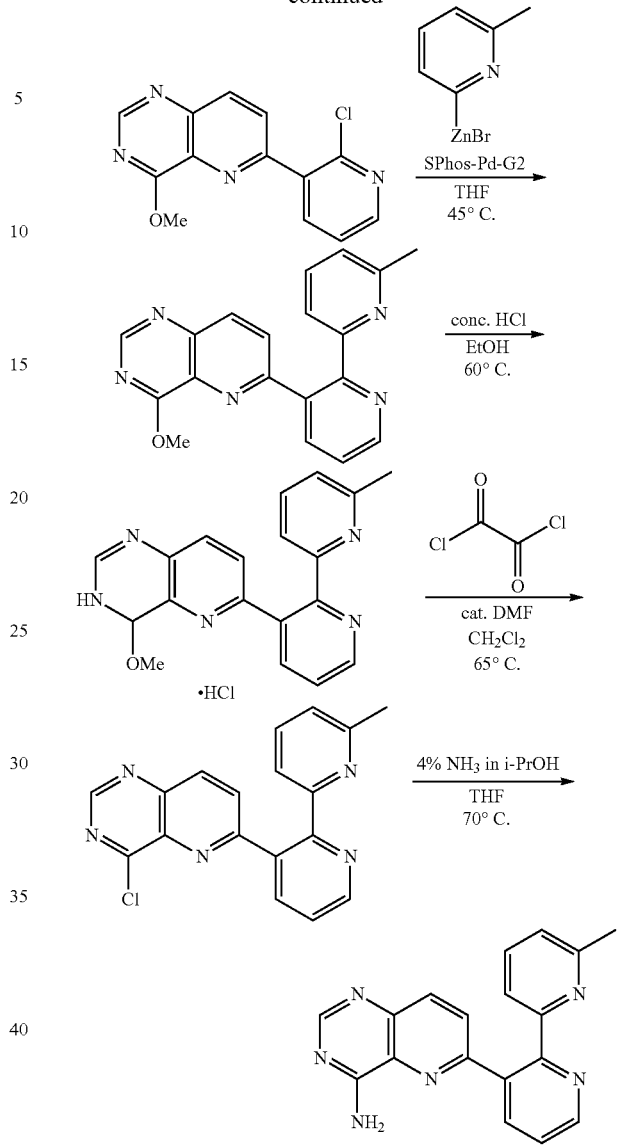

6-Chloro-4-methoxypyrido[3,2-d]pyrimidine 4,6-Dichloropyrido[3,2-d]pyrimidine (prepared from PCT Int. Appl., 2005058913, PCT Int. Appl., 2011131741, PCT Int. Appl., 201009469)-(2.5 g, 12.4 mmol) and NaHCO$_3$ (3.1 g, 31 mmol) in MeOH (20 mL) were heated at 70° C. for 12 h under nitrogen atmosphere. The reaction mixture was filtered and concentrated the filtrate. The crude concentrate was diluted with water and filtered. The suction dried solid was stirred in EtOAc (20 mL) and filtered to obtain 6-chloro-4-methoxypyrido[3,2-d]pyrimidine (1.8 g) as an off-white solid. $^1$H NMR (300 MHz, DMSO-$d_6$): δ 8.88 (s, 1H), 8.37 (d, J=8.8 Hz, 1H), 8.00 (d, J=8.8 Hz, 1H), 4.14 (s, 3H).

6-(2-Chloropyridin-3-yl)-4-methoxypyrido[3,2-d]pyrimidine

A reaction flask was charged 6-chloro-4-methoxypyrido[3,2-d]pyrimidine (3.5 g, 17.8 mmol), 2-chloro-3-pyridineboronic acid pinacol ester (4.35 g, 18.2 mmol), Na$_2$CO$_3$ (4.0 g, 38.2 mmol) and 1,4-dioxane (100 mL) and a stir bar. The contents were degassed by vacuum and back filled with argon three times while stirring. Subsequently, Pd(PPh$_3$)$_3$ (0.87 g, 0.75 mmol) was added to the reaction contents, repeated degassing cycles, and heated for overnight under argon at 98° C. The yellow heterogeneous reaction mixture was cooled to room temperature and suction filtered on a Buchner funnel. The collected solid on the funnel was washed with additional amount of dioxane (30 mL). The pale yellow clear filtrate solution was passed through a pad of Celite® and concentrated. The crude pale yellow solid residue thus obtained was partitioned between CH$_2$Cl$_2$ (150 mL)/water (50 mL). The organic layer was separated, dried over MgSO$_4$, filtered and concentrated. The crude concentrate was stirred in EtOAc (30 mL) and suction filtered. The filter cake was washed with EtOAc (10 mL) and dried to obtain 1.6 g of 6-(2-chloropyridin-3-yl)-4-methoxypyrido[3,2-d]pyrimidine (purity: 95%) as a white solid. The filtrate was concentrated and purified the concentrate by flash column chromatography (Combiflash® Companion System® with RediSep® silica gel column 40 g, 0-30-60% EtOAC/hexanes eluting solvent gradient) to obtain additional 0.65 g of titled compound. $^1$H NMR (300 MHz, DMSO-d$_6$): δ 8.92 (s, 1H), 8.57 (dd, J=4.8, 2.0 Hz, 1H), 8.45 (d, J=8.7 Hz, 1H), 8.28 (d, J=8.7 Hz, 1H), 8.13 (dd, J=7.6, 2.0 Hz, 1H), 7.63 (dd, J=7.6, 4.8 Hz, 1H), 4.16 (s, 3H).

4-Methoxy-6-(6'-methyl-[2,2'-bipyridin]-3-yl)pyrido[3,2-d]pyrimidine

A two necked round bottom flask containing a stir bar was fitted with reflux condenser to one of the necks and rubber septa to other neck. A three way stopcock was attached to reflux condenser and remaining two inlets were connected to argon balloon and vacuum pump hose. 6-(2-chloropyridin-3-yl)-4-methoxypyrido[3,2-d]pyrimidine (2.0 g, 7.3 mmol), and SPhos-Pd-G2 (0.16 g, 0.22 mmol) were transferred into reaction flask, introduced dry THF (20 mL) under vacuum, degassed by vacuum application followed by introduction of argon in three cycles and initiated heating yellow suspension reaction mixture simultaneously. Subsequently, 6-methyl-2-pyridylzinc bromide (0.5 M in THF, 22 mL, 11 mmol) was added under argon over a period of 10 min at 34° C. The resulting pale brown heterogeneous mixture was degassed again and stirred at 45° C. After 1 h, reaction mixture was turned to homogenous solution and indicated 7% of unreacted 6-(2-chloropyridin-3-yl)-4-methoxypyrido[3,2-d]pyrimidine as analyzed by LC/MS. Reaction mixture was cooled to room temperature after 5 h (<3% of unreacted 6-(2-chloropyridin-3-yl)-4-methoxypyrido[3,2-d]pyrimidine), concentrated under reduced pressure and stirred in a mixture of saturated aq. Na$_2$CO$_3$ (100 mL)/CH$_2$Cl$_2$ (300 mL). Organic layer was separated from semi-separable heterogeneous mixture and extracted aqueous layer with CH$_2$Cl$_2$ (3×200 mL). Combined organic layers were stirred over MgSO$_4$/Celite®, filtered and concentrated. The resultant crude mixture was adsorbed on silica gel, purified by Combiflash® on a RediSep® 40G silica gel column and eluted with 100% CH$_2$Cl$_2$-1% 7N NH$_3$ MeOH/CH$_2$Cl$_2$-3% 7N NH$_3$ MeOH/CH$_2$Cl$_2$. Two peaks were observed on UV trace containing product. Impure product fractions corresponding to low retention time peak were concentrated (1.2 g) and crystallized from EtOAc. Resulting crystalline white solid was collected by filtration and suction dried to provide 0.60 g of 4-methoxy-6-(6'-methyl-[2,2'-bipyridin]-3-yl) pyrido[3,2-d]pyrimidine with 96% purity. Filtrate was combined with impure product fractions from higher retention time peak and purified the concentrate (1.4 g) once again in a similar manner as above to obtain another lot of (0.78 g, 94% purity, white solid) 4-methoxy-6-(6'-methyl-[2,2'-bipyridin]-3-yl)pyrido[3,2-d]pyrimidine. Combined yield (61%). $^1$H NMR (300 MHz, DMSO-d$_6$) δ 8.84 (s, 1H), 8.80 (dd, J=4.7, 1.7 Hz, 1H), 8.10-8.07 (m, 2H), 7.90 (ddd, J=7.8, 1.2, 0.6 Hz, 1H), 7.77 (t, J=7.7 Hz, 1H), 7.61 (dd, J=7.8, 4.7 Hz, 1H), 7.53 (d, J=8.8 Hz, 1H), 7.12 (ddd, J=7.6, 1.1, 0.6 Hz, 1H), 4.12 (s, 3H), 1.81 (s, 3H). LCMS: rt 3.65 min (A), MS (m/e) 330 (MH$^+$).

6-(6'-Methyl-[2,2'-bipyridin]-3-yl)pyrido[3,2-d]pyrimidin-4(3H)-one hydrochloride salt Conc. HCl (0.0.5 ml) was added to a stirring heterogeneous slurry of 4-methoxy-6-(6'-methyl-[2,2'-bipyridin]-3-yl)pyrido[3,2-d]pyrimidine (1.1 g, 3.33 mmol) in EtOH (6 mL) at room temperature and heated the slurry gradually to 58° C. and monitored the progress of reaction. Additional amounts of conc. HCl were added to heterogeneous reaction mixture at 1 h (0.05 mL), 1 h 30 min (0.1 mL) and 2 h 30 min (0.05 mL) respectively to realize consumption of 4-methoxy-6-(6'-methyl-[2,2'-bipyridin]-3-yl)pyrido[3,2-d] pyrimidine. Upon conc. HCl addition at 2 h 30 min, reaction mixture was turned to homogeneous solution and converted back to heterogeneous mixture over a period of 30 min. At this stage, heating was continued for additional period of 2 h and cooled to room temperature. Crystalline solid from reaction mixture was collected by filtration and suction dried to provide 200 mg of 6-(6'-methyl-[2,2'-bipyridin]-3-yl) pyrido[3,2-d]pyrimidin-4(3H)-one as an HCl salt. Upon concentration of filtrate under reduced pressure provided pale yellow solid which was stirred in 10% EtOH/EtOAc (50 mL) for 20 min and collected by filtration to provide another lot of 6-(6'-methyl-[2,2'-bipyridin]-3-yl)pyrido[3,2-d]pyrimidin-4(3H)-one hydrochloride salt (0.81 g). Combined yield (1.1 g, 93%). LCMS: rt 2.80 min (A), purity 96%, MS (m/e) 316 (MH$^+$).

4-Chloro-6-(6'-methyl-[2,2'-bipyridin]-3-yl)pyrido[3,2-d]pyrimidine

To a stirring mixture of 6-(6'-methyl-[2,2'-bipyridin]-3-yl)pyrido[3,2-d]pyrimidin-4(3H)-one hydrochloride salt (1.0 g, 2.8 mmol) and dry CH$_2$Cl$_2$ (30 mL) under argon was added oxalyl chloride (2 mL, 3.0 g, 23.6 mmol) at room temperature. After 10 min of stirring the reaction contents, cat. DMF (0.1 mL) dissolved in dry CH$_2$Cl$_2$ (2 mL) was added to reaction mixture over a period of 10 min and heated at 65° C. for 3 h. Dark reaction mixture thus formed was analyzed to notice complete consumption of 6-(6'-methyl-[2,2'-bipyridin]-3-yl)pyrido[3,2-d]pyrimidin-4(3H)-one with minor product formation. Reaction mixture was cooled, concentrated, diluted with EtOAc (75 mL) and stirred in solid Na$_2$CO$_3$ (5.0 g) for 30 min. The dark slurry was diluted with ice water (30 mL), stirred for 20 min, separated organic layer and extracted aqueous layer with EtOAc (2×50 mL). Combined organic layers were dried over MgSO$_4$, filtered and concentrated. Crude concentrate was subjected to purification by Combiflash® on a RediSep® 40 g silica gel column and eluted with 30-60% EtOAc/hexanes to obtain 4-chloro-6-(6'-methyl-[2,2'-bipyridin]-3-yl)pyrido[3,2-d] pyrimidine as a off-white solid (120 mg, 12%). LCMS: rt 4.00 min (A), purity 95%, MS (m/e) 334 (MH$^+$).

6-(6'-Methyl-[2,2'-bipyridin]-3-yl)pyrido[3,2-d]pyrimidin-4-amine

4-Chloro-6-(6'-methyl-[2,2'-bipyridin]-3-yl)pyrido[3,2-d]pyrimidine (120 mg, 0.36 mmol), THF (3 mL) and 4% NH₃/i-PrOH (3 mL) in a screw capped vial was stirred at 70° C. for 4 h. Pale purple reaction mixture was concentrated and purified by Combiflash® on a RediSep® 4G silica gel column and eluted with 100% CH₂Cl₂-3% 7N NH₃ MeOH/CH₂Cl₂ to provide 6-(6'-methyl-[2,2'-bipyridin]-3-yl)pyrido[3,2-d]pyrimidin-4-amine (53 mg, 47%) as an off-white solid. ¹H NMR (300 MHz, DMSO-d₆) δ 8.76 (dd, J=4.7, 1.7 Hz, 1H), 8.38 (s, 1H), 8.23 (dd, J=7.8, 1.7 Hz, 1H), 7.88-7.72 (m, 4H), 7.61 (dd, J=7.8, 4.7 Hz, 1H), 7.50 (br s, 1H), 7.38 (d, J=8.7 Hz, 1H), 7.14 (dd, J=6.4, 2.3 Hz, 1H), 1.92 (s, 3H). LCMS: rt 1.93 min (A), purity 99%, MS (m/e) 315 (MH⁺).

Preparation of 2-chloro-3-(heteroaryl)pyridines

Preparation of 5-(2-chloropyridin-3-yl)-1H-indazole

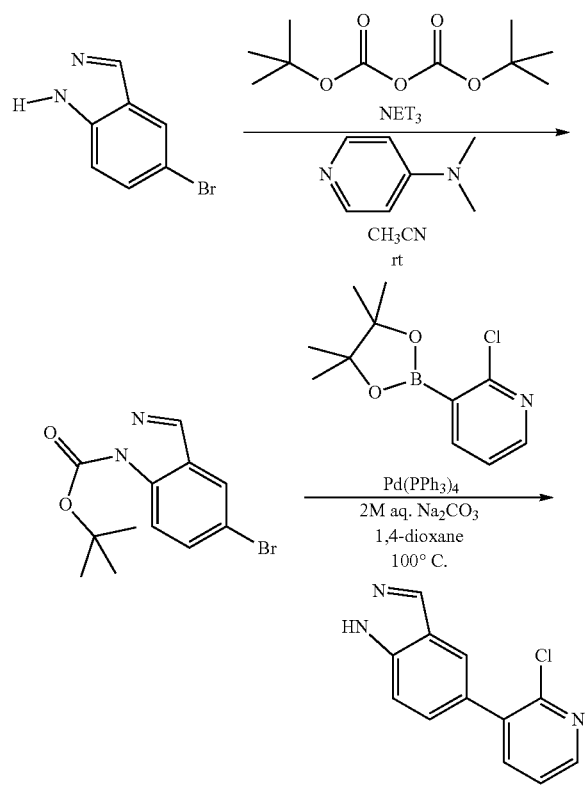

tert-Butyl 5-bromo-1H-indazole-carboxylate

A single necked round bottom flask containing a with a magnetic stir bar was charged with 5-bromo-1H-indazole (3.0 g, 15.2 mmol), di-tert-butyl dicarbonate (4.2 g, 19.2 mmol) and acetonitrile (30 mL) under mild stream of nitrogen at room temperature. Triethylamine (1.8 g, 2.5 mL, 17.7 mmol) was added in one portion to above stirred homogeneous solution followed by 4-(dimethylamino)pyridine (2.2 g, 18 mmol) over a period of 15 min in portions. The homogenous off-brown clear reaction mixture was stirred at room temperature under nitrogen and the progress of reaction monitored by TLC (50% EtOAc/hexanes). Stirring was discontinued after 3 h and the reaction mixture concentrated by rotary evaporator under vacuum. A clear viscous liquid was obtained and dissolved in EtOAc/hexanes (7:3, 200 mL), and diluted with water (75 mL). Organic layer was separated and the aqueous layer extracted with EtOAc/hexanes (1:1, 125 mL). The combined organic layers were washed with water (100 mL) followed by 1N aq. HCl (2×75 mL) to remove 4-(dimethylamino)pyridine. The combined organic layers were washed with water (2×75 mL), saturated aq. NaHCO₃ (2×75 mL) and saturated aqueous NaCl. Separated organic layers were dried over anhydrous MgSO₄, filtered, concentrated and dried under vacuum to provide tert-butyl 5-bromo-1H-indazole-carboxylate (4.5 g, purity 97%) as a pale yellow viscous liquid which was used without further purification. ¹H NMR (DMSO-d6): δ 8.36 (d, J=0.8 Hz, 1H), 8.11 (app d, J=0.8 Hz, 1H), 8.00 (d, J=8.8 Hz, 1H), 7.71 (app dd, J=8.8, 0.8 Hz, 1H), 1.62 (s, 9H). LCMS: 97%, MS (m/e) 241 (MH⁺-t-Bu). A single necked round bottom flask (250 mL) equipped with a magnetic stir bar was charged with tert-butyl 5-bromo-1H-indazole-carboxylate (4.0 g, 13.4 mmol) dissolved in 1,4-dioxane (130 mL), 2-chloro-3-pyridine boronic acid pinacol ester (4 g, 16.7 mmol), Pd(PPh₃)₄ (1.5 g, 1.3 mmol) and 2M aq. Na₂CO₃ (20 mL, 40 mmol) under nitrogen atmosphere. The rubber septum was replaced with reflux condenser containing three-way stopcock equipped with argon filled balloon. The reaction contents were stirred and air was removed from the closed reaction system by vacuum and back filled with argon. Following three cycles of degassing, the reaction mixture was heated at 100° C. (oil-bath) under argon. Inflated argon balloon was emptied, refilled with argon and remounted in the course of reaction. The initial pale yellow heterogeneous reaction mixture turned to clear biphasic off-brown solution. After 18 h with no additional change in the proportion of the product (62%) as analyzed by LC/MS, the reaction mixture was cooled to room temperature. Upon concentration of the reaction mixture, EtOAc/water (200 mL/75 mL) was transferred to the concentrate and stirred for 30 min. The organic layer was separated and the aqueous layer extracted with EtOAc (100 mL×2). MgSO₄ (20 g) and Celite® (20 g) were added to combined organic layers and the contents suction filtered after stirring for 1 h. The filter cake was washed with EtOAc (300 mL) and the combined filtrates concentrated by rotary evaporator under vacuum. The crude concentrate was dissolved in 1% MeOH/CH₂Cl₂ and absorbed on silica gel (20 g) by evaporating the solvent followed by drying. Subsequent purification by flash silica gel column purification of the dry powder (Combiflash® Companion System® with RediSep® silica gel column 120 g, 30-70% EtOAc/hexanes eluting solvent) provided 5-(2-chloropyridin-3-yl)-1H-indazole (1.5 g, 47%) as a white crystalline solid after concentration of the desired product fractions. ¹H NMR (DMSO-d6): δ 13.2 (s, 1H), 8.41 (dd, J=1.8 and 4.7 Hz, 1H), 8.13 (s, 1H), 7.90 (dd, J=4.7, 1.7 Hz, 1H), 7.84 (s, 1H), 7.62 (d, J=8.8 Hz, 1H), 7.51 (dd, J=7.3, 4.7 Hz, 1H), 7.42 (dd, J=8.5, 1.4 Hz, 1H). LCMS: 95%, MS (m/e) 230 (MH⁺).

4-(2-Chloropyridin-3-yl)quinoline

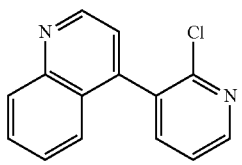 [SMILES: Clc1ncccc1-c1ccnc2ccccc12]

4-(2-Chloropyridin-3-yl)quinolone was prepared in the similar manner to the preparation of 5-(2-chloropyridin-3-yl)-1H-indazole by reacting 4-bromoquinoline (2.5 g, 12 mmol), 2-chloro-3-pyridine boronic acid pinacol ester (3.4 g, 14.4 mmol), Pd(PPh$_3$)$_4$ (0.7 g, 0.60 mmol) and 2M aq. Na$_2$CO$_3$ (21 mL, 42 mmol) in 1,4-dioxane (100 mL) at 100° C. $^1$H NMR (300 MHz, DMSO-d$_6$): δ 9.01 (d, J=4.4 Hz, 1H), 8.60 (dd, J=4.8, 1.9 Hz, 1H), 8.13 (d, J=8.5 Hz, 1H), 7.98 (dd, J=7.5, 1.9 Hz, 1H), 7.81 (ddd, J=8.4, 6.9, 1.4 Hz, 1H), 7.64 (dd, J=7.5, 4.8 Hz, 1H), 7.58 (dd, J=6.9, 1.3 Hz, 1H), 7.51 (d, J=4.4 Hz, 1H), 7.42 (dd, J=8.1, 1.1 Hz, 1H).

6-(2-Chloropyridin-3-yl)imidazo[1,2-a]pyridine-3-carbonitrile

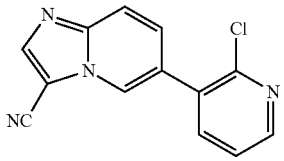 [SMILES: N#Cc1cnc2ccc(-c3cccnc3Cl)cn12]

6-(2-Chloropyridin-3-yl)imidazo[1,2-a]pyridine-3-carbonitrile was prepared in an analogous manner to 5-(2-chloropyridin-3-yl)-1H-indazole preparation from 6-bromoimidazo[1,2-a]pyridine-3-carbonitrile [*JMC* 54(7), 2455-2466, 2011] (1.5 g, 6.7 mmol), 2-chloro-3-pyridine boronic acid pinacol ester (1.9 g, 8.0 mmol), Pd(PPh$_3$)$_4$ (0.54 g, 0.46 mmol) and 2M aq. Na$_2$CO$_3$ (9.2 mL, 18.4 mmol) in 1,4-dioxane (100 mL) at 100° C. overnight. After extractive workup with CH$_2$Cl$_2$ followed by drying over MgSO$_4$/Celite® and filtration, filtrate was concentrated under reduced pressure. The resultant pale brown solid was stirred in EtOAc (25 mL) and filtered to provide 6-(2-chloropyridin-3-yl)imidazo[1,2-a]pyridine-3-carbonitrile as a white solid. $^1$H NMR (300 MHz, DMSO-d$_6$): δ 8.82 (d, J=1.9 Hz), 8.54-8.45 (m, 2H), 8.07 (dd, J=7.6, 1.9 Hz, 1H), 7.94 (d, J=9.3 Hz, 1H), 7.75 (dd, J=9.3, 1.7 Hz, 1H), 7.58 (dd, J=7.6, 4.8 Hz, 1H). LCMS: rt 5.34 min (B), purity 95%, MS (m/e) MH$^+$ 255.

6-(2-Chloropyridin-3-yl)-[1,2,4]triazolo[1,5-a]pyridine

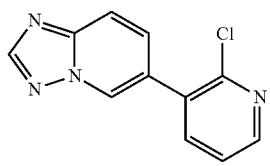 [SMILES: Clc1ncccc1-c1ccc2ncnn2c1]

6-(2-Chloropyridin-3-yl)-[1,2,4]triazolo[1,5-a]pyridine was prepared and isolated in the similar to 6-(2-chloropyridin-3-yl)imidazo[1,2-a]pyridine-3-carbonitrile preparation by the reaction of 6-bromo-[1,2,4]triazolo[1,5-a]pyridine (2.5 g, 12.5 mmol), 2-chloro-3-pyridine boronic acid pinacol ester (3.6 g, 15.0 mmol), Pd(PPh$_3$)$_4$ (0.58 g, 0.50 mmol) and 2M aq. Na$_2$CO$_3$ (17 mL, 34 mmol) in 1,4-dioxane (100 mL) at 100° C. overnight. White fluffy solid (1.76 g, 61%). $^1$H NMR (DMSO-d6): δ 9.18 (dd, J=1.7, 0.8 Hz, 1H), 8.57 (s, 1H), 8.50 (dd, J=4.9, 2.0 Hz, 1H), 8.05 (dd, J=7.6, 1.7 Hz, 1H), 7.97 (dd, J=9.1, 0.9 Hz, 1H), 7.80 (dd, J=9.1, 1.7 Hz, 1H), 7.57 (dd, J=7.6, 4.7 Hz, 1H). LCMS: rt 4.88 min (A), purity 95%, MS (m/e) MH$^+$ 231.

7-(2-Chloropyridin-3-yl)-[1,2,4]triazolo[1,5-a]pyridine

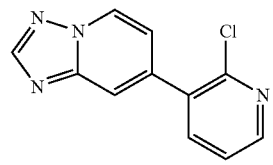 [SMILES: Clc1ncccc1-c1ccn2ncnc2c1]

7-(2-Chloropyridin-3-yl)-[1,2,4]triazolo[1,5-a]pyridine was prepared and isolated as in an analogous manner to 6-(2-chloropyridin-3-yl)imidazo[1,2-a]pyridine-3-carbonitrile preparation by the reaction of 7-bromo-[1,2,4]triazolo[1,5-a]pyridine (1.0 g, 5.0 mmol), 2-chloro-3-pyridine boronic acid pinacol ester (3.6 g, 8.3 mmol), Pd(PPh$_3$)$_4$ (0.3 g, 0.26 mmol) and 2M aq. Na$_2$CO$_3$ (8 mL, 16 mmol) in 1,4-dioxane (100 mL) at 100° C. overnight. White fluffy solid (0.67 g, 58%). $^1$H NMR (300 MHz, DMSO-d$_6$): δ 9.06 (d, J=6.5 Hz, 1H), 8.58 (s, 1H), 8.51 (dd, J=4.8, 1.9 Hz, 1H), 8.03 (dd, J=7.6, 1.9 Hz, 1H), 7.99 (s, 1H), 7.58 (dd, J=7.6, 4.8 Hz, 1H), 7.34 (dd, J=7.1, 1.8 Hz, 1H). LCMS: rt 4.83 min (A), purity 98%, MS (m/e) MH$^+$ 231.

Compound 2: 6-(6'-methyl-[2,2'-bipyridin]-3-yl)quinazolin-4-amine

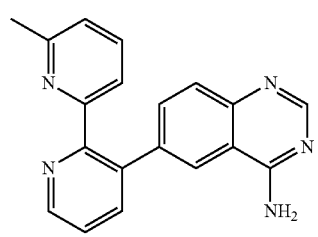 [SMILES: Cc1cccc(-c2ncccc2-c2ccc3ncnc(N)c3c2)n1]

LCMS: rt 2.15 min (A), MS (m/e) 314 MH$^+$.

$^1$H NMR (CD$_3$OD, 300 MHz): 8.71 (dd, J=5.1, 1.8 Hz, 1H),): 8.55 (dd, J=7.8, 1.5 Hz, 1H), 8.35 (s, 1H), 8.09-8.06 (m, 2H), 7.69-7.62 (m, 2H), 7.51 (d, J=8.7 Hz, 1H), 7.40 (dd, J=8.7, 1.8 Hz, 1H), 7.31 (d, J=7.5 Hz, 1H), 7.20 (d, J=7.5 Hz, 1H), 2.31 (m, 3H).

Compound 11: 6-(6'-fluoro-[2,2'-bipyridin]-3-yl)quinazolin-4-amine

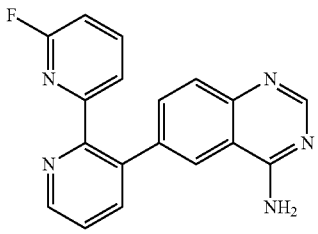 [SMILES: Nc1ncnc2ccc(-c3cccnc3-c3cccc(F)n3)cc12]

LCMS: rt 3.43 min (A), MS (m/e) 318 MH$^+$.
$^1$H NMR (CD$_3$OD, 300 MHz): 8.77 (m, 1H), 8.65 (m, 1H), 8.32 (m, 1H), 8.07-7.94 (m, 2H), 7.76-7.73 (m, 2H), 7.71-7.63 (m, 2H), 7.00 (dd, J=8.4, 2.7 Hz, 1H).

Compound 12: 6-([2,2'-bipyridin]-3-yl)quinazolin-4-amine

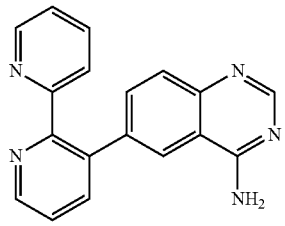 [SMILES: Nc1ncnc2ccc(-c3cccnc3-c3ccccn3)cc12]

LCMS: rt 1.07 min (A), MS (m/e) 300 MH$^+$.
$^1$H NMR (CD$_3$OD, 300 MHz): 8.72 (m, 1H), 8.38 (m, 2H), 8.12-8.06 (m, 2H), 7.85-7.80 (m, 1H), 7.67-7.58 (m, 2H), 7.52-7.49 (m, 1H), 7.44-7.40 (m, 1H), 7.37-7.32 (m, 1H).

Example 2: AlphaScreen® SureFire® SMAD3 (p-Ser423/425) Assay

The p-SMAD-3 (Ser423/425) SureFire® assay has been designed to measure the phosphorylation of endogenous cellular p-SMAD-3 (Ser423/425) in cell lysates and is a system for the screening of both modulators of receptor activation (e.g. agonists and antagonists) as well as agents acting intracellularly, such as small molecule inhibitors of upstream events. The assay will measure p-SMAD-3 (Ser423/425) activation by either cloned or endogenous receptors, and can be applied to primary cells.

P-SMAD-3 (Ser423/425) SureFire® Assay Protocols
Step A: Preparation of Buffers
  1× Lysis buffer: 1 ml of 5× Lysis buffer was diluted with 4 ml of sterile water. After dilution, excess 1× Lysis buffer can be frozen and thawed up to 5 times without loss in activity.
  Activation buffer: The buffer was warmed slowly to 37° C. and gently mixed to re-suspend. Activation buffer can be stored at room temperature with no loss in activity.
  Reaction buffer: The buffer was kept at 4° C. while in use.
  AlphaScreen® Protein A IgG Kit: The kit was stored at 4° C. in the dark.
  Reaction buffer+Activation buffer+AlphaScreen® Acceptor beads: Reaction buffer (40 parts), Activation Buffer (10 parts) and Acceptor beads (1 part) were mixed and the mixture was stored at room temperature and used the same day. Mixture was added to 384-well plates; excess mixture was discarded.
  Dilution buffer+AlphaScreen® Donor beads: Dilution buffer (20 parts) and Donor beads (1 part) were mixed and the mixture was stored at room temperature and used the same day. Excess mixture was discarded.
  Assay control samples: After reconstitution in 250 µl of water, lysates were at −20° C. in single use aliquots.

Step B: Preparation of Samples and Cells 96-well Assay Protocol for 293FT and RMS13 adherent cells can be carried out manually or in high throughput with liquid handling robots.

The cells (80 µL of cells for 96 well plates) were plated in collagen coated tissue culture plates in RPMI or FreeStyle medium (Invitrogen) and incubated overnight. For manual analysis, 6 plates for GDF8, 6 plates for TGFβ, and optionally 6 plates for Alk5ca (ALK5 constitutively active) were used.

The compound dilution plates were prepared as follows: 12 µL of DMSO was transferred into first column of 96-well plate, and 16 µL of DMSO was transferred into columns 2-12 of the 96-well plate. 12 µL of compound solution was transferred into first column of the DMSO-containing 96-well plate. Three-fold dilution was performed up to column 10 of the DMSO-containing 96-well plate.

Step C: Treatment and Analysis

The plate containing cells were treated with compounds for about 10 minutes, and then ligand was added. GDF8 or TGFb was added to plates to stimulate. 293FL cells were stimulated for 90 minutes at 37° C.; and RMS13 cells were stimulated for 60 minutes at 37° C. The medium was then removed from the cells, and 1× Lysis Buffer (about 25 µL) was added and the plate was gently agitated on plate shaker for 5-10 minutes.

The lysate (5 µL) was then placed into 384-well shallow plates avoiding the generation of bubbles. To this, the Reaction Buffer+Activation Buffer+AlphaScreen® Acceptor beadsmixture (5 µL) was added. The plate was sealed with adhesive cover and shielded from light (e.g., with metal foil), and agitated gently on plate shaker for 2 hours at room temperature.

Dilution buffer+AlphaScreen® Donor beads (2 µL) was then added, and the plate was intubated on the plate shaker for an additional 1½ hours. After completion, the plate was read on Synergy-4 or Enspire plate reader, using AlphaScreen® pSMAD3® settings.

Representative results for inhibition of TGF-β (data=TGF-β pSMAD (MPC-11) (µM)) and GDF8 (data=GDF pSMAD (MPC11)-(µM)) signaling are shown in Table 1:

| No. | TGF-β | GDF8 |
| --- | --- | --- |
| 1 | 10.58 | 19.66 |
| 2 | — | — |
| 2A | 0.2506 | 0.129 |
| 2B | 0.1115 | — |
| 3 | 1.707 | 0.7339 |
| 4 | 0.5014 | 0.2148 |
| 5 | 1.069 | 0.2803 |
| 6 | 0.0538 | 0.0286 |
| 7 | — | 8.509 |
| 8 | 23.56 | 8.058 |
| 9 | 0.2807 | 0.1194 |
| 10 | — | — |
| 11 | — | — |

-continued

| No. | TGF-β | GDF8 |
|-----|-------|------|
| 11A | 1.172 | 0.2288 |
| 12  | —     | —    |
| 12A | 5.477 | 1.307 |

Example 3: Synthesis and Characterization 2

Analytical LC-MS/HPLC retention time reported for each of the following compounds was generated using one of the following general analytical LC-MS/HPLC conditions:
LCMS Conditions:

A: Column: Waters Acquity UPLC BEH C18 (2.1×50 mm), 1.7μ; Mobile phase A: 0.1% TFA in water; Mobile phase B: 0.1% TFA in Acetonitrile; Gradient=20-90% B over 1.1 minute, then a 0.6 minute hold at 90% B; Temperature: 50° C.; Flow rate: 0.7 mL/min; Detection: UV at 220 nm.

B: Column: Waters Acquity UPLC BEH C18 (2.1×50 mm) 1.7μ, Mobile phase A: 10 mM $NH_4OAc$, Acetonitrile (95:5); Mobile phase B: 10 mM $NH_4OAc$: Acetonitrile (5:95), Gradient=20-90% B over 1.1 minute, then a 0.6 minute hold at 90% B; Temperature: 50° C.; Flow rate: 0.7 mL/min; Detection: UV at 220 nm C: Column: Ascentis Express C18 (2.1×50 mm), 2.7μ; Mobile phase A: 10 mM $NH_4OAc$, Acetonitrile (95:5), Mobile phase B: 10 mM $NH_4OAc$, Acetonitrile (5:95), Gradient=0-100% B over 3 minutes; Temperature: 50° C.; Flow rate: 1.1 mL/min; Detection: UV at 220 nm.

D: Column: Ascentis Express C18 (50×2.1 mm), 2.7μ; Mobile phase A: 0.1% TFA: Acetonitrile (95:5), Mobile phase B: 0.1% TFA: Acetonitrile (5:95), Gradient=0-100% B over 3 minutes; Temperature: 50° C.; Flow rate: 1.1 mL/min; Detection: UV at 220 nm.

E: Column: Kinetex XB-C18 (75×3 mm) 2.6μ; Mobile phase A: 10 mM Ammonium formate: Acetonitrile (98:2), Mobile phase B: 10 mM Ammonium formate: Acetonitrile (2:98), Gradient=20-100% B over 4 minutes, then a 0.6 minute hold at 100% B; Temperature: 27° C.; Flow rate: 1.0 mL/min; Detection: UV at 220 nm.
Preparative HPLC Conditions:

F: Column: Waters X-Bridge C18, 19×150 mm, 5μ; Mobile Phase A: 0.1% TFA in water; Mobile Phase B: Acetonitrile; Gradient: 10-100% B over 25 minutes, then a 5 minute hold at 100% B; Flow: 15 mL/min.

G: Column: Inertsil ODS, 250×20 mm ID, 5μ; Mobile Phase A: 0.1% TFA in water; Mobile Phase B: Acetonitrile; Gradient: 10-100% B over 25 minutes, then a 5 minute hold at 100% B; Flow: 17 mL/min.

H: Column: Inertsil ODS, 250×20 mm ID, 5μ; Mobile Phase A: 10 mM $NH_4OAc$ in water; Mobile Phase B: Methanol; Gradient: 10-100% B over 25 minutes, then a 5 minute hold at 100% B; Flow: 17 mL/min.

I: Column: DAD-1 X-Bridge phenyl, 150×4.6 mm 5μ; DAD-2 Sunfire C18, 150×4.6 mm 5μ; Mobile Phase A: 10 mM $NH_4OAc$ in water; Mobile Phase B: Acetonitrile; Gradient: 0-100% B over 18 minutes, then a 5 minute hold at 100% B; Flow: 1 mL/min.

J: Column: Sunfire C18, 150×4.6 mm, 5μ; Mobile Phase A: 0.05% TFA in water; Mobile Phase B: Acetonitrile; Gradient: 0-100% B over 18 minutes, then a 5 minute hold at 100% B; Flow: 1 mL/min.

K: Column: Inertsil ODS, 150×4.6 mm, 5μ; Mobile Phase A: 10 mM $NH_4OAc$ in water; Mobile Phase B: Acetonitrile; Gradient: 0-100% B over 18 minutes, then a 5 minute hold at 100% B; Flow: 17 mL/min.

L: Column: Sunfire C18, 150×19 mm ID, 5μ; Mobile Phase A: 10 mM $NH_4OAc$ in water; Mobile Phase B: Acetonitrile; Gradient: 0-100% B over 18 minutes, then a 5 minute hold at 100% B; Flow: 17 mL/min.

M: Column: Synergy Polar, 250×21.2 ID, 4μ; Mobile Phase A: 0.1% TFA in water; Mobile Phase B: Acetonitrile; Gradient: 0-100% B over 18 minutes, then a 5 minute hold at 100% B; Flow: 17 mL/min.

N: Column: Waters X-Bridge C18, 19×150 mm, 5μ; Mobile Phase A: 10 mM $NH_4OAc$ in water; Mobile Phase B: Acetonitrile; Gradient: 0-100% B over 18 minutes, then a 5 minute hold at 100% B; Flow: 17 mL/min.

O: Column: Symmetry C8, 300×19 mm ID, 7μ; Mobile Phase A: 10 mM $NH_4OAc$ in water; Mobile Phase B: Acetonitrile; Gradient: 0-100% B over 18 minutes, then a 5 minute hold at 100% B; Flow: 17 mL/min.

P: Column: X-Bridge Phenyl, 250×19 mm ID, 5μ; Mobile Phase A: 10 mM $NH_4OAc$ in water; Mobile Phase B: Acetonitrile; Gradient: 0-100% B over 18 minutes, then a 5 minute hold at 100% B; Flow: 17 mL/min.

Q: Column: DAD1—X-Bridge Phenyl, 4.6×250 mm, 5μ; DAD2—X-Terra RP18, 4.6×250 mm, 5μ; Mobile Phase A: 0.05% TFA in water; Mobile Phase B: Acetonitrile; Gradient: 0-100% B over 18 minutes, then a 5 minute hold at 100% B; Flow: 2 mL/min.

General Experimental Procedures for Stille Coupling

Scheme 1 (Method A:) Compound 13: 6-([2,2'-bipyridin]-3-yl)imidazo[1,2-a]pyridine-3-carbonitrile

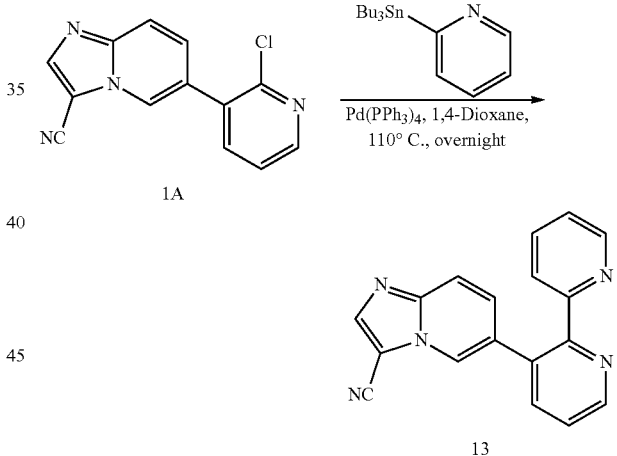

To a solution of compound 1A (reference: WO 2015157093 A1 and WO2014055955 A1)-(200 mg, 0.785 mmol) in 1,4-dioxane (10 mL) was added 2-(tributylstannyl)pyridine (318 mg, 0.864 mmol). The reaction mixture was degassed with argon. Then, $Pd(PPh_3)_4$ (91 mg, 0.079 mmol) was added and the reaction mixture was degassed once again and stirred at 110° C. for 36 h. It was then cooled to room temperature and the volatiles were removed under reduced pressure to give a brown solid. The crude residue was purified by preparative HPLC (condition N) to furnish 6-([2,2'-bipyridin]-3-yl)imidazo[1,2-a]pyridine-3-carbonitrile 13 (205 mg, 0.690 mmol, 88% yield). LCMS: m/z=298.1 [M+H]$^+$; ret. time 0.99 min; condition C. $^1$H NMR (400 MHz, DMSO-d$_6$) δ ppm 8.78 (dd, J=1.6, 4.8 Hz, 1H), 8.59 (dd, J=1.2, 1.6 Hz, 1H), 8.46 (s, 1H), 8.30-8.31 (m, 1H), 8.11 (dd, J=1.6, 7.6 Hz, 1H), 7.90-7.92 (m, 2H), 7.62-7.68 (m, 2H), 7.33-7.34 (m, 1H), 7.16 (dd, J=2.0, 9.6 Hz, 1H).

Scheme-2 (Method B): Compound 14: 6-(6'-(trifluoromethyl)-[2,2'-bipyridin]-3-yl)imidazo[1,2-a]pyridine-3-carbonitrile

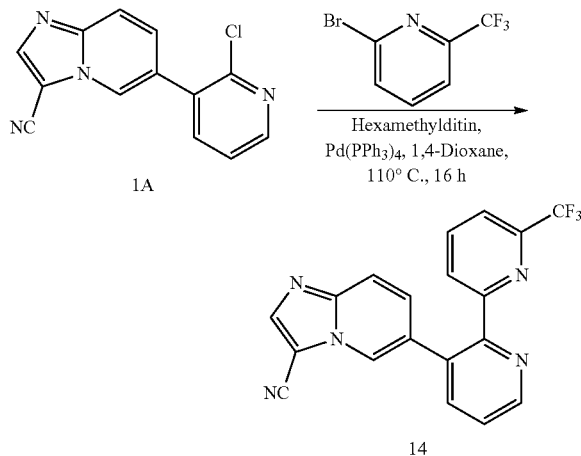

14

To a stirred solution of compound 1A (200 mg, 0.785 mmol) and 2-bromo-6-(trifluoromethyl)pyridine (195 mg, 0.864 mmol) in 1,4-dioxane (2 mL) was added hexamethylditin (0.326 mL, 1.571 mmol) and the reaction mixture was purged with nitrogen for 5 minutes. Then Pd(PPh$_3$)$_4$ (0.091 g, 0.079 mmol) was added and the mixture was again purged for 10 minutes. It was then heated at 110° C. for 16 h. The reaction mixture was filtered through syringe filter and the filtrate was concentrated. The crude residue was purified by preparative HPLC (condition N) to give 6-(6'-(trifluoromethyl)-[2,2'-bipyridin]-3-yl)imidazo[1,2-a]pyridine-3-carbonitrile 14 (0.15 g, 0.411 mmol, 52.3% yield) as a yellow solid. LCMS: m/z=366.1 [M+H]$^+$; ret. time 1.67 min; condition C. $^1$H NMR (400 MHz, DMSO-d$_6$) δ ppm 8.81-8.85 (m, 1H) 8.58-8.62 (m, 1H) 8.44-8.48 (m, 1H) 8.29-8.36 (m, 1H) 8.17-8.24 (m, 1H) 8.08-8.13 (m, 1H) 7.78-7.83 (m, 1H) 7.66-7.72 (m, 2H) 7.22-7.28 (m, 1H).

Scheme 3 (Method C): Compound 15: 6-(5'-(fluoro-6'-methyl-[2,2'-bipyridin]-3-yl)imidazo[1,2-a]pyridine-3-carbonitrile

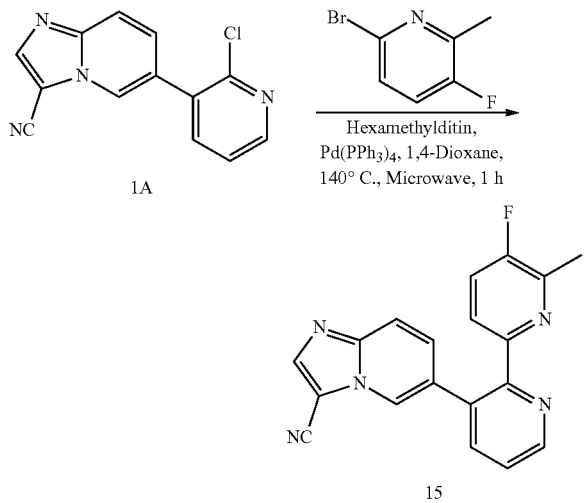

15

To a solution of compound 1A (50 mg, 0.196 mmol) and 6-bromo-3-fluoro-2-methylpyridine (37.3 mg, 0.196 mmol) in 1,4-dioxane (2 mL) was added hexamethylditin (0.041 mL, 0.196 mmol). The solution was degassed with argon and then Pd(PPh$_3$)$_4$ (22.69 mg, 0.020 mmol) was added. The reaction mixture was stirred at 140° C. for 1 h in a CEM microwave instrument. The reaction mixture was cooled, filtered off and the filtrate was evaporated under reduced pressure. The crude residue was purified by preparative HPLC (Method N) to yield 6-(5'-fluoro-6'-methyl-[2,2'-bipyridin]-3-yl)imidazo[1,2-a]pyridine-3-carbonitrile 15 (15.9 mg, 0.047 mmol, 24.1% yield). LCMS: m/z=330.1 [M+H]$^+$; ret. time 1.28 min; condition C. $^1$H NMR (400 MHz, DMSO-d$_6$) δ ppm 8.76 (dd, J=4.6, 1.7 Hz, 1H), 8.58 (dd, J=1.7, 1.0 Hz, 1H), 8.48-8.44 (m, 1H), 8.07 (dd, J=7.7, 1.6 Hz, 1H), 7.80 (dd, J=8.6, 3.7 Hz, 1H), 7.73-7.65 (m, 2H), 7.61 (dd, J=7.8, 4.6 Hz, 1H), 7.23 (dd, J=9.3, 1.7 Hz, 1H), 2.07 (d, J=2.9 Hz, 3H).

Scheme 4 (Method D): Compound 16: 6-(4'-fluoro-[2,2'-bipyridin]-3-yl)imidazo[1,2-a]pyridine-3-carbonitrile

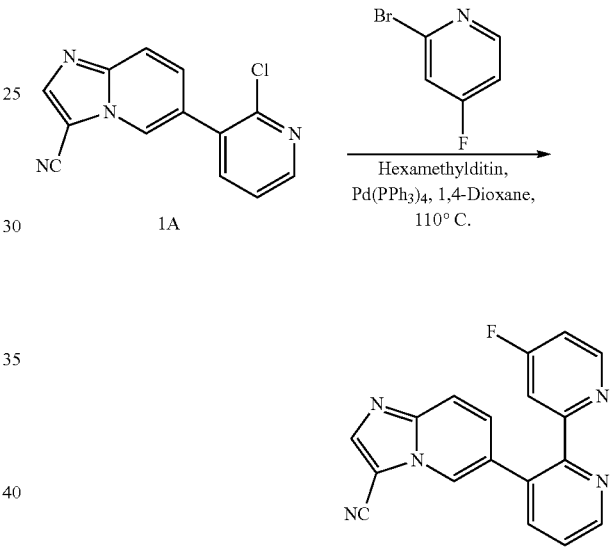

16

To a stirred solution of 2-bromo-4-fluoropyridine (0.3 g, 1.71 mmol) in 1,4-dioxane (5 mL) was added hexamethylditin (0.43 mL, 2.1 mmol). The reaction mixture was purged with N$_2$ for 10 min. and to it was added Pd(Ph$_3$P)$_4$ (0.20 g, 0.17 mmol). The reaction mixture was purged once again with N$_2$ for another 10 min and heated at 110° C. for 2 h. Then, after cooling to room temperature, compound 1A (0.43 g, 1.71 mmol) was added and the mixture was purged with N$_2$ for 5 min., followed by the addition of Pd(Ph$_3$P)$_4$ (0.2 g, 0.17 mmol). The reaction was again heated at 110° C. for 18 h. The reaction mixture was concentrated under vacuum to give a crude residue, which was purified by preparative HPLC (Condition N) to provide 6-(4'-fluoro-[2,2'-bipyridin]-3-yl)imidazo[1,2-a]pyridine-3-carbonitrile 16 (0.38 mg, 0.89 mmol, 52.3% yield). LC-MS: m/z=317.1 [M+H]$^+$; ret. time 1.41 min; condition C. $^1$H NMR (400 MHz, DMSO-d$_6$) δ ppm 8.93-8.89 (m, 1H), 8.60-8.57 (m, 1H), 8.27-8.19 (m, 3H), 8.03-7.97 (m, 1H), 7.77-7.72 (m, 1H), 7.42-7.37 (m, 1H), 7.34-7.27 (m, 1H).

Scheme 5 (Method E): Compound 17: 6-(6'-methoxy-[2,2'-bipyridin]-3-yl)imidazo[1,2-a]pyridine-3-carbonitrile

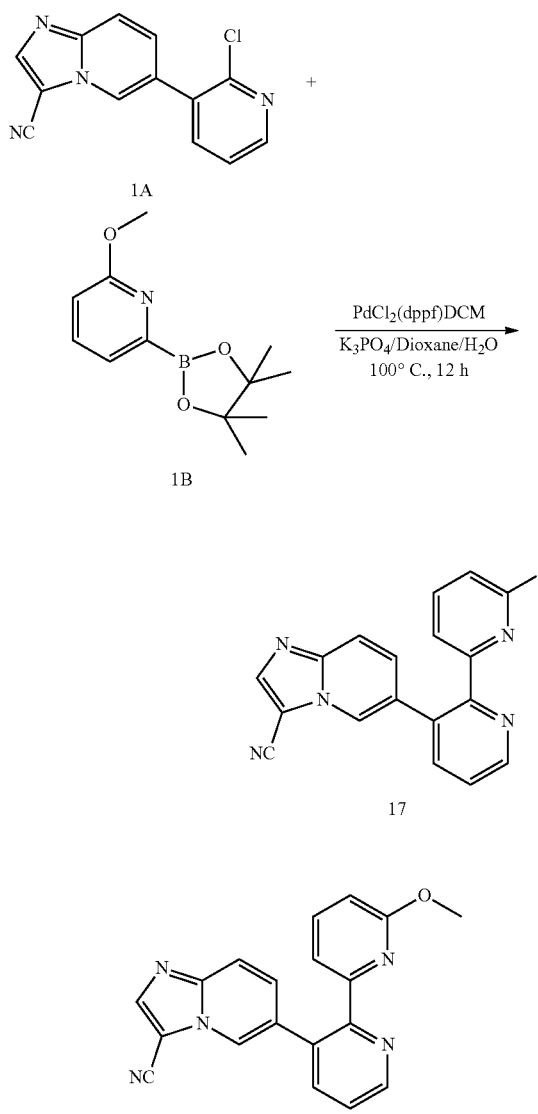

To a stirred solution of compound 1A (0.2 g, 0.79 mmol) and 2-methoxy-6-(4,4,5,5-tetramethyl-1,3,2-dioxaborolan-2-yl)pyridine 1B (0.24 g, 1.02 mmol) in 1,4-dioxane (10 mL)/H$_2$O (2 mL) was added K$_3$PO$_4$ (0.5 g, 2.36 mmol). The reaction mixture was degassed for 3 min. and then to it was added the PdCl$_2$(dppf)-CH$_2$Cl$_2$ adduct (0.032 g, 0.039 mmol), and the resultant mixture was heated at 100° C. for 12 h. The reaction mixture was then filtered through a Celite® pad, the filter cake washed with ethyl acetate and the combined filtrate evaporated under reduced pressure to give the crude compound, which was purified by preparative HPLC (condition N) to yield 6-(6'-methoxy-[2,2'-bipyridin]-3-yl)imidazo[1,2-a]pyridine-3-carbonitrile 17 (0.2 mg, 0.054 mmol, 68.5% yield). LCMS: m/z=328.1 [M+H]$^+$; ret. time 1.49 min; condition C. $^1$H NMR (400 MHz, DMSO-d$_6$) δ ppm 8.78 (dd, J=4.6, 1.7 Hz, 1H), 8.63 (dd, J=1.7, 1.0 Hz, 1H), 8.48 (s, 1H), 8.07 (dd, J=7.7, 1.6 Hz, 1H), 7.86-7.70 (m, 2H), 7.66-7.55 (m, 2H), 7.25 (dd, J=9.2, 1.8 Hz, 1H), 6.79-6.66 (m, 1H), 3.04 (s, 3H).

General Experimental Procedures for Hydrolysis of Nitrile to Amide

Scheme 6 (Method A): Compound 18: 6-(6'-trifluoromethyl-[2,2'-bipyridin]-3-yl)imidazo[1,2-a]pyridine-3-carboxamide

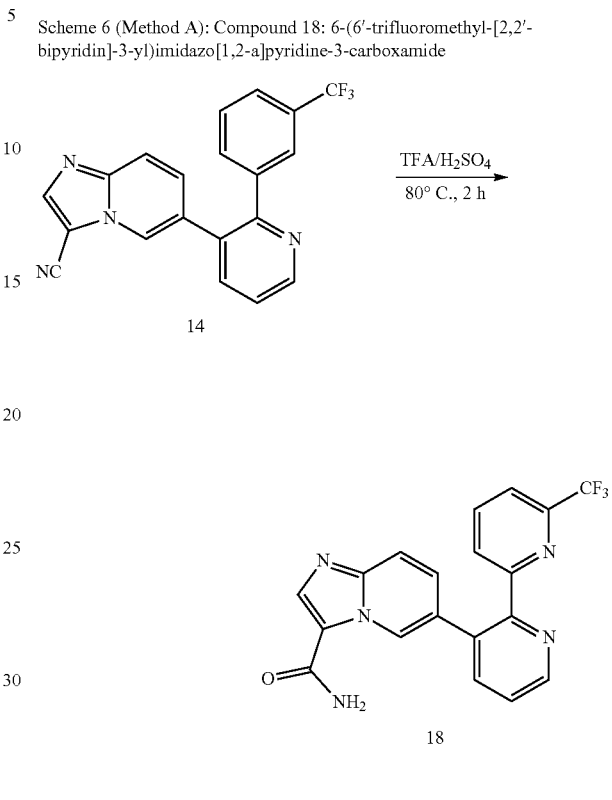

Compound 14 was added to a stirred solution of H$_2$SO$_4$ (0.066 mL, 1.232 mmol) in TFA (0.274 mL, 3.56 mmol) at room temperature and the resultant mixture was stirred for 10 min. Then it was heated at 85° C. for 2 h. After that, ice-cold water (5 mL) was added and the solution was basified with 10% aq. NaOH solution. The precipitated solid was filtered and purified by preparative HPLC (Condition H) to furnish 6-(6'-(trifluoromethyl)-[2,2'-bipyridin]-3-yl)imidazo[1,2-a]pyridine-3-carboxamide 18 (50 mg, 0.130 mmol, 47.6% yield) as an off-white solid. LCMS: m/z=384.0 [M+H]$^+$; ret. time 1.82 min; condition E. $^1$H NMR (400 MHz, DMSO-d$_6$) δ ppm 9.32-9.36 (m, 1H) 8.80-8.84 (m, 1H) 8.31-8.34 (m, 1H) 8.22-8.27 (m, 2H) 8.15-8.21 (m, 1H) 8.04-8.09 (m, 1H) 7.76-7.81 (m, 1H) 7.63-7.71 (m, 1H) 7.54-7.59 (m, 1H) 7.10-7.17 (m, 2H).

Scheme 7 (Method B): Compound 19: 6-(5'-fluoro-6'-methyl-[2,2'-bipyridin]-3-yl)imidazo[1,2-a]pyridine-3-carboxamide

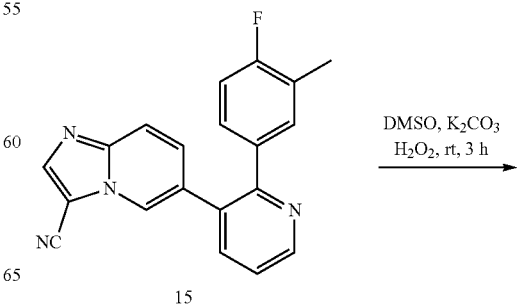

-continued

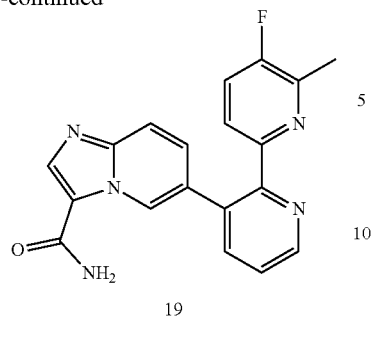

19

In a 25 mL round bottom flask was added 15 (140 mg, 0.425 mmol) and K$_2$CO$_3$ (176 mg, 1.275 mmol) in DMSO (2 mL). The mixture was cooled to 0° C. and H$_2$O$_2$ (0.977 mL, 12.75 mmol, 30% v/v) was added drop-wise. The reaction mixture was brought to room temperature and stirred for another 3 h. The reaction mixture was then diluted with ice water and the solid obtained was filtered, washed with water and dried to yield 6-(5'-fluoro-6'-methyl-[2,2'-bipyridin]-3-yl)imidazo[1,2-a]pyridine-3-carboxamide 19 (73 mg, 0.205 mmol, 48.2% yield) as an off-white solid. LCMS: m/z 348.2 [M+H]$^+$; ret. time 1.34 min; condition E. $^1$H NMR (400 MHz, DMSO-d$_6$) δ ppm 9.37 (dd, J=2.0, 1.0 Hz, 1H), 8.74 (dd, J=4.8, 1.8 Hz, 1H), 8.35-8.31 (m, 1H), 8.01-7.87 (m, 2H), 7.76-7.69 (m, 1H), 7.69-7.55 (m, 3H), 7.35 (br. s., 1H), 7.16-7.10 (m, 1H), 2.07 (d, J=3.0 Hz, 3H).

Compound 20: 6-(5'-fluoro-[2,2'-bipyridin]-3-yl)imidazo[1,2-a]pyridine-3-carbonitrile

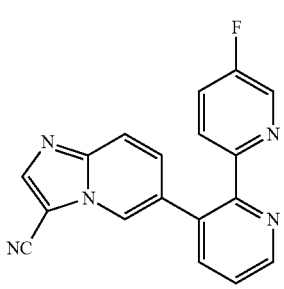 [SMILES: N#Cc1cnc2ccc(-c3cccnc3-c3ccc(F)cn3)cn12]

Compound 20 was synthesized by reacting 1A and 6-bromo-3-fluoropyridine and employing the experimental procedure described in Scheme 3 (Method C). The crude residue was purified by preparative HPLC (condition N) to yield 6-(5'-fluoro-[2,2'-bipyridin]-3-yl)imidazo[1,2-a]pyridine-3-carbonitrile 20 (14 mg, 0.044 mmol, 34.7% yield). LCMS: m/z=316.1 [M+H]$^+$; ret. time 1.49 min; condition C. $^1$H NMR (400 MHz, DMSO-d$_6$) δ ppm 8.76 (dd, J=4.6, 1.7 Hz, 1H), 8.60 (dd, J=1.7, 1.0 Hz, 1H), 8.45 (s, 1H), 8.30 (s, 1H), 8.13-8.07 (m, 1H), 8.03-7.95 (m, 1H), 7.87-7.78 (m, 1H), 7.70-7.56 (m, 2H), 7.15 (dd, J=9.3, 2.0 Hz, 1H).

Compound 21: 6-(5'-fluoro-[2,2'-bipyridin]-3-yl)imidazo[1,2-a]pyridine-3-carboxamide

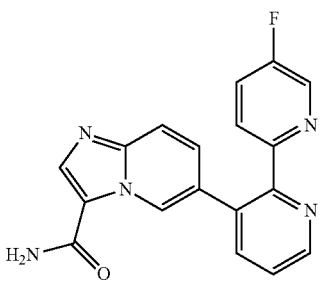 [SMILES: NC(=O)c1cnc2ccc(-c3cccnc3-c3ccc(F)cn3)cn12]

Compound 21 was synthesized from 20 in a manner similar to 19 employing the experimental procedure described in Scheme 7 (Method B). The crude residue was purified by preparative HPLC (condition-N) to yield 6-(5'-fluoro-[2,2'-bipyridin]-3-yl)imidazo[1,2-a]pyridine-3-carboxamide 21 (57.3 mg, 0.172 mmol, 24.8% yield). LCMS m/z=334.1 [M+H]$^+$; ret. time 0.98 min; condition C. $^1$H NMR (400 MHz, DMSO-d$_6$) δ ppm 9.39 (dd, J=1.8, 0.9 Hz, 1H), 8.77-8.72 (m, 1H), 8.34-8.26 (m, 2H), 8.03 (d, J=1.7 Hz, 1H), 7.94 (d, J=0.5 Hz, 2H), 7.82 (td, J=8.7, 2.9 Hz, 1H), 7.65-7.59 (m, 1H), 7.54 (s, 1H), 7.37 (d, J=7.3 Hz, 1H), 7.08 (d, J=2.0 Hz, 1H).

Compound 22: 6-(4'-fluoro-[2,2'-bipyridin]-3-yl)imidazo[1,2-a]pyridine-3-carboxamide

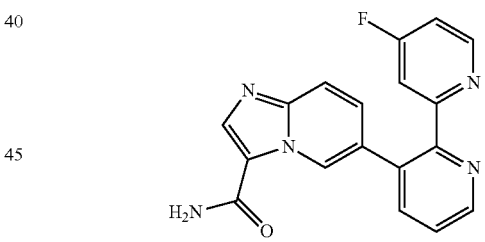

Compound 22 was synthesized from 16 in a manner similar to 19 employing the experimental procedure described in Scheme 7 (Method B). The crude residue was purified by preparative HPLC (condition-N) to yield 6-(4'-fluoro-[2,2'-bipyridin]-3-yl)imidazo[1,2-a]pyridine-3-carboxamide compound 22. (3.9 mg, 0.012 mmol, 0.96% yield). LCMS: m/z=334.1 [M+H]$^+$; ret. time 0.86 min; condition C. $^1$H NMR (400 MHz, DMSO-d$_6$) δ ppm 9.40 (dd, J=2.0, 1.0 Hz, 1H), 8.77 (dd, J=4.8, 1.6 Hz, 1H), 8.34-8.22 (m, 2H), 8.05 (d, J=1.7 Hz, 1H), 7.94 (d, J=4.4 Hz, 1H), 7.78 (d, J=2.7 Hz, 1H), 7.66 (d, J=4.6 Hz, 1H), 7.55 (dd, 1.0 Hz, 1H), 7.38 (br. s., 1H), 7.26 (ddd, J=8.9, 5.7, 2.4 Hz, 1H), 7.11 (dd, J=9.3, 2.0 Hz, 1H).

Compound 23: 6-(6'-(difluoromethyl)-5'-fluoro-[2,2'-bipyridin]-3-yl)imidazo[1,2-a]pyridine-3-carbonitrile

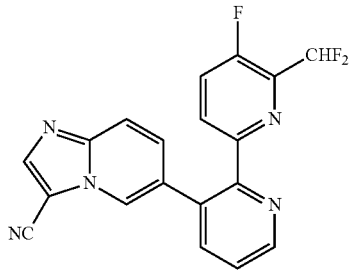 [SMILES: N#Cc1cnc2ccc(-c3cccnc3-c3ccc(F)c(C(F)F)n3)cn12]

Compound 23 was synthesized by reacting 1A and 6-bromo-2-(difluoromethyl)-3-fluoropyridine employing the experimental procedure described in Scheme 4 (Method-D). The crude residue was purified by preparative HPLC (condition-N) to yield 6-(6'-(difluoromethyl)-5'-fluoro-[2,2'-bipyridin]-3-yl)imidazo[1,2-a]pyridine-3-carbonitrile 23 (250 mg, 0.438 mmol, 33% yield). LCMS: m/z=366.1 [M+H]$^+$; ret. time 1.62 min; condition C. $^1$H NMR (400 MHz, DMSO-d$_6$) δ ppm 8.79 (dd, J=4.8, 1.6 Hz, 1H), 8.60 (d, J=1.0 Hz, 1H), 8.45 (s, 1H), 8.24 (dd, J=8.9, 3.8 Hz, 1H), 8.12-8.06 (m, 1H), 8.05-7.97 (m, 1H), 7.69-7.57 (m, 2H), 7.21 (dd, J=9.3, 1.7 Hz, 1H), 6.85-6.55 (m, 1H).

Compound 24: 6-(6'-(difluoromethyl)-5'-fluoro-[2,2'-bipyridin]-3-yl)imidazo[1,2-a]pyridine-3-carboxamide

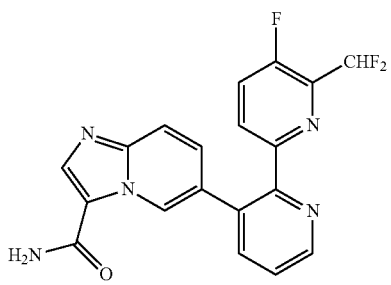 [SMILES: NC(=O)c1cnc2ccc(-c3cccnc3-c3ccc(F)c(C(F)F)n3)cn12]

Compound 24 was synthesized from 23 in a manner similar to 19 employing the experimental procedure described in Scheme 7 (Method B). The crude residue was purified by preparative HPLC (condition-N) to yield 6-(6'-(difluoromethyl)-5'-fluoro-[2,2'-bipyridin]-3-yl)imidazo[1,2-a]pyridine-3-carboxamide 24. (37.6 mg, 0.098 mmol, 25.6% yield). LCMS m/z=384.1 [M+H]$^+$; ret. time 1.24 min; condition C. $^1$H NMR (400 MHz, DMSO-d$_6$) δ ppm 9.66-9.58 (m, 1H), 9.06 (d, J=1.5 Hz, 1H), 8.59 (s, 1H), 8.40 (d, J=3.9 Hz, 1H), 8.33-8.22 (m, 2H), 8.20-8.09 (m, 1H), 7.93 (d, J=7.8 Hz, 1H), 7.83 (dd, J=9.3, 0.7 Hz, 1H), 7.66-7.55 (m, 1H), 7.41 (dd, J=9.2, 1.8 Hz, 1H), 7.13-6.96 (m, 1H).

Compound 25: methyl 3'-(3-cyanoimidazo[1,2-a]pyridin-6-yl)-[2,2'-bipyridine]-5-carboxylate

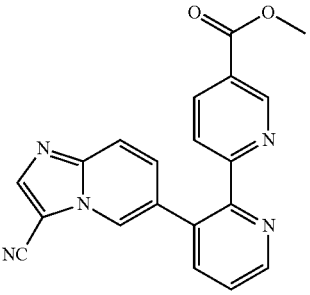

Compound 25 was synthesized by reacting 1A and methyl 6-bromonicotinate employing the experimental procedure described in Scheme 4 (Method-D). The crude residue was purified by preparative HPLC (condition-N) to yield methyl 3'-(3-cyanoimidazo[1,2-a]pyridin-6-yl)-[2,2'-bipyridine]-5-carboxylate 25 (150 mg, 0.35 mmol, 25.2% yield). LCMS m/z=356.2 [M+H]$^+$; ret. time 1.14 min; condition C. $^1$H NMR (400 MHz, DMSO-d$_6$) δ 8.81 (dd, 1.5 Hz, 1H), 8.78-8.73 (m, 1H), 8.68-8.62 (m, 1H), 8.47 (s, 1H), 8.40 (dd, J=8.3, 2.3 Hz, 1H), 8.19-8.13 (m, 1H), 8.11-8.06 (m, 1H), 7.71-7.62 (m, 2H), 7.19-7.12 (m, 1H), 3.86 (s, 3H).

Compounds 26 and 27: methyl 3'-(3-carbamoylimidazo[1,2-a]pyridin-6-yl)-[2,2'-bipyridine]-5-carboxylate and 3'-(3-carbamoylimidazo[1,2-a]pyridin-6-yl)-[2,2'-bipyridine]-5-carboxylic acid

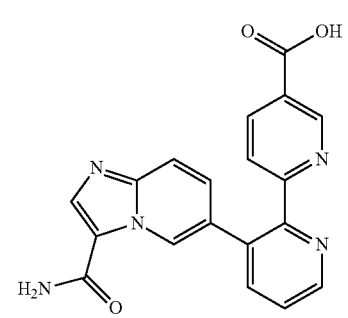

Compounds 26 and 27 were obtained from 25 when employing experimental procedure similar to the synthesis of 19 as described in Scheme 7 (Method B). The crude residue was purified by preparative HPLC (condition-N) to yield methyl 3'-(3-carbamoylimidazo[1,2-a]pyridin-6-yl)-

[2,2'-bipyridine]-5-carboxylate 26 (4 mg, 10.71 μmol, 3.8% yield) and 3'-(3-carbamoylimidazo[1,2-a]pyridin-6-yl)-[2,2'-bipyridine]-5-carboxylic acid 27 (20.1 mg, 0.056 mmol, 19.9% yield). Analysis of 26: LCMS: m/z=374.1 [M+H]+; ret. time 0.88 min; condition C. ¹H NMR (400 MHz, DMSO-d₆) δ ppm 9.70-9.67 (m, 1H), 9.08-9.02 (m, 2H), 8.66-8.62 (m, 1H), 8.60 (s, 1H), 8.36-8.27 (m, 2H), 8.25-8.19 (m, 1H), 7.94 (dd, J=7.8, 4.6 Hz, 1H), 7.82 (s, 1H), 7.65 (br. s., 1H), 7.33 (dd, J=9.0, 1.7 Hz, 1H), 4.12 (s, 3H). Analysis of 27: LCMS m/z=360.1 [M+H]+; ret. time 0.57 min; condition C. ¹H NMR (400 MHz, DMSO-d₆) δ ppm 13.68 (br. s., 1H), 9.72-9.64 (m, 1H), 9.09-8.97 (m, 2H), 8.62 (d, J=2.2 Hz, 2H), 8.35-8.18 (m, 3H), 7.93 (dd, J=7.7, 4.8 Hz, 1H), 7.81 (d, J=9.0 Hz, 1H), 7.66 (br. s., 1H), 7.32 (dd, J=9.2, 1.8 Hz, 1H).

Compound 28: 6-(6'-(difluoromethyl)-[2,2'-bipyridin]-3-yl)imidazo[1,2-a]pyridine-3-carbonitrile

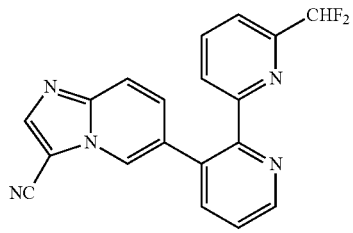 [SMILES: N#Cc1cnc2ccc(-c3cccnc3-c3cccc(C(F)F)n3)cn12]

Compound 28 was synthesized by reacting 1A and 2-bromo-6-(difluoromethyl)pyridine employing the experimental procedure described in Scheme 4 (Method-D). The crude residue was purified by preparative HPLC (method-N) to yield 6-(6'-(difluoromethyl)-[2,2'-bipyridin]-3-yl)imidazo[1,2-a]pyridine-3-carbonitrile 28 (0.22 g, 0.633 mmol, 81% yield) as a yellow solid. LCMS: m/z=348.1 [M+H]+; ret. time 1.35 min; conditions C. ¹H NMR (400 MHz, DMSO-d₆) δ ppm 8.79-8.83 (m, 1H) 8.53-8.57 (m, 1H) 8.41-8.47 (m, 1H) 8.07-8.13 (m, 3H) 7.56-7.72 (m, 3H) 7.18-7.24 (m, 1H) 6.33-6.66 (m, 1H).

Compound 29: 6-(6'-(difluoromethyl)-[2,2'-bipyridin]-3-yl)imidazo[1,2-a]pyridine-3-carboxamide

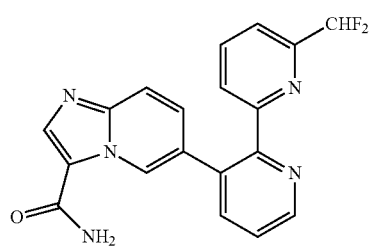 [SMILES: NC(=O)c1cnc2ccc(-c3cccnc3-c3cccc(C(F)F)n3)cn12]

Compound 29 was synthesized from 28 in a manner similar to 18 employing the experimental procedure described in Scheme 6 (Method A). The crude residue was purified by preparative HPLC (condition-H) to yield 6-(6'-(difluoromethyl)-[2,2'-bipyridin]-3-yl)imidazo[1,2-a]pyridine-3-carboxamide 29 (45 mg, 0.123 mmol, 28.5% yield) as an off-white solid. LCMS m/z=366.2 [M+H]+; ret. time 1.58 min; conditions E. ¹H NMR (400 MHz, DMSO-d₆) δ ppm 9.36-9.43 (m, 1H) 8.76-8.82 (m, 1H) 8.32 (s, 1H) 7.98-8.11 (m, 3H) 7.8 (s, 1H) 7.63-7.70 (m, 1H) 7.51-7.62 (m, 2H) 7.4 (s, 1H) 7.09-7.15 (m, 1H) 6.36-6.69 (m, 1H).

Compound 30: 6-(6'-ethyl-[2,2'-bipyridin]-3-yl)imidazo[1,2-a]pyridine-3-carbonitrile

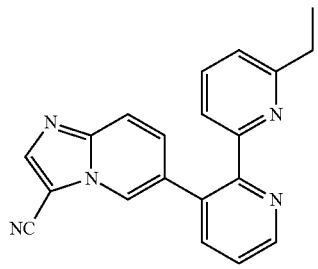 [SMILES: CCc1cccc(-c2ncccc2-c2ccc3ncc(C#N)n3c2)n1]

Compound 30 was synthesized by reacting 1A and 2-bromo-6-ethylpyridine employing the experimental procedure described in Scheme 4 (Method-D). The crude residue was purified by preparative HPLC (condition-N) to yield 6-(6'-ethyl-[2,2'-bipyridin]-3-yl)imidazo[1,2-a]pyridine-3-carbonitrile 30 (2.4 mg, 1% yield). LCMS m/z=326.1 [M+H]+; ret. time 1.46 min; conditions C. ¹H NMR (400 MHz, DMSO-d₆) δ ppm 9.02-9.05 (m, 1H) 8.75-8.78 (m, 1H) 8.70-8.72 (m, 1H) 8.31-8.36 (m, 1H) 8.04-8.08 (m, 2H) 7.94-7.99 (m, 1H) 7.85-7.90 (m, 1H) 7.49-7.52 (m, 1H) 7.41-7.44 (m, 1H) 2.57-2.66 (m, 2H) 0.76-0.83 (m, 3H).

Compound 31: 6-(6'-isopropyl-[2,2'-bipyridin]-3-yl)imidazo[1,2-a]pyridine-3-carbonitrile

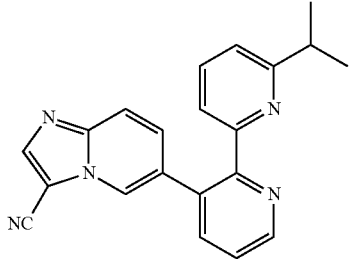 [SMILES: CC(C)c1cccc(-c2ncccc2-c2ccc3ncc(C#N)n3c2)n1]

Compound 31 was synthesized by reacting 1A and 2-bromo-6-isopropylpyridine employing the experimental procedure described in Scheme-2 (Method B). The crude residue was purified by preparative HPLC (condition-N) to yield 6-(6'-isopropyl-[2,2'-bipyridin]-3-yl)imidazo[1,2-a]pyridine-3-carbonitrile 31 (150 mg, 4.4 mmol, 45% yield) as a pale yellow solid. LCMS: m/z=340.1 [M+H]+; ret. time 1.58 min; condition C. ¹H NMR (400 MHz, DMSO-d₆) δ ppm 8.76-8.80 (m, 1H), 8.43-8.50 (m, 2H), 8.05-8.11 (m, 1H), 7.83-7.88 (m, 2H), 7.70-7.75 (m, 1H), 7.59-7.66 (m, 1H), 7.26 (dd, J=1.76, 9.29 Hz, 1H), 7.19 (dd, J=2.76, 5.77 Hz, 1H), 2.68 (td, J=1.63, 3.76 Hz, 1H), 0.64 (d, J=7.03 Hz, 6H).

Compound 32: 6-(6'-isopropyl-[2,2'-bipyridin]-3-yl)imidazo[1,2-a]pyridine-3-carboxamide

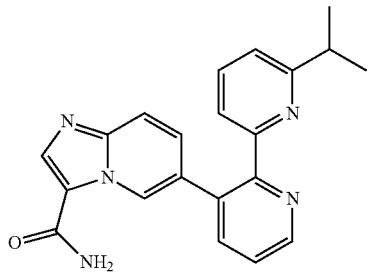

Compound 32 was synthesized from 31 in a manner similar to 19 employing the experimental procedure described in Scheme 7 (Method B). The crude residue was purified by preparative HPLC (condition-N) to yield 6-(6'-isopropyl-[2,2'-bipyridin]-3-yl)imidazo[1,2-a]pyridine-3-carboxamide 32 (59.7 mg, 0.164 mmol, 55.6% yield) as a pale yellow solid. LCMS: m/z=358.2 [M+H]$^+$; ret. time 1.15 min; condition C. $^1$H NMR (400 MHz, DMSO-d$_6$) δ ppm 9.40 (d, J=6.85 Hz, 6H), 7.44-7.36 (m, 1H), 2.96-2.87 (m, 2H), 2.49-2.38 (m, 2H), 2.28-2.18 (m, 2H), 2.03 (dd, J=1.59, 7.70 Hz, 1H), 1.71 (s, 1H), 1.26 (dd, J=1.71, 4.65 Hz, 1H), 0.69 (dd, J=0.98, 1.71 Hz, 1H).

Compound 33: 6-(6'-methoxy-[2,2'-bipyridin]-3-yl)imidazo[1,2-a]pyridine-3-carboxamide

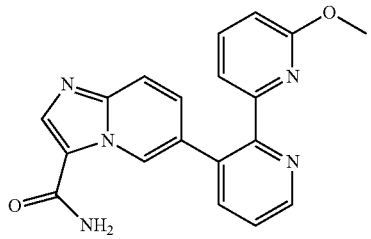

Compound 33 was synthesized from 17 in a manner similar to 19 employing the experimental procedure described in Scheme 7 (Method B). The crude residue was purified by preparative HPLC (condition-N) to yield 6-(6'-methoxy-[2,2'-bipyridin]-3-yl)imidazo[1,2-a]pyridine-3-carboxamide 33 (53 mg, 0.150 mmol, 24.6% yield) as a pale yellow solid. LCMS: m/z=346.1 [M+H]$^+$; ret. time 1.06 min; condition C. $^1$H NMR (400 MHz, DMSO-d$_6$) δ ppm 9.42 (dd, J=1.8, 0.9 Hz, 1H), 8.78-8.70 (m, 1H), 8.34 (s, 1H), 8.00-7.71 (m, 3H), 7.63-7.52 (m, 3H), 7.34 (br. s., 1H), 7.15 (dd, J=9.2, 1.8 Hz, 1H), 6.70 (dd, J=8.3, 0.7 Hz, 1H), 3.03 (s, 3H).

Compound 34: 6-(6'-cyclopropyl-[2,2'-bipyridin]-3-yl)imidazo[1,2-a]pyridine-3-carbonitrile

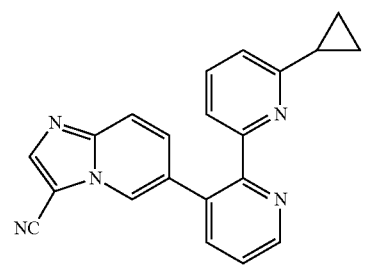 [SMILES: N#Cc1cnc2ccc(-c3cccnc3-c3cccc(C4CC4)n3)cn12]

Compound 34 was synthesized by reacting 1A and 2-bromo-6-cyclopropylpyridine the employing experimental procedure described in Scheme-2 (Method B). The crude residue was purified by preparative HPLC (condition-F) to yield 6-(6'-cyclopropyl-[2,2'-bipyridin]-3-yl)imidazo[1,2-a]pyridine-3-carbonitrile 34 (100 mg, 2.96 mmol, 30.2% yield) as a pale yellow solid. LCMS: m/z=338.1 [M+H]$^+$; ret. time 1.65 min; condition C. $^1$H NMR (400 MHz, DMSO-d$_6$) δ ppm 8.76 (dd, 1.5 Hz, 1H), 8.54 (s, 1H), 8.48 (s, 1H), 8.04 (dd, J=7.7, 1.6 Hz, 1H), 7.78-7.74 (m, 2H), 7.71 (d, J=9.3 Hz, 1H), 7.60 (dd, J=7.8, 4.6 Hz, 1H), 7.27-7.22 (m, 1H), 7.16 (dd, J=9.3, 1.7 Hz, 1H), 1.82 (ddd, J=12.5, 8.3, 4.6 Hz, 1H), 0.48-0.41 (m, 2H), 0.03-0.08 (m, 2H).

Compound 35: 6-(6'-cyclopropyl-[2,2'-bipyridin]-3-yl)imidazo[1,2-a]pyridine-3-carboxamide

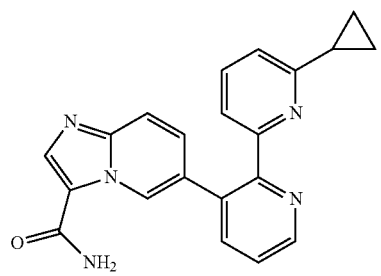 [SMILES: NC(=O)c1cnc2ccc(-c3cccnc3-c3cccc(C4CC4)n3)cn12]

Compound 35 was synthesized from 34 in a manner similar to 19 employing the experimental procedure described in Scheme 7 (Method B). The crude residue was purified by preparative HPLC (condition-N) to yield 6-(6'-cyclopropyl-[2,2'-bipyridin]-3-yl)imidazo[1,2-a]pyridine-3-carboxamide 35 (16.3 mg, 0.045 mmol, 30.6% yield) as a pale yellow solid. LCMS: m/z=356.1 [M+H]$^+$; ret. time 1.29 min; condition C. $^1$H NMR (400 MHz, DMSO-d$_6$) δ ppm 9.61 (d, J=0.7 Hz, 1H), 9.00 (dd, J=4.8, 1.6 Hz, 1H), 8.61 (s, 1H), 8.21 (dd, J=7.7, 1.6 Hz, 2H), 8.06-7.92 (m, 2H), 7.90-7.75 (m, 2H), 7.60 (br. s., 1H), 7.53-7.41 (m, 1H), 7.29 (dd, J=9.3, 1.7 Hz, 1H), 2.13-1.94 (m, 1H), 0.72-0.56 (m, 2H), 0.22-0.13 (m, 2H).

Compound 36: 6-(6'-fluoro-[2,2'-bipyridin]-3-yl)imidazo[1,2-a]pyridine-3-carbonitrile

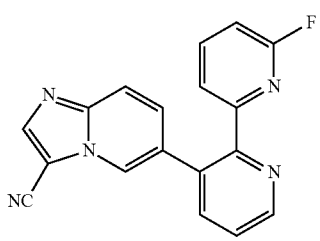

Compound 36 was synthesized by reacting 1A and 6-bromo-2-fluoropyridine employing experimental procedure described in Scheme-4 (Method D). The crude residue was purified by preparative HPLC (condition-N) to yield 6-(6'-fluoro-[2,2'-bipyridin]-3-yl)imidazo[1,2-a]pyridine-3-carbonitrile 36 (130 mg, 4.12 mmol, 52.4% yield) as a pale yellow solid. LCMS: m/z=316.1 [M+H]$^+$; ret. time 1.35 min; condition C. $^1$H NMR (400 MHz, DMSO-d$_6$) δ ppm 9.06 (dd, J=4.8, 1.6 Hz, 1H), 8.92 (s, 1H), 8.75 (s, 1H), 8.42-8.29 (m, 2H), 8.11 (dd, J=7.6, 2.2 Hz, 1H), 7.98 (d, J=9.3 Hz, 1H), 7.92 (dd, J=7.8, 4.9 Hz, 1H), 7.48 (dd, J=9.3, 1.7 Hz, 1H), 7.41 (dd, J=7.9, 2.6 Hz, 1H).

Compound 37: 6-(6'-fluoro-[2,2'-bipyridin]-3-yl)imidazo[1,2-a]pyridine-3-carboxamide

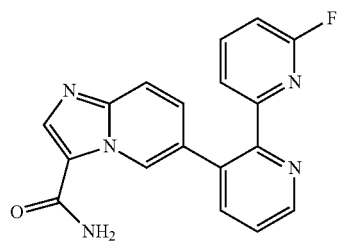 [SMILES: NC(=O)c1cnc2ccc(-c3cccnc3-c3cccc(F)n3)cn12]

Compound 37 was synthesized from 36 in a manner similar to 19 employing the experimental procedure described in Scheme 7 (Method B). The crude residue was purified by preparative HPLC (condition-N) to 6-(6'-fluoro-[2,2'-bipyridin]-3-yl)imidazo[1,2-a]pyridine-3-carboxamide 37 (13.5 mg, 0.040 mmol, 12.6% yield) as a pale yellow solid. LCMS: m/z=334.1 [M+H]$^+$; ret. time 1.06 min; condition C. $^1$H NMR (400 MHz, DMSO-d$_6$) δ ppm 9.39 (dd, J=0.98, 1.96 Hz, 1H), 8.77 (dd, J=1.59, 4.77 Hz, 1H), 8.34 (s, 1H), 8.01-8.09 (m, 2H), 7.89-7.99 (m, 1H), 7.77 (dd, J=2.32, 7.21 Hz, 1H), 7.56-7.68 (m, 2H), 7.36 (br. s., 1H), 7.06-7.15 (m, 2H).

Compound 38: 6-(6'-(benzyloxy)-[2,2'-bipyridin]-3-yl)imidazo[1,2-a]pyridine-3-carbonitrile

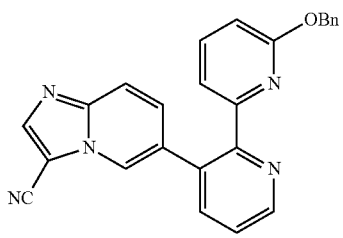 [SMILES: N#Cc1cnc2ccc(-c3cccnc3-c3cccc(OCc4ccccc4)n3)cn12]

Compound 38 was synthesized by reacting 1A and 2-(benzyloxy)-6-bromopyridine employing experimental procedure described in Scheme-2 (Method B). The crude residue was purified by preparative HPLC (condition-N) to yield 6-(6'-(benzyloxy)-[2,2'-bipyridin]-3-yl)imidazo[1,2-a]pyridine-3-carbonitrile 38 (24.1 mg, 0.06 mmol, 15.21%). LCMS m/z=404.1 [M+H]$^+$; ret. time 1.97; condition C. $^1$H NMR (400 MHz, DMSO-d$_6$) δ ppm 8.78 (dd, J=4.9, 1.7 Hz, 1H), 8.66 (dd, J=1.7, 1.0 Hz, 1H), 8.50 (s, 1H), 8.07 (dd, J=7.7, 1.6 Hz, 1H), 7.86 (dd, J=8.1, 7.3 Hz, 1H), 7.71-7.79 (m, 2H), 7.60-7.63 (m, 1H), 7.29-7.20 (m, 4H), 6.95-6.87 (m, 2H), 6.81 (dd, J=8.3, 0.7 Hz, 1H), 4.31 (s, 2H).

Compound 39: 6-([2,2'-bipyridin]-3-yl)imidazo[1,2-a]pyridine-3-carboxamide

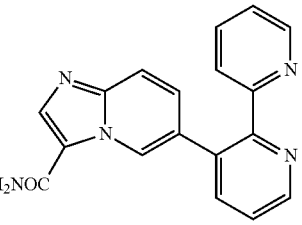

Compound 39 was synthesized from 13 in a manner similar to 18 employing the experimental procedure described in Scheme-6 (Method A). The crude compound was purified by preparative HPLC (condition-H) to yield 6-([2,2'-bipyridin]-3-yl)imidazo[1,2-a]pyridine-3-carbonoxamide 39 (14.3 g, 0.045 mmol, 13.3% yield). LCMS: m/z=316.2 [M+H]$^+$; ret. time 1.22 min; condition E. $^1$H NMR (400 MHz, DMSO-d$_6$) δ ppm 9.40 (d, J=0.8 Hz, 1H), 8.75 (dd, J=1.6, 4.8 Hz, 1H), 8.32 (s, 1H), 8.27 (d, J=4.4 Hz, 1H), 8.01 (dd, J=1.6, 7.6 Hz, 1H), 7.95 (bs, 1H), 7.83-7.90 (m, 2H), 7.61 (dd, J=4.8, 8.0 Hz, 1H), 7.52 (d, J=9.2 Hz, 1H), 7.35 (bs, 1H), 7.28-7.31 (m, 1H), 7.03 (dd, J=2.0, 9.2 Hz, 1H)

Compound 40: 6-(6'-acetyl-[2,2'-bipyridin]-3-yl)imidazo[1,2-a]pyridine-3-carbonitrile

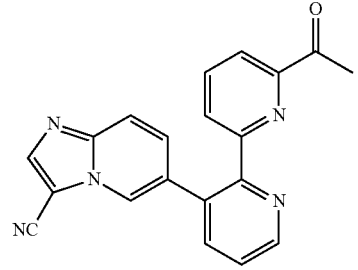 [SMILES: CC(=O)c1cccc(-c2ncccc2-c2ccc3ncc(C#N)n3c2)n1]

Compound 40 was synthesized by reacting 1A and 1-(6-bromopyridin-2-yl)ethanone employing the experimental procedure described in Scheme-2 (Method B). The crude residue was purified by preparative HPLC (condition-N) to yield 6-(6'-acetyl-[2,2'-bipyridin]-3-yl)imidazo[1,2-a]pyridine-3-carbonitrile 40 (6.5 mg, 0.019 mmol, 4.9%). LCMS: m/z=340.1 [M+H]$^+$; ret. time 1.38; condition C. $^1$H NMR (400 MHz, DMSO-d$_6$) δ ppm 8.83 (dd, J=4.6, 1.7 Hz, 1H), 8.73 (dd, J=1.7, 1.0 Hz, 1H), 8.47 (s, 1H), 8.33 (dd, J=7.8, 1.0 Hz, 1H), 8.16-8.10 (m, 2H), 7.86 (dd, J=7.7, 1.1 Hz, 1H), 7.73-7.65 (m, 2H), 7.24 (dd, J=9.3, 1.7 Hz, 1H), 1.72 (s, 3H).

Scheme-8:

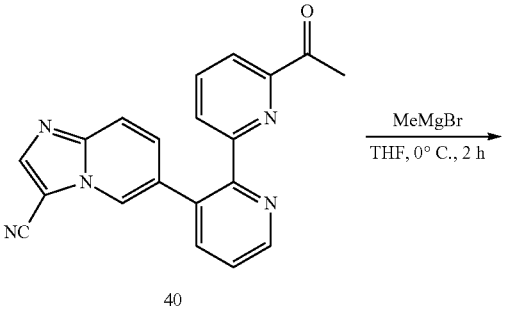

40

151

-continued

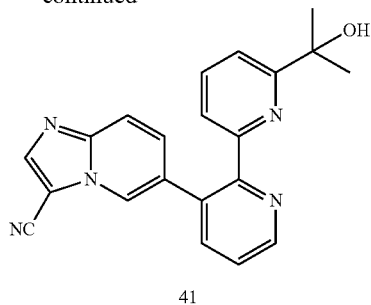

41

Compound 41: 6-(6'-6-(6'-(2-hydroxypropan-2-yl)-[2,2'-bipyridin]-3-yl)imidazo[1,2-a]pyridine-3-carbonitrile To a solution of compound 40 (0.09 g, 0.265 mmol) in THF (5 mL) at 0° C. was added 3.4M solution of methylmagnesium bromide (0.086 mL, 0.292 mmol) and the reaction was stirred for 2 h. It was then quenched with saturated aq. NH$_4$Cl solution and extracted with ethyl acetate (2×50 mL). The combined organic layer was washed with water, brine, dried over anhydrous sodium sulfate, filtered and the filtrate was concentrated under reduced pressure to afford a crude residue. It was purified by preparative HPLC (Condition N) to yield 6-(6'-6-(6'-(2-hydroxypropan-2-yl)-[2,2'-bipyridin]-3-yl)imidazo[1,2-a]pyridine-3-carbonitrile 41 (7.1 mg, 0.020 mmol, 7.46% yield). LCMS: m/z=356.1 [M+H]$^+$; ret. time 1.05; condition C. $^1$H NMR (400 MHz, DMSO-d$_6$) δ ppm 8.77 (s, 1H), 8.51-8.51 (m, 1H), 8.48 (dd, J=0.92, 1.59 Hz, 1H), 8.05 (d, J=7.76 Hz, 1H), 7.84-7.94 (m, 2H), 7.74-7.77 (m, 1H), 7.50-7.64 (m, 2H), 7.22-7.25 (m, 1H), 1.81 (s, 1H), 0.76 (s, 6H).

Compound 42: 6-(4',6'-dimethyl-[2,2'-bipyridin]-3-yl)imidazo[1,2-a]pyridine-3-carboxamide

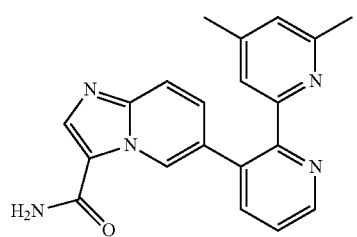 [SMILES: Cc1cc(C)nc(-c2ncccc2-c2ccc3ncc(C(N)=O)n3c2)c1]

Compound 42 was synthesized by reacting 1A and 2-bromo-4,6-dimethylpyridine employing the experimental procedure described in Scheme 4 (Method-D) and then the resultant cyano compound was hydrolyzed similar to 19 employing experimental procedures described in Scheme 7 (Method B). The crude residue was purified by preparative HPLC (condition P) to yield 6-(4',6'-dimethyl-[2,2'-bipyridin]-3-yl)imidazo[1,2-a]pyridine-3-carboxamide 42 (42.6 mg, 0.122 mmol, 39.6% yield). LCMS: m/z=344.2 [M+H]$^+$; ret. time 1.56 min; condition C. $^1$H NMR (400 MHz, DMSO-d$_6$) δ ppm 9.39 (d, J=0.7 Hz, 1H), 8.73 (dd, J=1.5 Hz, 1H), 8.32 (s, 1H), 7.96 (dd, J=7.7, 1.6 Hz, 2H), 7.58 (dd, J=7.7, 4.8 Hz, 1H), 7.55-7.49 (m, 2H), 7.37 (br. s., 1H), 7.12-7.06 (m, 1H), 6.96 (s, 1H), 2.29 (s, 3H), 2.02 (s, 3H).

152

Compound 44: N-(3'-(3-cyanoimidazo[1,2-a]pyridin-6-yl)-[2,2'-bipyridin]-6-yl)methanesulfonamide

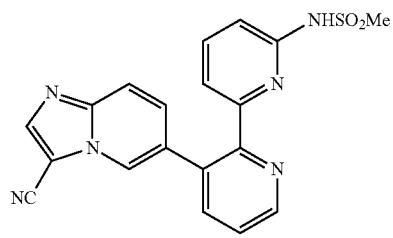

Compound 44 was synthesized by reacting 1A and N-(6-bromopyridin-2-yl)methanesulfonamide [Reference: WO2011141848 A1/Organic & Biomolecular Chemistry (2015), 13(25), 7050-7066] employing experimental procedure described in Scheme-2 (Method B). The crude residue was purified by preparative HPLC (Method: N) to yield N-(3'-(3-cyanoimidazo[1,2-a]pyridin-6-yl)-[2,2'-bipyridin]-6-yl)methanesulfonamide 44 (0.07 g, 0.179 mmol, 22.8% yield) as a yellow solid. LCMS: m/z=391.1 [M+H]$^+$; ret. time 1.03 min; condition C. $^1$H NMR (400 MHz, DMSO-d$_6$) δ ppm 10.31 (s, 1H) 8.68-8.89 (m, 1H) 8.55-8.58 (m, 1H) 8.41-8.44 (m, 1H) 8.08-8.14 (m, 1H) 7.82-7.89 (m, 1H) 7.60-7.67 (m, 2H) 7.55-7.59 (m, 1H) 7.07-7.13 (m, 1H) 6.87-6.92 (m, 1H) 2.72-2.76 (m, 3H).

Scheme 9:

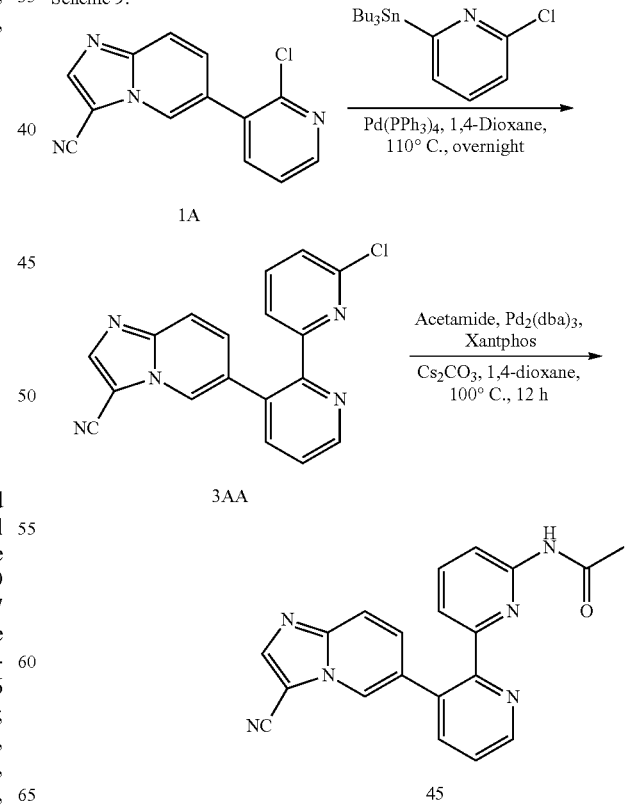

-continued

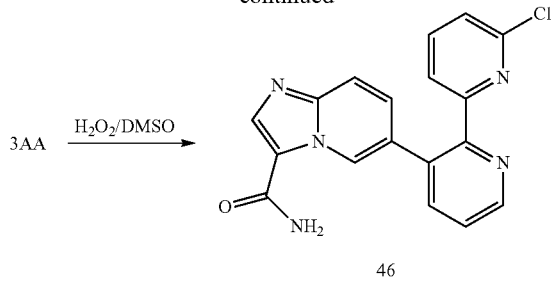

Compound 3AA: 6-(6'-chloro-[2,2'-bipyridin]-3-yl)imidazo[1,2-a]pyridine-3-carbonitrile

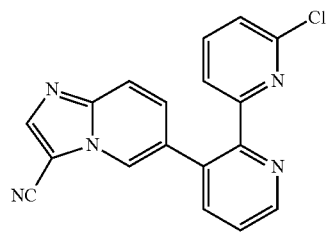 [SMILES: N#Cc1cnc2ccc(-c3cccnc3-c3cccc(Cl)n3)cn12]

Compound 3AA was synthesized by reacting 1A and 2-chloro-6-(tributylstannyl)pyridine employing experimental procedure described in Scheme 1 (Method A). The crude residue was purified by silica gel chromatography (40 g RediSep® column, eluted with a gradient of 20-30% ethyl acetate in petroleum ether) to yield 6-(6'-chloro-[2,2'-bipyridin]-3-yl)imidazo[1,2-a]pyridine-3-carbonitrile 3AA (0.25 g, 0.460 mmol, 29.3% yield) as colorless liquid. LCMS: m/z=332.2 [M+H]⁺; ret. time 2.46 min; condition E.

Compound 45: N-(3'-(3-cyanoimidazo[1,2-a]pyridin-6-yl)-[2,2'-bipyridin]-6-yl)acetamide

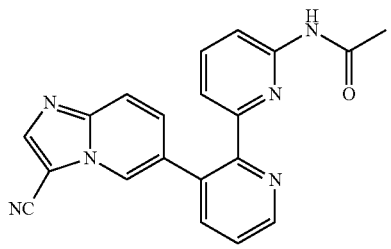 [SMILES: CC(=O)Nc1cccc(-c2ncccc2-c2ccc3ncc(C#N)n3c2)n1]

Tris(dibenzylideneacetone)dipalladium(O)-(27.6 mg, 0.030 mmol) was added to a stirred solution of 6-(6'-chloro-[2,2'-bipyridin]-3-yl)imidazo[1,2-a]pyridine-3-carbonitrile 3AA (100 mg, 0.301 mmol), acetamide (26.7 mg, 0.452 mmol), 4,5-bis(diphenylphosphino)-9,9-dimethylxanthaneacetamide (34.9 mg, 0.060 mmol) and Cs₂CO₃ (196 mg, 0.603 mmol) in 1,4-dioxane (10 mL). The reaction mixture was heated at 100° C. for 12 h. The mixture was cooled to room temperature and filtered through a Celite® pad, the filter cake was washed with ethyl acetate and the combined filtrate was evaporated under reduced pressure to give crude compound, which was purified by preparative HPLC (condition N) to yield N-(3'-(3-cyanoimidazo[1,2-a]pyridin-6-yl)-[2,2'-bipyridin]-6-yl)acetamide 45 (17.4 mg, 0.048 mmol, 15.8% yield). LCMS: m/z=355.1 [M+H]⁺; ret. time 1.22 min; condition C. ¹H NMR (400 MHz, DMSO-d₆) δ ppm 10.14 (s, 1H), 8.76 (d, J=4.5 Hz, 1H), 8.66-8.57 (m, 1H), 8.46 (s, 1H), 8.15 (d, J=9.5 Hz, 1H), 8.01 (d, J=8.0 Hz, 1H), 7.79 (d, J=15.6 Hz, 1H), 7.67-7.50 (m, 2H), 7.35 (d, J=7.5 Hz, 1H), 7.12-6.94 (m, 1H), 1.95 (s, 3H).

Compound 46: 6-(6'-chloro-[2,2'-bipyridin]-3-yl)imidazo[1,2-a]pyridine-3-carboxamide

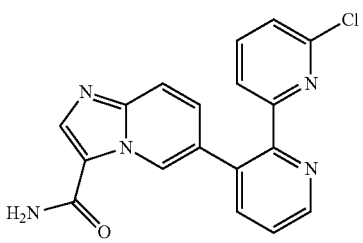 [SMILES: NC(=O)c1cnc2ccc(-c3cccnc3-c3cccc(Cl)n3)cn12]

Compound 46 was synthesized from 3AJ in a manner similar to 19 employing the experimental procedure described in Scheme 7 (Method B). The crude residue was purified by preparative HPLC (condition-H) to yield compound 6-(6'-chloro-[2,2'-bipyridin]-3-yl)imidazo[1,2-a]pyridine-3-carboxamide 46 (7.3 mg, 0.020 mmol, 5.6% yield). LCMS: m/z=350.1 [M+H]⁺; ret. time 1.13 min; condition C. ¹H NMR ¹H NMR (400 MHz, DMSO-d₆) δ 9.38 (d, J=0.7 Hz, 1H), 8.77 (dd, 1.5 Hz, 1H), 8.33 (s, 1H), 8.05-7.97 (m, 1H), 7.95-7.86 (m, 2H), 7.85-7.80 (m, 1H), 7.67-7.61 (m, 2H), 7.58 (s, 1H), 7.42 (dd, J=7.8, 0.7 Hz, 1H), 7.12 (dd, J=9.2, 1.8 Hz, 1H).

Scheme 10:

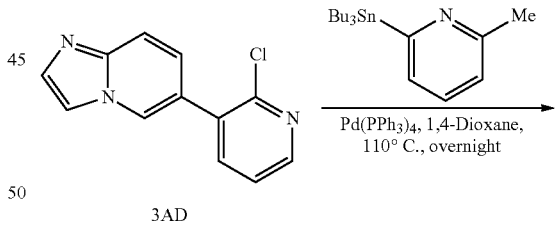

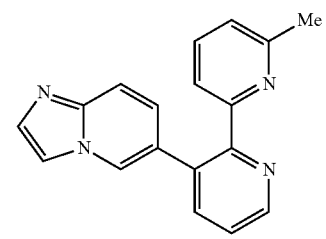 [SMILES: Cc1cccc(-c2ncccc2-c2ccc3nccn3c2)n1]

Compound 47: 6-(6'-methyl-[2,2'-bipyridin]-3-yl)imidazo[1,2-a]pyridine

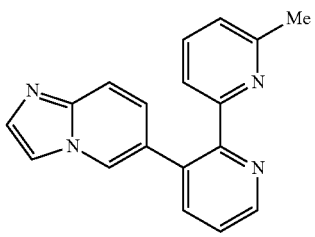

Compound 47 was synthesized by reacting 3AD (Reference: WO 2015157093 A1/WO 2014055955 A1) and 2-methyl-6-(tributylstannyl)pyridine in a manner similar to compound 13 employing the experimental procedure described in Scheme-1 (Method A). The crude residue was purified by preparative HPLC (method: I) to yield 6-(6'-methyl-[2,2'-bipyridin]-3-yl)imidazo[1,2-a]pyridine 47 (17 mg, 0.069 mmol, 15.80% yield). LCMS: m/z=287.1 [M+H]$^+$; ret. time 1.16 min; condition C. $^1$H NMR (400 MHz, DMSO-d$_6$) δ ppm 8.72 (dd, 1.5 Hz, 1H), 8.53 (s, 1H), 7.97 (dd, 1.5 Hz, 1H), 7.89 (s, 1H), 7.75-7.69 (m, 1H), 7.60-7.53 (m, 3H), 7.36 (d, J=9.3 Hz, 1H), 7.15 (d, J=7.6 Hz, 1H), 6.78 (dd, 1.7 Hz, 1H), 2.13 (s, 3H).

Compound 48: 6-(6'-(difluoromethyl)-5'-fluoro-[2,2'-bipyridin]-3-yl)imidazo[1,2-a]pyridine

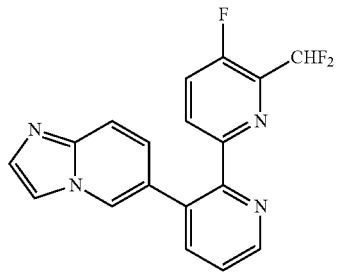 [SMILES: Fc1ccc(-c2ncccc2-c2ccc3nccn3c2)nc1C(F)F]

Compound 48 was synthesized by reacting 3AD and 6-bromo-2-(difluoromethyl)-3-fluoropyridine employing the experimental procedure described in Scheme-2 (Method B). The crude residue was purified by preparative HPLC (method I) to yield 6-(6'-(difluoromethyl)-5'-fluoro-[2,2'-bipyridin]-3-yl)imidazo[1,2-a]pyridine 48 (6.8 mg, 0.020 mmol, 3.3% yield). LCMS: m/z=341.1 [M+H]$^+$; ret. time 1.43 min; condition C. $^1$H NMR (400 MHz, DMSO-d$_6$) δ=8.76 (dd, J=4.6, 1.5 Hz, 1H), 8.56 (s, 1H), 8.10 (dd, J=8.7, 3.8 Hz, 1H), 8.05-7.99 (m, 2H), 7.89 (s, 1H), 7.64 (dd, J=7.7, 4.8 Hz, 1H), 7.56 (s, 1H), 7.42-7.34 (m, 1H), 6.92-6.56 (m, 2H).

Scheme 11:

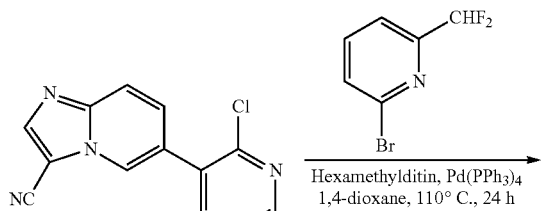

Compound 49: 6-(6'-(difluoromethyl)-[2,2'-bipyridin]-3-yl)imidazo[1,2-b]pyridazine-3-carbonitrile

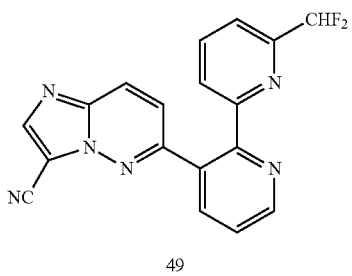

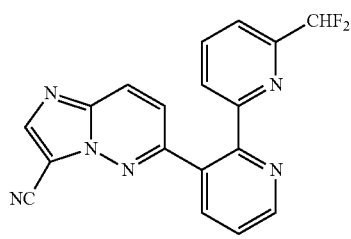 [SMILES: N#Cc1cnc2ccc(-c3cccnc3-c3cccc(C(F)F)n3)nn12]

Compound 49 was synthesized by reacting 4 (reference: WO 2015157093 A1 and WO 2014055955 A1) and 2-bromo-6-(difluoromethyl)pyridine employing the experimental procedure described in Scheme 4 (Method-D). The crude residue was purified by preparative HPLC (condition-H) to yield 6-(6'-(difluoromethyl)-[2,2'-bipyridin]-3-yl)imidazo[1,2-b]pyridazine-3-carbonitrile 49 (242 mg, 0.0604 mmol, 62.9% yield). LCMS: m/z=349.1 [M+H]$^+$; ret. time 1.53 min. condition C. $^1$H NMR (400 MHz, DMSO-d$_6$) δ ppm 8.92 (dd, J=4.6, 1.7 Hz, 1H), 8.36 (dd, J=8.1, 1.0 Hz, 1H), 8.25 (d, J=9.3 Hz, 1H), 8.21-8.18 (m, 2H), 8.16 (t, J=7.8 Hz, 1H), 7.74 (dd, J=7.7, 4.8 Hz, 1H), 7.61 (d, J=7.8 Hz, 1H), 7.43 (d, J=9.5 Hz, 1H), 6.26 (s, 1H).

Scheme-12:

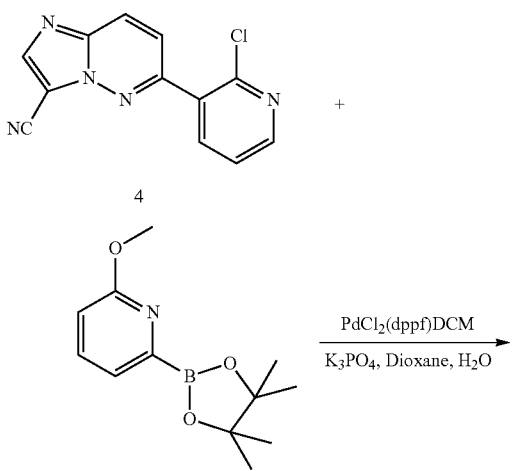

-continued

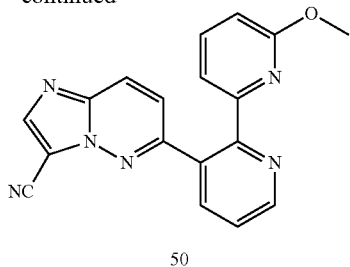

50

Compound 50: 6-(6'-methoxy-[2,2'-bipyridin]-3-yl)imidazo[1,2-b]pyridazine-3-carbonitrile

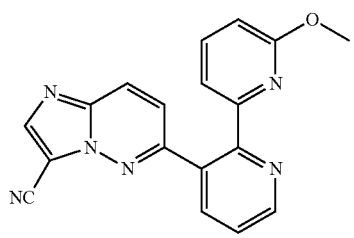 [SMILES: COc1cccc(-c2ncccc2-c2ccc3ncc(C#N)n3n2)n1]

Compound 50 was synthesized by reacting 4 and 2-methoxy-6-(4,4,5,5-tetramethyl-1,3,2-dioxaborolan-2-yl)pyridine employing the experimental procedure described in Scheme-5 (Method E). The crude product was purified by preparative HPLC (condition L) to yield 6-(6'-methoxy-[2,2'-bipyridin]-3-yl)imidazo[1,2-b]pyridazine-3-carbonitrile 50 (125 mg, 0.35 mmol, 44.8% yield). LCMS: m/z=329.2 [M+1]$^+$; ret. time 1.54 min; condition C. $^1$H NMR (400 MHz, DMSO-d$_6$) δ ppm 8.48 (dd, J=4.8, 1.6 Hz, 1H), 8.21 (s, 1H), 7.89 (d, J=9.5 Hz, 2H), 7.77-7.63 (m, 1H), 7.45 (d, J=5.9 Hz, 1H), 7.33-7.21 (m, 1H), 6.98 (d, J=9.3 Hz, 1H), 6.42-6.19 (m, 1H), 2.91 (s, 3H).

Compound 51: 6-(6'-methoxy-[2,2'-bipyridin]-3-yl)imidazo[1,2-b]pyridazine-3-carboxamide

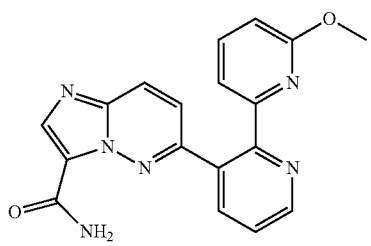 [SMILES: COc1cccc(-c2ncccc2-c2ccc3ncc(C(N)=O)n3n2)n1]

Compound 51 was synthesized from 50 and employing the experimental procedure described in Scheme 6 (Method A). The crude residue was purified by preparative HPLC (condition L) to yield compound 51. (28.9 mg, 0.083 mmol, 27.1% yield). LCMS: m/z=347.2 [M+H]$^+$; ret. time 1.02 min; condition E. $^1$H NMR (400 MHz, DMSO-d$_6$) δ ppm 8.88-8.82 (m, 1H), 8.29-8.19 (m, 3H), 7.89-7.82 (m, 1H), 7.79-7.73 (m, 2H), 7.70-7.65 (m, 1H), 7.63-7.59 (m, 1H), 7.37 (s, 1H), 6.77-6.71 (m, 1H), 2.89 (s, 3H).

Compound 52: 6-(6'-(difluoromethyl)-[2,2'-bipyridin]-3-yl)imidazo[1,2-b]pyridazine-3-carboxamide

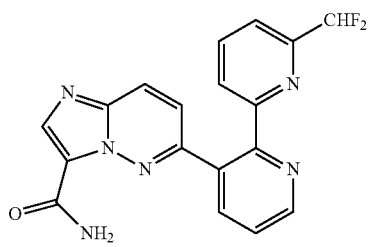

Compound 52 was synthesized from 5 in a manner similar to 19 employing the experimental procedure described in Scheme 7 (Method B). The crude residue was purified by preparative HPLC (condition H) to yield 6-(6'-(difluoromethyl)-[2,2'-bipyridin]-3-yl)imidazo[1,2-b]pyridazine-3-carboxamide 52 (38.7 mg, 0.105 mmol, 36.4% yield). LCMS: m/z=367.2 [M+H]$^+$; ret. time 1.18 min.; condition E. $^1$H NMR (400 MHz, DMSO-d$_6$) δ ppm 8.91 (dd, J=4.8, 1.8 Hz, 1H), 8.32-8.21 (m, 4H), 8.15 (s, 1H), 7.75 (dd, J=7.8, 4.8 Hz, 1H), 7.70-7.65 (m, 1H), 7.62 (s, 1H), 7.49-7.44 (m, 1H), 7.39 (d, J=9.5 Hz, 1H), 6.39 (s, 1H).

Compound 53: 6-(5'-fluoro-[2,2'-bipyridin]-3-yl)imidazo[1,2-b]pyridazine-3-carbonitrile

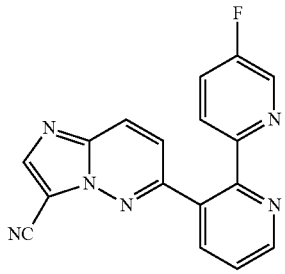 [SMILES: N#Cc1cnc2ccc(-c3cccnc3-c3ccc(F)cn3)nn12]

Compound 53 was synthesized by reacting 4 and 2-bromo-5-fluoropyridine employing the experimental procedure described in Scheme 4 (Method-D). The crude residue was purified by preparative HPLC (condition-N) to yield 6-(5'-fluoro-[2,2'-bipyridin]-3-yl)imidazo[1,2-b]pyridazine-3-carbonitrile 53 (220 mg, 0.58 mmol, 34.3% yield). LCMS=m/z 317.1 [M+H]$^+$; ret. time 1.24 min; condition C. $^1$H NMR (400 MHz, DMSO-d$_6$) δ ppm 8.89 (dd, J=4.8, 1.8 Hz, 1H), 8.60 (s, 1H), 8.27-8.22 (m, 3H), 8.20-8.16 (m, 1H), 7.94-7.87 (m, 1H), 7.71 (dd, J=7.8, 4.8 Hz, 1H), 7.33 (d, J=9.5 Hz, 1H).

Compound 54: 6-(5'-fluoro-[2,2'-bipyridin]-3-yl)imidazo[1,2-b]pyridazine-3-carboxamide

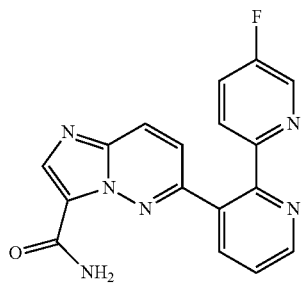 [SMILES: NC(=O)c1cnc2ccc(-c3cccnc3-c3ccc(F)cn3)nn12]

Compound 54 was synthesized from 53 employing the experimental procedure described in Scheme 6 (Method A). The crude residue was purified by preparative HPLC (condition-M) to yield 6-(5'-fluoro-[2,2'-bipyridin]-3-yl)imidazo[1,2-b]pyridazine-3-carboxamide 54 (10.3 mg, 0.031 mmol, 6.4% yield). LCMS: m/z=335.1 [M+H]$^+$; ret. time 0.77 min; condition C. $^1$H NMR (400 MHz, DMSO-d$_6$) δ ppm 8.86 (dd, J=4.8, 1.6 Hz, 1H), 8.26 (s, 3H), 8.22-8.18 (m, 1H), 8.17-8.12 (m, 1H), 7.87 (td, J=8.8, 2.9 Hz, 1H), 7.79 (br. s., 1H), 7.70 (dd, J=7.8, 4.9 Hz, 1H), 7.57 (br. s., 1H), 7.30-7.26 (m, 1H).

Compound 55: 6-(5'-methyl-[2,2'-bipyridin]-3-yl)imidazo[1,2-b]pyridazine-3-carbonitrile

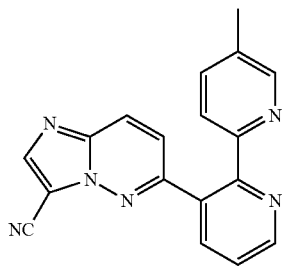 [SMILES: Cc1ccc(-c2ncccc2-c2ccc3ncc(C#N)n3n2)nc1]

Compound 55 was synthesized by reacting 4 and 2-bromo-5-methylpyridine employing the experimental procedure described in Scheme 4 (Method-D). The crude residue was purified by preparative HPLC (condition N) to yield 6-(5'-methyl-[2,2'-bipyridin]-3-yl)imidazo[1,2-b]pyridazine-3-carbonitrile 55 (65 mg, 0.2 mmol, 21.5% yield). LCMS: m/z=313.1 [M+H]$^+$; ret. time 1.42 min; condition C. $^1$H NMR (400 MHz, DMSO-d$_6$) δ ppm 8.88 (dd, J=4.9, 1.7 Hz, 1H), 8.59 (s, 1H), 8.20 (s, 1H), 8.16-8.09 (m, 2H), 8.05-8.03 (m, 1H), 7.81-7.77 (m, 1H), 7.70-7.65 (m, 1H), 7.25 (d, J=9.5 Hz, 1H), 2.27 (s, 3H).

Compound 56: 6-(5'-methyl-[2,2'-bipyridin]-3-yl)imidazo[1,2-b]pyridazine-3-carboxamide

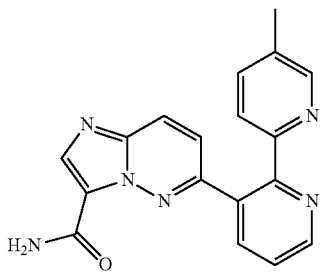 [SMILES: Cc1ccc(-c2ncccc2-c2ccc3ncc(C(N)=O)n3n2)nc1]

Compound 56 was synthesized from 55 in a manner similar to 19 employing the experimental procedure described in Scheme 7 (Method B). The crude residue was purified by preparative HPLC (condition H) to yield 6-(5'-methyl-[2,2'-bipyridin]-3-yl)imidazo[1,2-b]pyridazine-3-carboxamide 56 (12 mg, 0.036 mmol, 28.4% yield). LCMS: m/z=331.1 [M+H]$^+$; ret. time 1.04 min; condition C. $^1$H NMR (400 MHz, DMSO-d$_6$) δ ppm 8.86 (dd, J=5.0, 1.5 Hz, 1H), 8.28 (s, 1H), 8.24 (dd, J=8.0, 1.5 Hz, 1H), 8.18 (d, J=9.5 Hz, 1H), 8.07 (d, J=1.5 Hz, 1H), 8.02 (d, J=8.0 Hz, 1H), 7.81 (br. s., 1H), 7.78 (dd, J=8.0, 1.5 Hz, 1H), 7.68 (dd, J=7.8, 4.8 Hz, 2H), 7.21 (d, J=9.5 Hz, 1H), 2.27 (s, 3H).

Compound 57: 6-(6'-methyl-[2, 2'-bipyridin]-3-yl)imidazo[1,2-b]pyridazine-3-carbonitrile

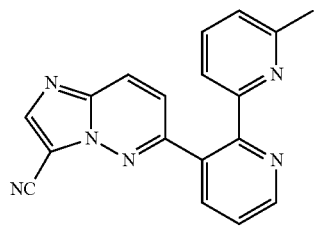 [SMILES: Cc1cccc(-c2ncccc2-c2ccc3ncc(C#N)n3n2)n1]

Compound 57 was synthesized by reacting 4 and 2-methyl-6-(tributylstannyl)pyridine employing the experimental procedure described in Scheme 1 (Method-A). The crude residue was purified by preparative HPLC (condition Q) to yield 6-(6'-methyl-[2, 2'-bipyridin]-3-yl) imidazo[1,2-b]pyridazine-3-carbonitrile 57 (3.4 mg, 10.89 μmol, 2.8% yield). LC-MS: m/z=313.2 [M+H]$^+$; ret. time 1.40 min; condition C. $^1$H NMR (400 MHz, DMSO-d$_6$) δ ppm 8.92-8.86 (m, 1H), 8.60-8.56 (m, 1H), 8.26-8.20 (m, 1H), 8.18-8.11 (m, 1H), 8.08-8.02 (m, 1H), 7.88-7.79 (m, 1H), 7.72-7.64 (m, 1H), 7.38-7.31 (m, 1H), 7.23-7.15 (m, 1H), 1.87 (s, 3H).

Compound 58: 6-(6'-methyl-[2,2'-bipyridin]-3-yl)imidazo[1,2-b]pyridazine-3-carboxamide

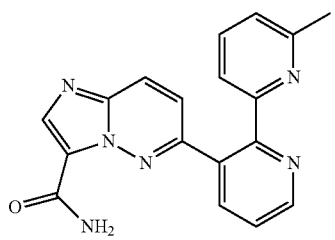 [SMILES: Cc1cccc(-c2ncccc2-c2ccc3ncc(C(N)=O)n3n2)n1]

Compound 58 was synthesized from 57 in a manner similar to 19 employing the experimental procedure described in Scheme 7 (Method B). The crude residue was purified by preparative HPLC (condition-N) to yield 6-(6'-methyl-[2,2'-bipyridin]-3-yl)imidazo[1,2-b]pyridazine-3-carboxamide 58 (5.1 mg, 0.015 mmol, 12.1% yield). LC-MS: m/z=331.1 [M+H]$^+$; ret. time 1.01 min; condition C, $^1$H NMR (400 MHz, DMSO-d$_6$) δ ppm 9.15-9.10 (m, 1H), 8.54-8.45 (m, 3H), 8.22-8.17 (m, 1H), 8.07 (s, 1H), 8.04-7.99 (m, 1H), 7.97-7.92 (m, 1H), 7.89-7.85 (m, 1H), 7.56 (d, J=9.5 Hz, 1H), 7.46-7.40 (m, 1H), 2.15 (s, 3H).

Compound 59: 6-(4'-fluoro-[2,2'-bipyridin]-3-yl)imidazo[1,2-b]pyridazine-3-carbonitrile

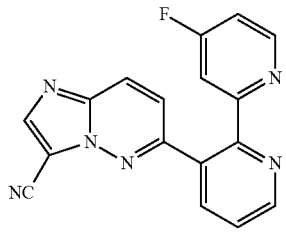 [SMILES: N#Cc1cnc2ccc(-c3cccnc3-c3cc(F)ccn3)nn12]

Compound 59 was synthesized by reacting 4 and 2-bromo-4-fluoropyridine employing the experimental procedure described in Scheme 4 (Method D). The crude residue was purified by preparative HPLC (condition-N) to yield compound 59. (4.3 mg, 0.013 mmol, 3.1% yield), LC-MS: m/z=317 [M+H]$^+$; ret. time 1.41 min; condition C, $^1$H NMR (400 MHz, DMSO-d6) δ ppm 8.93-8.89 (m, 1H), 8.60-8.57 (m, 1H), 8.27-8.19 (m, 3H), 8.03-7.97 (m, 1H), 7.77-7.72 (m, 1H), 7.42-7.37 (m, 1H), 7.34-7.27 (m, 1H).

Compound 60: 6-(4'-fluoro-[2,2'-bipyridin]-3-yl)imidazo[1,2-b]pyridazine-3-carboxamide

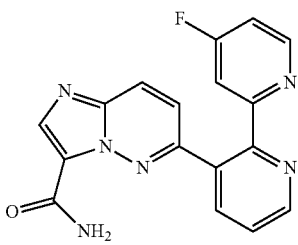 [SMILES: NC(=O)c1cnc2ccc(-c3cccnc3-c3cc(F)ccn3)nn12]

Compound 60 was synthesized from 59 in a manner similar to 19 employing the experimental procedure described in Scheme 7 (Method B). The crude residue was purified by preparative HPLC (condition-N) to yield compound 60 (7.9 mg, 0.023 mmol, 18.3% yield). LC-MS: m/z=335.1 [M+H]$^+$; ret. time 1.03 min; condition C. $^1$H NMR (400 MHz, DMSO-d$_6$) δ ppm 8.93-8.87 (m, 1H), 8.32-8.20 (m, 4H), 7.98-7.92 (m, 1H), 7.85-7.80 (m, 1H), 7.78-7.72 (m, 1H), 7.68-7.61 (m, 1H), 7.34 (d, J=9.3 Hz, 2H).

Compound 61: 6-(5'-fluoro-6'-methyl-[2,2'-bipyridin]-3-yl)imidazo[1,2-b]pyridazine-3-carbonitrile

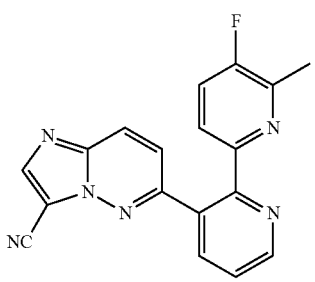 [SMILES: Cc1nc(-c2ncccc2-c2ccc3ncc(C#N)n3n2)ccc1F]

Compound 61 was synthesized by reacting 4 and 6-bromo-3-fluoro-2-methylpyridine employing the experimental procedure described in Scheme 3 (Method C). The crude residue was purified by preparative HPLC (condition-N) to yield compound 61 (140 mg, 0.424 mmol, 54.2% yield). LCMS: m/z=331.1 [M+H]$^+$; ret. time 1.59 min; condition C. $^1$H NMR (400 MHz, DMSO-d$_6$) δ ppm 8.88 (dd, J=4.8, 1.6 Hz, 1H), 8.60 (s, 1H), 8.25 (d, J=9.5 Hz, 1H), 8.17-8.09 (m, 2H), 7.77 (t, J=9.0 Hz, 1H), 7.68 (dd, J=7.8, 4.9 Hz, 1H), 7.38 (d, J=9.5 Hz, 1H), 1.86 (d, J=2.7 Hz, 3H).

Compound 43: 6-(5'-fluoro-6'-methyl-[2,2'-bipyridin]-3-yl)imidazo[1,2-b]pyridazine-3-carboxamide

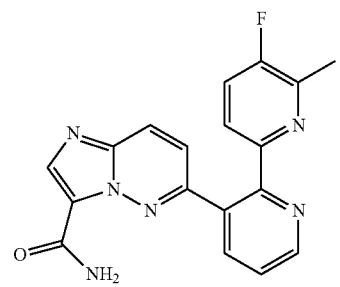 [SMILES: Cc1nc(-c2ncccc2-c2ccc3ncc(C(N)=O)n3n2)ccc1F]

Compound 43 was synthesized from 61 in a manner similar to 19 employing the experimental procedure described in Scheme 7 (Method B). The crude residue was purified by preparative HPLC (condition-N) to yield 6-(5'-fluoro-6'-methyl-[2,2'-bipyridin]-3-yl)imidazo[1,2-b]pyridazine-3-carboxamide 43 (20 mg, 0.057 mmol, 19.0% yield). LCMS: m/z=349.1; ret. time 1.13 min; condition C. $^1$H NMR (400 MHz, DMSO-d$_6$) δ ppm 8.86 (dd, J=4.8, 1.6 Hz, 1H), 8.28 (s, 1H), 8.26-8.20 (m, 2H), 8.03 (dd, J=8.7, 3.8 Hz, 1H), 7.82-7.58 (m, 4H), 7.32 (d, J=9.3 Hz, 1H), 1.88 (d, J=2.7 Hz, 3H).

Compound 63: 6-(6'-isopropyl-[2,2'-bipyridin]-3-yl)imidazo[1,2-b]pyridazine-3-carbonitrile

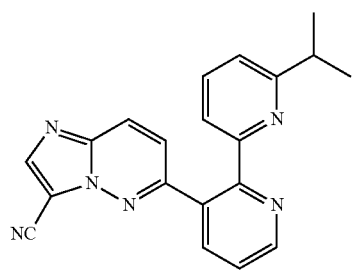

Compound 63 was synthesized from 4 and 2-bromo-6-isopropylpyridine employing the experimental procedure described in Scheme-2 (Method B). The crude residue was purified by preparative HPLC (condition-F) to yield 6-(6'-isopropyl-[2,2'-bipyridin]-3-yl)imidazo[1,2-b]pyridazine-3-carbonitrile 63 (125 mg, 3.67 mmol, 37.5% yield) as a pale yellow solid. LCMS: m/z=341.1 [M+H]$^+$; ret. time 1.64 min; condition C. $^1$H NMR (400 MHz, DMSO-d$_6$) δ ppm 8.87-8.91 (m, 1H), 8.58 (s, 1H), 8.28 (d, J=9.54 Hz, 1H), 8.12-8.17 (m, 1H), 8.01-8.06 (m, 1H), 7.84-7.91 (m, 1H), 7.65-7.73 (m, 1H), 7.39 (d, J=9.04 Hz, 1H), 7.16-7.24 (m, 1H), 2.68 (td, J=1.95, 3.64 Hz, 1H), 0.58 (d, J=7.03 Hz, 6H).

Compound 64: 6-(6'-isopropyl-[2,2'-bipyridin]-3-yl)imidazo[1,2-b]pyridazine-3-carboxamide

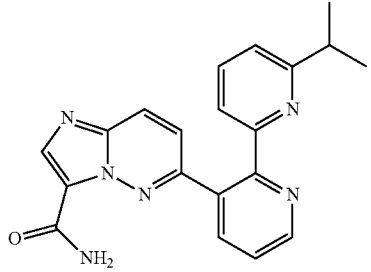 [SMILES: CC(C)c1cccc(-c2ncccc2-c2ccc3ncc(C(N)=O)n3n2)n1]

Compound 64 was synthesized from 4 in a manner similar to 19 employing the experimental procedure described in Scheme 7 (Method B). The crude residue was purified by preparative HPLC (condition-N) to yield 6-(6'-isopropyl-[2,2'-bipyridin]-3-yl)imidazo[1,2-b]pyridazine-3-carboxamide 64 (34.9 mg, 0.096 mmol, 32.8%) as a pale yellow solid. LCMS: m/z=359.2 [M+H]+; ret. time 1.13 min; condition C. $^1$H NMR (400 MHz, DMSO-d$_6$) δ ppm 1.15 (dd, J=1.59, 4.77 Hz, 1H), 1.82-1.72 (m, 3H), 2.09-2.04 (m, 1H), 2.20-2.12 (m, 1H), 2.33 (dd, J=4.77, 7.70 Hz, 2H), 2.65-2.57 (m, 2H), 2.84 (dd, J=0.98, 7.83 Hz, 1H), 7.48-7.40 (m, 1H), 9.49 (d, J=6.85 Hz, 6H).

Compound 65: 6-(6'-fluoro-[2,2'-bipyridin]-3-yl)imidazo[1,2-b]pyridazine-3-carbonitrile

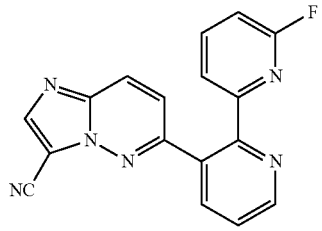

Compound 65 was synthesized by reacting 4 and 6-bromo-2-fluoropyridine employing experimental procedure described in Scheme 4 (Method D). The crude residue was purified by preparative HPLC (condition-N) to yield 6-(6'-fluoro-[2,2'-bipyridin]-3-yl)imidazo[1,2-b]pyridazine-3-carbonitrile 65 (1.4 mg, 4.38 μmol, 0.38% yield) as a pale yellow solid. LCMS: m/z=317.1 [M+H]+; ret. time 1.41 min; condition C. $^1$H NMR (400 MHz, DMSO-d$_6$) δ ppm 8.91 (dd, J=1.71, 4.65 Hz, 1H), 8.60 (s, 1H), 8.31 (d, J=9.54 Hz, 1H), 8.17-8.22 (m, 1H), 8.15 (d, J=8.07 Hz, 1H), 8.08-8.13 (m, 1H), 7.73 (dd, J=4.89, 7.83 Hz, 1H), 7.47 (d, J=9.54 Hz, 1H), 7.11-7.18 (m, 1H).

Scheme-13:

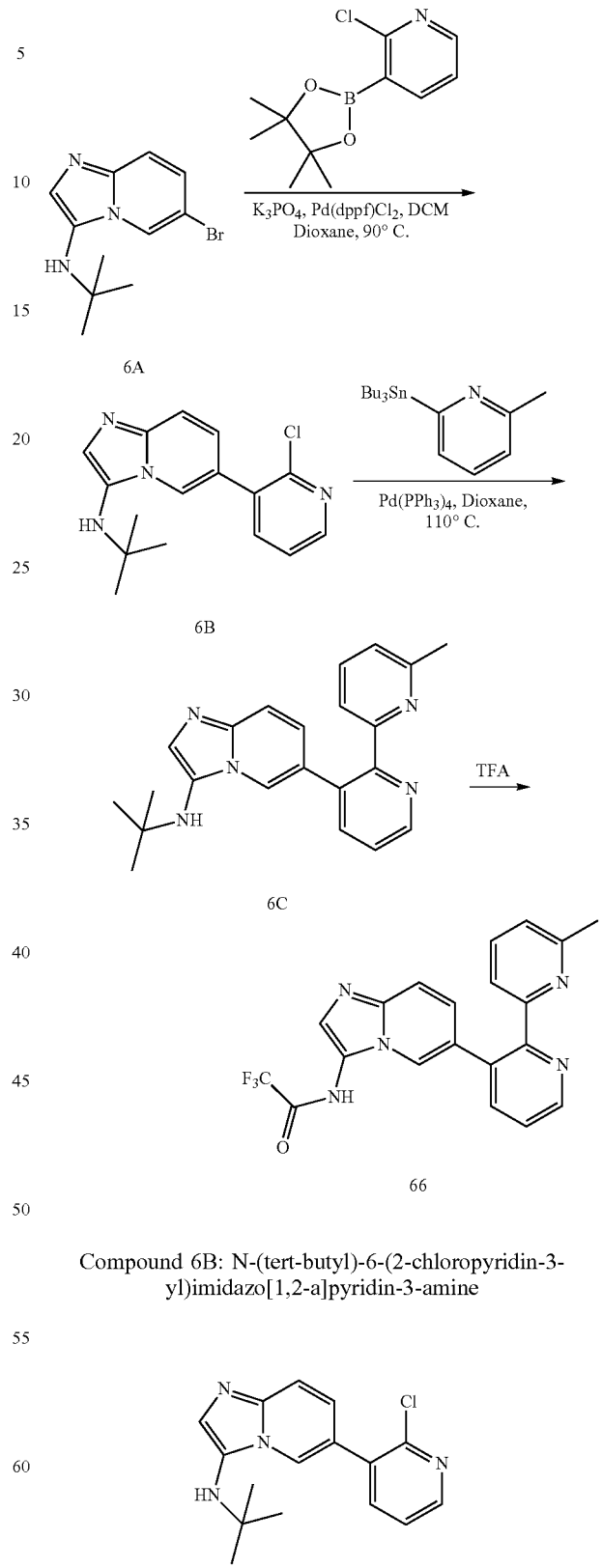

Compound 6B: N-(tert-butyl)-6-(2-chloropyridin-3-yl)imidazo[1,2-a]pyridin-3-amine Compound 6B was synthesized by reacting 6A (reference: WO 2013064984 A1) and 2-chloro-3-(4,4,5,5-tetramethyl- 1,3,2-dioxaborolan-2-yl)pyridine (reference: WO 2015157093 A1/WO 2015044172 A1/WO 2014055955 A1) employing the experimental procedure described in Scheme-5 compound 17. The crude product was purified by silica gel chromatography (24 g RediSep® column, eluting with a gradient of 20-60% ethyl acetate in petroleum ether) to yield compound 6B (180 mg, 0.59 mmol, 16.1% yield) as a light yellow solid. LCMS: m/z=301.2 [M–H]+; ret. time 2.13 min; condition-E.

Compound 6C: N-(tert-butyl)-6-(6'-methyl-[2,2'-bipyridin]-3-yl)imidazo[1,2-a]pyridin-3-amine

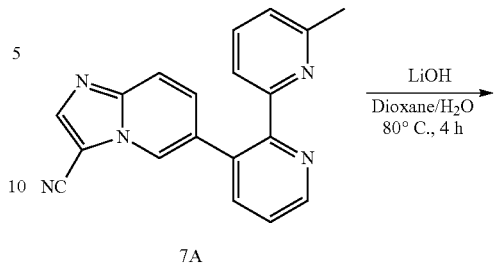

Compound 6C was synthesized by reacting 6B and 2-methyl-6-(tributylstannyl)pyridine employing the experimental procedure described in Scheme 1 (Method A). The crude residue was purified by silica gel chromatography (RediSep® column, eluting with a gradient of 20% ethyl acetate in petroleum ether) to yield N-(tert-butyl)-6-(6'-methyl-[2,2'-bipyridin]-3-yl)imidazo[1,2-a]pyridin-3-amine 6C (0.07 g, 0.20 mmol, 39.3%). LCMS: m/z=358.2 [M+H]+; ret. time 1.73; conditions E.

Compound 66: 2,2,2-trifluoro-N-(6-(6'-methyl-[2,2'-bipyridin]-3-yl)imidazo[1,2-a]pyridin-3-yl)acetamide

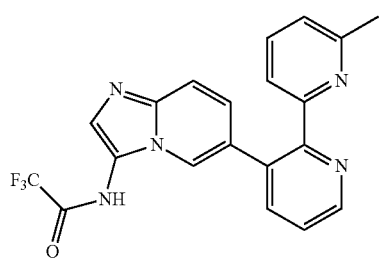

A mixture of N-(tert-butyl)-6-(6'-methyl-[2,2'-bipyridin]-3-yl)imidazo[1,2-a]pyridin-3-amine 6C (0.05 g, 0.140 mmol) and TFA (2 mL, 26.0 mmol) was stirred overnight at room temperature. TFA was evaporated under reduced pressure and the residue was purified by preparative HPLC (condition N). The fractions containing the product were combined and concentrated under reduced pressure to yield 2,2,2-trifluoro-N-(6-(6'-methyl-[2,2'-bipyridin]-3-yl)imidazo[1,2-a]pyridin-3-yl)acetamide 66 (5.7 mg, 0.14 mmol, 9.7% yield). LCMS: m/z=398.1 [M+H]+; ret. time 1.27; condition C. 1H NMR (400 MHz, DMSO-d6) δ ppm 13.63 (br s, 1H), 8.75-8.81 (m, 1H), 8.39 (br s, 1H), 7.98-8.06 (m, 2H), 7.59-7.75 (m, 5H), 7.14-7.19 (m, 1H), 2.12 (s, 3H).

Scheme-14:

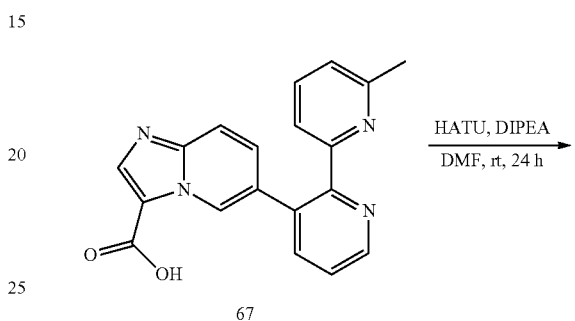

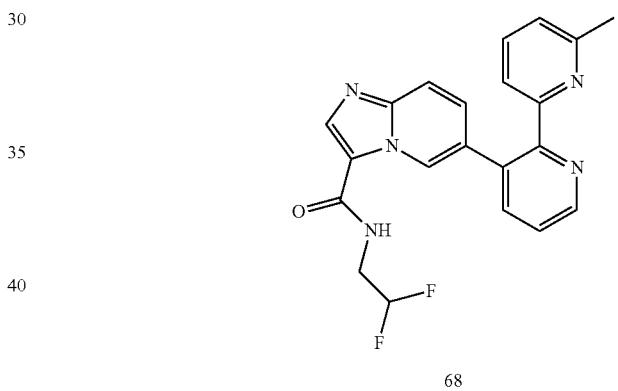

Compound 67: 6-(6'-methyl-[2,2'-bipyridin]-3-yl)imidazo[1,2-a]pyridine-3-carboxylic acid To a solution of 6-(6'-methyl-[2,2'-bipyridin]-3-yl)imidazo[1,2-a]pyridine-3-carbonitrile 7A (100 mg, 0.321 mmol) in 1,4-dioxane (5 mL) and H2O (2 mL) mixture was added LiOH (61.5 mg, 2.57 mmol). The reaction mixture was heated at 80° C. for 4 h. The reaction mixture was then diluted with water (20 mL), acidified with 1.5N aq. HCl solution to pH-5.0 and passed through a Celite® bed. The filtrate was evaporated to dryness. The crude residue was purified by preparative HPLC (method N) to yield 6-(6'-methyl-[2,2'-bipyridin]-3-yl)imidazo[1,2-a]pyridine-3-carboxylic acid 67 (4.4 mg, 0.013 mmol, 4.1% yield) as a pale yellow solid. LCMS: m/z=330.1 [M+H]+; ret. time 1.02 min; condition C. 1H NMR (400 MHz, DMSO-d6) δ ppm 9.39 (dd, J=0.98, 1.71 Hz, 1H), 8.75 (dd, J=1.59, 4.77 Hz, 1H), 8.32 (s, 1H), 7.98 (dd, J=1.47, 7.83 Hz, 1H), 7.67-7.76 (m, 1H), 7.50-7.64 (m, 3H), 7.05-7.16 (m, 2H), 2.09 (s, 3H).

Compound 68: N-(2,2-difluoroethyl)-6-(6'-methyl-[2,2'-bipyridin]-3-yl)imidazo[1,2-a]pyridine-3-carboxamide

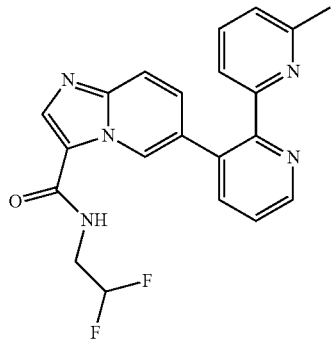 [SMILES: Cc1cccc(-c2ncccc2-c2ccc3ncc(C(=O)NCC(F)F)n3c2)n1]

To a stirred solution of compound 67 (0.0.1 g, 0.303 mmol) in DMF (2 mL) was added HATU (0.23 g, 0.605 mmol) and DIPEA (0.16 mL, 0.908 mmol), followed by 2,2-difluoroethanamine (29.4 mg, 0.363 mmol). The reaction mixture was stirred at room temperature for 18 h. The reaction mixture concentrated under reduced pressure to give a crude residue, which was purified by preparative HPLC (condition N) to yield N-(2,2-difluoroethyl)-6-(6'-methyl-[2,2'-bipyridin]-3-yl)imidazo[1,2-a]pyridine-3-carboxamide 68 (3.2 mg, 8.05 μmol, 2.7% yield) as a pale yellow solid. LCMS: m/z=394.1 [M+H]$^+$; ret. time 1.40 min; condition C. $^1$H NMR (400 MHz, DMSO-d$_6$) δ ppm 9.35 (dd, J=1.00, 2.01 Hz, 1H), 8.87 (t, J=6.02 Hz, 1H), 8.75 (dd, J=1.51, 4.52 Hz, 1H), 8.40 (s, 1H), 7.95-8.01 (m, 1H), 7.68-7.75 (m, 1H), 7.53-7.65 (m, 3H), 7.08-7.17 (m, 1H), 5.95-6.29 (m, 1H), 3.63-3.76 (m, 2H), 2.09 (s, 3H).

Compound 69: 6-(6'-methyl-[2,2'-bipyridin]-3-yl)-N-(2,2,2-trifluoroethyl)imidazo[1,2-a]pyridine-3-carboxamide

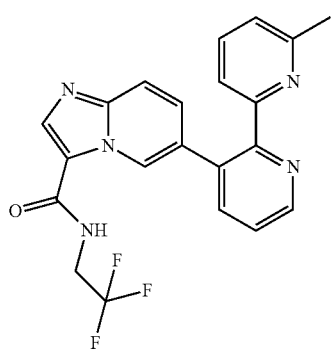 [SMILES: Cc1cccc(-c2ncccc2-c2ccc3ncc(C(=O)NCC(F)(F)F)n3c2)n1]

Compound 69 was synthesized by reacting 67 and 2,2,2-trifluoroethanamine employing the experimental procedure described for 68 in Scheme 14. The crude residue was purified by preparative HPLC (condition-N) to yield 6-(6'-methyl-[2,2'-bipyridin]-3-yl)-N-(2,2,2-trifluoroethyl)imidazo[1,2-a]pyridine-3-carboxamide 69 (2.1 mg, 5.05 μmol, 1.7% yield) as a pale yellow solid. LCMS: m/z=412.1 [M+H]$^+$; ret. time 1.53 min; condition C. $^1$H NMR (400 MHz, DMSO-d$_6$) δ ppm 9.32-9.36 (m, 1H), 9.08 (t, J=6.53 Hz, 1H), 8.75 (dd, J=1.76, 4.77 Hz, 1H), 8.45 (s, 1H), 7.97-8.02 (m, 1H), 7.68-7.74 (m, 1H), 7.56-7.64 (m, 3H), 7.09-7.18 (m, 2H), 4.05-4.16 (m, 2H), 2.08 (s, 3H).

Compound 70: N-(2-methoxyethyl)-6-(6'-methyl-[2,2'-bipyridin]-3-yl)imidazo[1,2-a]pyridine-3-carboxamide

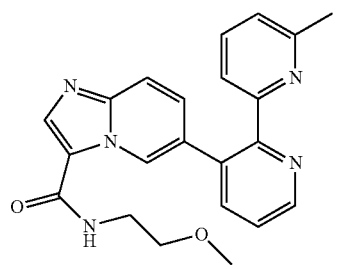 [SMILES: COCCNC(=O)c1cnc2ccc(-c3cccnc3-c3cccc(C)n3)cn12]

Compound 70 was synthesized by reacting 67 and 2-methoxyethanamine employing the experimental procedure described for 68 in Scheme 14. The crude residue was purified by preparative HPLC (condition-N) to yield N-(2-methoxyethyl)-6-(6'-methyl-[2,2'-bipyridin]-3-yl)imidazo[1,2-a]pyridine-3-carboxamide 70 (1.7 mg, 4.34 μmol, 1.4% yield) as a pale yellow solid. LCMS: m/z=388.2 [M+H]$^+$; ret. time 1.3 min; condition C. $^1$H NMR (400 MHz, DMSO-d$_6$) δ ppm 9.39 (dd, J=1.00, 2.01 Hz, 1H), 8.73-8.76 (m, 1H), 8.56 (d, J=4.02 Hz, 1H), 8.33 (d, J=8.03 Hz, 1H), 7.95-8.01 (m, 1H), 7.68-7.75 (m, 1H), 7.57-7.63 (m, 2H), 7.51-7.56 (m, 1H), 7.14 (d, J=7.53 Hz, 1H), 7.04-7.10 (m, 1H), 3.40-3.49 (m, 4H), 3.28 (s, 3H), 2.10 (s, 3H).

Compound 71: N—($^2$H$_3$)methyl-6-[2-(6-methylpyridin-2-yl)pyridin-3-yl]imidazo[1,2-a]pyridine-3-carboxamide

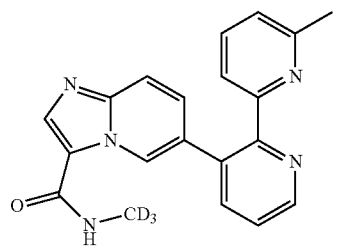 [SMILES: [2H]C([2H])([2H])NC(=O)c1cnc2ccc(-c3cccnc3-c3cccc(C)n3)cn12]

Compound 71 was synthesized by reacting 67 and ($^2$H$_3$) methylamine employing the experimental procedure described for 68 in Scheme 14. The crude residue was purified by preparative HPLC (condition-N) to yield compound 71 (0.4 mg, 1.120 μmol, 0.4% yield) as a pale yellow solid. LCMS: m/z=347.1 [M+H]$^+$; ret. time 0.90 min; condition D. $^1$H NMR (400 MHz, DMSO-d$_6$) δ ppm 9.36 (s, 1H), 8.74 (dd, J=1.59, 4.77 Hz, 1H), 8.41 (s, 1H), 8.25 (s, 1H), 7.97 (dd, J=1.59, 7.70 Hz, 1H), 7.67-7.75 (m, 1H), 7.56-7.63 (m, 2H), 7.53 (d, J=9.05 Hz, 1H), 7.13 (d, J=7.83 Hz, 1H), 7.06 (dd, J=1.71, 9.29 Hz, 1H), 2.08 (s, 3H).

Compound 72: methyl-6-(6'-methyl-[2,2'-bipyridin]-3-yl)imidazo[1,2-a]pyridine-3-carboxamide

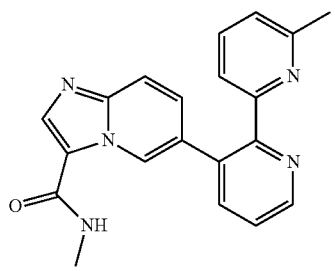 [SMILES: CNC(=O)c1cnc2ccc(-c3cccnc3-c3cccc(C)n3)cn12]

Compound 72 was synthesized by reacting 67 and methylamine employing experimental procedure described for 68 in Scheme 14. The crude residue was purified by preparative HPLC (condition-N) to yield compound 72 (2.4 mg, 6.64 μmol, 2.2% yield) as a pale yellow solid. LCMS: m/z=344.1 [M+H]$^+$; ret. time 1.22 min; condition C. $^1$H NMR (400 MHz, DMSO-d$_6$) δ ppm 9.38 (dd, J=1.00, 2.01 Hz, 1H), 8.73-8.76 (m, 1H), 8.40-8.46 (m, 1H), 8.26 (s, 1H), 7.98 (dd, J=1.76, 7.78 Hz, 1H), 7.69-7.75 (m, 1H), 7.57-7.63 (m, 2H), 7.50-7.56 (m, 1H), 7.14 (d, J=7.53 Hz, 1H), 7.04-7.10 (m, 1H), 2.79 (d, J=4.52 Hz, 3H), 2.09 (s, 3H).

Scheme 15:

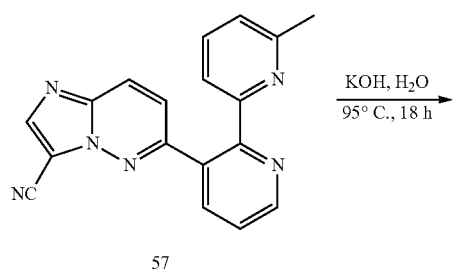

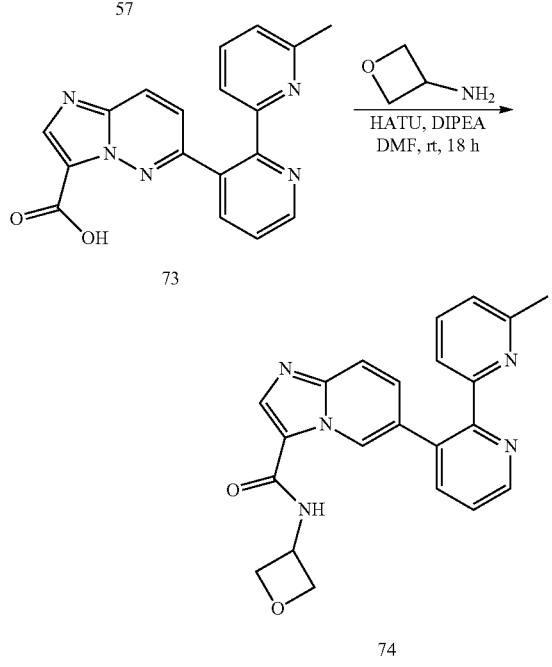

Compound 73: 6-(6'-methyl-[2,2'-bipyridin]-3-yl)imidazo[1,2-b]pyridazine-3-carboxylic acid

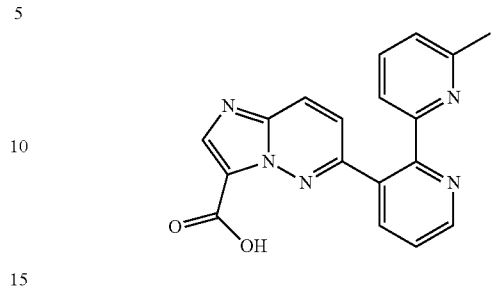

To a solution of 57 (0.02 g, 0.064 mmol) in water (5 mL) was added KOH (0.018 g, 0.32 mmol). The reaction mixture was heated up to 95° C. over 5 min. and was stirred for 18 h. The reaction mixture was cooled to room temperature, the precipitated solid was filtered off and the filtrate was acidified to pH 6 with 1N aq. HCl. The precipitated product was filtered through a sintered funnel and dried under vacuum to get a crude residue, which was purified by preparative HPLC (condition N) to yield (6'-methyl-[2,2'-bipyridin]-3-yl)imidazo[1,2-b]pyridazine-3-carboxylic acid 73 (8.7 mg, 0.026 mmol, 41.0% yield). LCMS: m/z=332.1 [M+H]$^+$; ret. time 0.71 min; condition C, $^1$H NMR (400 MHz, DMSO-d$_6$) δ ppm 12.94 (bs, 1H), 8.89-8.86 (m, 1H), 8.32 (s, 1H), 8.13 (s, 2H), 8.01-7.95 (m, 1H), 7.87-7.82 (m, 1H), 7.72-7.66 (m, 1H), 7.26-7.19 (m, 2H), 1.97 (s, 3H).

Compound 74: 6-(6'-methyl-[2,2'-bipyridin]-3-yl)-N-(oxetan-3-yl)imidazo[1,2-b]pyridazine-3-carboxamide

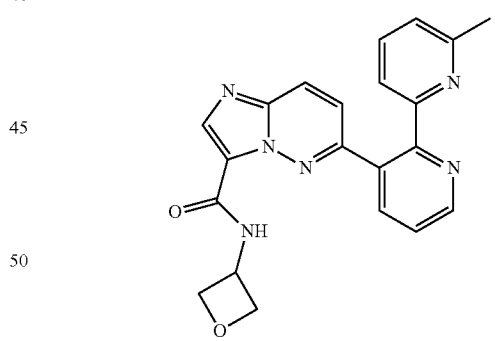

Compound 74 was synthesized by reacting 73 and oxetan-3-amine employing the experimental procedure described for 68 in Scheme 14. The crude product was purified by preparative HPLC (Condition N) to yield 6-(6'-methyl-[2,2'-bipyridin]-3-yl)-N-(oxetan-3-yl)imidazo[1,2-b]pyridazine-3-carboxamide 6M (11.3 mg, 0.029 mmol, 16.15% yield). LCMS: m/z=387.2 [M+H]$^+$; ret. time 1.07 min; condition C, $^1$H NMR (400 MHz, DMSO-d$_6$) δ ppm 8.89-8.86 (m, 1H), 8.69-8.66 (m, 1H), 8.28 (s, 2H), 8.26-8.21 (m, 1H), 7.99-7.95 (m, 1H), 7.86-7.81 (m, 1H), 7.73-7.68 (m, 1H), 7.37-7.31 (m, 1H), 7.21-7.15 (m, 1H), 4.95-4.88 (m, 1H), 4.76 (s, 2H), 4.38 (s, 2H), 1.86 (s, 3H).

Compound 75: N-cyclopropyl-6-(6'-methyl-[2,2'-bipyridin]-3-yl)imidazo[1,2-b]pyridazine-3-carboxamide

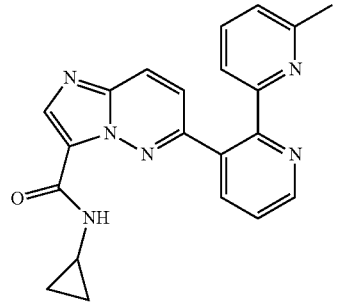 [SMILES: Cc1cccc(-c2ncccc2-c2ccc3ncc(C(=O)NC4CC4)n3n2)n1]

Compound 75 was synthesized by reacting 73 and cyclopropyl amine employing the experimental procedure described for 68 in Scheme 14. The crude residue was purified by HPLC (condition N) to yield N-cyclopropyl-6-(6'-methyl-[2,2'-bipyridin]-3-yl)imidazo[1,2-b]pyridazine-3-carboxamide 75 (7.6 mg, 0.020 mmol, 16.8% yield). LCMS: m/z=371.2 [M+H]$^+$; ret. time 1.26 min; condition C. $^1$H NMR (400 MHz, DMSO-d$_6$) δ ppm 8.90-8.83 (m, 1H), 8.25 (d, J=2.4 Hz, 3H), 8.15-8.10 (m, 1H), 7.98-7.93 (m, 1H), 7.87-7.81 (m, 1H), 7.73-7.68 (m, 1H), 7.37-7.31 (m, 1H), 7.19-7.13 (m, 1H), 2.77-2.70 (m, 1H), 1.85 (s, 3H), 0.75-0.69 (m, 2H), 0.39-0.33 (m, 2H).

Scheme 16:

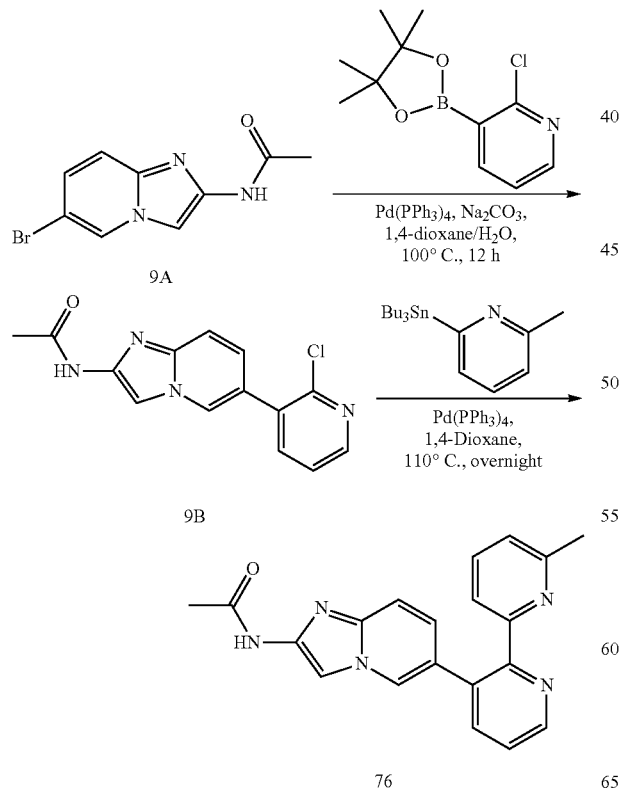

Compound 9B: N-(6-(2-chloropyridin-3-yl)imidazo[1,2-a]pyridin-2-yl)acetamide

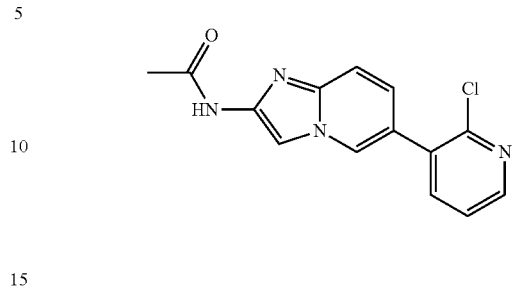

To a stirred solution of compound 9A (reference: US 2009/0163489 A1)-(0.315 g, 1.24 mmol) and 2-chloro-3-(4,4,5,5-tetramethyl-1,3,2-dioxaborolan-2-yl)pyridine (Reference WO 2015157093 A1/WO 2015044172 A1/WO 2014055955 A1)-(0.445, 1.86 mmol) in 1,4-dioxane (9 mL) and water (3 mL) was added Na$_2$CO$_3$ (0.394 g, 3.72 mmol). The reaction mixture was degassed for 3 min. and then to it was added Pd(PPh$_3$)$_4$ (0.143 g, 0.124 mmol), and the resultant mixture was heated at 100° C. for 12 h. The reaction mixture was then filtered through a Celite® pad, the filter cake washed with ethyl acetate and the combined filtrate evaporated under reduced pressure to give the crude compound. It was purified via silica gel chromatography (24 g RediSep® column, eluted with 60% ethyl acetate in petroleum ether) to furnish N-(6-(2-chloropyridin-3-yl)imidazo[1,2-a]pyridin-2-yl)acetamide 9B (211 mg, 0.736 mmol, 59.4% yield) as a light yellow solid. LCMS: m/z=385.0 [M+H]$^+$; ret. time 1.49 min; condition C.

Compound 76: N-(6-(6'-methyl-[2,2'-bipyridin]-3-yl)imidazo[1,2-a]pyridin-2-yl)acetamide

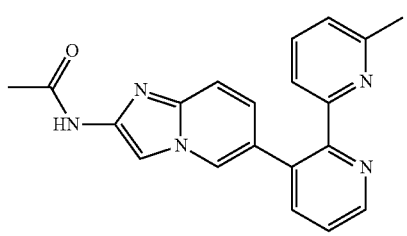 [SMILES: CC(=O)Nc1cn2cc(-c3cccnc3-c3cccc(C)n3)ccc2n1]

Compound 76 was synthesized by reacting 9B and 2-methyl-6-(tributylstannyl)pyridine employing the experimental procedure described in Scheme 1 (Method A). The crude compound was purified by preparative HPLC (Condition-N) to yield N-(6-(6'-methyl-[2,2'-bipyridin]-3-yl)imidazo[1,2-a]pyridin-2-yl)acetamide 76 (7.6 mg, 0.022 mmol, 12.4% yield). LCMS: m/z=344.1 [M+H]$^+$; ret. time 1.17 min; condition C. $^1$H NMR (400 MHz, DMSO-d$_6$) δ ppm 10.65 (s, 1H), 8.70-8.71 (m, 1H), 8.50 (s, 1H), 8.02 (s, 1H), 7.93-7.95 (m, 1H), 7.69-7.73 (m, 1H), 7.53-7.58 (m, 2H), 7.21 (d, J=9.2 Hz, 1H), 7.15 (d, J=7.6 Hz, 1H), 6.77 (d, J=1.6 Hz, 1H) 2.15 (s, 3H), 2.07 (s, 3H).

Compound 77: N-(6-(5'-fluoro-6'-methyl-[2,2'-bi-pyridin]-3-yl)imidazo[1,2-a]pyridin-2-yl)acetamide

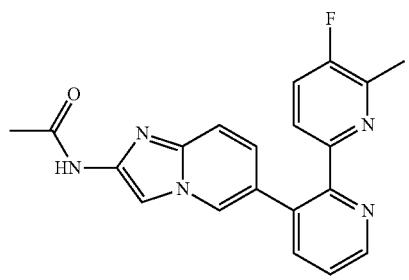 [SMILES: CC(=O)Nc1cn2cc(-c3cccnc3-c3ccc(F)c(C)n3)ccc2n1]

Compound 77 was synthesized by reacting 9B and 6-bromo-3-fluoro-2-methylpyridine employing the experimental procedure described in Scheme-2 (Method B). The crude compound was purified by preparative HPLC (Condition-G) to yield N-(6-(5'-fluoro-6'-methyl-[2,2'-bipyridin]-3-yl)imidazo[1,2-a]pyridin-2-yl)acetamide 77 (27.3 mg, 0.073 mmol, 21.0% yield). LCMS: m/z=362.1 [M+H]$^+$; ret. time 1.29 min; condition C. $^1$H NMR (400 MHz, DMSO-d$_6$) δ ppm 10.8 (s, 1H), 8.72 (dd, J=1.6, 4.8 Hz, 1H), 8.57 (s, 1H), 8.05 (s, 1H), 7.96 (dd, J=1.2, 7.6, 1H), 7.65-7.72 (m, 2H), 7.58-7.61 (m, 1H), 7.32 (d, J=9.2 Hz, 1H), 6.90 (d, J=8.8 Hz, 1H), 2.11 (s, 3H), 2.09 (s, 3H).

Scheme 17:

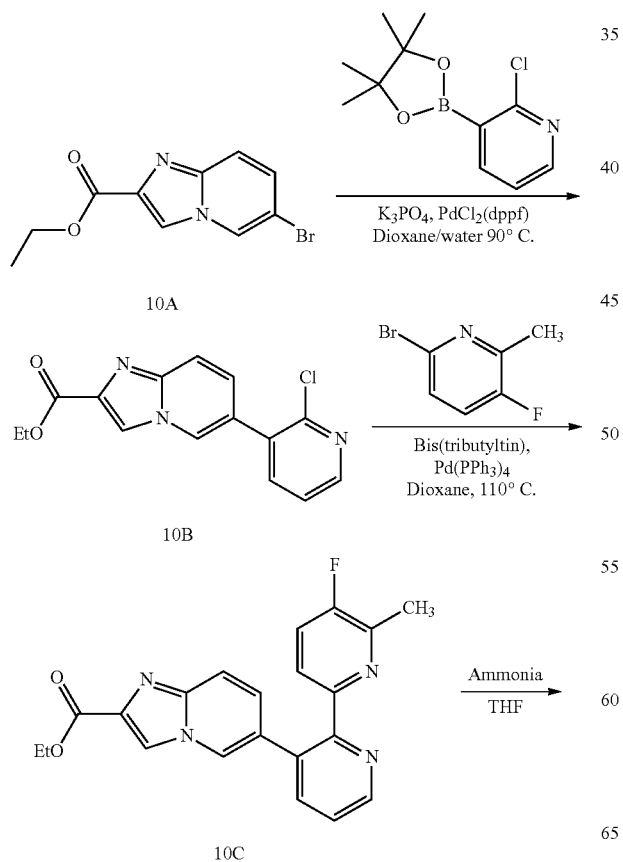

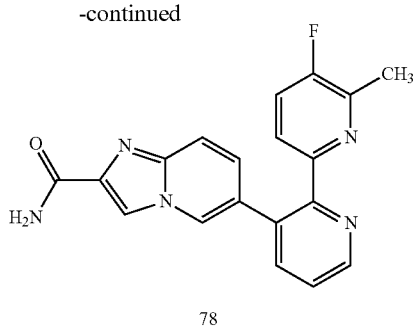

78

Compound 10B: ethyl 6-(2-chloropyridin-3-yl)imidazo[1,2-a]pyridine-2-carboxylate

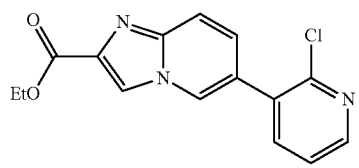 [SMILES: CCOC(=O)c1cn2cc(-c3cccnc3Cl)ccc2n1]

Compound 10B was synthesized by reacting 10A (reference: WO 2015086526 A1, WO 2011050245 A1 and WO 2009112651 A1) and 2-chloro-3-(4,4,5,5-tetramethyl-1,3,2-dioxaborolan-2-yl)pyridine (reference: WO 2015157093 A1, WO 2015044172 A1 and WO 2014055955 A1) employing the experimental procedure described for 50 in Scheme-12. The crude product was purified by silica gel chromatography (24 g RediSep® column, eluting with 50% ethyl acetate in petroleum ether). The fractions containing the product were combined and concentrated under reduced pressure to yield ethyl 6-(2-chloropyridin-3-yl)imidazo[1,2-a]pyridine-2-carboxylate 74 (0.5 g, 1.65 mmol, 55.7% yield). LCMS: m/z=302.1 [M+H]$^+$; ret. time 2.21 min; condition E.

Compound 10C: ethyl 6-(5'-fluoro-6'-methyl-[2,2'-bipyridin]-3-yl)imidazo[1,2-a]pyridine-2-carboxylate

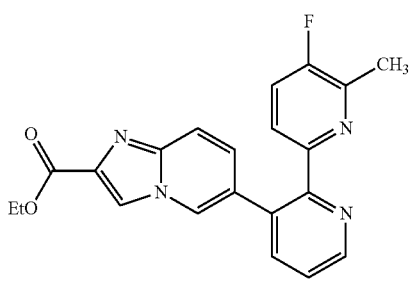 [SMILES: CCOC(=O)c1cn2cc(-c3cccnc3-c3ccc(F)c(C)n3)ccc2n1]

Compound 10C was synthesized by reacting 10B and 6-bromo-3-fluoro-2-methylpyridine and bis-(tributyltin) employing the experimental procedure described in Scheme-2 (Method B). The crude product was purified by silica gel chromatography (24 g RediSep® column, eluting with 40% ethyl acetate in petroleum ether). The fractions containing the product were combined and concentrated under reduced pressure to yield ethyl 6-(5'-fluoro-6'-methyl-[2,2'-bipyridin]-3-yl)imidazo[1,2-a]pyridine-2-carboxylate 10C (0.05 g, 0.133 mmol, 25.1% yield). LCMS: m/z=377.2 [M+H]$^+$; ret. time 1.50 min; condition E.

Compound 78: 6-(5'-fluoro-6'-methyl-[2,2'-bipyridin]-3-yl)imidazo[1,2-a]pyridine-2-carboxamide

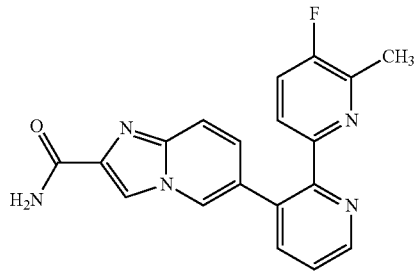 [SMILES: Cc1nc(-c2ncccc2-c2ccc3nc(C(N)=O)cn3c2)ccc1F]

To a solution of ethyl 6-(5'-fluoro-6'-methyl-[2,2'-bipyridin]-3-yl)imidazo[1,2-a]pyridine-2-carboxylate 10C (0.05 g, 0.133 mmol) in THF (2 mL) was added ammonia (1 mL of 2.5M) and the reaction was stirred overnight at room temperature. The solvent was evaporated under reduced pressure and the residue was purified by preparative HPLC (condition N) to yield compound 8D (1.5 mg, 4.32 µmol 3.3% yield). LCMS: m/z=348.2 [M+H]$^+$; ret. time 1.13 min; condition C. $^1$H NMR (400 MHz, DMSO-d$_6$) δ ppm 8.74 (dd, J=1.31, 4.68 Hz, 1H), 8.57 (s, 1H), 8.30 (s, 1H), 7.99 (dd, J=1.35, 7.76 Hz, 1H), 7.75-7.81 (m, 1H), 7.66-7.72 (m, 2H), 7.59 (dd, J=4.71, 7.76 Hz, 1H), 7.36-7.46 (m, 2H), 6.92 (dd, J=9.45, 1.62 Hz, 1H), 2.07 (d, J=2.75 Hz, 3H).

Compound 10E: ethyl 6-(6'-(trifluoromethyl)-[2,2'-bipyridin]-3-yl)imidazo[1,2-a]pyridine-2-carboxylate

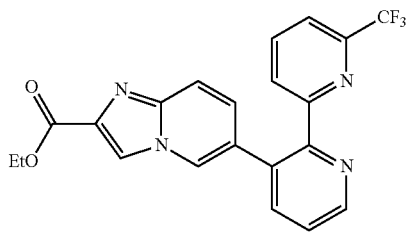

Compound 10E was synthesized by reacting 10B and 2-bromo-6-(trifluoromethyl)pyridine and bis-(tributyltin) employing experimental procedure described in Scheme-2 (Method B). The crude residue was purified by silica gel chromatography (12 g, RediSep® column, eluting with 40% ethyl acetate in petroleum ether). The fractions containing the product were combined and evaporated under reduced pressure to yield ethyl 6-(6'-(trifluoromethyl)-[2,2'-bipyridin]-3-yl)imidazo[1,2-a]pyridine-2-carboxylate 10E (0.2 g, 48.7% yield). LCMS: m/z=413.3 [M+H]$^+$; ret. time 1.14 min.; condition B.

Compound 79: 6-(6'-(trifluoromethyl)-[2,2'-bipyridin]-3-yl)imidazo[1,2-a]pyridine-2-carboxamide

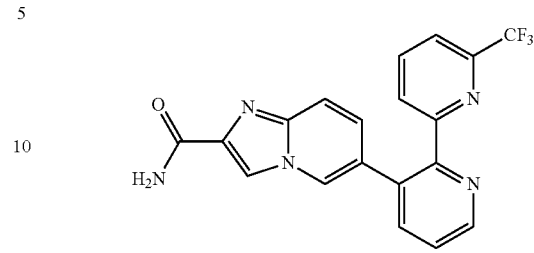

Compound 79 was synthesized by reacting 10E and ammonia employing the experimental procedure described for the synthesis of 78. The crude residue was purified by preparative HPLC (method-N) to yield compound 79 (6.5 mg, 0.017 mmol, 6.9%). LCMS m/z=384.1 [M+H]$^+$; ret. time 1.40 min; conditions C. $^1$H NMR (400 MHz, DMSO-d$_6$) δ ppm 8.78-8.83 (m, 1H), 8.57-8.60 (m, 1H), 8.26 (s, 2H), 8.17-8.23 (m, 1H), 8.03-8.07 (m, 1H), 7.79-7.84 (m, 1H), 7.64-7.74 (m, 2H), 7.37-7.43 (m, 2H), 6.88-6.94 (m, 1H).

Compound 10G: ethyl 6-(6'-methyl-[2,2'-bipyridin]-3-yl)imidazo[1,2-a]pyridine-2-carboxylate

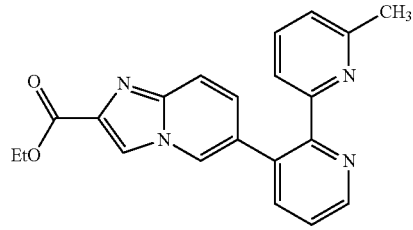 [SMILES: CCOC(=O)c1cn2cc(-c3cccnc3-c3cccc(C)n3)ccc2n1]

Compound 10G was synthesized by reacting 10B and 2-methyl-6-(tributylstannyl)pyridine employing the experimental procedure described in Scheme-1 (Method A). The crude product was purified by silica gel chromatography (12 g RediSep® column, eluting with 40% ethyl acetate in petroleum ether). The fractions containing the product were combined and concentrated under reduced pressure to yield compound 10G (0.06 g, 0.17 mmol, 38.9% yield). LCMS: m/z=359.2 [M+H]$^+$; ret. time 1.39 min; condition E.

Compound 80: 6-(6'-methyl-[2,2'-bipyridin]-3-yl)imidazo[1,2-a]pyridine-2-carboxamide

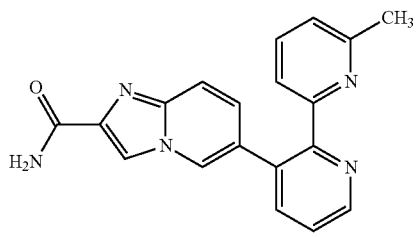 [SMILES: Cc1cccc(-c2ncccc2-c2ccc3nc(C(N)=O)cn3c2)n1]

Compound 80 was synthesized by reacting 10G and ammonia employing experimental procedure described for the synthesis of 78. The crude residue was purified by preparative HPLC (method N) to yield 6-(6'-methyl-[2,2'-bipyridin]-3-yl)imidazo[1,2-a]pyridine-2-carboxamide 80 (21.5 mg, 11.46% yield). LCMS: m/z=330.1 [M+H]+; ret. time 1.13 min; condition C. $^1$H NMR (400 MHz, DMSO-d$_6$) δ ppm 8.73-8.77 (m, 1H), 8.58 (s, 1H), 8.30 (s, 1H), 7.97-8.02 (m, 1H), 7.64-7.79 (m, 3H), 7.57-7.63 (m, 1H), 7.40 (d, J=9.35 Hz, 2H), 7.18 (s, 1H), 6.88-6.93 (m, 1H), 2.11 (s, 3H).

Scheme 18:

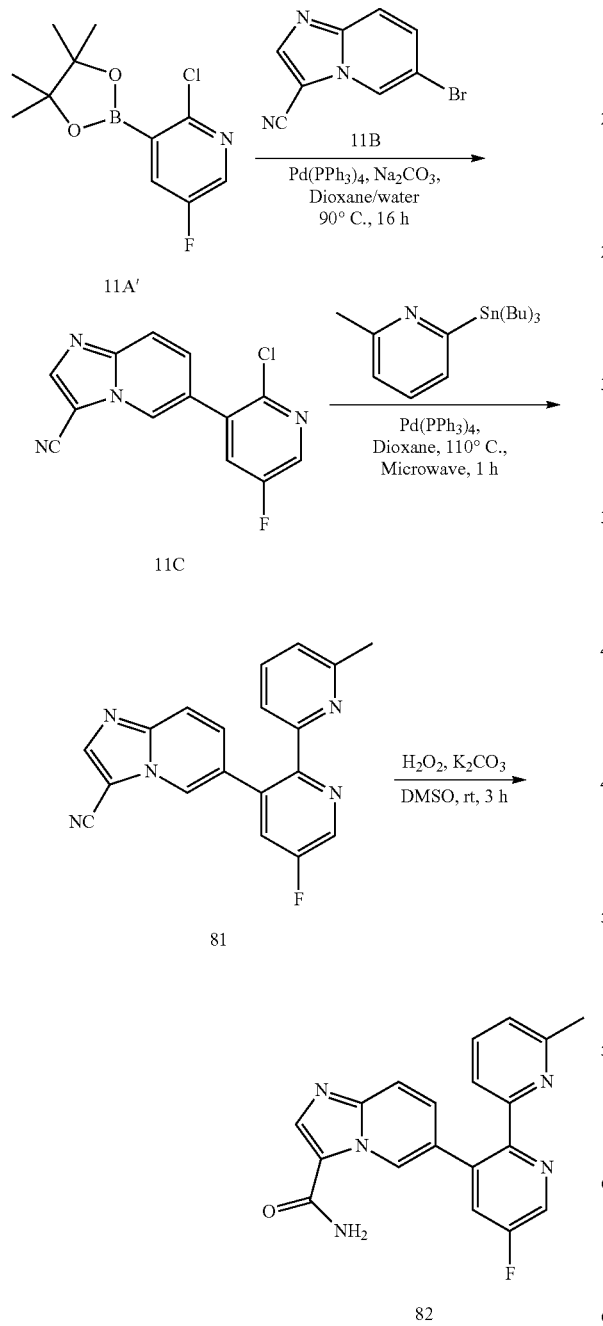

Compound 11C: 6-(2-chloro-5-fluoropyridin-3-yl)imidazo[1,2-a]pyridine-3-carbonitrile

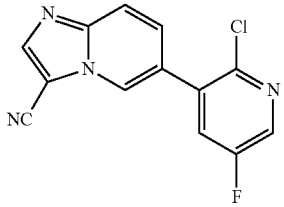 [SMILES: N#Cc1cnc2ccc(-c3cc(F)cnc3Cl)cn12]

Compound 11C was synthesized by reacting 11A' (reference: WO2013171640 A1) and 6-bromoimidazo[1,2-a]pyridine-3-carbonitrile 11B employing the experimental procedure described for 9B in Scheme-16. The crude product was purified via silica gel chromatography (24 g RediSep® column, eluting with 50% ethyl acetate in petroleum ether). Fractions containing the product were combined and evaporated to get compound 11C (0.32 g, 1.17 mmol, 45.3% yield) as a white solid. LCMS: m/z=273.2 [M+H]+; ret. time 1.73 min; conditions E.

Compound 81: 6-(5-fluoro-6'-methyl-[2,2'-bipyridin]-3-yl)imidazo[1,2-a]pyridine-3-carbonitrile

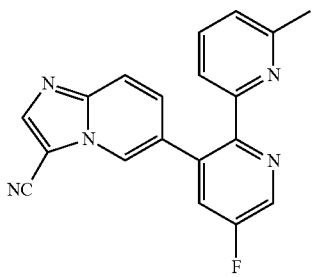 [SMILES: Cc1cccc(-c2ncc(F)cc2-c2ccc3ncc(C#N)n3c2)n1]

To a degassed solution of 6-(2-chloro-5-fluoropyridin-3-yl)imidazo[1,2-a]pyridine-3-carbonitrile 11C (0.05 g, 0.183 mmol) and 2-methyl-6-(tributylstannyl)pyridine (0.070 g, 0.183 mmol) in 1,4-dioxane (2 mL), tetrakis(triphenylphosphine)palladium(O)-(0.127 g, 0.110 mmol) was added under nitrogen. The reaction mixture was stirred at 120° C. for 1 h in a microwave oven to obtain a crude residue, which was purified by preparative HPLC (condition-N) to yield 6-(5-fluoro-6'-methyl-[2,2'-bipyridin]-3-yl)imidazo[1,2-a]pyridine-3-carbonitrile 81 as an off-white solid (4.5 mg, 0.014 mmol, 7.5% yield). LCMS m/z=330.1 [M+H]+; ret. time 1.55 min; conditions C. $^1$H NMR (400 MHz, DMSO-d$_6$) δ ppm 8.77-8.80 (m, 1H) 8.68-8.71 (m, 1H) 8.48 (s, 1H) 8.11 (dd, J=9.29, 2.76 Hz, 1H) 7.61-7.78 (m, 3H) 7.15-7.24 (m, 2H) 2.10 (s, 3H).

Compound 82: 6-(5-fluoro-6'-methyl-[2,2'-bipyridin]-3-yl)imidazo[1,2-a]pyridine-3-carboxamide

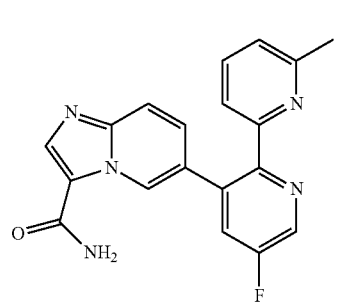 [SMILES: Cc1cccc(-c2ncc(F)cc2-c2ccc3ncc(C(N)=O)n3c2)n1]

Compound 82 was synthesized from 81 in a manner similar to 19 employing the experimental procedure described in Scheme 7 (Method B). The crude residue was purified by preparative HPLC (condition-I) to yield compound 82 (22 mg, 0.063 mmol, 17.38% yield). LCMS m/z=348.1 [M+H]$^+$; ret. time 0.84 min; condition C. $^1$H NMR (400 MHz, DMSO-d$_6$) δ ppm 9.39 (d, J=0.73 Hz, 1H) 8.32 (s, 1H) 8.02 (dd, J=9.29, 2.93 Hz, 1H) 7.86-7.96 (m, 1H) 7.94 (br. s., 1H) 7.70 (d, J=15.41 Hz, 1H) 7.28-7.45 (m, 1H) 7.36 (br. s., 1H) 7.07-7.09 (m, 2H) 2.08 (s, 3H).

Compound 83: 6-(6'-(difluoromethyl)-5-fluoro-[2,2'-bipyridin]-3-yl)imidazo[1,2-a]pyridine-3-carbonitrile

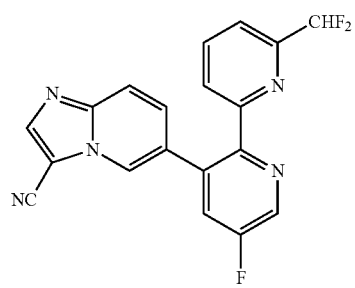 [SMILES: N#Cc1cnc2ccc(-c3cc(F)cnc3-c3cccc(C(F)F)n3)cn12]

Compound 9F was synthesized by reacting 11C and 2-bromo-6-(difluoromethyl)pyridine employing experimental procedure described in Scheme 3 (Method C). The crude residue was purified by preparative HPLC (condition-N) to yield compound 83 (65 mg, 0.18 mmol, 97% yield). LCMS: m/z=366.1 [M+H]$^+$; ret. time 1.73 min; condition C. $^1$H NMR (400 MHz, DMSO-d$_6$) δ ppm 8.79 (d, J=2.69 Hz, 1H) 8.65 (d, J=0.73 Hz, 1H) 8.47 (s, 1H) 8.00-8.14 (m, 3H) 7.55-7.66 (m, 2H) 7.16 (dd, J=9.17, 1.83 Hz, 1H) 6.32-6.62 (m, 1H).

Compound 84: 6-(6'-(difluoromethyl)-5-fluoro-[2,2'-bipyridin]-3-yl)imidazo[1,2-a]pyridine-3-carboxamide

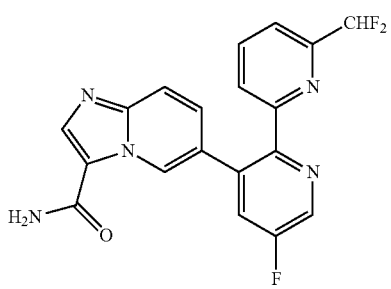 [SMILES: NC(=O)c1cnc2ccc(-c3cc(F)cnc3-c3cccc(C(F)F)n3)cn12]

Compound 84 was synthesized from 83 employing the experimental procedure described in Scheme-7 (Method B). The crude residue was purified by preparative HPLC (condition-N) to yield compound 84 (7 mg, 0.018 mmol, 13.3% yield). LCMS: m/z=384.1 [M+H]$^+$; ret. time 1.12 min; conditions C. $^1$H NMR (400 MHz, DMSO-d$_6$) δ ppm 9.41 (s, 1H) 8.81 (d, J=2.69 Hz, 1H) 8.32 (s, 1H) 8.03-8.12 (m, 2H) 7.97 (d, J=7.83 Hz, 2H) 7.52-7.62 (m, 2H) 7.36 (br. s., 1H) 7.15 (dd, J=9.17, 1.83 Hz, 1H) 6.35-6.68 (m, 1H).

Compound 85: 6-(5,5'-difluoro-6'-methyl-[2,2'-bipyridin]-3-yl)imidazo[1,2-a]pyridine-3-carboxamide

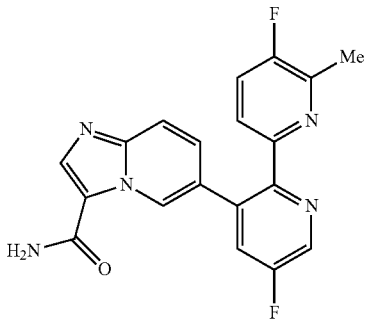 [SMILES: Cc1nc(-c2ncc(F)cc2-c2ccc3ncc(C(N)=O)n3c2)ccc1F]

Compound 85 was synthesized by reacting 11C and 6-bromo-3-fluoro-2-methylpyridine employing the experimental procedure described in Scheme 3 (Method C), and the resultant cyano compound was hydrolyzed similar to 19 employing experimental procedures described in Scheme 7 (Method B). The crude residue was purified by preparative HPLC (condition-N) to yield compound 85 (12 mg, 0.033 mmol, 19.1% yield). LCMS: m/z=366.1 [M+H]$^+$; ret. time 1.32 min; conditions C. $^1$H NMR (400 MHz, DMSO-d$_6$) δ ppm 9.39 (d, J=0.73 Hz, 1H)) 8.77 (d, J=2.4 Hz, 1H) 8.32 (s, 1H) 8.02 (dd, J=9.29, 2.93 Hz, 1H) 7.86-7.96 (br. s., 1H) 7.70 (m, 1H) 7.36 (br. s., 1H) 7.07-7.09 (m, 1H) 2.08 (s, 3H)

Scheme 19:

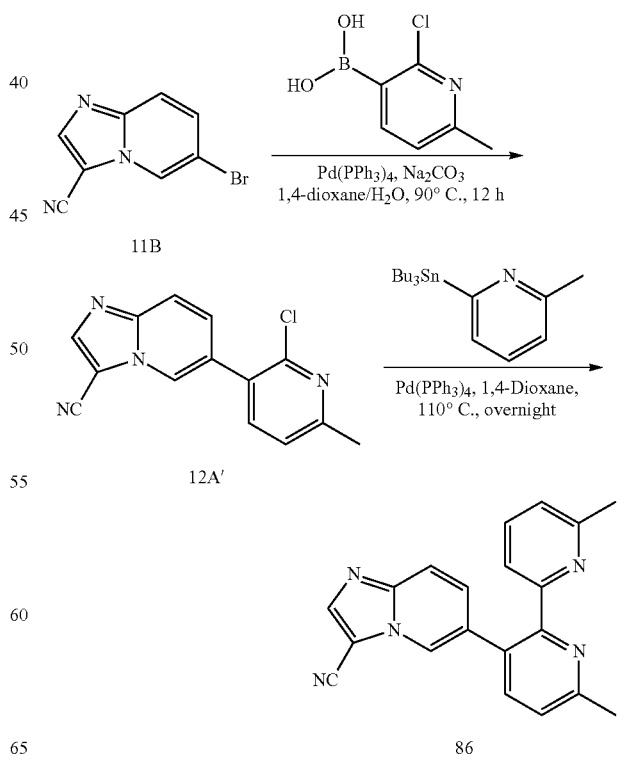

86

Compound: 12A': 6-(2-chloro-6-methylpyridin-3-yl)imidazo[1,2-a]pyridine-3-carbonitrile

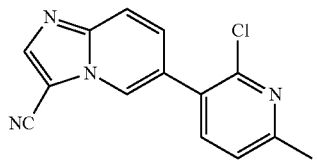 [SMILES: Cc1ccc(-c2ccc3ncc(C#N)n3c2)c(Cl)n1]

Intermediate 12A' was synthesized by reacting 11B and (2-chloro-6-methylpyridin-3-yl)boronic acid employing the experimental procedure described for 9B as shown in Scheme-16. The crude product was purified by silica gel chromatography (40 g RediSep® column, eluted with a gradient of 20-30% ethyl acetate in petroleum ether) to yield compound 12A' (150 mg, 0.497 mmol, 31.5% yield) as an off-white solid. LCMS: m/z=269 [M+H]$^+$; ret. time 1.7 min; condition E

Compound 86: 6-(6,6'-dimethyl-[2,2'-bipyridin]-3-yl)imidazo[1,2-a]pyridine-3-carbonitrile

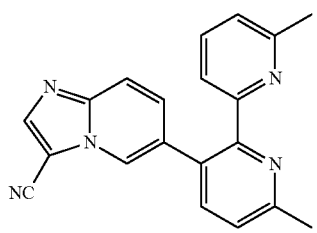 [SMILES: Cc1cccc(-c2nc(C)ccc2-c2ccc3ncc(C#N)n3c2)n1]

Compound 86 was synthesized by reacting 12A' and 2-methyl-6-(tributylstannyl)pyridine employing the experimental procedure described in Scheme-1 (Method A). The crude residue was purified by preparative HPLC (condition-H) to yield 6-(6,6'-dimethyl-[2,2'-bipyridin]-3-yl)imidazo[1, 2-a]pyridine-3-carbonitrile 86 (85 mg, 0.149 mmol, 57.2% yield). LCMS: m/z=326.1 [M+H]$^+$; ret. time 1.45 min; condition C. $^1$H NMR (400 MHz, DMSO-d$_6$) δ ppm 8.49 (dd, J=1.7, 1.0 Hz, 1H), 8.44 (s, 1H), 7.95 (d, J=7.8 Hz, 1H), 7.74-7.65 (m, 2H), 7.62 (s, 1H), 7.47 (d, J=8.1 Hz, 1H), 7.23-7.14 (m, 2H), 2.61 (s, 3H), 2.13 (s, 3H).

Compound 87: 6-(6,6'-dimethyl-[2,2'-bipyridin]-3-yl)imidazo[1,2-a]pyridine-3-carbonitrile

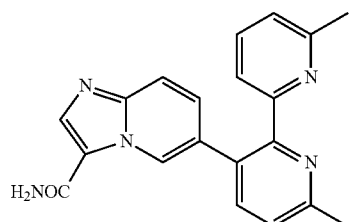

Compound 87 was synthesized from 86 similar to 19 employing experimental procedure described in Scheme 7 (Method B). The crude residue was purified by preparative HPLC (condition-O) to yield 6-(6,6'-dimethyl-[2,2'-bipyridin]-3-yl)imidazo[1,2-a]pyridine-3-carbonitrile 87 (16.9 mg, 0.049 mmol, 24.6% yield). LCMS: m/z=344.2 [M+H]$^+$; ret. time 1.17 min; condition C. $^1$H NMR (400 MHz, DMSO-d$_6$) δ ppm 9.36 (d, J=1.0 Hz, 1H), 8.31 (s, 1H), 7.91-7.81 (m, 1H), 7.71-7.64 (m, 1H), 7.56-7.49 (m, 2H), 7.46 (s, 1H), 7.34 (br. s., 1H), 7.15-7.03 (m, 2H), 2.60 (s, 3H), 2.12 (s, 3H).

Compound 88: 6-(6'-(difluoromethyl)-6-methyl-[2,2'-bipyridin]-3-yl)imidazo[1,2-a]pyridine-3-carboxamide

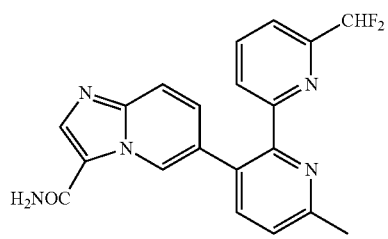 [SMILES: Cc1ccc(-c2ccc3ncc(C(N)=O)n3c2)c(-c2cccc(C(F)F)n2)n1]

Compound 88 was synthesized by reacting 12A' and 2-bromo-6-(difluoromethyl)pyridine employing the experimental procedure described in Scheme-2 (Method B) and then the resultant cyano compound was hydrolyzed similar to 19 employing experimental procedures described in Scheme 7 (Method B). The crude residue was purified by preparative HPLC (condition-H) to yield compound 88 (14.1 mg, 0.036 mmol, 19.8% yield). LCMS: m/z=380.2 [M+H]$^+$; ret. time 1.33 min; condition C. $^1$H NMR (400 MHz, DMSO-d$_6$) δ ppm 9.36 (s, 1H), 8.30 (s, 1H), 8.06 (s, 1H), 7.97-7.85 (m, 3H), 7.61-7.45 (m, 3H), 7.38-7.25 (m, 1H), 7.08 (dd, J=9.3, 1.7 Hz, 1H), 6.69-6.32 (m, 1H), 2.62 (s, 3H).

Scheme 20:

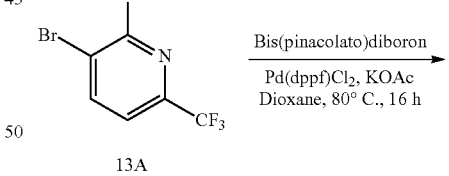

13A

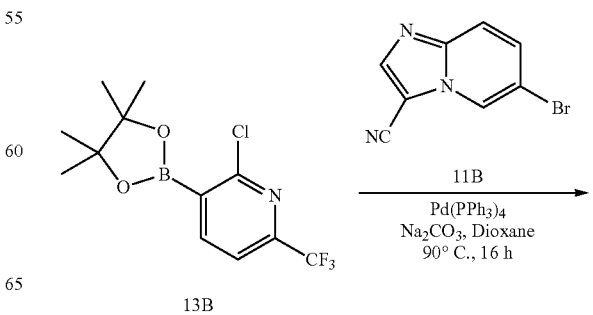

13B

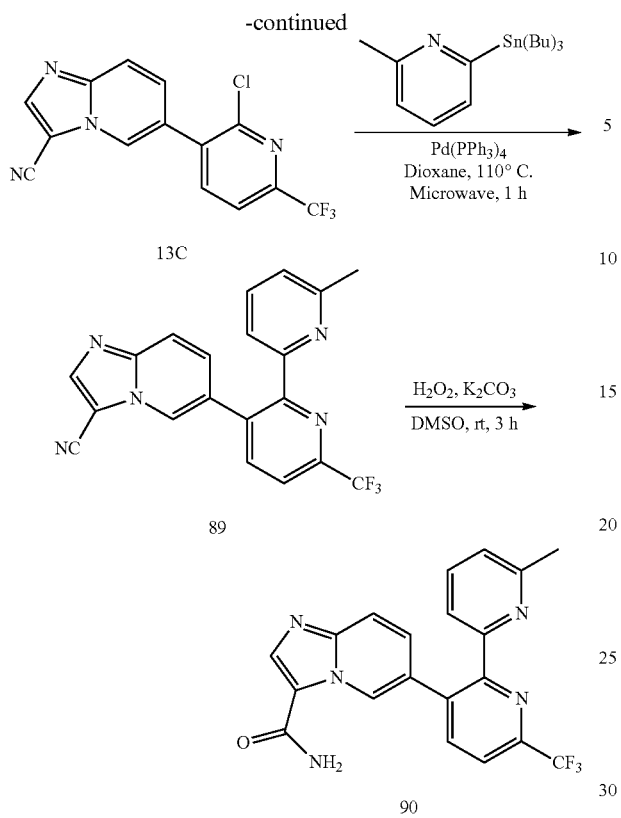

Compound 13B: N-(4-((2-(6-(difluoromethyl)pyridin-2-yl)-5-methyl-7H-pyrrolo[2,3-d]pyrimidin-4-yl)amino)pyridin-2-yl)acetamide

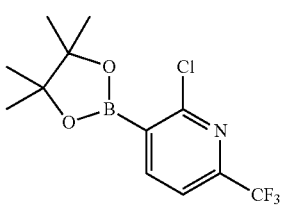 [SMILES: CC1(C)OB(c2ccc(C(F)(F)F)nc2Cl)OC1(C)C]

In a 50 mL flask, a solution of 3-bromo-2-chloro-6-(trifluoromethyl)pyridine 13A (reference: WO 2015052264 A1)-(0.3 g, 1.15 mmol), bis(pinacolato)diborane (0.44 g, 173 mmol) and potassium acetate (0.19 g, 2.3 mmol) in 1,4-dioxane (3 mL) was degassed under nitrogen for 10 min, prior to the addition of PdCl$_2$(dppf)-CH$_2$Cl$_2$ adduct (0.094 g, 0.115 mmol) under nitrogen. The reaction mixture was stirred at 80° C. for 16 h. It was quenched with water (8 mL) and the organic layer separated. The aqueous layer was back extracted with diethyl ether (3×20 mL). The combined organic layer was washed with water (2×20 mL), brine, dried over anhydrous Na$_2$SO$_4$, filtered and the filtrate concentrated under reduced pressure to afford compound 13B (0.25 g, 0.813 mmol, 70.6% yield) as a brown solid, which was carried to the next step without purification. $^1$H NMR (400 MHz, CDCl3) δ ppm 7.76-7.90 (m, 1H) 7.47-7.56 (m, 1H) 1.27 (s, 12H).

Compound 13C: 6-(2-chloro-6-(trifluoromethyl)pyridin-3-yl)imidazo[1,2-a]pyridine-3-carbonitrile

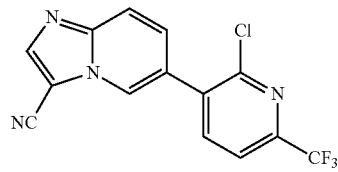 [SMILES: N#Cc1cnc2ccc(-c3ccc(C(F)(F)F)nc3Cl)cn12]

Compound 13C was synthesized by reacting 13B and 6-bromoimidazo[1,2-a]pyridine-3-carbonitrile 11B employing experimental procedure described for 67 in Scheme 16. The crude residue was purified by silica gel chromatography (24 g RediSep® column, eluting with 50% ethyl acetate in petroleum ether) to afford 6-(2-chloro-6-(trifluoromethyl)pyridin-3-yl)imidazo[1,2-a]pyridine-3-carbonitrile 13C (0.2 g, 062 mmol, 57.2% yield) as a white solid. LCMS: m/z=323.0 [M+H]$^+$; ret. time 2.43 min; conditions E.

Compound 89: 6-(6'-methyl-6-(trifluoromethyl)-[2,2'-bipyridin]-3-yl)imidazo[1,2-a]pyridine-3-carbonitrile

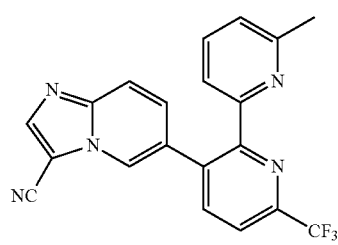

Compound 89 was synthesized by reacting 13C and 2-methyl-6-(tributylstannyl)pyridine employing experimental procedure described for 81 in Scheme 18. The crude residue was purified by preparative HPLC (condition-N) to yield compound 89 (0.15 g, 0.395 mmol, 63.8%). LCMS m/z=380.1 [M+H]$^+$; ret. time 1.95 min; condition C. $^1$H NMR (400 MHz, DMSO-d$_6$) δ 8.72 (s, 1H) 8.48 (s, 1H) 8.37 (d, J=8.07 Hz, 1H) 8.13 (d, J=8.07 Hz, 1H) 7.66-7.82 (m, 3H) 7.20-7.31 (m, 2H) 2.14 (s, 3H).

Compound 90: 6-(6'-methyl-6-(trifluoromethyl)-[2,2'-bipyridin]-3-yl)imidazo[1,2-a]pyridine-3-carboxamide

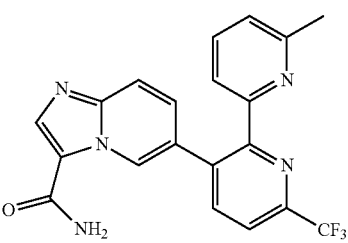 [SMILES: Cc1cccc(-c2nc(C(F)(F)F)ccc2-c2ccc3ncc(C(N)=O)n3c2)n1]

Compound 90 was synthesized from 89 similar to 19 employing experimental procedure described in Scheme 7

(Method B). The crude residue was purified by preparative HPLC (condition K) to yield compound 90 (11 mg, 0.027 mmol, 8.66% yield). LCMS m/z=398.1 [M+H]+; ret. time 1.19 min; condition C. 1H NMR (400 MHz, DMSO-d6) 9.45 (s, 1H) 8.30-8.35 (m, 2H) 8.10 (d, J=8.07 Hz, 1H) 7.95 (br. s., 1H) 7.72-7.79 (m, 1H) 7.60 (dd, J=8.56, 6.11 Hz, 2H) 7.39 (br. s., 1H) 7.10-7.23 (m, 2H) 2.14 (s, 3H).

Scheme 21:

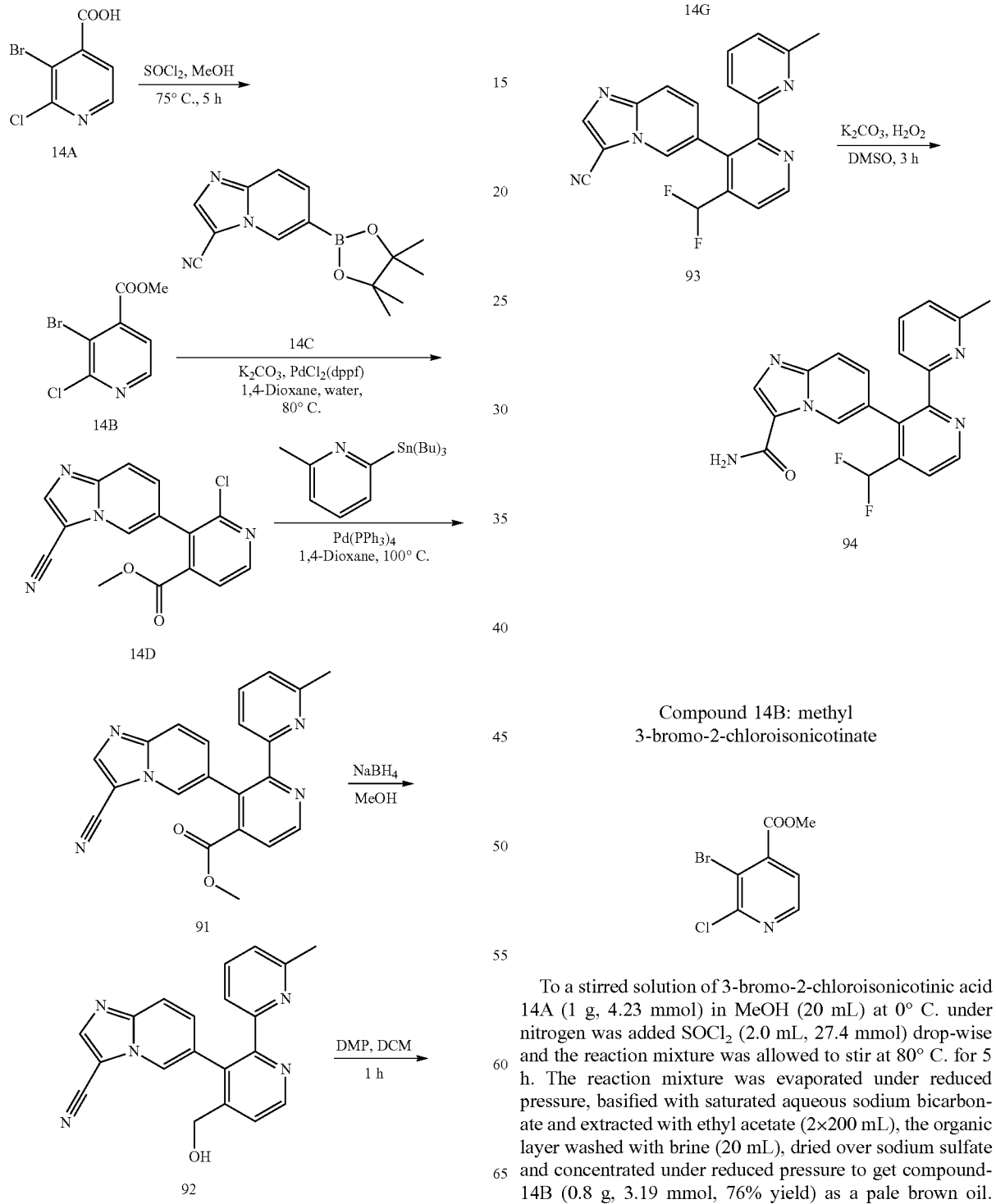

Compound 14B: methyl 3-bromo-2-chloroisonicotinate

To a stirred solution of 3-bromo-2-chloroisonicotinic acid 14A (1 g, 4.23 mmol) in MeOH (20 mL) at 0° C. under nitrogen was added SOCl2 (2.0 mL, 27.4 mmol) drop-wise and the reaction mixture was allowed to stir at 80° C. for 5 h. The reaction mixture was evaporated under reduced pressure, basified with saturated aqueous sodium bicarbonate and extracted with ethyl acetate (2×200 mL), the organic layer washed with brine (20 mL), dried over sodium sulfate and concentrated under reduced pressure to get compound-14B (0.8 g, 3.19 mmol, 76% yield) as a pale brown oil. LCMS: m/z=252.2 [M+H]+; ret. time 0.9 min; condition B.

Compound 14D: methyl 2-chloro-3-(3-cyanoimi-
dazo[1,2-a]pyridin-6-yl)isonicotinate

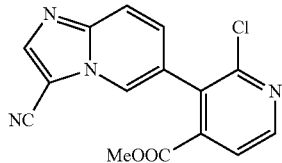 [SMILES: COC(=O)c1ccnc(Cl)c1-c1ccc2ncc(C#N)n2c1]

Compound 14D was synthesized by reacting 14B and 6-(4,4,5,5-tetramethyl-1,3,2-dioxaborolan-2-yl)imidazo[1,2-a]pyridine-3-carbonitrile 14C employing the experimental procedure described in Scheme 5 (Method-E). The crude compound was purified by silica gel chromatography (24 g RediSep® column, eluting with a gradient of 2-4% methanol in chloroform) to get compound 14D (0.25 g, 0.799 mmol, 40.0% yield) as pale yellow solid. LCMS m/z 313.3 [M+H]$^+$; ret. time 0.75 min; condition B.

Compound 91: methyl 3-(3-cyanoimidazo[1,2-a]
pyridin-6-yl)-6'-methyl-[2,2'-bipyridine]-4-carboxy-
late

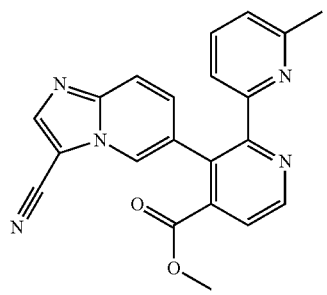 [SMILES: COC(=O)c1ccnc(-c2cccc(C)n2)c1-c1ccc2ncc(C#N)n2c1]

Compound 91 was synthesized by reacting 14D and 2-methyl-6-(tributylstannyl)pyridine employing experimental procedure described in Scheme 1 (Method A). The crude residue was purified by preparative HPLC (Method: N) to yield compound 91 (215 mg, 77% yield). LCMS: m/z=370.1 [M+H]$^+$; ret. time 1.22 min; condition C. $^1$H NMR (400 MHz, DMSO-d$_6$): δ ppm 8.93-8.91 (m, 1H), 8.40 (s, 1H), 7.92-7.91 (m, 1H), 7.73-7.67 (m, 2H), 7.61-7.59 (m, 1H), 7.43-7.40 (m, 1H), 7.08-7.07 (m, 1H), 7.40 (d, J=8.00 Hz, 1H), 3.65 (s, 3H), 2.00 (s, 3H).

Compound 92: 6-(4-(hydroxymethyl)-6'-methyl-[2,
2'-bipyridin]-3-yl)imidazo[1,2-a]pyridine-3-carboni-
trile

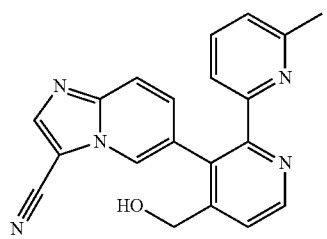 [SMILES: Cc1cccc(-c2nccc(CO)c2-c2ccc3ncc(C#N)n3c2)n1]

To a stirred solution of methyl 3-(3-cyanoimidazo[1,2-a]pyridin-6-yl)-6'-methyl-[2,2'-bipyridine]-4-carboxylate 91 (0.05 g, 0.135 mmol) in a mixture of methanol (0.5 mL) tetrahydrofuran (0.5 mL) was added NaBH$_4$ (5.12 mg, 0.135 mmol) at 0° C. stirred for 10 minutes, and the reaction mixture was allowed to stir at room temperature for 1 h. The reaction mixture was diluted with water (5 mL) and extracted with ethyl acetate (2×25 mL). The organic layer was washed with brine (1×10 mL), dried over anhydrous Na$_2$SO$_4$, filtered and concentrated under reduced pressure. The residue was purified by preparative HPLC (condition N) to yield 6-(4-(hydroxymethyl)-6'-methyl-[2,2'-bipyridin]-3-yl)imidazo[1,2-a]pyridine-3-carbonitrile 92 (6 mg, 12% yield); LCMS: m/z=342.1 [M+H]$^+$; ret. time 1.11 min; condition C. $^1$H NMR (400 MHz, DMSO-d$_6$): δ ppm 8.74 (d, J=4.00 Hz, 1H), 8.43 (s, 2H), 7.76-7.60 (m, 4H), 7.37-7.40 (m, 1H), 7.02-7.04 (m, 1H), 5.4 (bs, 1H) 4.37-4.40 (m, 2H), 1.99 (s, 3H).

Compound 14G: 6-(4-formyl-6'-methyl-[2,2'-bipyri-
din]-3-yl)imidazo[1,2-a]pyridine-3-carbonitrile

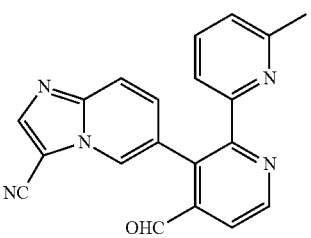 [SMILES: Cc1cccc(-c2nccc(C=O)c2-c2ccc3ncc(C#N)n3c2)n1]

To a stirred solution of 6-(4-(hydroxymethyl)-6'-methyl-[2,2'-bipyridin]-3-yl)imidazo[1,2-a]pyridine-3-carbonitrile 92 (0.05 g, 0.527 mmol) in CH$_2$Cl$_2$ (1 mL) was added Dess-Martin periodinane (0.093 g, 0.22 mmol) at 0° C. under nitrogen and the reaction mixture was allowed to stir at room temperature for 1 h. The reaction mixture was quenched with saturated aqueous sodium bicarbonate, extracted with DCM (2×250 mL), dried over sodium sulfate and concentrated to yield crude 6-(4-formyl-6'-methyl-[2,2'-bipyridin]-3-yl)imidazo[1,2-a]pyridine-3-carbonitrile 14G (0.053 g, 0.016 mmol, 11.5% yield), which was used without further purification in the next step. LCMS: m/z=340.1 [M+H]$^+$; ret. time 0.54 min; condition B.

Compound 93: 6-(4-(difluoromethyl)-6'-methyl-[2,
2'-bipyridin]-3-yl)imidazo[1,2-a]pyridine-3-carboni-
trile

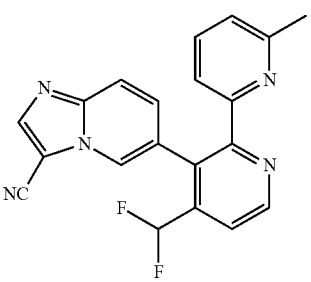 [SMILES: Cc1cccc(-c2nccc(C(F)F)c2-c2ccc3ncc(C#N)n3c2)n1]

To a stirred solution of 6-(4-formyl-6'-methyl-[2,2'-bipyridin]-3-yl)imidazo[1,2-a]pyridine-3-carbonitrile 14G (0.2 g, 0.589 mmol) in CH$_2$Cl$_2$ (2 mL) was added DAST (0.156 mL, 1.179 mmol) drop-wise at −78° C. under nitrogen. The reaction mixture was allowed to stir at room temperature for 4 h. The reaction mixture was cooled to 0° C., quenched with saturated aqueous sodium bicarbonate solution and extracted with ethyl acetate (2×200 mL). The organic layer was washed with brine (25 mL), dried over sodium sulfate and concentrated to obtain crude product, which was purified by preparative HPLC using (condition-N) to provide 6-(4-(difluoromethyl)-6'-methyl-[2,2'-bipyridin]-3-yl)imidazo[1,2-a]pyridine-3-carbonitrile 93 (115 mg, 0.30 mmol, 53% yield); LCMS: m/z=362.1 [M+H]$^+$; ret. time 1.54 min; condition C.; $^1$H NMR (400 MHz, DMSO-d$_6$): δ 8.96 (d, J=4.00 Hz, 1H), 8.57 (s, 1H), 8.46 (s, 1H), 7.83 (d, J=4.00 Hz, 1H), 7.67-7.70 (m, 3H), 7.35-7.37 (m, 1H), 6.88-7.14 (m, 2H), 2.00 (s, 3H).

Compound 94: 6-(4-(difluoromethyl)-6'-methyl-[2,2'-bipyridin]-3-yl)imidazo[1,2-a]pyridine-3-carboxamide

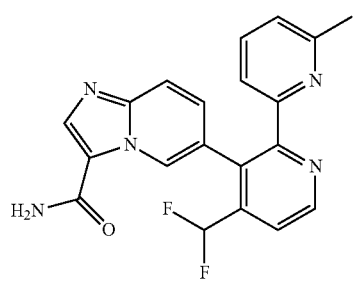 [SMILES: Cc1cccc(-c2nccc(C(F)F)c2-c2ccc3ncc(C(N)=O)n3c2)n1]

Compound 94 was synthesized from 93 in a manner similar to 19 employing the experimental procedure described in Scheme 7 (Method B). The crude product was purified by preparative HPLC (condition N) to yield 6-(4-(difluoromethyl)-6'-methyl-[2,2'-bipyridin]-3-yl)imidazo[1,2-a]pyridine-3-carboxamide 94 (9.1 mg, 0.024 mmol, 8.7% yield). LCMS: m/z=380.1 [M+H]$^+$; ret. time 1.09 min; condition C. $^1$H NMR (400 MHz, DMSO-d$_6$): δ 9.26 (s, 1H) 8.94 (d, J=8.00 Hz, 1H), 8.31 (s, 1H), 8.01-7.82 (m, 2H), 7.57-7.68 (m, 3H), 7.25-7.40 (m, 2H), 6.77-7.01 (m, 2H), 2.01 (s, 3H).

Scheme 22:

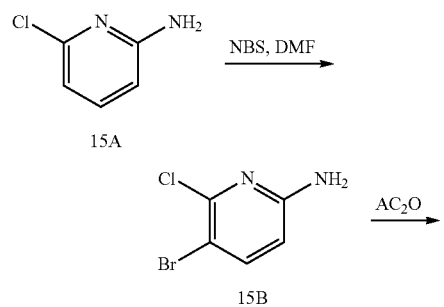

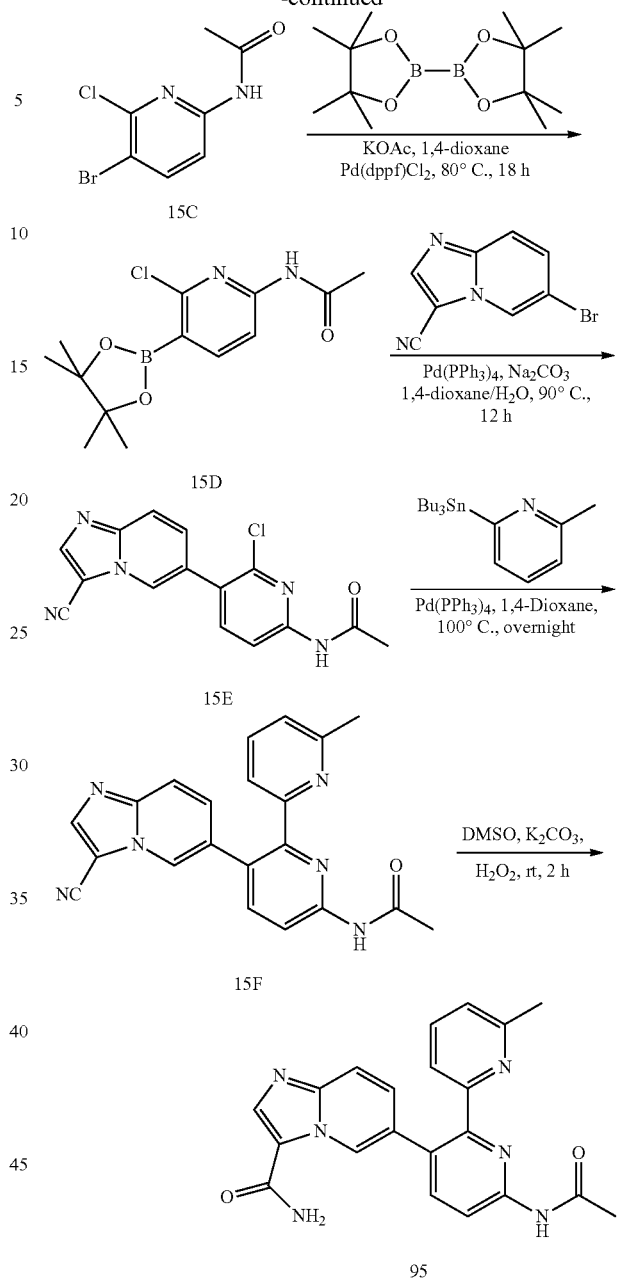

Compound 15B: 5-bromo-6-chloropyridin-2-amine

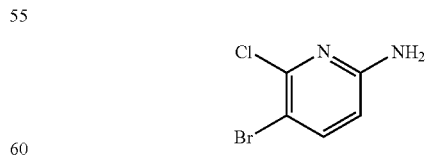

To a solution of 6-chloropyridin-2-amine 13A (reference: WO2014055955A1)-(1.0 g, 7.78 mmol) in DMF (10 mL) was added NBS (1.384 g, 7.78 mmol) portion-wise at room temperature and stirring was continued for 2 h. The reaction mixture was then evaporated under reduced pressure to give a crude residue. To this was added aqueous ammonia (60 mL, 25% solution) and the mixture was extracted with ethyl acetate (3×100 mL). The combined organic layer was dried over anhydrous sodium sulfate, filtered and the filtrate was evaporated under reduced pressure to give crude residue which was purified by silica gel chromatography (24 g RediSep® column, eluting with a gradient of 27-29% ethyl acetate in petroleum ether) to yield 5-bromo-6-chloropyridin-2-amine 15B (0.4 g, 1.928 mmol, 24.79% yield) as a brown solid. LCMS: m/z=207.0 [M+H]⁺; ret. time 1.74 min; condition-E. ¹H NMR (400 MHz, DMSO-d₆) δ ppm 7.63 (d, J=8.5 Hz, 1H), 6.59 (s, 2H), 6.36 (d, J=9.0 Hz, 1H).

Compound 15C:
N-(5-bromo-6-chloropyridin-2-yl)acetamide

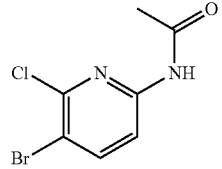

A solution of 5-bromo-6-chloropyridin-2-amine 15B (0.37 g, 1.784 mmol) in Ac₂O (5 mL, 53.0 mmol) was stirred at room temperature for 1 h. The reaction was then poured into ice-cold water, stirred for 20 min. and the precipitate obtained was filtered to yield N-(5-bromo-6-chloropyridin-2-yl)acetamide 15C (0.33 g, 1.323 mmol, 74.2% yield). LCMS: m/z=249.0 [M+H]⁺; ret. time 1.86 min; condition E. ¹H NMR (400 MHz, DMSO-d₆) δ ppm 10.94 (s, 1H), 8.16 (d, J=8.5 Hz, 1H), 8.01 (d, J=8.5 Hz, 1H), 2.09 (s, 3H).

Compound 15D: N-(6-chloro-5-(4,4,5,5-tetramethyl-1,3,2-dioxaborolan-2-yl)pyridin-2-yl)acetamide

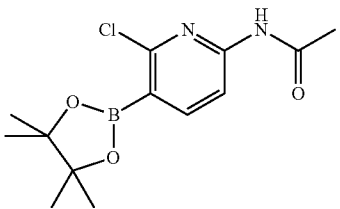 [SMILES: CC(=O)Nc1ccc(B2OC(C)(C)C(C)(C)O2)c(Cl)n1]

Compound 89 was synthesized from N-(5-bromo-6-chloropyridin-2-yl)acetamide 15C similar to 13B as shown in Scheme 20. The crude product N-(6-chloro-5-(4,4,5,5-tetramethyl-1,3,2-dioxaborolan-2-yl)pyridin-2-yl)acetamide 15D (0.29 g, 46.2% yield) was taken for the next step without further purification. LCMS: m/z=295.2 [M−H]⁺; ret. time 1.27 min; condition-C.

Compound 15E: N-(6-chloro-5-(3-cyanoimidazo[1,2-a]pyridin-6-yl)pyridin-2-yl)acetamide

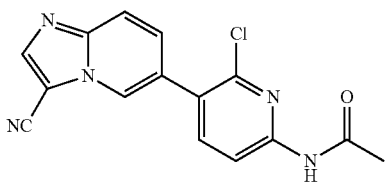 [SMILES: CC(=O)Nc1ccc(-c2ccc3ncc(C#N)n3c2)c(Cl)n1]

Compound 15E was synthesized by reacting N-(6-chloro-5-(4,4,5,5-tetramethyl-1,3,2-dioxaborolan-2-yl)pyridin-2-yl)acetamide 15D and 6-bromoimidazo[1,2-a]pyridine-3-carbonitrile 11B employing the experimental procedure described for compound 9B as shown in Scheme 16. The crude product 15E (0.18 g, 16% yield) was used for next reaction without further purification. LCMS: m/z=310.2 [M−H]⁺; ret. time 0.65 min; condition C.

Compound 15F: N-(3-(3-cyanoimidazo[1,2-a]pyridin-6-yl)-6'-methyl-[2,2'-bipyridin]-6-yl)acetamide

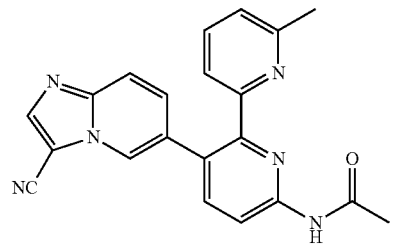 [SMILES: CC(=O)Nc1ccc(-c2ccc3ncc(C#N)n3c2)c(-c2cccc(C)n2)n1]

Compound 15F was synthesized by reacting N-(6-chloro-5-(3-cyanoimidazo[1,2-a]pyridin-6-yl)pyridin-2-yl)acetamide 15E and 2-methyl-6-(tributylstannyl)pyridine employing experimental procedure described in Scheme 1 (Method A). The crude product N-(3-(3-cyanoimidazo[1,2-a]pyridin-6-yl)-6'-methyl-[2,2'-bipyridin]-6-yl)acetamide 15F (0.04 g, 18.8% yield) was used for next reaction without further purification. LCMS: m/z=369.5 [M−H]⁺; ret. time 0.54 min; condition D.

Compound 95: 6-(6-acetamido-6'-methyl-[2,2'-bipyridin]-3-yl)imidazo[1,2-a]pyridine-3-carboxamide

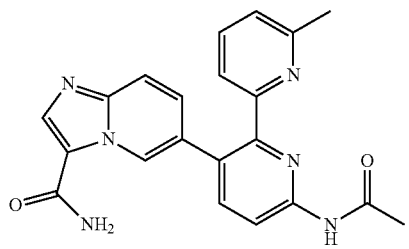 [SMILES: CC(=O)Nc1ccc(-c2ccc3ncc(C(N)=O)n3c2)c(-c2cccc(C)n2)n1]

Compound 95 was synthesized from 15F in a manner similar to 19 employing the experimental procedure described in Scheme 7 (Method B). The crude product was purified by preparative HPLC (method N) to yield 6-(6-acetamido-6'-methyl-[2,2'-bipyridin]-3-yl)imidazo[1,2-a]pyridine-3-carboxamide 95 (6.6 mg, 0.017 mmol, 15.7% yield). LC-MS: m/z=387.2 [M+H]⁺; ret. time 1.08 min; condition C. ¹H NMR (400 MHz, DMSO-d₆) δ ppm 10.79-10.73 (m, 1H), 9.38-9.32 (m, 1H), 8.31 (s, 1H), 8.26-8.21 (m, 1H), 7.97 (s, 1H), 7.67 (s, 1H), 7.57-7.50 (m, 1H), 7.48-7.28 (m, 2H), 7.19-7.05 (m, 2H), 2.19 (s, 3H), 2.14 (s, 3H).

Scheme 23:

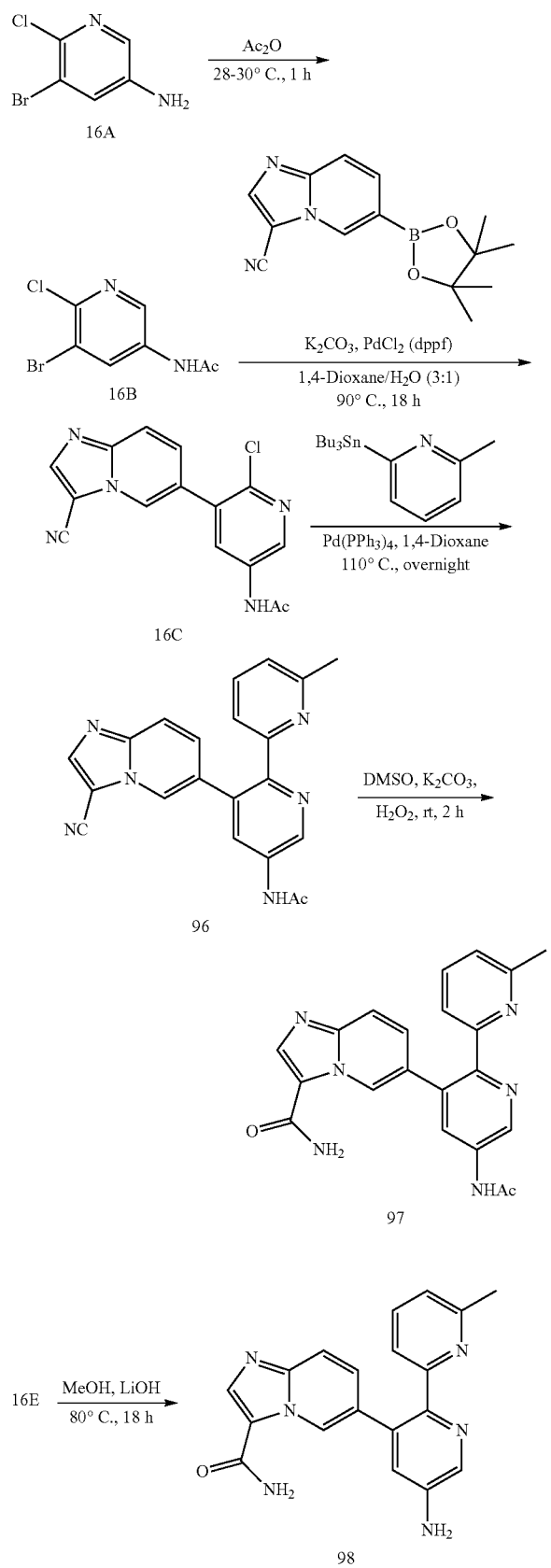

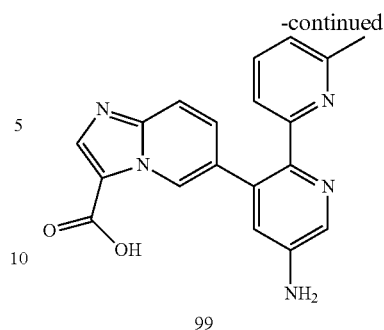

99

Compound 16B: N-(5-bromo-6-chloropyridin-3-yl)acetamide

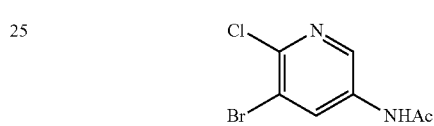

Compound 16B was synthesized from 5-bromo-6-chloropyridin-3-amine 16A employing experimental procedure for compound 15C in Scheme 22 to yield N-(5-bromo-6-chloropyridin-3-yl)acetamide 16B (0.25 g, 1.002 mmol, 49.5% yield) as a brown solid. LCMS: m/z=249.0 [M+H]⁺; ret. time 1.53 min; condition E.

Compound 16C: N-(6-chloro-5-(3-cyanoimidazo[1,2-a]pyridin-6-yl)pyridin-3-yl)acetamide

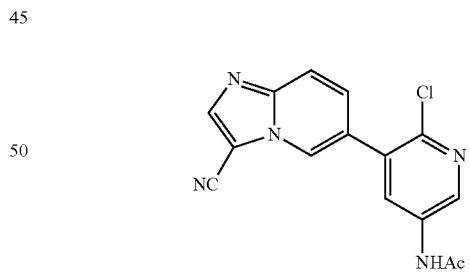

Compound 16C was synthesized by reacting bromo-6-chloropyridin-3-yl)acetamide 16B and 6-(4,4,5,5-tetramethyl-1,3,2-dioxaborolan-2-yl)imidazo[1,2-a]pyridine-3-carbonitrile employing the experimental procedure described in Scheme 5 (Method-E). The crude compound was purified by silica gel chromatography (24 g RediSep® column, eluting with a gradient of 42-48% ethyl acetate in petroleum ether) to yield N-(6-chloro-5-(3-cyanoimidazo[1,2-a]pyridin-6-yl)pyridin-3-yl)acetamide 16C (0.3 g, 0.962 mmol, 48.0% yield) as a brown solid. LCMS: m/z=312.2 [M+H]⁺; ret. time 1.23 min; condition E.

Compound 96: N-(3-(3-cyanoimidazo[1,2-a]pyridin-6-yl)-6'-methyl-[2,2'-bipyridin]-5-yl)acetamide

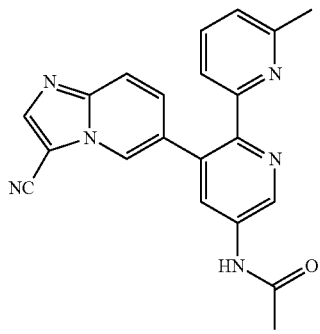

Compound 96 was synthesized by reacting 16C and 2-methyl-6-(tributylstannyl)pyridine employing experimental procedure described in Scheme 1 (Method A). The crude residue was purified by preparative HPLC (condition-N) to yield compound 96 (12.5 mg, 0.033 mmol, 17.3% yield). LCMS: m/z=369.2 [M+H]$^+$; ret. time 1.12 min; condition C. $^1$H NMR (400 MHz, DMSO-d$_6$) δ ppm 10.45 (s, 1H), 8.90 (d, J=2.2 Hz, 1H), 8.61-8.49 (m, 1H), 8.47-8.39 (m, 1H), 8.23 (d, J=2.4 Hz, 1H), 7.76-7.61 (m, 3H), 7.26 (dd, J=9.3, 1.7 Hz, 1H), 7.12 (d, J=7.3 Hz, 1H), 2.14 (s, 3H), 2.06 (s, 3H).

Compound 97: 6-(5-acetamido-6'-methyl-[2,2'-bipyridin]-3-yl)imidazo[1,2-a]pyridine-3-carboxamide

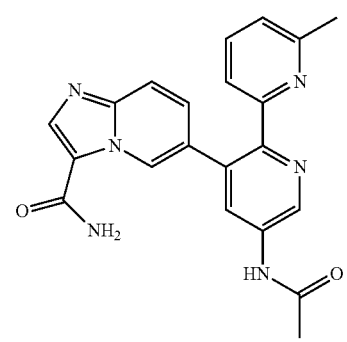 [SMILES: CC(=O)Nc1cnc(-c2cccc(C)n2)c(-c2ccc3ncc(C(N)=O)n3c2)c1]

Compound 97 was synthesized from 96 in a manner similar to 19 employing the experimental procedure described in Scheme 7 (Method B). The crude residue was purified by preparative HPLC (condition-N) to yield compound 97 (15.6 mg, 0.040 mmol, 13.5% yield). LCMS: m/z=387.1 [M+H]$^+$; ret. time 0.94 min; condition C. $^1$H NMR (400 MHz, DMSO-d$_6$) δ ppm 10.45 (s, 1H), 9.40 (s, 1H), 8.88 (d, J=2.2 Hz, 1H), 8.30 (s, 1H), 8.18 (d, J=2.4 Hz, 1H), 7.95 (br. s., 1H), 7.73-7.64 (m, 1H), 7.63-7.57 (m, 1H), 7.54 (d, J=9.3 Hz, 1H), 7.36 (br. s., 1H), 7.12-7.01 (m, 2H), 2.12 (s, 3H), 2.06-2.01 (s, 3H).

Compounds 98 and 99: 6-(5-amino-6'-methyl-[2,2'-bipyridin]-3-yl)imidazo[1,2-a]pyridine-3-carboxamide 98 and 6-(5-amino-6'-methyl-[2,2'-bipyridin]-3-yl)imidazo[1,2-a]pyridine-3-carboxylic acid 99

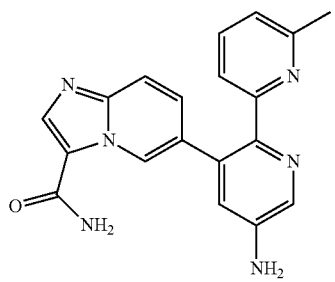

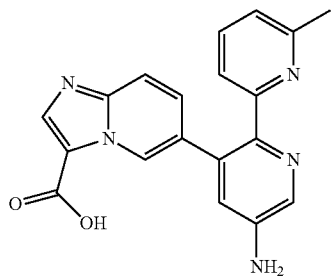

To a solution of N-(3-(3-cyanoimidazo[1,2-a]pyridin-6-yl)-6'-methyl-[2,2'-bipyridin]-5-yl)acetamide 97 (0.055 g, 0.149 mmol) in MeOH (4 mL) was added LiOH (1 mL, 2.0 mmol). The reaction mixture was heated at 80° C. for 18 h. It was then filtered through Celite® bed and the filtrate was concentrated under high vacuum to get a brown oil, which was purified by preparative HPLC (condition-N) to provide compounds 98 and 99

6-(5-amino-6'-methyl-[2,2'-bipyridin]-3-yl)imidazo[1,2-a]pyridine-3-carboxamide 98

(4.6 mg, 0.013 mmol, 8.95% yield). LCMS: m/z=345.1 [M+H]$^+$; ret. time 0.44 min; condition C. $^1$H NMR (400 MHz, DMSO-d$_6$) δ ppm 9.37 (s, 1H), 8.54 (s, 1H), 8.32 (s, 1H), 8.09 (s, 1H), 7.91 (br. s., 1H), 7.67-7.47 (m, 3H), 7.36 (s, 1H), 7.08-6.93 (m, 2H), 5.76 (s, 2H), 1.98 (s, 3H).

6-(5-amino-6'-methyl-[2,2'-bipyridin]-3-yl)imidazo[1,2-a]pyridine-3-carboxylic acid 14G (3.3 mg, 9.56 μmol, 6.40% yield). LCMS: m/z 346.1 [M+H]$^+$; ret. time 0.5 min; condition C. $^1$H NMR (400 MHz, DMSO-d$_6$) δ ppm 9.72 (br. s, 1H), 8.41-8.28 (m, 1H), 8.14 (br. s., 1H), 7.91-7.82 (m, 1H), 7.79-7.71 (m, 1H), 7.65 (d, J=9.0 Hz, 1H), 7.32-7.21 (m, 2H), 7.17 (br. s., 1H), 6.01-5.84 (s, 2H), 2.33 (s, 3H).

Scheme 24:

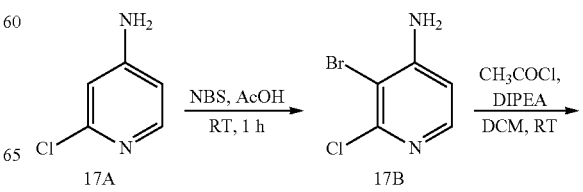

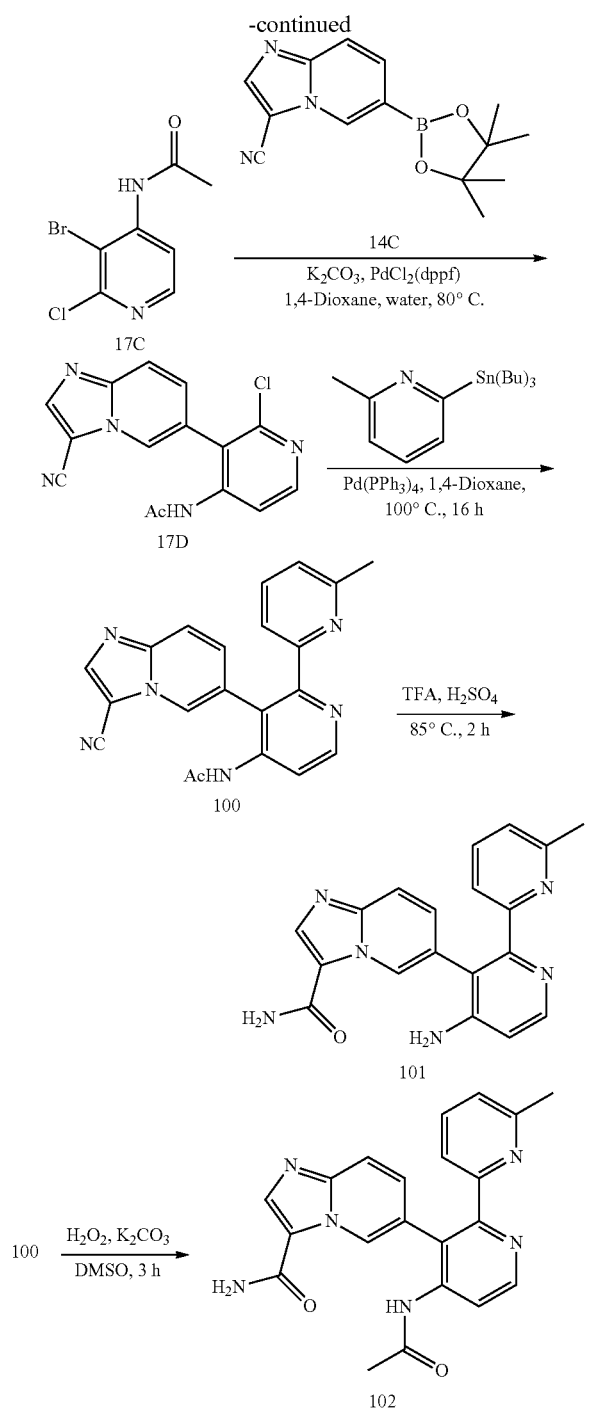

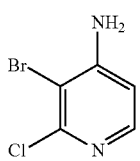

Compound 17B: 3-bromo-2-chloropyridin-4-amine

To a stirred solution of 2-chloropyridin-4-amine 17A (2 g, 15.56 mmol) in acetic acid (20 mL) was added NB S (2.77 g, 15.56 mmol) portion-wise at 0° C. under nitrogen. Then reaction mixture was allowed to stir at room temperature for 1 h. The solvent was removed under reduced pressure, followed by azeotropic distillation with ethanol. The crude compound was purified by silica gel chromatography (40 g RediSep® column, eluting with a gradient of 10-20% ethyl acetate in petroleum ether) to yield Compound 15B (2 g, 9.64 mmol, 62.0% yield) as a white solid. LCMS: m/z=209.0 [M+H]$^+$; ret. time 0.84 min; condition B.

Compound 17C:
N-(3-bromo-2-chloropyridin-4-yl)acetamide

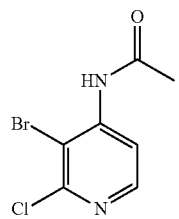

To a stirred solution of 3-bromo-2-chloropyridin-4-amine 17B (1 g, 4.82 mmol) in DCM (20 mL) at 0° C. was added DIPEA (1.684 mL, 9.64 mmol), followed by acetyl chloride (0.514 mL, 7.23 mmol) under nitrogen. Then reaction mixture was allowed to stir at room temperature for 1 h. The solvent was evaporated at reduced pressure, diluted with ethyl acetate (300 mL). Ethyl acetate layer was washed with saturated sodium bicarbonate (50 mL) and brine (50 mL). The organic layer was dried over anhydrous Na$_2$SO$_4$, filtered and concentrated under reduced pressure to yield crude N-(3-bromo-2-chloropyridin-4-yl)acetamide 17C (0.8 g. 66% yield). LCMS: m/z=251.3 [M+H]$^+$; ret. time 0.92 min; condition B, which was used without further purification.

Compound 17D: N-(2-chloro-3-(3-cyanoimidazo[1,2-a]pyridin-6-yl)pyridin-4-yl)acetamide

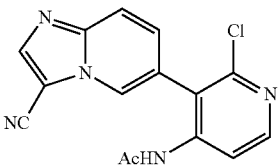 [SMILES: CC(=O)Nc1ccnc(Cl)c1-c1ccc2ncc(C#N)n2c1]

Compound 17D was synthesized from 17C similar to 17 employing the experimental procedure described in Scheme 5 (Method-E). The crude product was purified by silica gel chromatography (12 g RediSep® column, eluting with 4% methanol in chloroform). The fractions containing the product were collected and evaporated under reduced pressure to afford compound 17D (0.13 g, 0.417 mmol, 20.8% yield) as a white solid. LCMS: m/z=312.4 [M+H]$^+$; ret. time 0.85 min; condition B.

Compound 100: N-(3-(3-cyanoimidazo[1,2-a]pyridin-6-yl)-6'-methyl-[2,2'-bipyridin]-4-yl)acetamide

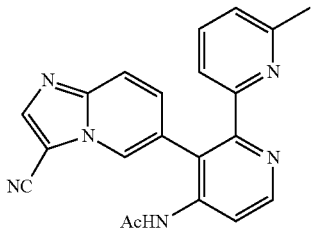

Compound 100 was synthesized by reacting 17D and 2-methyl-6-(tributylstannyl)pyridine employing the experimental procedure described in Scheme 1 (Method-A). The crude residue was purified by preparative HPLC (condition N) to yield N-(3-(3-cyanoimidazo[1,2-a]pyridin-6-yl)-6'-methyl-[2,2'-bipyridin]-4-yl)acetamide 100 (110 mg, 65% yield). LCMS: m/z=369.2 [M+H]$^+$; ret. time 1.19 min; condition C. $^1$H NMR (400 MHz, DMSO-d$_6$) δ ppm 9.02 (s, 1H), 8.62 (d, J=4.00 Hz, 1H), 8.46 (s, 2H), 8.16 (d, J=4.00 Hz, 1H), 7.74 (d, J=8.00 Hz, 1H), 7.64 (t, J=16.00 Hz, 1H), 7.53 (d, J=8.00 Hz, 1H), 7.27-7.25 (m, 1H), 7.04 (d, J=8.00 Hz, 1H), 2.03 (s, 3H), 1.97 (s, 3H).

Compound 101: 6-(4-amino-6'-methyl-[2,2'-bipyridin]-3-yl)imidazo[1,2-a]pyridine-3-carboxamide

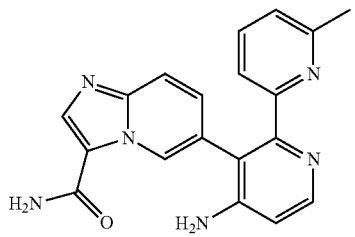 [SMILES: Cc1cccc(-c2nccc(N)c2-c2ccc3ncc(C(N)=O)n3c2)n1]

Compound 101 was synthesized from 100 in a manner similar to 3A employing the experimental procedure described in Scheme 6 (Method A). The crude residue was purified by preparative HPLC (condition N) to yield 6-(4-amino-6'-methyl-[2,2'-bipyridin]-3-yl)imidazo[1,2-a]pyridine-3-carboxamide 101 (10 mg, 34% yield). LCMS: m/z=345.1 [M+H]$^+$; ret. time 0.66 min; condition C. $^1$H NMR (400 MHz, DMSO-d$_6$): δ ppm 9.17 (s, 1H), 8.26 (s, 1H), 8.10-8.13 (m, 1H), 7.8 (bs, 1H), 7.53-7.58 (m, 2H), 7.41-7.43 (m, 1H), 7.25 (bs, 1H) 7.12-7.14 (m, 1H), 6.94 (d, J=8.00 Hz, 1H), 6.73 (d, J=4.00 Hz, 1H), 5.8 (s, 2H) 2.01 (s, 3H).

Compound 102: 6-(4-acetamido-6'-methyl-[2,2'-bipyridin]-3-yl)imidazo[1,2-a]pyridine-3-carboxamide

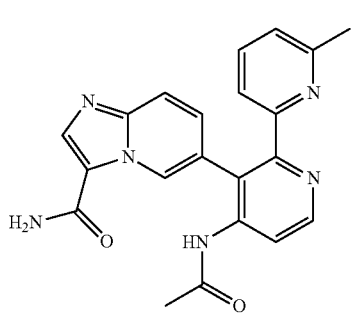 [SMILES: CC(=O)Nc1ccnc(-c2cccc(C)n2)c1-c1ccc2ncc(C(N)=O)n2c1]

Compound 102 was synthesized from 100 in a manner similar to 19 employing the experimental procedure described in Scheme 7 (Method B). The crude residue was purified by preparative HPLC (condition N) to yield 102 (14 mg, 32% yield). LCMS: m/z=387.1 [M+H]$^+$; ret. time 0.86 min; condition C. $^1$H NMR (400 MHz, DMSO-d$_6$) δ ppm 9.21-9.20 (m, 1H), 9.10 (s, 1H), 8.60 (d, J=4.00 Hz, 1H), 8.29 (s, 1H), 8.11 (d, J=8.00 Hz, 1H) 8.1 (bs, 1H), 7.61-7.57 (m, 2H), 7.40 (d, J=8.00 Hz, 1H), 7.14 (dd, J=12.00, Hz, 1H), 7.00 (d, J=8.00 Hz, 1H), 6.9 (m, 1H) 2.05 (s, 3H), 1.96 (s, 3H).

Scheme 25:

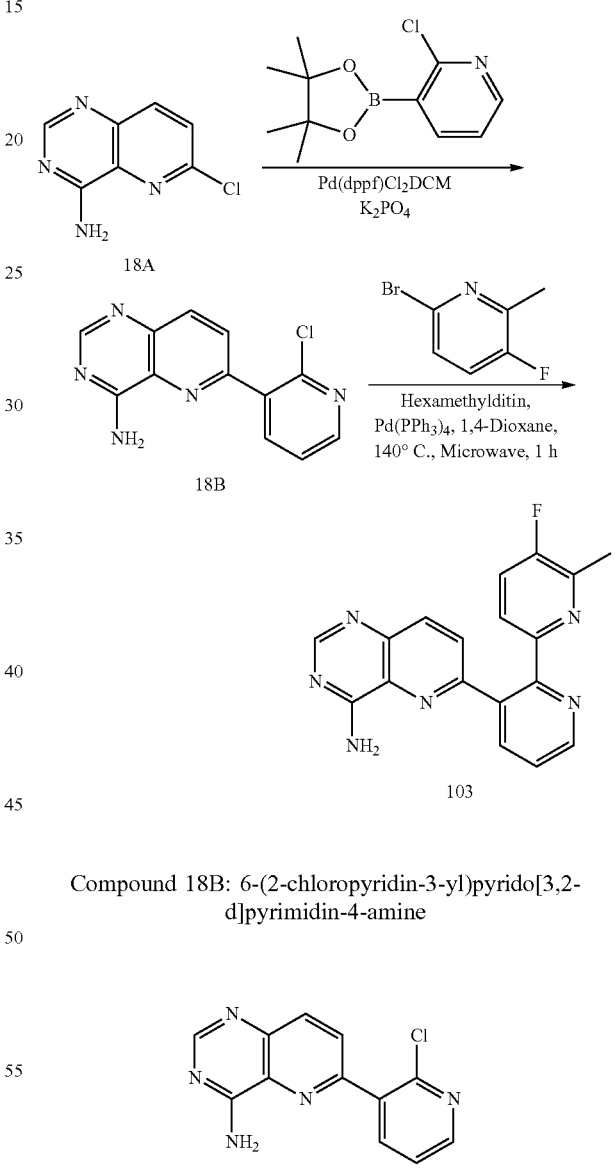

Compound 18B: 6-(2-chloropyridin-3-yl)pyrido[3,2-d]pyrimidin-4-amine

Compound 18B was synthesized by reacting 18A (reference: Journal of Medicinal Chemistry, 2014, 57, 3484-3493) and 2-chloro-3-(4,4,5,5-tetramethyl-1,3,2-dioxaborolan-2-yl)pyridine (reference: WO 2015157093 A1, WO 2015044172 A1 and WO 2014055955 A1) employing experimental procedure described in Scheme 5 (Method-E). The crude residue was purified by silica gel chromatography (24 g RediSep® column, eluting with a gradient of 3-10% methanol in chloroform). The fractions containing the product were combined and concentrated under reduced pressure to yield compound 18B (320 mg, 1.242 mmol, 37.4% yield) as a yellow solid. LCMS: m/z=258.0 [M+H]$^+$; ret. time 1.08 min; condition E.

Compound 103: 6-(5'-fluoro-6'-methyl-[2,2'-bipyridin]-3-yl)pyrido[3,2-d]pyrimidin-4-amine

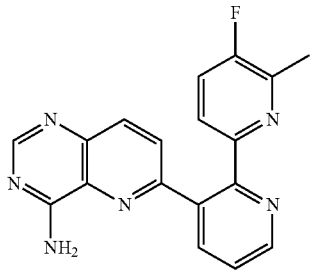

Compound 103 was synthesized by reacting 18B and 6-bromo-3-fluoro-2-methylpyridine employing the experimental procedure described for compound 15 as shown in Scheme 3 (Method C). The crude residue was purified by preparative HPLC (condition K) to yield 103 (13.9 mg, 0.041 mmol, 14.23% yield). LCMS: m/z=333.2 [M+H]$^+$; ret. time 1.24 min; condition C. $^1$H NMR (400 MHz, DMSO-d$_6$) δ ppm 8.77 (dd, J=4.77, 1.59 Hz, 1H) 8.40 (s, 1H) 8.25 (dd, J=7.70, 1.59 Hz, 1H) 7.76-7.87 (m, 4H) 7.63 (dd, J=7.83, 4.65 Hz, 1H) 7.52 (br. s., 1H) 7.40 (d, J=8.80 Hz, 1H) 1.94 (s, 3H).

Compound 104: 6-(5'-fluoro-[2,2'-bipyridin]-3-yl)pyrido[3,2-d]pyrimidin-4-amine

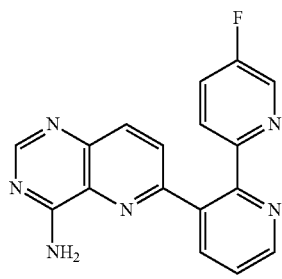 [SMILES: Nc1ncnc2ccc(-c3cccnc3-c3ccc(F)cn3)nc12]

Compound 104 was synthesized by reacting 18B and 6-bromo-3-fluoropyridine employing the experimental procedure described for compound 15 as shown in Scheme 3 (Method C). The crude residue was purified by preparative HPLC (method Q) to yield compound 104 (35.6 mg, 0.111 mmol, 36% yield). LCMS: m/z=319.2 [M+H]$^+$; ret. time 1.09 min; condition C. $^1$H NMR (400 MHz, DMSO-d$_6$) δ ppm 8.78 (dd, J=4.65, 1.47 Hz, 1H) 8.40 (s, 1H) 8.27-8.32 (m, 1H) 8.21 (d, J=2.69 Hz, 1H) 8.09 (dd, J=8.80, 4.65 Hz, 1H) 7.84-7.91 (m, 3H) 7.65 (dd, J=7.83, 4.89 Hz, 1H) 7.49 (br. s., 1H) 7.44 (d, J=8.56 Hz, 1H).

Compound 105: 6-(6'-(difluoromethyl)-[2,2'-bipyridin]-3-yl)pyrido[3,2-d]pyrimidin-4-amine

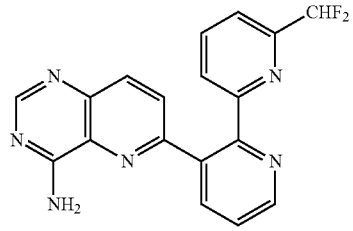

Compound 105 was synthesized by reacting 18B and 2-bromo-6-(difluoromethyl)pyridine employing the experimental procedure described for compound 15 as shown in Scheme 3 (Method C). The crude residue was purified by preparative HPLC (method K) to yield compound 105. (30.1 mg, 0.085 mmol, 28% yield). LCMS: m/z=351.1 [M+H]$^+$; ret. time 1.32 min; condition C. $^1$H NMR (400 MHz, DMSO-d$_6$) δ ppm 8.82 (dd, J=4.77, 1.59 Hz, 1H) 8.38 (s, 1H) 8.30 (dd, J=7.83, 1.71 Hz, 1H) 8.09-8.18 (m, 2H) 7.89 (d, J=8.56 Hz, 1H) 7.80 (br. s., 1H) 7.69 (dd, J=7.83, 4.89 Hz, 1H) 7.60 (d, J=6.85 Hz, 1H) 7.53 (d, J=8.80 Hz, 1H) 7.32 (br. s., 1H) 6.19-6.48 (t, J=54.8 Hz, 1H).

Compound 106: 6-(6'-cyclopropyl-[2,2'-bipyridin]-3-yl)pyrido[3,2-d]pyrimidin-4-amine

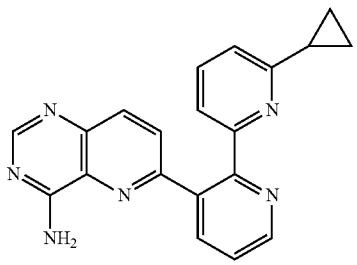

Compound 106 was synthesized by reacting 18B and 2-bromo-6-cyclopropylpyridine employing experimental procedure described for compound 15 as shown in Scheme 3 (Method C). The crude residue was purified by preparative HPLC (method: K) to yield compound 106 (48 mg, 0.141 mmol, 45% yield). LCMS: m/z=341.1 [M+H]$^+$; ret. time 1.42 min; condition C. $^1$H NMR (400 MHz, DMSO-d$_6$) δ ppm 8.76 (dd, J=4.77, 1.59 Hz, 1H) 8.41 (s, 1H) 8.17 (dd, J=7.83, 1.71 Hz, 1H) 7.87 (d, J=8.80 Hz, 1H) 7.75-7.85 (m, 3H) 7.61 (dd, J=7.83, 4.65 Hz, 1H) 7.55 (br. s., 1H) 7.34 (d, J=8.80 Hz, 1H) 7.25 (dd, J=7.34, 1.22 Hz, 1H) 1.73-1.77 (m, 1H) 0.402-0.358 (m, 2H) 0.137-0.164 (m, 2H).

Scheme 26:

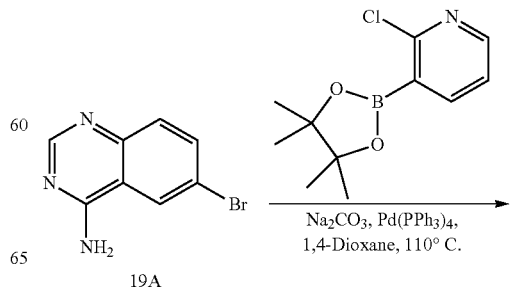

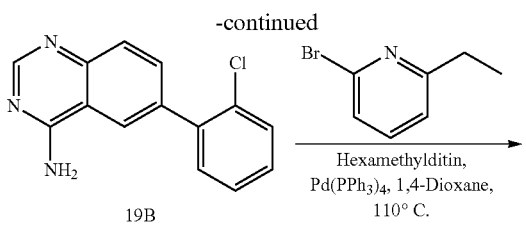

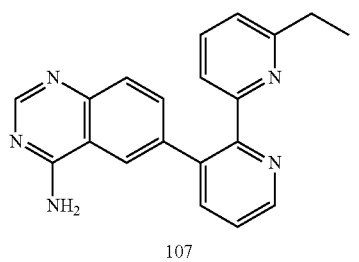

107

Compound 19B:
6-(2-chloropyridin-3-yl)quinazolin-4-amine

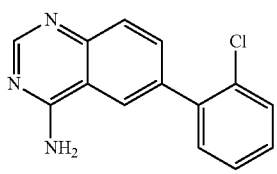 [SMILES: Nc1ncnc2ccc(-c3ccccc3Cl)cc12]

Compound 19B was synthesized by reacting 19A (reference: *Angew. Chem. Int. Ed.* 2014, 53, 305-309) and 2-chloro-3-(4,4,5,5-tetramethyl-1,3,2-dioxaborolan-2-yl) pyridine employing the experimental procedure described for compound 9B as shown in Scheme 16. The crude residue was purified by silica gel chromatography (40 g RediSep® column, eluting with a gradient of 35% ethyl acetate in petroleum ether) to yield 6-(2-chloropyridin-3-yl)quinazolin-4-amine 18B (0.6 g, 2.337 mmol, 52.4% yield). LCMS: m/z=257.2 [M+H]⁺; ret. time 1.06 min; condition E.

Compound 107: 6-(6'-ethyl-[2,2'-bipyridin]-3-yl) quinazolin-4-amine

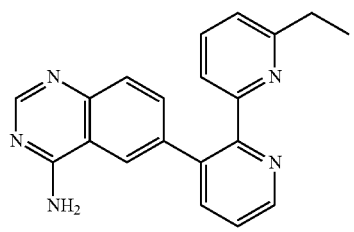 [SMILES: CCc1cccc(-c2ncccc2-c2ccc3ncnc(N)c3c2)n1]

Compound 107 was synthesized by reacting 19B and 6-bromo-2-ethylpyridine employing the experimental procedure described in Scheme 2 (Method B). The crude residue was purified by preparative HPLC (method: F) to yield compound 107 (4.2 mg, 0.012 mmol, 2.09% yield). LCMS: m/z=328.2 [M+H]⁺; ret. time 1.21 min; condition C. ¹H NMR (400 MHz, DMSO-d₆) δ ppm 8.83 (s, 1H), 8.80-8.76 (m, 1H), 8.41 (s, 1H), 7.97 (dd, J=7.9, 1.6 Hz, 1H), 7.83-7.78 (m, 2H), 7.67-7.61 (m, 3H), 7.26-6.93 (m, 3H), 2.30 (d, J=7.6 Hz, 2H), 0.60-0.50 (m, 3H).

Compound 108: 6-(6'-isopropyl-[2,2'-bipyridin]-3-yl)quinazolin-4-amine

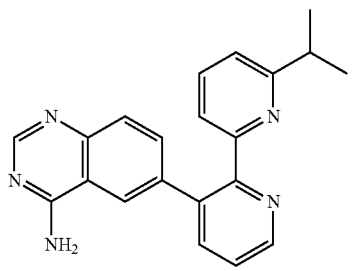 [SMILES: CC(C)c1cccc(-c2ncccc2-c2ccc3ncnc(N)c3c2)n1]

Compound 108 was synthesized by reacting 19B and 2-bromo-6-isopropylpyridine employing the experimental procedure described in Scheme-2 (Method B). The crude residue was purified by preparative HPLC (method N) to yield compound 108 (14.6 mg, 0.04 mmol, 7.03% yield). LCMS: m/z=342.2 [M+H]⁺; ret. time 1.36 min; condition C. ¹H NMR (400 MHz, DMSO-d₆) δ ppm 8.75-8.67 (m, 1H), 8.33 (s, 1H), 8.17 (d, J=1.5 Hz, 1H), 8.00-7.90 (m, 1H), 7.83-7.71 (m, 2H), 7.69-7.52 (m, 3H), 7.43 (d, J=8.6 Hz, 1H), 7.25 (dd, J=8.6, 1.7 Hz, 1H), 7.10 (d, J=7.3 Hz, 1H), 2.65-2.54 (m, 1H), 0.62 (d, J=6.8 Hz, 6H).

Compound 109: 6-(6'-(difluoromethyl)-[2,2'-bipyridin]-3-yl)quinazolin-4-amine

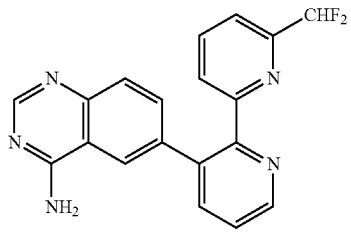 [SMILES: Nc1ncnc2ccc(-c3cccnc3-c3cccc(C(F)F)n3)cc12]

Compound 109 was synthesized by reacting 19B and 2-bromo-6-(difluoromethyl)pyridine employing the experimental procedure described in Scheme-2 (Method B). The crude residue was purified by preparative HPLC (method K) to yield compound 109 (0.015 g, 0.042 mmol, 10.7% yield). LCMS: m/z=350.2 [M+H]⁺; ret. time 1.08 min; condition E. ¹H NMR (400 MHz, DMSO-d₆) δ ppm 8.77 (dd, 1.5 Hz, 1H), 8.36 (s, 1H), 8.21 (d, J=1.5 Hz, 1H), 8.08-8.00 (m, 2H), 7.93 (d, J=8.0 Hz, 1H), 7.67 (dd, J=8.0, 4.5 Hz, 3H), 7.59 (d, J=8.0 Hz, 1H), 7.44 (d, J=9.0 Hz, 1H), 7.29 (dd, J=8.8, 1.8 Hz, 1H), 1.82 (s, 1H).

Compound 110: 6-(5'-fluoro-6'-methyl-[2,2'-bipyridin]-3-yl)imidazo[1,2-a]pyridine-2-carboxamide

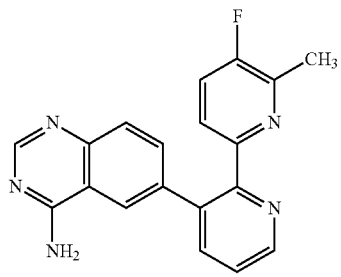

Compound 110 was synthesized by reacting 19B and 6-bromo-3-fluoro-2-methylpyridine employing the experimental procedure described in Scheme-2 (Method B). The crude residue was purified by preparative HPLC (method K) to yield compound 110 (15 mg, 0.044 mmol, 11.3% yield). LCMS: m/z=332.2 [M+H]$^+$; ret. time 1.03 min; condition E. $^1$H NMR (400 MHz, DMSO-d$_6$) δ ppm 8.72 (dd, J=4.8, 1.8 Hz, 1H), 8.37 (s, 1H), 8.20 (d, J=2.0 Hz, 1H), 7.97 (dd, J=7.8, 1.8 Hz, 1H), 7.74-7.63 (m, 4H), 7.60 (dd, J=7.5, 4.5 Hz, 1H), 7.47 (d, J=8.5 Hz, 1H), 7.30 (dd, J=8.5, 2.0 Hz, 1H), 2.03 (d, J=3.0 Hz, 3H).

Compound 111: 6-(6'-isopropyl-[2,2'-bipyridin]-3-yl)quinazolin-4-amine

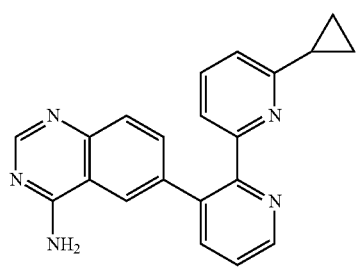 [SMILES: Nc1ncnc2ccc(-c3cccnc3-c3cccc(C4CC4)n3)cc12]

Compound 111 was synthesized by reacting 19B and 2-bromo-6-cyclopropylpyridine employing the experimental procedure described in Scheme-2 (Method B). The crude residue was purified by preparative HPLC (method: N) to yield compound 111 (31.2 mg, 0.091 mmol, 11.7% yield). LCMS: m/z=340.1 [M+H]$^+$; ret. time 1.38 min; condition C. $^1$H NMR (400 MHz, DMSO-d$_6$) δ ppm 8.68-8.72 (m, 1H), 8.35-8.38 (m, 1H), 8.15-8.19 (m, 1H), 7.89-7.94 (m, 1H), 7.62-7.77 (m, 4H), 7.55-7.61 (m, 1H), 7.43-7.47 (m, 1H), 7.16-7.23 (m, 2H), 1.70-1.79 (m, 1H), 0.33-0.41 (m, 2H), −0.13-0.06 (m, 2H).

Scheme 27:

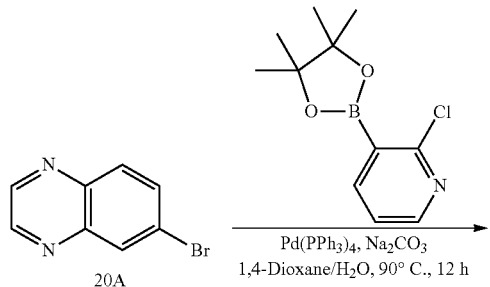

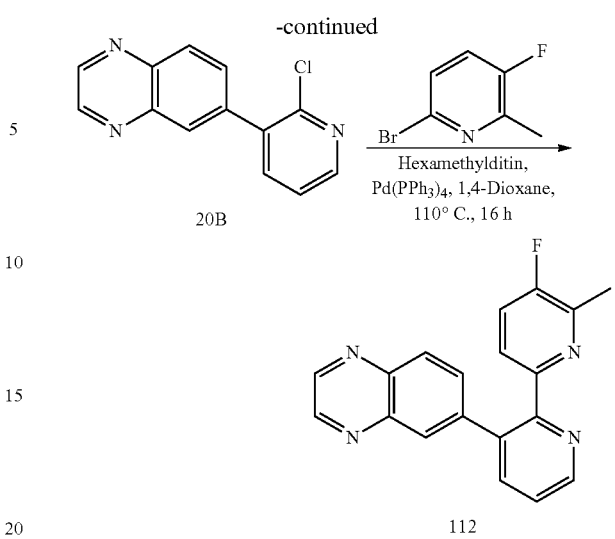

Compound 20B:
6-(2-chloropyridin-3-yl)quinoxaline

Compound 20B was synthesized by reacting 20A and 2-chloro-3-(4,4,5,5-tetramethyl-1,3,2-dioxaborolan-2-yl)pyridine (reference: WO 2015157093 A1, WO 2015044172 A1 and WO 2014055955 A1) employing the experimental procedure described in Scheme-5 (Method E). The crude product was purified by silica gel chromatography (40 g RediSep® column, eluting with 50% ethyl acetate in petroleum ether) to yield compound 20B (2.32 g, 9.61 mmol, 67.0% yield) as a light yellow solid. LCMS: m/z=242.0 [M+H]$^+$; ret. time 1.66 min; condition C.

Compound 112: 6-(5'-fluoro-6'-methyl-[2,2'-bipyridin]-3-yl)quinoxaline

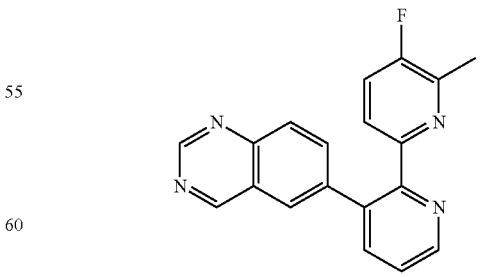

Compound 112 was synthesized by reacting 20B and 2-methyl-3-Flouro-6-bromopyridine employing experimental procedure described in Scheme-2 (Method B). The crude residue was purified by preparative HPLC (method: N) to yield compound 112 (79.9 mg, 0.253 mmol, 40.7% yield). LCMS: m/z=317.2 [M+H]+; ret. time 1.51 min.; condition-C. $^1$H NMR (400 MHz, DMSO-$d_6$): δ ppm 8.94 (s, 2H), 8.76 (dd, J=1.2, 4.8 Hz, 1H), 8.05-8.07 (m, 1H), 7.92-7.97 (m, 2H), 7.74-7.77 (m, 1H), 7.61-7.69 (m, 2H), 7.51-7.53 (m, 1H), 1.93 (d, J=2.8 Hz, 3H).

Compound 113: 6-(6'-methyl-[2,2'-bipyridin]-3-yl)quinoxaline

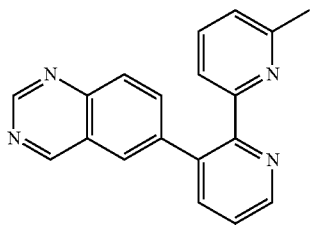 [SMILES: Cc1cccc(-c2ncccc2-c2ccc3ncncc3c2)n1]

Compound 113 was synthesized by reacting 20B and 2-methyl-6-(tributylstannyl)pyridine employing the experimental procedure described in Scheme 1 (Method A). The crude residue was purified by preparative HPLC (method: N) to yield 6-(6'-methyl-[2,2'-bipyridin]-3-yl)quinoxaline 113 (68.6 mg, 0.230 mmol, 55.6% yield). LCMS: m/z=299.1 [M+H]+; ret. time 1.41 min; conditions-C. $^1$H NMR (400 MHz, DMSO-$d_6$): δ ppm 8.92 (s, 2H), 8.74-8.76 (m, 1H), 8.05-8.07 (m, 1H), 7.90-7.94 (m, 2H), 7.69-7.73 (m, 1H), 7.60-7.63 (m, 2H), 7.51 (dd, J=2.0, 8.8 Hz, 1H), 7.11 (d, J=7.6 Hz, 1H), 1.97 (s, 3H).

Compound 114: 6-(6'-(trifluoromethyl)-[2,2'-bipyridin]-3-yl)quinoxaline

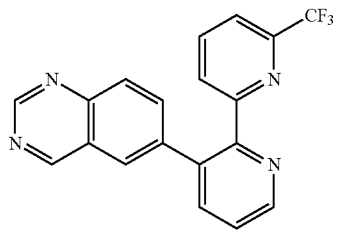 [SMILES: FC(F)(F)c1cccc(-c2ncccc2-c2ccc3ncncc3c2)n1]

Compound 114 was synthesized by reacting 20B and 2-bromo-6-(trifluoromethyl)pyridine employing the experimental procedure described in Scheme-2 (Method B). The crude residue was purified by preparative HPLC (method: H) to yield 6-(6'-(trifluoromethyl)-[2,2'-bipyridin]-3-yl)quinoxaline 114 (56.9 mg, 0.162 mmol, 39.0% yield). LCMS: m/z=353.1 [M+H]+; ret. time 1.75 min; condition C. 1H NMR (400 MHz, DMSO-$d_6$): δ ppm 8.93 (s, s, 2H), 8.83-8.84 (m, 1H), 8.26 (d, J=8.0 Hz, 1H), 8.12-8.20 (m, 2H), 7.96 (d, J=8.4 Hz, 1H), 7.98 (d, J=1.6 Hz, 1H), 7.76 (d, 7.6 Hz, 1H), 7.71 (dd, J=4.8, 7.6 Hz, 1H), 7.54 (dd, J=2.0, 8.8 Hz, 1H).

Scheme 28:

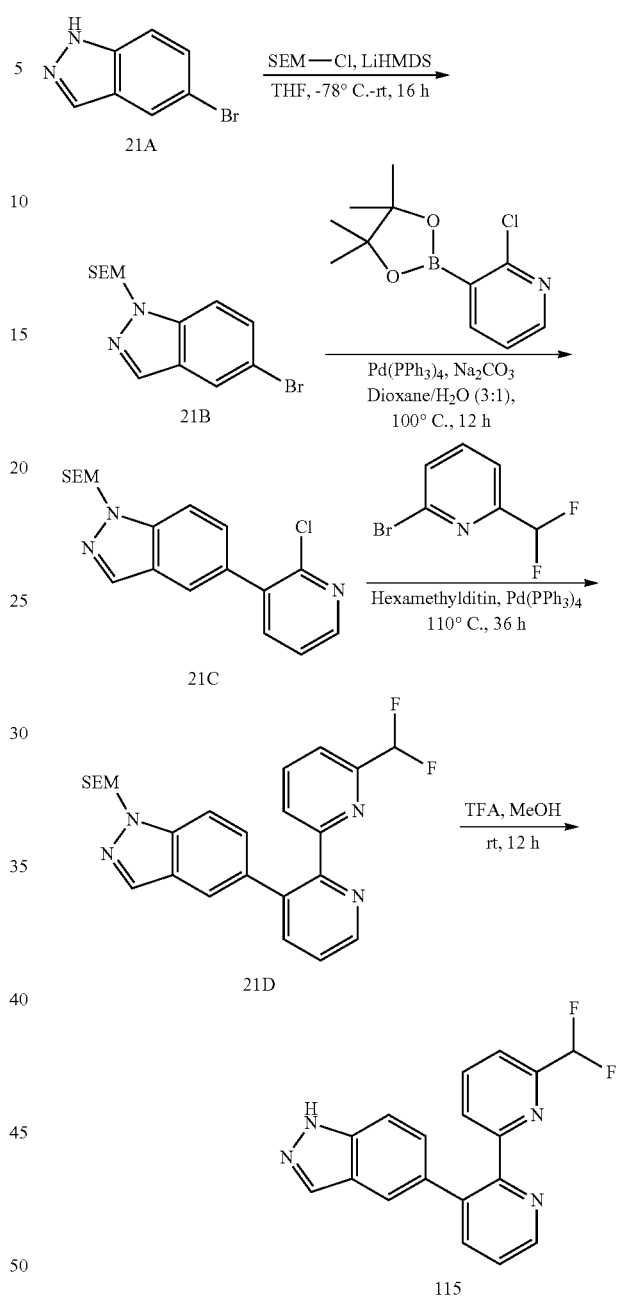

Compound 21B: 5-bromo-1-((2-(trimethylsilyl)ethoxy)methyl)-1H-indazole

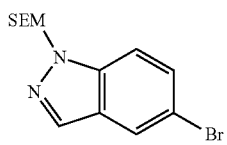 [SMILES: C[Si](C)(C)CCOCn1ncc2cc(Br)ccc21]

To a solution of 5-bromo-1H-indazole 20 (5 g, 25.4 mmol) in THF (100 mL) was added LiHMDS (30.5 mL, 30.5 mmol) at −78° C. and the reaction mixture was stirred at the same temperature for 30 min. Then 2-(trimethylsilanyl)ethoxymethyl chloride (6.75 mL, 38.1 mmol) was added and the reaction mixture was slowly allowed to attain room temperature and stirred for 16 h. The reaction mixture was quenched with saturated NH$_4$Cl. The aqueous layer was back extracted with ethyl acetate (3×100 mL). The combined organic layers was washed with 10% NaHCO$_3$ (3×150 mL) solution and brine. The organic layer was dried over Na$_2$SO$_4$, filtered and concentrated to afford crude product as pale yellow liquid. The crude residue was purified by silica gel chromatography (120 g RediSep® column, eluted with a gradient of 1-5% ethyl acetate in petroleum ether) to yield 5-bromo-1-((2-(trimethylsilyl)ethoxy)methyl)-1H-indazole 21B (8.13 g, 24.84 mmol, 98% yield) as a light yellow liquid. LCMS: m/z=327.0 [M+H]$^+$; ret. time 3.76 min; condition E.

Compound 21C: 5-(2-chloropyridin-3-yl)-1-((2-(trimethylsilyl)ethoxy)methyl)-1H-indazole

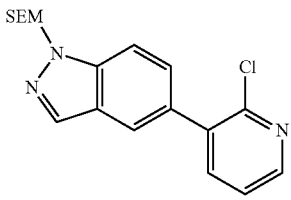 [SMILES: C[Si](C)(C)CCOCn1ncc2cc(-c3cccnc3Cl)ccc21]

Compound 21C was synthesized by reacting 21B and 2-chloro-3-(4,4,5,5-tetramethyl-1,3,2-dioxaborolan-2-yl) employing the experimental procedure described for compound 9B as shown in Scheme 16. The crude residue was purified by silica gel chromatography (40 g RediSep® column, eluted with a gradient of 5-10% ethyl acetate in petroleum ether) to yield 5-(2-chloropyridin-3-yl)-1-((2-(trimethylsilyl)ethoxy)methyl)-1H-indazole 21C (1.925 g, 5.35 mmol, 50.0% yield) as light yellow solid. LCMS: m/z=360.3 [M+H]$^+$; ret. time 1.21 min; condition B.

Compound 21D: 5-(6'-(difluoromethyl)-[2,2'-bipyridin]-3-yl)-1-((2-(trimethylsilyl)ethoxy)methyl)-1H-indazole

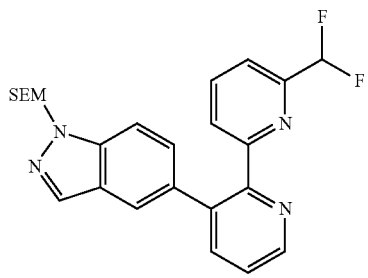 [SMILES: C[Si](C)(C)CCOCn1ncc2cc(-c3cccnc3-c3cccc(C(F)F)n3)ccc21]

Compound 21D was synthesized by reacting 21C and 2-bromo-6-(difluoromethyl)pyridine (95 mg, 0.458 mmol) employing the experimental procedure described in Scheme-2 (Method B). The crude residue was purified by silica gel chromatography (24 g RediSep® column, eluted with a gradient of 5-10% methanol in chloroform) to yield 5-(6'-(difluoromethyl)-[2,2'-bipyridin]-3-yl)-1-((2-(trimethylsilyl)ethoxy)methyl)-1H-indazole 21D (93 mg, 0.205 mmol, 49.3% yield). LCMS: m/z=453.7 [M+H]$^+$; ret. time 1.1 min; condition B.

Compound 115: 5-(6'-(difluoromethyl)-[2,2'-bipyridin]-3-yl)-1H-indazole

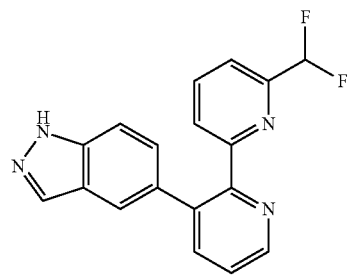

5-(6'-(Difluoromethyl)-[2,2'-bipyridin]-3-yl)-1-((2-(trimethylsilyl)ethoxy)methyl)-1H-indazole 21D (110 mg, 0.243 mmol) was treated with TFA (8 mL, 104 mmol) and the reaction mixture was stirred at room temperature for 12 h. The volatiles were removed under reduced pressure and the residue was dissolve in methanol (10 mL) and ammonium hydroxide (8 mL, 205 mmol) and stirred for 12 h. After that, the reaction mixture was evaporated under reduced pressure to obtain the crude compound, which was purified by preparative HPLC (method: H) to yield 5-(6'-(difluoromethyl)-[2,2'-bipyridin]-3-yl)-1H-indazole 115 (37.5 mg, 0.116 mmol, 47.9% yield). LCMS: m/z=323.1 [M+H]$^+$; ret. time 1.14 min; condition C. $^1$H NMR (400 MHz, DMSO-d$_6$) δ ppm 13.03 (s, 1H), 8.71 (dd, J=1.6, 4.8 Hz, 1H), 7.93-8.01 (m, 3H), 7.61-7.68 (m, 3H), 7.57 (d, J=7.6 Hz, 1H), 7.36 (d, J=8.8 Hz, 1H), 6.96-7.00 (m, 1H), 6.58 (t, J=55.2 Hz, 1H).

Compound 21F: 5-(5'-fluoro-[2,2'-bipyridin]-3-yl)-1-((2-(trimethylsilyl)ethoxy)methyl)-1H-indazole

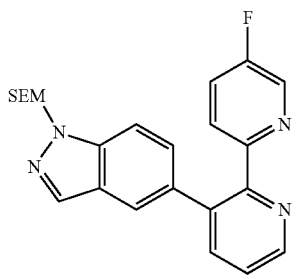 [SMILES: C[Si](C)(C)CCOCn1ncc2cc(-c3cccnc3-c3ccc(F)cn3)ccc21]

Compound 21F was synthesized by reacting 21C and 2-bromo-5-fluoropyridine employing the experimental procedure described in Scheme-2 (Method B). The crude residue was purified by silica gel chromatography (24 g RediSep® column, eluted with a gradient of 5-10% methanol in chloroform) to yield 5-(5'-fluoro-[2,2'-bipyridin]-3-yl)-1-((2-(trimethylsilyl)ethoxy)methyl)-1H-indazole 21F (105 mg, 0.250 mmol, 59.9% yield). LCMS: m/z=421.1 [M+H]$^+$; ret. time 3.13 min; condition E.

Compound 116: 5-(5'-fluoro-[2,2'-bipyridin]-3-yl)-1H-indazole

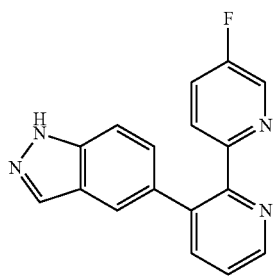 [SMILES: Fc1ccc(-c2ncccc2-c2ccc3[nH]ncc3c2)nc1]

Compound 116 was synthesized by reacting 21F employing the experimental procedure described in for compound 115 in Scheme 28. The crude residue was purified by preparative HPLC (method: H) to yield 5-(5'-fluoro-[2,2'-bipyridin]-3-yl)-1H-indazole 116 (23.2 mg, 0.080 mmol, 28.0% yield). LCMS: m/z=291.1 [M+H]$^+$; ret. time 1.32 min; condition C. $^1$H NMR (400 MHz, DMSO-d$_6$) δ ppm 8.65-8.67 (m, 1H), 8.29 (d, J=2.8 Hz, 1H), 8.02 (s, 1H), 7.92-7.95 (m, 1H), 7.68-7.76 (m, 2H), 7.60 (s, 1H), 7.55-7.58 (m, 1H), 7.37 (d, J=8.8 Hz, 1H), 6.95-6.98 (m, 1H).

Compound 21H: 5-(5'-fluoro-6'-methyl-[2,2'-bipyridin]-3-yl)-1-((2-(trimethylsilyl)ethoxy)methyl)-1H-indazole

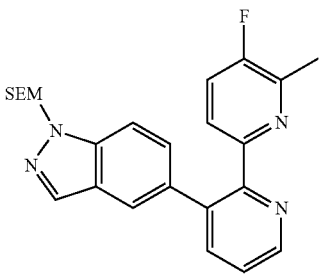 [SMILES: Cc1nc(-c2ncccc2-c2ccc3c(cnn3COCC[Si](C)(C)C)c2)ccc1F]

Compound 21H was synthesized by reacting 21C and 6-bromo-3-fluoro-2-methylpyridine employing the experimental procedure described in Scheme-2 (Method B). The crude residue was purified by silica gel chromatography (24 g RediSep® column, eluted with a gradient of 5-10% methanol in chloroform) to get 5-(5'-fluoro-6'-methyl-[2,2'-bipyridin]-3-yl)-1-((2-(trimethylsilyl)ethoxy)methyl)-1H-indazole 21H (135 mg, 0.311 mmol, 74.5% yield) as a light yellow solid. LCMS: m/z=435.4 [M+H]$^+$; ret. time 3.3 min; condition E.

Compound 117: 5-(5'-fluoro-6'-methyl-[2,2'-bipyridin]-3-yl)-1H-indazole

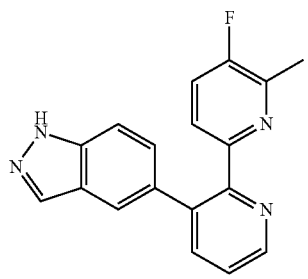 [SMILES: Cc1nc(-c2ncccc2-c2ccc3[nH]ncc3c2)ccc1F]

Compound 117 was synthesized by reacting 21H employing the experimental procedure described for compound 115 as shown in Scheme 28. The crude residue was purified by preparative HPLC (method: H) to yield 5-(5'-fluoro-6'-methyl-[2,2'-bipyridin]-3-yl)-1H-indazole 117 (13 mg, 0.043 mmol, 14.28% yield). LCMS: m/z=305.1 [M+H]$^+$; ret. time 1.24 min; condition C. $^1$H NMR (400 MHz, DMSO-d$_6$) δ ppm 13.03 (s, 1H), 8.65 (dd, J=1.6, 4.8 Hz, 1H), 8.03 (s, 1H), 7.92 (dd, J=1.6, 8.0 Hz, 1H), 7.53-7.60 (m, 3H), 7.37-7.42 (m, 2H), 6.97-7.00 (m, 1H), 2.13 (d, J=2.8 Hz, 3H).

Scheme 29:

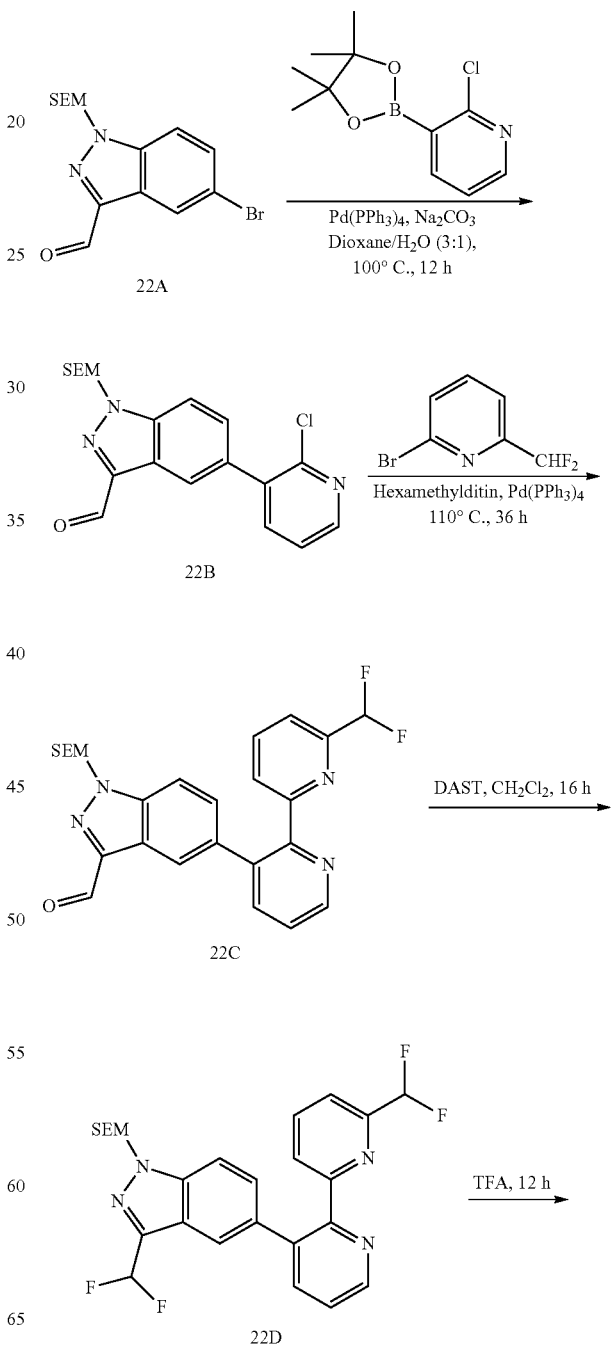

-continued

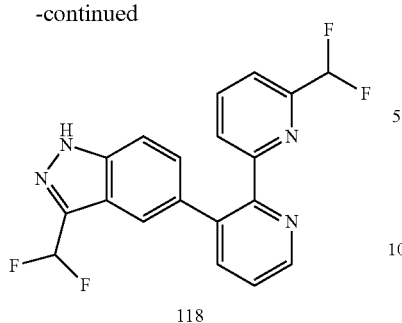

118

Compound 22B: 5-(2-chloropyridin-3-yl)-1-((2-(trimethylsilyl)ethoxy)methyl)-1H-indazole-3-carbaldehyde

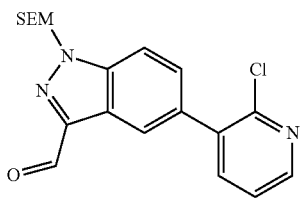 [SMILES: C[Si](C)(C)CCOCn1nc(C=O)c2cc(-c3cccnc3Cl)ccc21]

Compound 22B was synthesized by reacting 22A (reference: US 20140194441 A1) and 2-chloro-3-(4,4,5,5-tetramethyl-1,3,2-dioxaborolan-2-yl)pyridine employing the experimental procedure described for compound 9B as shown in Scheme 16. The crude residue was purified by silica gel chromatography (40 g RediSep® column, eluted with a gradient of 5-10% ethyl acetate in petroleum ether) to yield 5-(2-chloropyridin-3-yl)-1-((2-(trimethylsilyl)ethoxy)methyl)-1H-indazole-3-carbaldehyde 22B (1.202 g, 3.10 mmol, 73.4% yield). LCMS: m/z=388.2 [M+H]$^+$; ret. time 3.52 min; condition E.

Compound 22C: 5-(6'-(difluoromethyl)-[2,2'-bipyridin]-3-yl)-1-((2-(trimethylsilyl)ethoxy)methyl)-1H-indazole-3-carbaldehyde

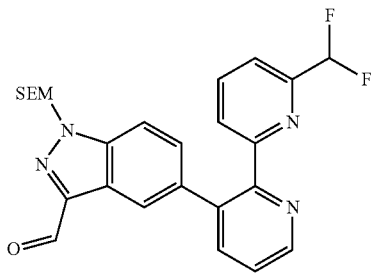 [SMILES: C[Si](C)(C)CCOCn1nc(C=O)c2cc(-c3cccnc3-c3cccc(C(F)F)n3)ccc21]

Compound 22C was synthesized by reacting 22B and 2-bromo-6-(difluoromethyl)pyridine employing the experimental procedure described in Scheme 2 (Method 2). The crude residue was purified by silica gel chromatography (24 g RediSep® column, eluted with a gradient of 5-10% ethyl acetate in petroleum ether) to yield 5-(6'-(difluoromethyl)-[2,2'-bipyridin]-3-yl)-1-((2-(trimethylsilyl)ethoxy)methyl)-1H-indazole-3-carbaldehyde 22C (335 mg, 0.697 mmol, 49.2% yield). LCMS: m/z=481.2 [M+H]$^+$; ret. time 3.56 min; condition E.

Compound 22D: 3-(difluoromethyl)-5-(6'-(difluoromethyl)-[2,2'-bipyridin]-3-yl)-1-((2-(trimethylsilyl)ethoxy)methyl)-1H-indazole

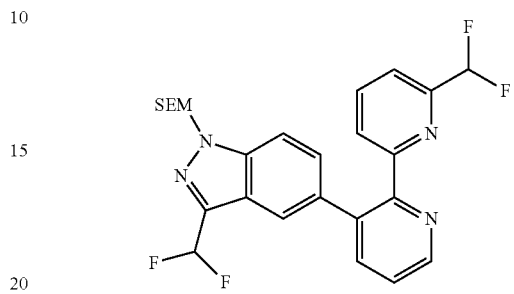

To a stirred solution of 5-(6'-(difluoromethyl)-[2,2'-bipyridin]-3-yl)-1-((2-(trimethylsilyl)ethoxy)methyl)-1H-indazole-3-carbaldehyde 22C (100 mg, 0.208 mmol) in DCM (5 mL) was added DAST (0.055 mL, 0.416 mmol) at 0° C. The reaction mixture was warmed to room temperature and stirred for 16 h. The reaction mixture was diluted with DCM (20 mL) and poured into an ice cooled 10% aq. NaHCO$_3$ solution (20 mL). The organic layer was separated and the aqueous layer was back extracted with DCM (3×15 mL). The combined organic layer were dried over Na$_2$SO$_4$, concentrated under reduced pressure to give a light yellow semi-solid mass. The crude residue was purified by silica gel chromatography (24 g RediSep® column, eluted with a gradient of 10-30% ethyl acetate in petroleum ether) to yield 3-(difluoromethyl)-5-(6'-(difluoromethyl)-[2,2'-bipyridin]-3-yl)-1-((2-(trimethylsilyl)ethoxy)methyl)-1H-indazole 22D (72 mg, 0.143 mmol, 68.8% yield). LCMS: m/z=503.2 [M+H]$^+$; ret. time 3.47 min; condition E.

Compound 118: 3-(difluoromethyl)-5-(6'-(difluoromethyl)-[2,2'-bipyridin]-3-yl)-1H-indazole

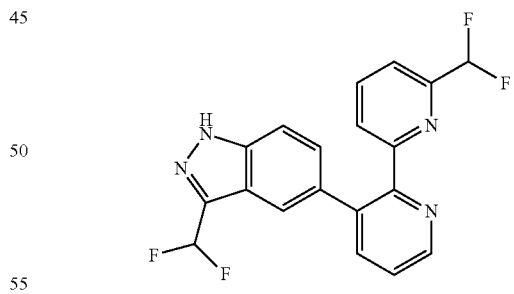

Compound 118 was synthesized from 22D employing the experimental procedure described for compound 115 as shown in Scheme 29. The crude residue was purified by preparative HPLC (method: H) to yield 3-(difluoromethyl)-5-(6'-(difluoromethyl)-[2,2'-bipyridin]-3-yl)-1H-indazole 115 (9.7 mg, 0.026 mmol, 12.35% yield). LCMS: m/z=373.1 [M+H]$^+$; ret. Time 1.8 min; condition C. $^1$H NMR (400 MHz, DMSO-d$_6$) δ=13.57 (s, 1H), 8.72-8.74 (m, 1H), 7.97-8.00 (m, 2H), 7.74-7.76 (m, 1H), 7.56-7.64 (m, 4H), 7.27 (t, J=54.0 Hz, 1H), 7.14-7.18 (m, 1H), 6.52 (J=54.8 Hz, 1H).

Scheme 30:

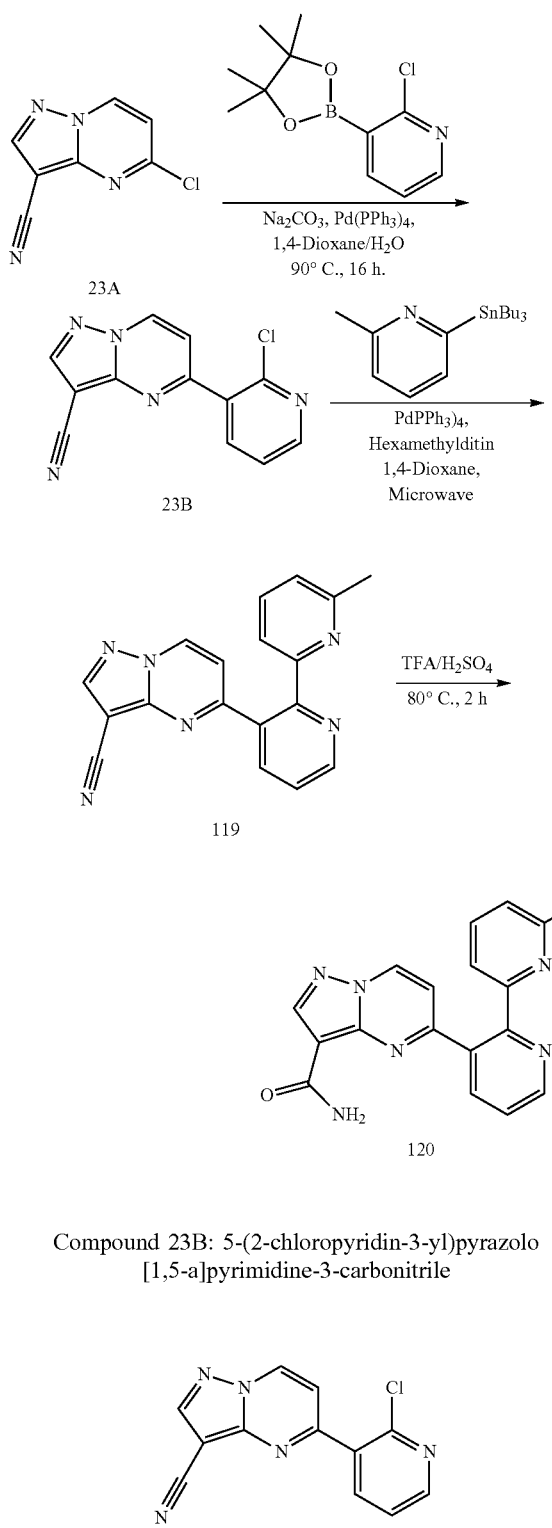

with a gradient of 50% ethyl acetate in petroleum ether). The fractions containing the product were combined and evaporated under reduced pressure to afford compound 5-(2-chloropyridin-3-yl)pyrazolo[1,5-a]pyrimidine-3-carbonitrile 23B (900 mg, 3.52 mmol, 62.9% yield). LCMS: m/z=256.1 [M+H]⁺; ret. time 0.64 min; condition B.

Compound 119: 5-(6'-methyl-[2,2'-bipyridin]-3-yl)pyrazolo[1,5-a]pyrimidine-3-carbonitrile

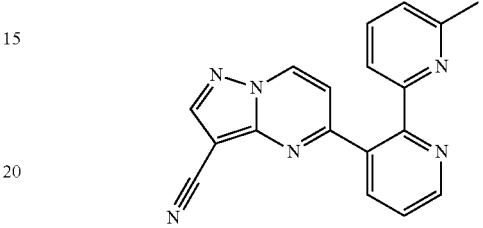

Compound 119 was synthesized by reacting 23B and 2-methyl-6-(tributylstannyl)pyridine employing the experimental procedure described for compound 81 in Scheme 18. The crude compound was purified by preparative HPLC (Condition-N) to yield 5-(6'-methyl-[2,2'-bipyridin]-3-yl)pyrazolo[1,5-a]pyrimidine-3-carbonitrile 119 (120 mg, 0.384 mmol, 49.1% yield). LCMS: m/z=313.1 [M+H]⁺; ret. time 1.44 min; condition C. ¹H NMR (400 MHz, DMSO-d₆) δ=9.19 (d, J=7.3 Hz, 1H), 8.85 (dd, J=4.6, 1.7 Hz, 1H), 8.81 (s, 1H), 8.14 (dd, J=7.8, 1.7 Hz, 1H), 8.00 (d, J=7.8 Hz, 1H), 7.83 (t, J=7.7 Hz, 1H), 7.66 (dd, J=7.7, 4.8 Hz, 1H), 7.19 (d, J=7.6 Hz, 1H), 7.07 (d, J=7.1 Hz, 1H), 1.90 (s, 3H)

Compound 120: 5-(6'-methyl-[2,2'-bipyridin]-3-yl)pyrazolo[1,5-a]pyrimidine-3-carboxamide

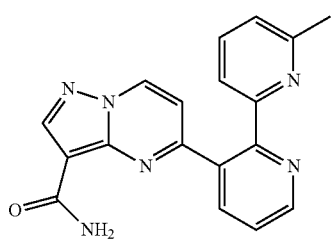

Compound 23B: 5-(2-chloropyridin-3-yl)pyrazolo[1,5-a]pyrimidine-3-carbonitrile

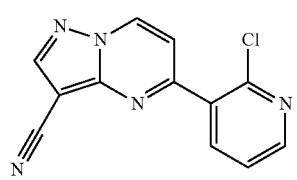 [SMILES: N#Cc1cnn2ccc(-c3cccnc3Cl)nc12]

Compound 23B was synthesized by reacting 23A [reference: Heterocycles (2010), 80(2), 1359-1379] and 2-chloro-3-(4,4,5,5-tetramethyl-1,3,2-dioxaborolan-2-yl)pyridine employing experimental procedure described for compound 9B as shown in Scheme 16. The crude was purified using silica gel chromatography (24 g RediSep® column, eluting Compound 120 was synthesized from 119 similar to 3A employing experimental procedure described in Scheme-6 (Method A). The crude compound was purified by preparative HPLC (Condition-N) to yield 5-(6'-methyl-[2,2'-bipyridin]-3-yl)pyrazolo[1,5-a]pyrimidine-3-carboxamide 120 (10.6 mg, 0.032 mmol, 10% yield). LCMS: m/z=332.1 [M+H]⁺; ret. time 1.1 min; condition C. ¹H NMR (400 MHz, DMSO-d₆) δ ppm 9.16 (d, J=7.1 Hz, 1H), 8.83 (dd, J=4.8, 1.6 Hz, 1H), 8.51 (s, 1H), 8.25 (dd, J=7.7, 1.6 Hz, 1H), 7.90-7.77 (m, 2H), 7.67 (dd, J=7.7, 4.8 Hz, 1H), 7.31 (br. s., 1H), 7.19 (d, J=7.3 Hz, 1H), 7.08-6.98 (m, 2H), 1.95 (s, 3H).

Compound 121: 5-(6'-(trifluoromethyl)-[2,2'-bipyridin]-3-yl)pyrazolo[1,5-a]pyrimidine-3-carbonitrile Scheme 31:

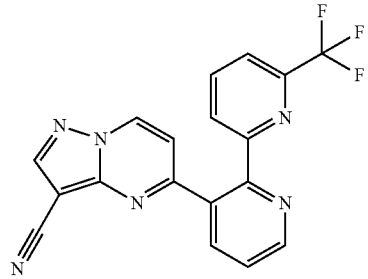 [SMILES: N#Cc1cnn2ccc(-c3cccnc3-c3cccc(C(F)(F)F)n3)nc12]

Compound 121 was synthesized by reacting 23B and 2-bromo-6-(trifluoromethyl)pyridine employing the experimental procedure described in Scheme 2 (Method B). The crude compound was purified by preparative HPLC (Condition-N) to yield 5-(6'-(trifluoromethyl)-[2,2'-bipyridin]-3-yl)pyrazolo[1,5-a]pyrimidine-3-carbonitrile 121 (140 mg, 0.382 mmol, 48.9% yield). LCMS: m/z=367.1 [M+H]$^+$; ret. time 1.72 min; condition C. $^1$H NMR (400 MHz, DMSO-d$_6$) δ ppm 9.30 (d, J=7.1 Hz, 1H), 8.92 (dd, J=4.6, 1.5 Hz, 1H), 8.79 (s, 1H), 8.49 (d, J=7.8 Hz, 1H), 8.29-8.19 (m, 2H), 7.83 (d, J=7.8 Hz, 1H), 7.75 (dd, J=7.7, 4.8 Hz, 1H), 7.31 (d, J=7.1 Hz, 1H).

Compound 122: 5-(5'-fluoro-6'-methyl-[2,2'-bipyridin]-3-yl)pyrazolo[1,5-a]pyrimidine-3-carbonitrile

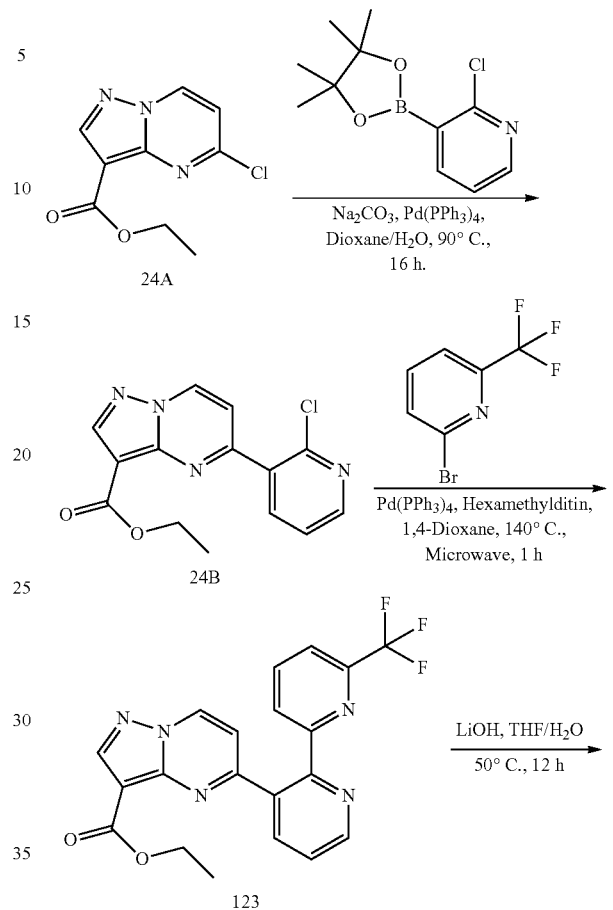

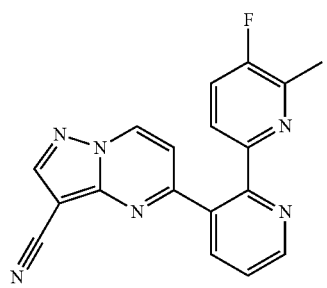 [SMILES: Cc1nc(-c2ncccc2-c2ccn3ncc(C#N)c3n2)ccc1F]

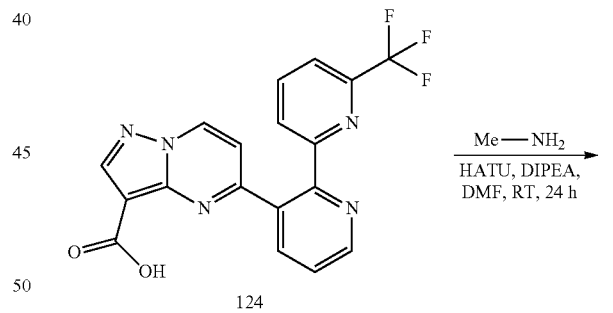

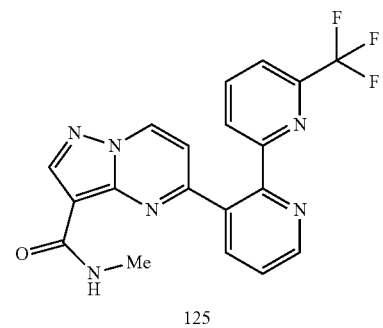

Compound 122 was synthesized by reacting 23B and 6-bromo-3-fluoro-2-methylpyridine employing the experimental procedure described in Scheme 3 (Method C). The crude compound was purified by preparative HPLC (Condition-N) to yield 5-(5'-fluoro-6'-methyl-[2,2'-bipyridin]-3-yl)pyrazolo[1,5-c]pyrimidine-3-carbonitrile 122 (130 mg, 0.394 mmol, 50.3% yield). LCMS: m/z=331.2 [M+H]$^+$; ret. time 1.55 min; condition C. $^1$H NMR (400 MHz, DMSO-d$_6$) δ ppm 9.30 (d, J=7.1 Hz, 1H), 8.92 (dd, J=4.6, 1.5 Hz, 1H), 8.79 (s, 1H), 8.49 (d, J=7.8 Hz, 1H), 8.29-8.19 (m, 2H), 7.83 (d, J=7.8 Hz, 1H), 7.75 (dd, J=7.7, 4.8 Hz, 1H), 7.31 (d, J=7.1 Hz, 1H).

Compound 24B: ethyl 5-(2-chloropyridin-3-yl)pyrazolo[1,5-a]pyrimidine-3-carboxylate

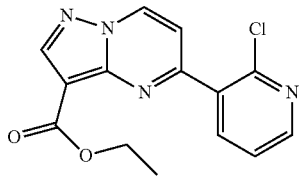 [SMILES: CCOC(=O)c1cnn2ccc(-c3cccnc3Cl)nc12]

Compound 24B was synthesized by reacting 24A (reference: WO 2013059587 A1) and 2-chloro-3-(4,4,5,5-tetramethyl-1,3,2-dioxaborolan-2-yl)pyridine employing the experimental procedure described for compound 9B as shown in Scheme 16. The crude was purified using silica gel chromatography (24 g RediSep® column, eluting with a gradient of 50% ethyl acetate in petroleum ether). The fractions containing the product were combined and evaporated under reduced pressure to afford ethyl 5-(2-chloropyridin-3-yl)pyrazolo[1,5-c]pyrimidine-3-carboxylate 24B (1 g, 3.30 mmol, 83% yield). LCMS: m/z=303.1 [M+H]$^+$; ret. time 0.82 min; condition B.

Compound 123: ethyl 5-(6'-(trifluoromethyl)-[2,2'-bipyridin]-3-yl)pyrazolo[1,5-a]pyrimidine-3-carboxylate

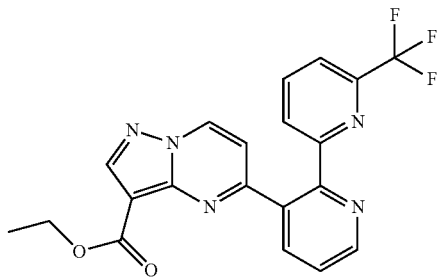

Compound 123 was synthesized by reacting 24B and 2-bromo-6-(trifluoromethyl)pyridine employing the experimental procedure described in Scheme 3 (Method C). The crude compound was purified by preparative HPLC (Condition-N) to yield ethyl 5-(6'-(trifluoromethyl)-[2,2'-bipyridin]-3-yl)pyrazolo[1,5-a]pyrimidine-3-carboxylate 123 (180 mg, 0.435 mmol, 65.9% yield). LCMS: m/z=414.1 [M+H]$^+$; ret. time 1.81 min; condition C. $^1$H NMR (400 MHz, DMSO-d$_6$) δ ppm 9.18 (d, J=7.1 Hz, 1H), 8.90 (dd, J=4.8, 1.6 Hz, 1H), 8.58 (s, 1H), 8.45 (d, J=8.1 Hz, 1H), 8.28-8.17 (m, 2H), 7.82-7.72 (m, 2H), 7.18 (d, J=7.1 Hz, 1H), 4.19 (q, J=7.1 Hz, 2H), 1.22 (t, J=7.1 Hz, 3H).

Compound 124: 5-(6'-(trifluoromethyl)-[2,2'-bipyridin]-3-yl)pyrazolo[1,5-a]pyrimidine-3-carboxylic acid

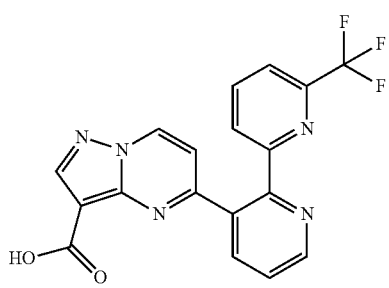 [SMILES: O=C(O)c1cnn2ccc(-c3cccnc3-c3cccc(C(F)(F)F)n3)nc12]

In a 8 mL vial, was added ethyl 5-(6'-(trifluoromethyl)-[2,2'-bipyridin]-3-yl)pyrazolo[1,5-a]pyrimidine-3-carboxylate 23B (120 mg, 0.290 mmol) in THF (2 mL) and water (1 mL). The mixture was cooled to 0° C. and LiOH (6.95 mg, 0.290 mmol) was added. Then, the reaction mixture was heated at 50° C. for 12 h. The reaction mixture was acidified using 1N aqueous HCl and evaporated completely to get the crude product, which was purified by preparative HPLC (Condition-N) to yield 5-(6'-(trifluoromethyl)-[2,2'-bipyridin]-3-yl) pyrazolo[1,5-a]pyrimidine-3-carboxylic acid 124 (22.5 mg, 0.058 mmol, 20.1% yield). LCMS: m/z=386.1 [M+H]$^+$; ret. time 0.97 min; condition C. $^1$H NMR (400 MHz, DMSO-d$_6$) δ ppm 9.06 (d, J=7.3 Hz, 1H), 8.89 (d, J=3.7 Hz, 1H), 8.46 (d, J=7.6 Hz, 2H), 8.27-8.14 (m, 2H), 7.80 (d, J=7.6 Hz, 1H), 7.73 (dd, J=7.6, 4.9 Hz, 1H), 6.99 (d, J=6.6 Hz, 1H).

Compound 125: N-methyl-5-(6'-(trifluoromethyl)-[2,2'-bipyridin]-3-yl)pyrazolo[1,5-a]pyrimidine-3-carboxamide

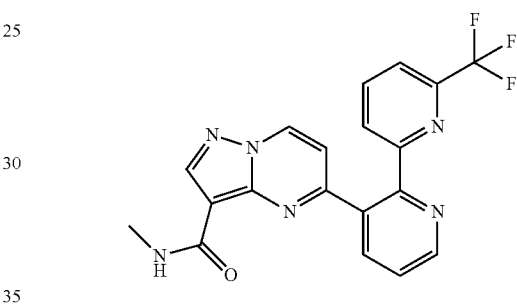

Compound 125 was synthesized by reacting 124 and methylamine, employing the experimental procedure described for compound 68 as shown in Scheme 14. The crude compound was purified by preparative HPLC (Condition-N) to yield N-methyl-5-(6'-(trifluoromethyl)-[2,2'-bipyridin]-3-yl)pyrazolo[1,5-a]pyrimidine-3-carboxamide 125 (1.1 mg, 2.76 μmol, 3.6% yield). LCMS: m/z=399.1 [M+H]$^+$; ret. time 1.466 min; condition C. $^1$H NMR (400 MHz, DMSO-d$_6$) δ ppm 9.26 (d, J=7.3 Hz, 1H), 8.93-8.88 (m, 1H), 8.49 (s, 1H), 8.42 (d, J=8.1 Hz, 1H), 8.37-8.24 (m, 2H), 7.84-7.73 (m, 2H), 7.33-7.27 (m, 1H), 7.14 (d, J=4.6 Hz, 1H), 2.71-2.65 (m, 3H).

Compound 126: N-cyclopropyl-5-(6'-(trifluoromethyl)-[2,2'-bipyridin]-3-yl)pyrazolo[1,5-a]pyrimidine-3-carboxamide

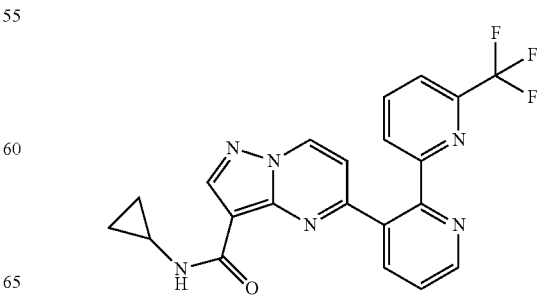

Compound 126 was synthesized by reacting 124 and cyclopropanamine, employing experimental procedure described for compound 68 as shown in Scheme 14. The crude compound was purified by preparative HPLC (Condition-N) to yield N-cyclopropyl-5-(6'-(trifluoromethyl)-[2,2'-bipyridin]-3-yl) pyrazolo[1,5-c]pyrimidine-3-carboxamide 126 (5.8 mg, 0.014 mmol, 17.55% yield. LCMS: m/z=425.1 [M+H]$^+$; ret. time 1.617 min; condition C. $^1$H NMR (400 MHz, DMSO-d$_6$) δ ppm 9.30 (d, J=7.1 Hz, 1H), 8.91 (dd, J=4.6, 1.5 Hz, 1H), 8.50 (s, 1H), 8.43 (d, J=7.8 Hz, 1H), 8.34-8.25 (m, 2H), 7.83 (d, J=7.8 Hz, 1H), 7.77 (dd, J=7.8, 4.9 Hz, 1H), 7.35 (d, J=7.3 Hz, 1H), 7.20 (d, J=3.2 Hz, 1H), 2.65-2.57 (m, 1H), 0.71-0.63 (m, 2H), 0.29-0.22 (m, 2H).

Compound 24G: ethyl 5-(6'-methyl-[2,2'-bipyridin]-3-yl)pyrazolo[1,5-a]pyrimidine-3-carboxylate

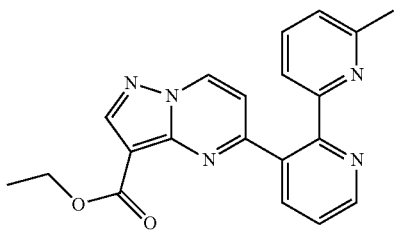 [SMILES: CCOC(=O)c1cnn2ccc(-c3cccnc3-c3cccc(C)n3)nc12]

Compound 24G was synthesized by reacting 24B and 2-methyl-6-(tributylstannyl)pyridine employing the experimental procedure described for compound 81 as sown in Scheme 18. The crude compound was purified using silica gel chromatography (24 g RediSep® column, eluting with a gradient of 50% ethyl acetate in petroleum ether). The fractions containing the product were combined and evaporated under reduced pressure to afford ethyl 5-(6'-methyl-[2,2'-bipyridin]-3-yl)pyrazolo[1,5-a]pyrimidine-3-carboxylate 24G (200 mg, 0.557 mmol, 67.4% yield). LCMS: m/z=360.1 [M+H]$^+$; ret. time 0.84 min; condition B.

Compound 24H: 5-(6'-methyl-[2,2'-bipyridin]-3-yl)pyrazolo[1,5-a]pyrimidine-3-carboxylic acid

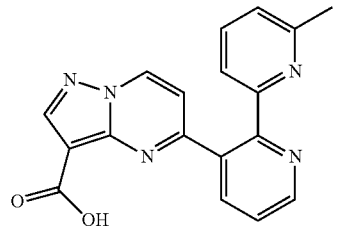 [SMILES: Cc1cccc(-c2ncccc2-c2ccn3ncc(C(=O)O)c3n2)n1]

Compound 24H was synthesized from 24G employing the experimental procedure described for compound 124 as shown in Scheme 31. The crude compound was purified by preparative HPLC (Condition-N) to yield 5-(6'-methyl-[2,2'-bipyridin]-3-yl)pyrazolo[1,5-a]pyrimidine-3-carboxylic acid 23G (120 mg, 0.362 mmol, 100% yield). LCMS: m/z=332.1 [M+H]$^+$; ret. time 0.86 min; condition C. $^1$H NMR (400 MHz, DMSO-d$_6$) δ ppm 8.99 (d, J=7.1 Hz, 1H), 8.83 (dd, J=4.8, 1.6 Hz, 1H), 8.49 (s, 1H), 8.11 (dd, J=7.7, 1.6 Hz, 1H), 7.97 (d, J=7.8 Hz, 1H), 7.81 (t, J=7.7 Hz, 1H), 7.65 (dd, J=7.8, 4.9 Hz, 1H), 7.18 (d, J=7.6 Hz, 1H), 6.78 (d, J=7.1 Hz, 1H), 1.93 (s, 3H).

Compound 127: N-methyl-5-(6'-methyl-[2,2'-bipyridin]-3-yl)pyrazolo[1,5-a]pyrimidine-3-carboxamide

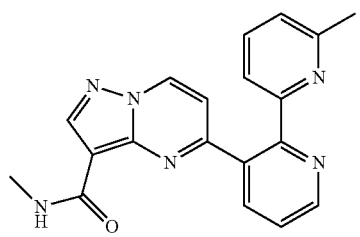

Compound 127 was synthesized from 24H employing the experimental procedure described for compound 68 as shown in Scheme 14. The crude compound was purified by preparative HPLC (Condition-N) to yield N-methyl-5-(6'-methyl-[2,2'-bipyridin]-3-yl)pyrazolo[1,5-a]pyrimidine-3-carboxamide 127 (1 mg, 2.90 μmol, 3.2% yield). LCMS: m/z=345.2 [M+H]$^+$; ret. time 1.08 min; condition C. $^1$H NMR (400 MHz, DMSO-d$_6$) δ ppm 9.17 (d, J=7.3 Hz, 1H), 8.83 (dd, J=4.8, 1.6 Hz, 1H), 8.50 (s, 1H), 8.27 (dd, J=7.8, 1.7 Hz, 1H), 7.91-7.80 (m, 2H), 7.67 (dd, J=7.8, 4.6 Hz, 1H), 7.31 (d, J=4.9 Hz, 1H), 7.18 (d, J=7.3 Hz, 1H), 7.14-7.09 (m, 1H), 2.74 (d, J=4.9 Hz, 4H), 1.94-1.90 (m, 3H).

Compound 128: N-cyclopropyl-5-(6'-methyl-[2,2'-bipyridin]-3-yl)pyrazolo[1,5-a]pyrimidine-3-carboxamide

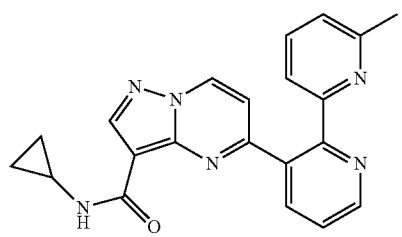 [SMILES: Cc1cccc(-c2ncccc2-c2ccn3ncc(C(=O)NC4CC4)c3n2)n1]

Compound 128 was synthesized from 24H employing the experimental procedure described in Scheme 14 (compound 68). The crude compound was purified by preparative HPLC (Condition-N) to N-cyclopropyl-5-(6'-methyl-[2,2'-bipyridin]-3-yl)pyrazolo[1,5-a]pyrimidine-3-carboxamide 231 (3.4 mg, 9.18 μmol, 10.1% yield). LCMS: m/z=371.1 [M+H]$^+$; ret. time 1.13 min; condition C. $^1$H NMR (400 MHz, DMSO-d$_6$) δ ppm 9.21 (d, J=7.1 Hz, 1H), 8.84 (dd, J=4.8, 1.6 Hz, 1H), 8.51 (s, 1H), 8.24 (dd, J=7.7, 1.6 Hz, 1H), 7.94-7.80 (m, 2H), 7.68 (dd, J=7.7, 4.8 Hz, 1H), 7.41 (d, J=3.4 Hz, 1H), 7.21-7.11 (m, 2H), 2.72-2.65 (m, 1H), 1.90 (s, 2H), 1.94-1.86 (m, 3H), 0.73-0.65 (m, 1H), 0.38-0.27 (m, 1H).

Compound 129: 5-(6'-methyl-[2,2'-bipyridin]-3-yl)-N-(oxetan-3-yl)pyrazolo[1,5-a]pyrimidine-3-carboxamide

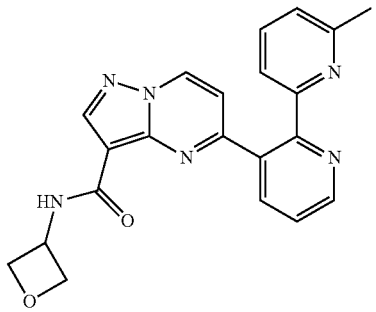 [SMILES: Cc1cccc(-c2ncccc2-c2ccn3ncc(C(=O)NC4COC4)c3n2)n1]

Compound 129 was synthesized from 24H employing the experimental procedure described for compound 68 as shown in Scheme 14. The crude compound was purified by preparative HPLC (Condition-N) to yield 5-(6'-methyl-[2, 2'-bipyridin]-3-yl)-N-(oxetan-3-yl)pyrazolo[1,5-a]pyrimidine-3-carboxamide 129 (16.5 mg, 0.043 mmol, 47.2% yield). LCMS: m/z=387.1 [M+H]$^+$; ret. time 0.99 min; condition C. $^1$H NMR (400 MHz, DMSO-d$_6$) δ ppm 9.22 (d, J=7.3 Hz, 1H), 8.85 (dd, J=4.8, 1.6 Hz, 1H), 8.54 (s, 1H), 8.31 (dd, J=7.8, 1.7 Hz, 1H), 7.95 (dd, J=12.2, 7.1 Hz, 2H), 7.87-7.80 (m, 1H), 7.70 (dd, J=7.8, 4.9 Hz, 1H), 7.22-7.12 (m, 2H), 4.90 (dq, J=13.8, 6.6 Hz, 1H), 4.75 (t, J=7.0 Hz, 2H), 4.36 (t, J=6.5 Hz, 2H), 1.91 (s, 3H).

Compound 130: ethyl 5-(5'-fluoro-6'-methyl-[2,2'-bipyridin]-3-yl)pyrazolo[1,5-a]pyrimidine-3-carboxylate

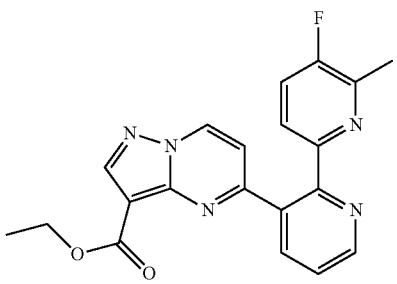 [SMILES: CCOC(=O)c1cnn2ccc(-c3cccnc3-c3ccc(F)c(C)n3)nc12]

Compound 130 was synthesized by reacting 24B and 6-bromo-3-fluoro-2-methylpyridine employing the experimental procedure described in Scheme 3 (Method C). The crude compound was purified by preparative HPLC (Condition-N) to yield ethyl 5-(5'-fluoro-6'-methyl-[2, 2'-bipyridin]-3-yl) pyrazolo[1,5-a]pyrimidine-3-carboxylate 130 (180 mg, 0.477 mmol, 72.2% yield). LCMS: m/z=378.1 [M+H]$^+$; ret. time 1.66 min; condition C. $^1$H NMR (400 MHz, DMSO-d$_6$) δ=9.37 (d, J=7.1 Hz, 1H), 9.10 (dd, J=4.8, 1.6 Hz, 1H), 8.87 (s, 1H), 8.40 (dd, J=7.8, 1.7 Hz, 1H), 8.32 (dd, J=8.4, 4.0 Hz, 1H), 8.03 (t, J=9.0 Hz, 1H), 7.93 (dd, J=7.8, 4.9 Hz, 1H), 7.25 (d, J=7.3 Hz, 1H), 4.51 (q, J=7.1 Hz, 2H), 2.16 (d, J=2.7 Hz, 3H), 1.53 (t, J=7.1 Hz, 3H).

Compound 131: 5-(5'-fluoro-6'-methyl-[2,2'-bipyridin]-3-yl)pyrazolo[1,5-a]pyrimidine-3-carboxylic acid

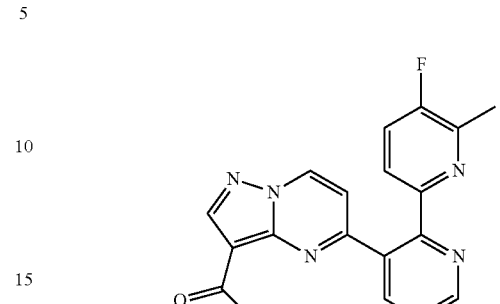

Compound 131 was synthesized from 130 employing the experimental procedure described for Compound 124 as shown in Scheme 31. The crude compound was purified by preparative HPLC (Condition N) to yield 5-(5'-fluoro-6'-methyl-[2,2'-bipyridin]-3-yl)pyrazolo[1,5-a]pyrimidine-3-carboxylic acid 131 (15.4 mg, 0.044 mmol, 13.8% yield). LCMS: m/z=350.2 [M+H]$^+$; ret. time 0.67 min; condition C. $^1$H NMR (400 MHz, DMSO-d$_6$) δ ppm 8.87 (d, J=7.1 Hz, 1H), 8.80 (dd, J=4.6, 1.7 Hz, 1H), 8.32 (s, 1H), 8.11 (dd, J=7.7, 1.6 Hz, 1H), 8.02 (dd, J=8.6, 3.7 Hz, 1H), 7.74 (t, J=9.0 Hz, 1H), 7.63 (dd, J=7.7, 4.8 Hz, 1H), 6.63 (d, J=7.1 Hz, 1H), 1.96 (d, J=2.7 Hz, 3H).

Compound 132: N-cyclopropyl-5-(5'-fluoro-6'-methyl-[2,2'-bipyridin]-3-yl)pyrazolo[1,5-a]pyrimidine-3-carboxamide

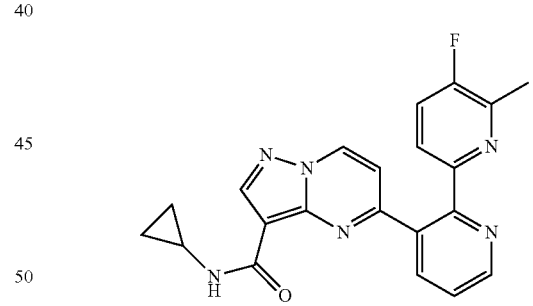

Compound 132 was synthesized from 131 employing the experimental procedure described for compound 68 as shown in Scheme 14. The crude compound was purified by preparative HPLC (Condition-N) to yield N-cyclopropyl-5-(5'-fluoro-6'-methyl-[2,2'-bipyridin]-3-yl)pyrazolo[1,5-a] pyrimidine-3-carboxamide 132 (1.8 mg, 4.63 μmol, 5.40% yield). LCMS: m/z=389.1 [M+H]$^+$; ret. time 1.475 min; condition C. $^1$H NMR (400 MHz, DMSO-d$_6$) δ ppm 9.21 (d, J=7.3 Hz, 1H), 8.84 (dd, J=4.6, 1.2 Hz, 1H), 8.53 (s, 1H), 8.26 (d, J=7.6 Hz, 1H), 8.00 (dd, J=8.7, 3.8 Hz, 1H), 7.80 (t, J=9.0 Hz, 1H), 7.69 (dd, J=7.8, 4.6 Hz, 1H), 7.45 (d, J=3.7 Hz, 1H), 7.16 (d, J=7.1 Hz, 1H), 1.90 (d, J=2.7 Hz, 3H), 0.77-0.67 (m, 2H), 0.38-0.30 (m, 2H).

Compound 133: 5-(5'-fluoro-6'-methyl-[2,2'-bipyridin]-3-yl)-N-(oxetan-3-yl)pyrazolo[1,5-a]pyrimidine-3-carboxamide

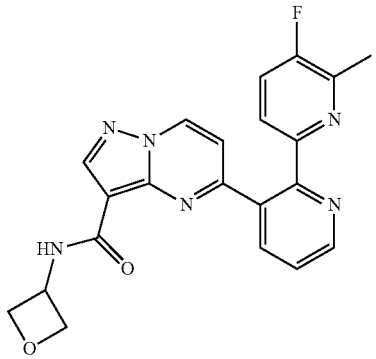 [SMILES: Cc1nc(-c2ncccc2-c2ccn3ncc(C(=O)NC4COC4)c3n2)ccc1F]

Compound 133 was synthesized from 131 employing the experimental procedure described for compound 68 as shown in Scheme 14. The crude compound was purified by preparative HPLC (Condition-N) to yield 5-(5'-fluoro-6'-methyl-[2,2'-bipyridin]-3-yl)-N-(oxetan-3-yl)pyrazolo[1,5-a]pyrimidine-3-carboxamide 133 (2.2 mg, 5.44 µmol, 6.3% yield). LCMS: m/z=405.1 [M+H]$^+$; ret. time 1.31 min; condition C. $^1$H NMR (400 MHz, DMSO-d$_6$) δ ppm 9.02 (d, J=7.3 Hz, 1H), 8.83 (dd, J=4.8, 1.6 Hz, 1H), 8.53 (s, 1H), 8.13-8.03 (m, 2H), 7.76 (t, J=9.2 Hz, 1H), 7.66 (dd, J=7.8, 4.6 Hz, 1H), 6.86 (d, J=7.3 Hz, 1H), 4.80 (t, J=5.5 Hz, 1H), 4.38-4.31 (m, 1H), 4.28-4.12 (m, 2H), 3.59 (dt, J=10.0, 5.0 Hz, 1H), 3.46-3.37 (m, 1H), 1.91 (d, J=2.7 Hz, 3H).

Compound 134: ethyl 5-(6'-(difluoromethyl)-[2,2'-bipyridin]-3-yl)pyrazolo[1,5-a]pyrimidine-3-carboxylate

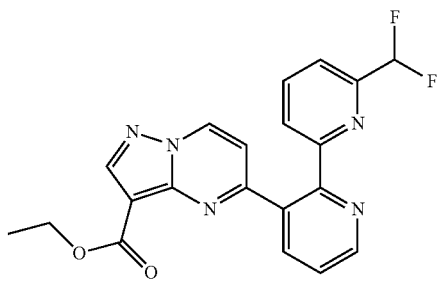

Compound 134 was synthesized by reacting 24B and 2-bromo-6-(difluoromethyl)pyridine employing the experimental procedure described in Scheme 3 (Method C). The crude compound was purified by preparative HPLC (Condition-N) to yield ethyl 5-(6'-(difluoromethyl)-[2,2'-bipyridin]-3-yl)pyrazolo[1,5-a]pyrimidine-3-carboxylate 134 (26 mg, 0.066 mmol, 19.91% yield). LCMS: m/z=396.1 [M+H]$^+$; ret. time 1.63 min; condition C. $^1$H NMR (400 MHz, DMSO-d$_6$) δ=9.10 (d, J=7.3 Hz, 1H), 8.88 (dd, J=4.8, 1.6 Hz, 1H), 8.57 (s, 1H), 8.30 (d, J=7.1 Hz, 1H), 8.22-8.10 (m, 2H), 7.72 (dd, J=7.8, 4.6 Hz, 1H), 7.59 (d, J=7.6 Hz, 1H), 7.04 (d, J=7.1 Hz, 1H), 6.58-6.24 (m, 1H), 4.21 (q, J=7.1 Hz, 1H), 1.24 (t, J=7.1 Hz, 3H).

Compound 135: 5-(6'-(difluoromethyl)-[2,2'-bipyridin]-3-yl)pyrazolo[1,5-a]pyrimidine-3-carboxylic acid

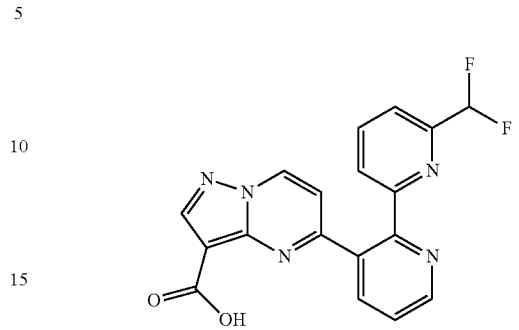

Compound 135 was synthesized from 134 employing experimental procedure described for compound 124 as shown in Scheme 31. The crude compound was purified by preparative HPLC (Condition-N) to yield 5-(6'-(difluoromethyl)-[2,2'-bipyridin]-3-yl)pyrazolo[1,5-a]pyrimidine-3-carboxylic acid 135 (6.2 mg, 0.017 mmol, 35.1% yield). LCMS: m/z=368.1 [M+H]$^+$; ret. time 0.91 min; condition C. $^1$H NMR (400 MHz, DMSO-d$_6$) δ ppm 8.92 (d, J=7.5 Hz, 1H), 8.88-8.85 (m, 1H), 8.40 (s, 1H), 8.31-8.26 (m, 1H), 8.19-8.11 (m, 2H), 7.70 (dd, J=7.8, 4.8 Hz, 1H), 7.61 (d, J=7.5 Hz, 1H), 6.75 (d, J=7.5 Hz, 1H), 6.59-6.26 (m, 1H).

Scheme 32:

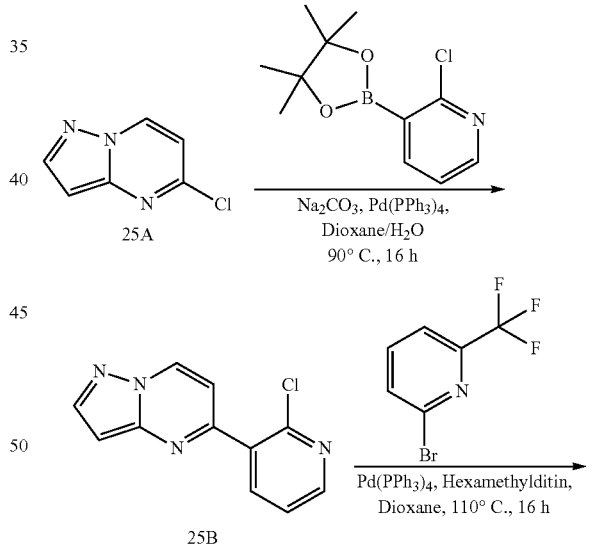

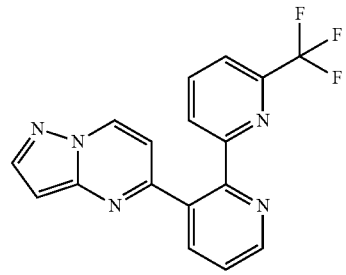

136

227

Compound 25B: 5-(2-chloropyridin-3-yl)pyrazolo[1,5-a]pyrimidine

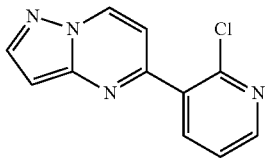 [SMILES: Clc1ncccc1-c1ccn2nccc2n1]

Compound 25B was synthesized by reacting 25A (reference: WO 2014074657 A1) and 2-chloro-3-(4,4,5,5-tetramethyl-1,3,2-dioxaborolan-2-yl)pyridine employing the experimental procedure described for compound 9B as shown in Scheme 16. The crude product was purified using silica gel chromatography (24 g RediSep® column, eluting with a gradient of 50% ethyl acetate in petroleum ether). The fractions containing the product were combined and evaporated under reduced pressure to afford 5-(2-chloropyridin-3-yl)pyrazolo[1,5-a]pyrimidine 24A (1 g, 4.34 mmol, 66.6% yield). LCMS: m/z=231.3 [M+H]$^+$; ret. time 0.76 min; condition B.

Compound 136: 5-(6'-(trifluoromethyl)-[2,2'-bipyridin]-3-yl)pyrazolo[1,5-a]pyrimidine

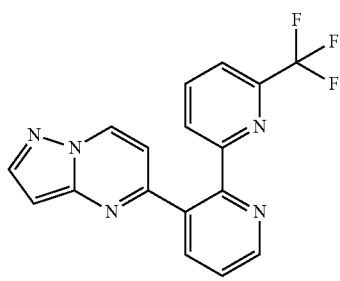 [SMILES: FC(F)(F)c1cccc(-c2ncccc2-c2ccn3nccc3n2)n1]

Compound 136 was synthesized by reacting 25B and 2-bromo-6-(trifluoromethyl)pyridine employing the experimental procedure described in Scheme 2 (Method B). The crude compound was purified by preparative HPLC (Condition-N) to yield 5-(6'-(trifluoromethyl)-[2,2'-bipyridin]-3-yl)pyrazolo[1,5-a]pyrimidine 136 (11.8 mg, 0.035 mmol, 7.97% yield). LCMS: m/z=342.1 [M+H]$^+$; ret. time 1.61 min; condition C. $^1$H NMR (400 MHz, DMSO-d$_6$) δ ppm 8.99 (d, J=7.3 Hz, 1H), 8.86 (dd, J=4.8, 1.6 Hz, 1H), 8.41 (d, J=7.8 Hz, 1H), 8.27-8.12 (m, 3H), 7.80 (d, J=7.8 Hz, 1H), 7.70 (dd, J=7.8, 4.9 Hz, 1H), 6.85 (d, J=7.3 Hz, 1H), 6.57 (d, J=2.2 Hz, 1H).

Compound 137: 5-(5'-fluoro-6'-methyl-[2,2'-bipyridin]-3-yl)pyrazolo[1,5-a]pyrimidine

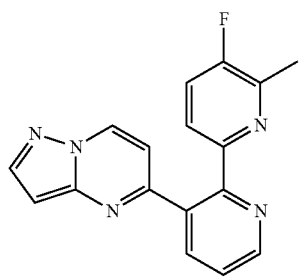 [SMILES: Cc1nc(-c2ncccc2-c2ccn3nccc3n2)ccc1F]

228

Compound 137 was synthesized by reacting 25B and 6-bromo-3-fluoro-2-methylpyridine employing experimental procedure described in Scheme 3 (Method C). The crude compound was purified by preparative HPLC (Condition-N) to yield 5-(5'-fluoro-6'-methyl-[2,2'-bipyridin]-3-yl)pyrazolo[1,5-c]pyrimidine 137 (10.2 mg, 0.033 mmol, 7.7% yield). LCMS: m/z=306.1 [M+H]$^+$; ret. time 1.423 min; condition C. $^1$H NMR (400 MHz, DMSO-d$_6$) δ=8.94 (d, J=7.1 Hz, 1H), 8.79 (dd, J=4.8, 1.6 Hz, 1H), 8.20 (d, J=2.4 Hz, 1H), 8.11 (dd, J=7.7, 1.6 Hz, 1H), 8.00 (dd, J=8.6, 3.9 Hz, 1H), 7.75 (t, J=9.2 Hz, 1H), 7.62 (dd, J=7.8, 4.6 Hz, 1H), 6.72-6.64 (m, 2H), 1.92 (d, J=2.7 Hz, 3H).

Compound 138: 5-(6'-methyl-[2,2'-bipyridin]-3-yl)pyrazolo[1,5-a]pyrimidine

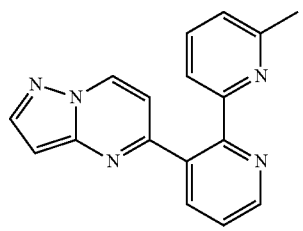 [SMILES: Cc1cccc(-c2ncccc2-c2ccn3nccc3n2)n1]

Compound 138 was synthesized by reacting 25B and 2-methyl-6-(tributylstannyl)pyridine employing the experimental procedure described for compound 81 as shown in Scheme 18. The crude compound was purified by preparative HPLC (Condition N) to yield 5-(6'-methyl-[2,2'-bipyridin]-3-yl)pyrazolo[1,5-a]pyrimidine 138 (61 mg, 0.212 mmol, 98% yield). LCMS: m/z=288.1 [M+H]$^+$; ret. time 1.28 min; condition C. $^1$H NMR (400 MHz, DMSO-d$_6$) δ ppm 8.91 (dd, J=7.3, 0.7 Hz, 1H), 8.80 (dd, J=4.6, 1.7 Hz, 1H), 8.19 (d, J=2.4 Hz, 1H), 8.10 (dd, J=7.6, 1.7 Hz, 1H), 7.90 (d, J=7.6 Hz, 1H), 7.84-7.76 (m, 1H), 7.61 (dd, J=7.8, 4.9 Hz, 1H), 7.17 (d, J=7.3 Hz, 1H), 6.68-6.60 (m, 2H), 1.94 (s, 3H).

Example 4: Biological Assay

Assays for the compounds reported below were conducted in 1536-well plates and 2 mL reactions are prepared from addition of HIS-TGFβR1 T204D or HIS-TGFβR2 WT, anti-HIS detection antibody, a labeled small molecule probe ($K_d$=<100 nM; $k_{off}$=<0.001 s$^{-1}$.) and test compounds in assay buffer (20 mM HEPES pH 7.4, 10 mM MgCl$_2$, 0.015% Brij35, 4 mM DTT, and 0.05 mg/ml BSA). The reaction is incubated for 1 hour at room temperature and the HTRF signal was measured on an Envision plate reader (Ex: 340 nm; Em: 520 nm/495 nm). Inhibition data were calculated by comparison to no enzyme control reactions for 100% inhibition and vehicle-only reactions for 0% inhibition. The final concentration of reagents in the assay are 1 nM HIS-TGFβR1 T204D or HIS-TGFβR2 WT, 0.2 nM anti-HIS detection antibody, labeled small molecule probe (at $K_d$) and 0.5% DMSO. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis.

| No. | TGF BR1T20 4D IC50 (μM) | TGF BR2WT IC50 (μM) |
|---|---|---|
| 13 | 0.103 | >15 |
| 14 | 0.011 | >15 |
| 15 | 0.010 | >15 |
| 16 | 0.207 | >15 |
| 17 | 0.009 | >15 |
| 18 | 0.001 | >15 |
| 19 | 0.001 | 9.617 |
| 20 | 0.103 | >15 |
| 21 | 0.005 | 3.632 |
| 22 | 0.005 | 12.717 |
| 23 | 0.130 | >15 |
| 24 | — | >15 |
| 25 | 4.477 | >15 |
| 26 | 7.651 | >15 |
| 27 | 14.348 | >15 |
| 28 | 0.009 | >15 |
| 29 | 0.001 | >15 |
| 30 | — | >15 |
| 31 | 0.307 | >15 |
| 32 | 0.016 | >15 |
| 33 | 0.001 | 14.638 |
| 34 | 0.019 | >15 |
| 35 | 0.001 | >15 |
| 36 | 0.120 | >15 |
| 37 | 0.004 | 1.600 |
| 38 | 1.925 | >15 |
| 39 | 0.006 | 3.723 |
| 40 | 0.821 | >15 |
| 41 | 15.000 | >15 |
| 42 | 0.021 | >15 |
| 43 | 0.017 | >15 |
| 44 | 1.977 | >15 |
| 45 | 0.907 | >15 |
| 46 | 0.0004 | >15 |
| 47 | 0.003 | >15 |
| 48 | 0.026 | >15 |
| 49 | 0.061 | >15 |
| 50 | 0.043 | >15 |
| 51 | 0.021 | >15 |
| 52 | 0.030 | >15 |
| 53 | 0.605 | >15 |
| 54 | 0.254 | >15 |
| 55 | 5.232 | >15 |
| 56 | 5.295 | >15 |
| 57 | 0.035 | >15 |
| 58 | 0.019 | >15 |
| 59 | 0.918 | >15 |
| 60 | 0.161 | >15 |
| 61 | 0.032 | >15 |
| 63 | 1.948 | >15 |
| 64 | 0.563 | >15 |
| 65 | 0.397 | >15 |
| 66 | 0.037 | >15 |
| 67 | 0.004 | — |
| 68 | 0.004 | >15 |
| 69 | 0.007 | >15 |
| 70 | 0.004 | >15 |
| 71 | — | — |
| 72 | 0.002 | >15 |
| 73 | 0.026 | >15 |
| 74 | 0.108 | >15 |
| 75 | 0.025 | >15 |
| 76 | 0.001 | >15 |
| 77 | 0.004 | >15 |
| 78 | 15.000 | >15 |
| 79 | 15.000 | >15 |
| 80 | 1.019 | >15 |
| 81 | 0.016 | >15 |
| 82 | 0.001 | 7.296 |
| 83 | 0.022 | >15 |
| 84 | 0.001 | >15 |
| 85 | 0.002 | 14.309 |
| 86 | 0.187 | >15 |
| 87 | 0.015 | >15 |
| 88 | 0.013 | >15 |
| 89 | 3.362 | >15 |
| 90 | 0.084 | >15 |
| 91 | 0.652 | >15 |
| 92 | 0.487 | >15 |
| 93 | 15.000 | >15 |
| 94 | 15.000 | >15 |
| 95 | 0.353 | >15 |
| 96 | 0.043 | >15 |
| 97 | 0.005 | 5.215 |
| 98 | 0.002 | 0.562 |
| 99 | 0.004 | 2.499 |
| 100 | 11.130 | >15 |
| 101 | 0.005 | >15 |
| 102 | 0.716 | >15 |
| 103 | 0.004 | >15 |
| 104 | 0.042 | >15 |
| 105 | 0.003 | >15 |
| 106 | 0.004 | >15 |
| 107 | 0.009 | >15 |
| 108 | 0.172 | >15 |
| 109 | 0.002 | >15 |
| 110 | 0.002 | >15 |
| 111 | 0.002 | >15 |
| 112 | 0.012 | >15 |
| 113 | 0.009 | >15 |
| 114 | 0.016 | >15 |
| 115 | 0.003 | >15 |
| 116 | 0.014 | >15 |
| 117 | 0.002 | >15 |
| 118 | 0.427 | >15 |
| 119 | 0.059 | >15 |
| 120 | 0.006 | >15 |
| 121 | 0.854 | >15 |
| 122 | 0.242 | >15 |
| 123 | 0.046 | >15 |
| 124 | 0.137 | >15 |
| 125 | 0.339 | >15 |
| 126 | 0.094 | >15 |
| 127 | 0.128 | >15 |
| 128 | 0.033 | >15 |
| 129 | 0.029 | >15 |
| 130 | 0.014 | >15 |
| 131 | 0.211 | >15 |
| 132 | 0.036 | >15 |
| 133 | 0.024 | >15 |
| 134 | 0.028 | >15 |
| 135 | 0.107 | >15 |
| 136 | 0.015 | >15 |
| 137 | 0.008 | >15 |
| 138 | 0.005 | >15 |
What is claimed:
1. A compound having the structure of formula)(I°):
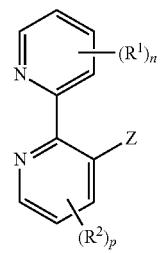
(I°)
or a pharmaceutically acceptable salt, prodrug, or N-oxide thereof, or a solvate or hydrate thereof, wherein
n is 1, 2, 3 or 4;
R$^1$ is hydrogen, halogen, cyano, nitro, C$_{1-6}$alkyl, C$_{1-6}$haloalkyl, C$_{3-8}$cycloalkyl, C$_{3-8}$ cycloalkenyl, heterocyclyl, aryl, heteroaryl, —R$^a$, or —C$_{1-6}$ alkyl-R$^a$, wherein R$^a$ is —OR$^{S1}$, —SR$^{S1}$, —NR$^{S1}$R$^{S1}$, —C(O)R$^{S1}$, —C(O)OR$^{S1}$, —C(O)NR$^{S1}$R$^{S1}$, —S(O)$_2$NR$^{S1}$R$^{S1}$, —OC(O)R$^{S1}$, —N(R$^{S1}$)C(O)R$^{S1}$, —OC(O)OR$^{S1}$, —O(CH$_2$)$_m$C(O)NR$^{S1}$R$^{S1}$, —N(R$^{S1}$)C(O)OR$^{S1}$, —N(R)C(O)NR$^{S1}$R$^{S1}$, —N(R$^{S1}$)S(O)$_2$NR$^{S1}$R$^{S1}$, or —N(R$^{S1}$)S(O)$_2$R$^{S1}$;
wherein m is 0, 1, 2 or 3; and
wherein each R$^{S1}$ is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano;
p is 1, 2, 3 or 4;
R$^2$ is hydrogen, halogen, cyano, nitro, C$_{1-6}$alkyl, C$_{1-6}$haloalkyl, C$_{3-8}$cycloalkyl, C$_{3-8}$cycloalkenyl, heterocyclyl, aryl, heteroaryl, —R$^b$, or —C$_{1-6}$alkyl-R$^b$, wherein R$^b$ is —OR$^{S4}$, —SR$^{S4}$; —NR$^{S4}$R$^{S4}$, —C(O)R$^{S4}$, —C(O)OR$^{S4}$, —C(O)NR$^{S4}$R$^{S4}$, —S(O)$_2$NR$^{S4}$R$^{S4}$, —OC(O)R$^{S4}$, —N(R$^{S4}$)C(O)R$^{S4}$, —OC(O)OR$^{S4}$, —O(CH$_2$)$_q$C(O)NR$^{S4}$R$^{S4}$, —N(R$^{S4}$)C(O)OR$^{S4}$, —N(R)C(O)NR$^{S4}$R$^{S4}$, —N(R$^{S4}$)S(O)$_2$NR$^{S4}$R$^{S4}$ or —N(R$^{S4}$)S(O)$_2$R$^{S4}$;
wherein q is 0, 1, 2 or 3; and
wherein each R$^{S4}$ is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano;
Z is
a fused bicyclic ring of the formula,

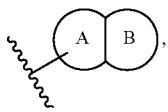

wherein
ring A is Ar or 6-membered Het,
ring B is 5- or 6-membered Het,
wherein
Z is optionally substituted by one or two —R$^Z$ groups that are each independently halogen, cyano, C$_{1-6}$alkyl, C$_{1-6}$haloalkyl, —C$_1$-C$_6$alkoxy, —OR$^{S2}$, —SR$^{S2}$, —NR$^{S2}$$_2$, —C(O)R$^{S2}$, —C(O)OR$^{S2}$, —C(O)NR$^{S2}$$_2$, —S(O)$_2$NR$^{S2}$$_2$, —S(O)$_2$R$^{S2}$, —OC(O)R$^{S2}$, —N(R$^{S2}$)C(O)R$^{S2}$, —OC(O)OR$^{S2}$, —OC(O)NR$^{S2}$$_2$, —N(R$^{S2}$)C(O)OR$^{S2}$, —N(R$^{S2}$)C(O)NR$^{S2}$$_2$, —N(R$^{S2}$)S(O)$_2$R$^{S2}$, —OP(O)(OR$^{S2}$)$_2$ or —CH$_2$—OP(O)(OR$^{S2}$), wherein each alkyl, haloalkyl and alkoxy is optionally substituted by one or two —R$^{Z2}$ groups;
wherein each R$^{S2}$ is independently hydrogen, C$_1$-C$_6$alkyl, C$_1$-C$_6$haloalkyl, C$_1$-C$_6$alkyl-O—C$_1$-C$_6$alkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano; and
each —R$^{Z2}$ is independently halogen, cyano, C$_{1-6}$alkyl, C$_{1-6}$haloalkyl, —C$_1$-C$_6$alkoxy, —OR$^{S3}$, —SR$^{S3}$, —NR$^{S3}$$_2$, —C(O)R$^{S3}$, —C(O)OR$^{S3}$, —C(O)NR$^{S3}$$_2$, —S(O)$_2$NR$^{S3}$$_2$, —S(O)$_2$R$^{S3}$, —OC(O)R$^{S3}$, —N(R$^{S3}$)C(O)R$^{S3}$, —OC(O)OR$^{S3}$, —OC(O)NR$^{S3}$$_2$, —N(R$^{S3}$)C(O)OR$^{S3}$, —N(R$^{S3}$)C(O)NR$^{S3}$$_2$, —N(R$^{S3}$)S(O)$_2$R$^{S3}$, —OP(O)(OR$^{S3}$)$_2$ or —CH$_2$—OP(O)(OR$^{S3}$); and
wherein each R$^{S3}$ is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano.

2. The compound of claim 1, wherein
Z is

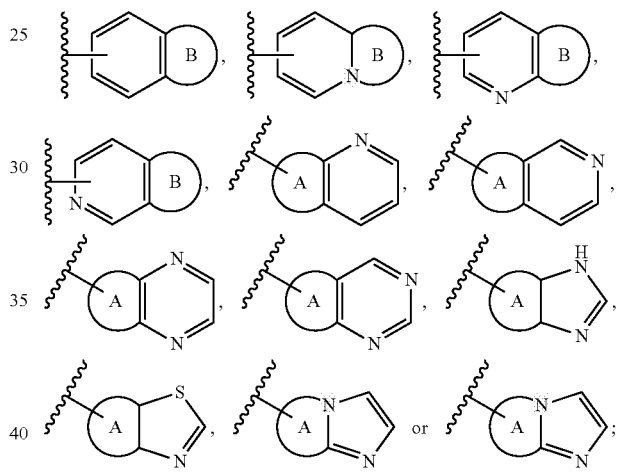

wherein Z is optionally substituted by one or two —R$^Z$ groups.

3. The compound of claim 1, wherein
Z is

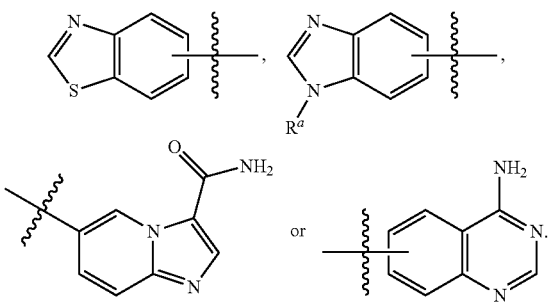

4. The compound of claim 1, wherein n is 1 or 2 and each R$^1$ is independently halogen, C$_{1-6}$alkyl, C$_{1-6}$haloalkyl, or C$_{3-8}$cycloalkyl.

5. The compound of claim 1, wherein the compound has the structure of one of Formulae (Ia)-(Ih):

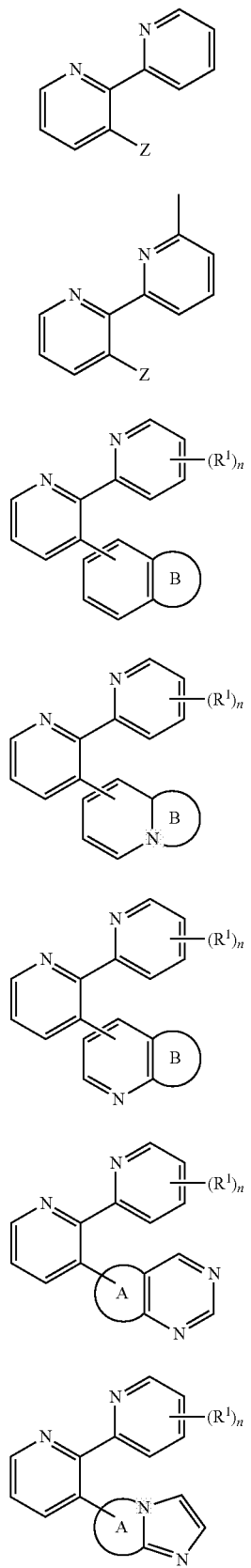

6. A compound according to claim 1 that is:
6-(6'-methyl-[2,2'-bipyridin]-3-yl)quinazolin-4-amine;
6-(6'-methyl-[2,2'-bipyridin]-3-yl)quinazolin-4-aminium 2,2,2-trifluoroacetate;
6-(6'-methyl-[2,2'-bipyridin]-3-yl)quinazolin-4-aminium formate;
6-(6'-Methyl-[2,2'-bipyridin]-3-yl)imidazo[1,2-a]pyridine-3-carbonitrile;
6-(6'-Methyl-[2,2'-bipyridin]-3-yl)-[1,2,4]triazolo[1,5-a]pyridine;
7-(6'-Methyl-[2,2'-bipyridin]-3-yl)-[1,2,4]triazolo[1,5-a]pyridine;
6-(6'-Methyl-[2,2'-bipyridin]-3-yl)imidazo[1,2-a]pyridine-3-carboxamide;
6-([2,2'-Bipyridin]-3-yl)imidazo[1,2-a]pyridine-3-carbonitrile;
6-([2,2'-Bipyridin]-3-yl)-[1,2,4]triazolo[1,5-a]pyridine;
6-([2,2'-Bipyridin]-3-yl)imidazo[1,2-a]pyridine-3-carboxamide;
6-(6'-methyl-[2,2'-bipyridin]-3-yl)pyrido[3,2-d]pyrimidin-4-amine;
6-(6'-fluoro-[2,2'-bipyridin]-3-yl)quinazolin-4-amine;
6-(6'-fluoro-[2,2'-bipyridin]-3-yl)quinazolin-4-aminium 2,2,2-trifluoroacetate;
6-([2,2'-bipyridin]-3-yl)quinazolin-4-amine;
6-([2,2'-bipyridin]-3-yl)quinazolin-4-aminium formate;
or a pharmaceutically acceptable salt, prodrug, or N-oxide thereof, or a solvate or hydrate thereof.

7. A compound according to claim 1 having the structure of formula (II):

(II)

or a pharmaceutically acceptable salt, prodrug or N-oxide thereof, or solvate or hydrate thereof,
wherein
R¹ is hydrogen, halogen, cyano, nitro, $C_{1-6}$alkyl or $C_{1-6}$haloalkyl;

Z is
a fused bicyclic ring of the formula,

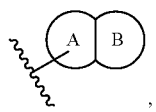

wherein
ring A is Ar or 6-membered Het,
ring B is 5- or 6-membered Het,
wherein
Z is optionally substituted by one or two —R$^Z$ groups that are each independently halogen, cyano, C$_{1-6}$alkyl, C$_{1-6}$haloalkyl, —C$_1$-C$_6$alkoxy, —OR$^{S2}$, —SR$^{S2}$, —NR$^{S2}$$_2$, —C(O)R$^{S2}$, —C(O)OR$^{S2}$, —C(O)NR$^{S2}$$_2$, —S(O)$_2$NR$^{S2}$$_2$, —S(O)$_2$R$^{S2}$, —OC(O)R$^{S2}$, —N(R$^{S2}$)C(O)R$^{S2}$, —OC(O)OR$^{S2}$, —OC(O)NR$^{S2}$$_2$, —N(R$^{S2}$)C(O)OR$^{S2}$, —N(R$^{S2}$)C(O)NR$^{S2}$$_2$, —NR$^{S2}$S(O)$_2$R$^{S2}$, —OP(O)(OR$^{S2}$)$_2$ or —CH$_2$—OP(O)(OR$^{S2}$);
wherein each R$^{S2}$ is independently hydrogen, C$_1$-C$_6$alkyl, C$_1$-C$_6$haloalkyl, —(C$_0$-C$_6$alkyl)-Ar, —(C$_0$-C$_6$alkyl)-Het, —(C$_0$-C$_6$alkyl)-Cak, or —(C$_0$-C$_6$alkyl)-Hca, wherein Ar, Het, Cak, Hca, alkyl, and haloalkyl are optionally substituted with C$_1$-C$_6$alkyl, halogen, C$_1$-C$_6$haloalkyl or cyano;

provided that the compound is not 5-(6'-methyl-[2,2'-bipyridin]-3-yl)-1H-indazole.

8. The compound of claim 7, wherein
Z is

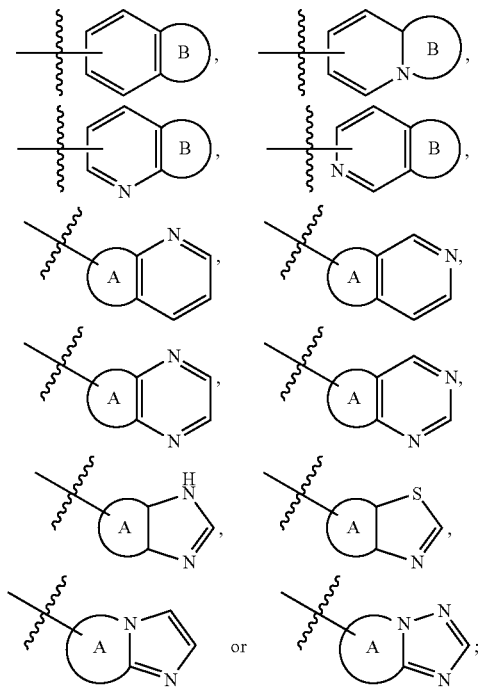

wherein Z is optionally substituted by one or two —R$^Z$ groups.

9. The compound of claim 7, wherein
Z is

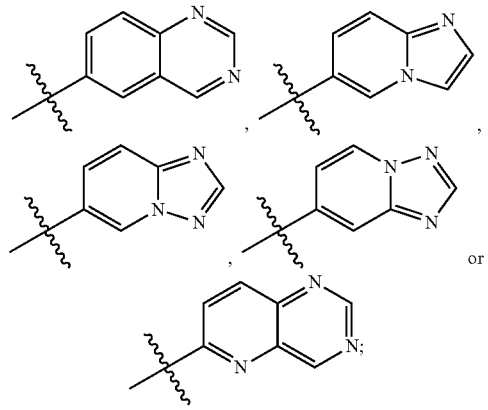

wherein Z is optionally substituted by one or two —R$^Z$ groups.

10. The compound of claim 7, wherein R$^1$ is hydrogen or methyl.

11. The compound of claim 7, wherein the compound has the structure of Formulae (IIa)-(IIh):

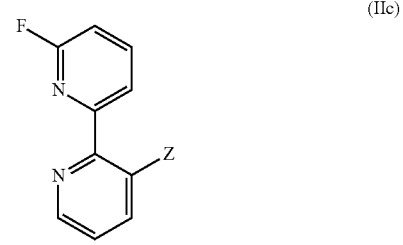
(IIc)

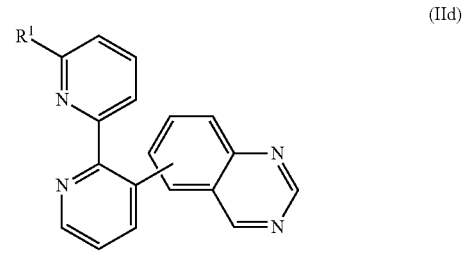
(IId)

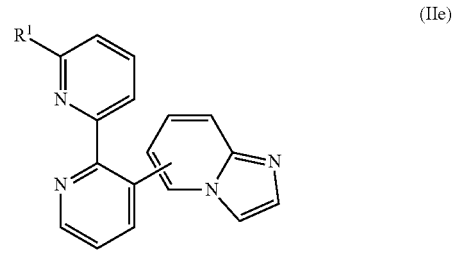
(IIe)

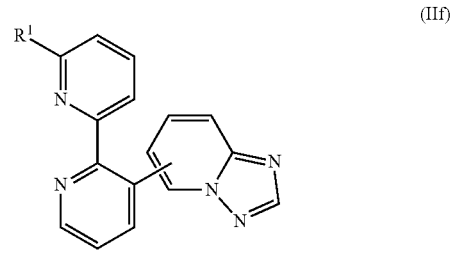
(IIf)

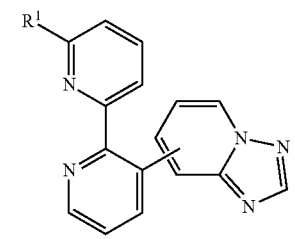

(IIg)

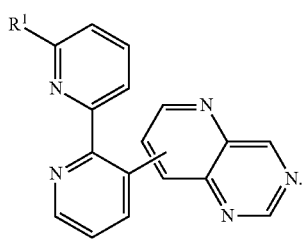

(IIh)

12. The compound according to claim 1 that is 6-(6'-methyl-[2,2'-bipyridin]-3-yl)quinazolin-4-amine;

6-(6'-methyl-[2,2'-bipyridin]-3-yl)quinazolin-4-aminium 2,2,2-trifluoroacetate;

6-(6'-methyl-[2,2'-bipyridin]-3-yl)imidazo[1,2-a]pyridine-3-carbonitrile;

6-(6'-Methyl-[2,2'-bipyridin]-3-yl)-[1,2,4]triazolo[1,5-a]pyridine;

7-(6'-Methyl-[2,2'-bipyridin]-3-yl)-[1,2,4]triazolo[1,5-a]pyridine;

6-(6'-methyl-[2,2'-bipyridin]-3-yl)imidazo[1,2-a]pyridine-3-carboxamide;

6-([2,2'-Bipyridin]-3-yl)imidazo[1,2-a]pyridine-3-carboxamide;

6-(6'-fluoro-[2,2'-bipyridin]-3-yl)quinazolin-4-amine;

6-(6'-fluoro-[2,2'-bipyridin]-3-yl)quinazolin-4-aminium 2,2,2-trifluoroacetate;

6-([2,2'-bipyridin]-3-yl)quinazolin-4-amine;

6-([2,2'-bipyridin]-3-yl)quinazolin-4-aminium formate;

or a pharmaceutically acceptable salt, prodrug, or N-oxide thereof, or a solvate or hydrate thereof.

13. A pharmaceutical composition comprising a compound or pharmaceutically acceptable salt according to claim 1 and a pharmaceutically acceptable carrier, excipient, or diluent.

14. A method for inhibiting GDF-8 in a cell comprising contacting the cell with an effective amount of a compound according to claim 1.

15. A method for increasing muscle mass in a mammal in need thereof comprising administering a therapeutically effective amount of a compound according to claim 1.

16. A method for increasing muscle strength in a mammal in need thereof comprising administering a therapeutically effective amount of a compound according to claim 1.

17. A method for increasing trabecular bone density in a patient in need thereof, comprising administering a therapeutically effective amount of a compound according to claim 1.

18. The compound of claim 1, wherein the compound has the structure of one of Formulae (Ii)-(Im), (IIi)-(IIk), and (III):

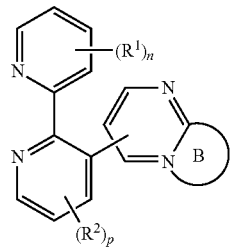

(Ii)

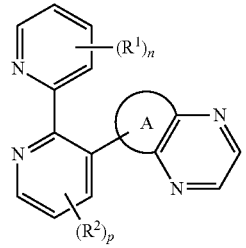

(Ij)

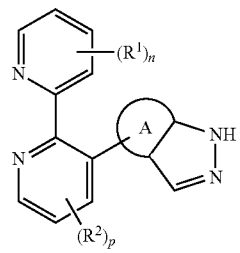

(Ik)

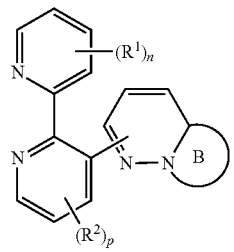

(Il)

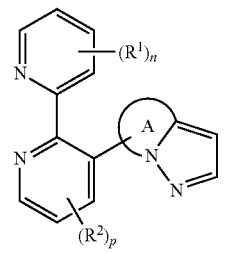

(Im)

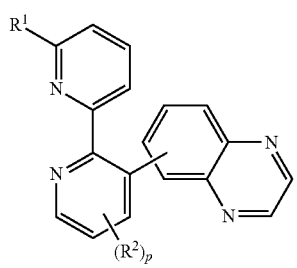

(IIi)

-continued

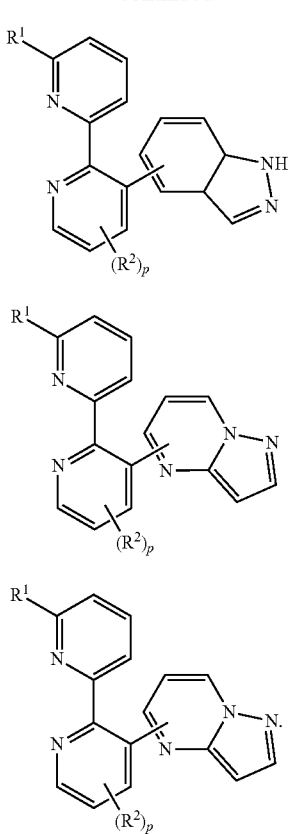

(IIj)

(IIk)

(III)

19. The compound according to claim 1 that is
6-([2,2'-bipyridin]-3-yl)imidazo[1,2-a]pyridine-3-carbonitrile
6-(6'-(trifluoromethyl)-[2,2'-bipyridin]-3-yl)imidazo[1,2-a]pyridine-3-carbonitrile
6-(5'-fluoro-6'-methyl-[2,2'-bipyridin]-3-yl)imidazo[1,2-a]pyridine-3-carbonitrile
6-(4'-fluoro-[2,2'-bipyridin]-3-yl)imidazo[1,2-a]pyridine-3-carbonitrile
6-(6'-methoxy-[2,2'-bipyridin]-3-yl)imidazo[1,2-a]pyridine-3-carbonitrile
6-(6'-(trifluoromethyl)-[2,2'-bipyridin]-3-yl)imidazo[1,2-a]pyridine-3-carboxamide
6-(5'-fluoro-6'-methyl-[2,2'-bipyridin]-3-yl)imidazo[1,2-a]pyridine-3-carboxamide
6-(5'-fluoro-[2,2'-bipyridin]-3-yl)imidazo[1,2-a]pyridine-3-carbonitrile
6-(5'-fluoro-[2,2'-bipyridin]-3-yl)imidazo[1,2-a]pyridine-3-carboxamide
6-(4'-fluoro-[2,2'-bipyridin]-3-yl)imidazo[1,2-a]pyridine-3-carboxamide
6-(6'-(difluoromethyl)-5'-fluoro-[2,2'-bipyridin]-3-yl)imidazo[1,2-a]pyridine-3-carbonitrile
6-(6'-(difluoromethyl)-5'-fluoro-[2,2'-bipyridin]-3-yl)imidazo[1,2-a]pyridine-3-carboxamide methyl 3'-(3-cyanoimidazo[1,2-a]pyridin-6-yl)-[2,2'-bipyridine]-5-carboxylate
methyl 3'-(3-carbamoylimidazo[1,2-a]pyridin-6-yl)-[2,2'-bipyridine]-5-carboxylate
3'-(3-carbamoylimidazo[1,2-a]pyridin-6-yl)-[2,2'-bipyridine]-5-carboxylic acid
6-(6'-(difluoromethyl)-[2,2'-bipyridin]-3-yl)imidazo[1,2-a]pyridine-3-carbonitrile
6-(6'-(difluoromethyl)-[2,2'-bipyridin]-3-yl)imidazo[1,2-a]pyridine-3-carboxamide
6-(6'-ethyl-[2,2'-bipyridin]-3-yl)imidazo[1,2-a]pyridine-3-carbonitrile
6-(6'-isopropyl-[2,2'-bipyridin]-3-yl)imidazo[1,2-a]pyridine-3-carbonitrile
6-(6'-isopropyl-[2,2'-bipyridin]-3-yl)imidazo[1,2-a]pyridine-3-carboxamide
6-(6'-methoxy-[2,2'-bipyridin]-3-yl)imidazo[1,2-a]pyridine-3-carboxamide
6-(6'-cyclopropyl-[2,2'-bipyridin]-3-yl)imidazo[1,2-a]pyridine-3-carbonitrile
6-(6'-cyclopropyl-[2,2'-bipyridin]-3-yl)imidazo[1,2-a]pyridine-3-carboxamide
6-(6'-fluoro-[2,2'-bipyridin]-3-yl)imidazo[1,2-a]pyridine-3-carbonitrile
6-(6'-fluoro-[2,2'-bipyridin]-3-yl)imidazo[1,2-a]pyridine-3-carboxamide
6-(6'-(benzyloxy)-[2,2'-bipyridin]-3-yl)imidazo[1,2-a]pyridine-3-carbonitrile
6-([2,2'-bipyridin]-3-yl)imidazo[1,2-a]pyridine-3-carboxamide
6-(6'-acetyl-[2,2'-bipyridin]-3-yl)imidazo[1,2-a]pyridine-3-carbonitrile
6-(6'-6-(6'-(2-hydroxypropan-2-yl)-[2,2'-bipyridin]-3-yl)imidazo[1,2-a]pyridine-3-carbonitrile
6-(4',6'-dimethyl-[2,2'-bipyridin]-3-yl)imidazo[1,2-a]pyridine-3-carboxamide
6-(5'-fluoro-6'-methyl-[2,2'-bipyridin]-3-yl)imidazo[1,2-b]pyridazine-3-carboxamide
N-(3'-(3-cyanoimidazo[1,2-a]pyridin-6-yl)-[2,2'-bipyridin]-6-yl)methanesulfonamide
N-(3'-(3-cyanoimidazo[1,2-a]pyridin-6-yl)-[2,2'-bipyridin]-6-yl)acetamide
6-(6'-chloro-[2,2'-bipyridin]-3-yl)imidazo[1,2-a]pyridine-3-carboxamide
6-(6'-methyl-[2,2'-bipyridin]-3-yl)imidazo[1,2-a]pyridine
6-(6'-(difluoromethyl)-5'-fluoro-[2,2'-bipyridin]-3-yl)imidazo[1,2-a]pyridine
6-(6'-(difluoromethyl)-[2,2'-bipyridin]-3-yl)imidazo[1,2-b]pyridazine-3-carbonitrile
6-(6'-methoxy-[2,2'-bipyridin]-3-yl)imidazo[1,2-b]pyridazine-3-carbonitrile
6-(6'-methoxy-[2,2'-bipyridin]-3-yl)imidazo[1,2-b]pyridazine-3-carboxamide
6-(6'-(difluoromethyl)-[2,2'-bipyridin]-3-yl)imidazo[1,2-b]pyridazine-3-carboxamide
6-(5'-fluoro-[2,2'-bipyridin]-3-yl)imidazo[1,2-b]pyridazine-3-carbonitrile
6-(5'-fluoro-[2,2'-bipyridin]-3-yl)imidazo[1,2-b]pyridazine-3-carboxamide
6-(5'-methyl-[2,2'-bipyridin]-3-yl)imidazo[1,2-b]pyridazine-3-carbonitrile
6-(5'-methyl-[2,2'-bipyridin]-3-yl)imidazo[1,2-b]pyridazine-3-carboxamide
6-(6'-methyl-[2, 2'-bipyridin]-3-yl) imidazo[1,2-b]pyridazine-3-carbonitrile
6-(6'-methyl-[2,2'-bipyridin]-3-yl)imidazo[1,2-b]pyridazine-3-carboxamide
6-(4'-fluoro-[2,2'-bipyridin]-3-yl)imidazo[1,2-b]pyridazine-3-carbonitrile
6-(4'-fluoro-[2,2'-bipyridin]-3-yl)imidazo[1,2-b]pyridazine-3-carboxamide
6-(5'-fluoro-6'-methyl-[2,2'-bipyridin]-3-yl)imidazo[1,2-b]pyridazine-3-carbonitrile
6-(6'-isopropyl-[2,2'-bipyridin]-3-yl)imidazo[1,2-b]pyridazine-3-carbonitrile 6-(6'-isopropyl-[2,2'-bipyridin]-3-yl)imidazo[1,2-b]pyridazine-3-carboxamide
6-(6'-fluoro-[2,2'-bipyridin]-3-yl)imidazo[1,2-b]pyridazine-3-carbonitrile
2,2,2-trifluoro-N-(6-(6'-methyl-[2,2'-bipyridin]-3-yl)imidazo[1,2-a]pyridin-3-yl)acetamide
6-(6'-methyl-[2,2'-bipyridin]-3-yl)imidazo[1,2-a]pyridine-3-carboxylic acid
N-(2,2-difluoroethyl)-6-(6'-methyl-[2,2'-bipyridin]-3-yl)imidazo[1,2-a]pyridine-3-carboxamide
6-(6'-methyl-[2,2'-bipyridin]-3-yl)-N-(2,2,2-trifluoroethyl)imidazo[1,2-a]pyridine-3-carboxamide
N-(2-methoxyethyl)-6-(6'-methyl-[2,2'-bipyridin]-3-yl)imidazo[1,2-a]pyridine-3-carboxamide
N—($^2$H$_3$)methyl-6-[2-(6-methylpyridin-2-yl)pyridin-3-yl]imidazo[1,2-a]pyridine-3-carboxamide
methyl-6-(6'-methyl-[2,2'-bipyridin]-3-yl)imidazo[1,2-a]pyridine-3-carboxamide
6-(6'-methyl-[2,2'-bipyridin]-3-yl)imidazo[1,2-b]pyridazine-3-carboxylic acid
6-(6'-methyl-[2,2'-bipyridin]-3-yl)-N-(oxetan-3-yl)imidazo[1,2-b]pyridazine-3-carboxamide
N-cyclopropyl-6-(6'-methyl-[2,2'-bipyridin]-3-yl)imidazo[1,2-b]pyridazine-3-carboxamide
N-(6-(6'-methyl-[2,2'-bipyridin]-3-yl)imidazo[1,2-a]pyridin-2-yl)acetamide
N-(6-(5'-fluoro-6'-methyl-[2,2'-bipyridin]-3-yl)imidazo[1,2-a]pyridin-2-yl)acetamide
6-(5'-fluoro-6'-methyl-[2,2'-bipyridin]-3-yl)imidazo[1,2-a]pyridine-2-carboxamide
6-(6'-(trifluoromethyl)-[2,2'-bipyridin]-3-yl)imidazo[1,2-a]pyridine-2-carboxamide
6-(6'-methyl-[2,2'-bipyridin]-3-yl)imidazo[1,2-a]pyridine-2-carboxamide
6-(5-fluoro-6'-methyl-[2,2'-bipyridin]-3-yl)imidazo[1,2-a]pyridine-3-carbonitrile
6-(5-fluoro-6'-methyl-[2,2'-bipyridin]-3-yl)imidazo[1,2-a]pyridine-3-carboxamide
6-(6'-(difluoromethyl)-5-fluoro-[2,2'-bipyridin]-3-yl)imidazo[1,2-a]pyridine-3-carbonitrile
6-(6'-(difluoromethyl)-5-fluoro-[2,2'-bipyridin]-3-yl)imidazo[1,2-a]pyridine-3-carboxamide
6-(5,5'-difluoro-6'-methyl-[2,2'-bipyridin]-3-yl)imidazo[1,2-a]pyridine-3-carboxamide
6-(6,6'-dimethyl-[2,2'-bipyridin]-3-yl)imidazo[1,2-a]pyridine-3-carbonitrile
6-(6,6'-dimethyl-[2,2'-bipyridin]-3-yl)imidazo[1,2-a]pyridine-3-carbonitrile
6-(6'-(difluoromethyl)-6-methyl-[2,2'-bipyridin]-3-yl)imidazo[1,2-a]pyridine-3-carboxamide
6-(6'-methyl-6-(trifluoromethyl)-[2,2'-bipyridin]-3-yl)imidazo[1,2-a]pyridine-3-carbonitrile
6-(6'-methyl-6-(trifluoromethyl)-[2,2'-bipyridin]-3-yl)imidazo[1,2-a]pyridine-3-carboxamide methyl 3-(3-cyanoimidazo[1,2-a]pyridin-6-yl)-6'-methyl-[2,2'-bipyridine]-4-carboxylate
6-(4-(hydroxymethyl)-6'-methyl-[2,2'-bipyridin]-3-yl)imidazo[1,2-a]pyridine-3-carbonitrile
6-(4-(difluoromethyl)-6'-methyl-[2,2'-bipyridin]-3-yl)imidazo[1,2-a]pyridine-3-carbonitrile
6-(4-(difluoromethyl)-6'-methyl-[2,2'-bipyridin]-3-yl)imidazo[1,2-a]pyridine-3-carboxamide
6-(6-acetamido-6'-methyl-[2,2'-bipyridin]-3-yl)imidazo[1,2-a]pyridine-3-carboxamide
N-(3-(3-cyanoimidazo[1,2-a]pyridin-6-yl)-6'-methyl-[2,2'-bipyridin]-5-yl)acetamide
6-(5-acetamido-6'-methyl-[2,2'-bipyridin]-3-yl)imidazo[1,2-a]pyridine-3-carboxamide
6-(5-amino-6'-methyl-[2,2'-bipyridin]-3-yl)imidazo[1,2-a]pyridine-3-carboxamide
6-(5-amino-6'-methyl-[2,2'-bipyridin]-3-yl)imidazo[1,2-a]pyridine-3-carboxylic acid
N-(3-(3-cyanoimidazo[1,2-a]pyridin-6-yl)-6'-methyl-[2,2'-bipyridin]-4-yl)acetamide
6-(4-amino-6'-methyl-[2,2'-bipyridin]-3-yl)imidazo[1,2-a]pyridine-3-carboxamide
6-(4-acetamido-6'-methyl-[2,2'-bipyridin]-3-yl)imidazo[1,2-a]pyridine-3-carboxamide
6-(5'-fluoro-6'-methyl-[2,2'-bipyridin]-3-yl)pyrido[3,2-d]pyrimidin-4-amine
6-(5'-fluoro-[2,2'-bipyridin]-3-yl)pyrido[3,2-d]pyrimidin-4-amine
6-(6'-(difluoromethyl)-[2,2'-bipyridin]-3-yl)pyrido[3,2-d]pyrimidin-4-amine
6-(6'-cyclopropyl-[2,2'-bipyridin]-3-yl)pyrido[3,2-d]pyrimidin-4-amine
6-(6'-ethyl-[2,2'-bipyridin]-3-yl)quinazolin-4-amine
6-(6'-isopropyl-[2,2'-bipyridin]-3-yl)quinazolin-4-amine
6-(6'-(difluoromethyl)-[2,2'-bipyridin]-3-yl)quinazolin-4-amine
6-(5'-fluoro-6'-methyl-[2,2'-bipyridin]-3-yl)imidazo[1,2-a]pyridine-2-carboxamide
6-(6'-isopropyl-[2,2'-bipyridin]-3-yl)quinazolin-4-amine
6-(5'-fluoro-6'-methyl-[2,2'-bipyridin]-3-yl)quinoxaline
6-(6'-methyl-[2,2'-bipyridin]-3-yl)quinoxaline
6-(6'-(trifluoromethyl)-[2,2'-bipyridin]-3-yl)quinoxaline
5-(6'-(difluoromethyl)-[2,2'-bipyridin]-3-yl)-1H-indazole
5-(5'-fluoro-[2,2'-bipyridin]-3-yl)-1H-indazole
5-(5'-fluoro-6'-methyl-[2,2'-bipyridin]-3-yl)-1H-indazole
3-(difluoromethyl)-5-(6'-(difluoromethyl)-[2,2'-bipyridin]-3-yl)-1H-indazole
5-(6'-methyl-[2,2'-bipyridin]-3-yl)pyrazolo[1,5-a]pyrimidine-3-carbonitrile
5-(6'-methyl-[2,2'-bipyridin]-3-yl)pyrazolo[1,5-a]pyrimidine-3-carboxamide
5-(6'-(trifluoromethyl)-[2,2'-bipyridin]-3-yl)pyrazolo[1,5-a]pyrimidine-3-carbonitrile
5-(5'-fluoro-6'-methyl-[2,2'-bipyridin]-3-yl)pyrazolo[1,5-a]pyrimidine-3-carbonitrile ethyl 5-(6'-(trifluoromethyl)-[2,2'-bipyridin]-3-yl)pyrazolo[1,5-a]pyrimidine-3-carboxylate
5-(6'-(trifluoromethyl)-[2,2'-bipyridin]-3-yl)pyrazolo[1,5-a]pyrimidine-3-carboxylic acid
N-methyl-5-(6'-(trifluoromethyl)-[2,2'-bipyridin]-3-yl)pyrazolo[1,5-a]pyrimidine-3-carboxamide
N-cyclopropyl-5-(6'-(trifluoromethyl)-[2,2'-bipyridin]-3-yl)pyrazolo[1,5-a]pyrimidine-3-carboxamide
N-methyl-5-(6'-methyl-[2,2'-bipyridin]-3-yl)pyrazolo[1,5-a]pyrimidine-3-carboxamide
N-cyclopropyl-5-(6'-methyl-[2,2'-bipyridin]-3-yl)pyrazolo[1,5-a]pyrimidine-3-carboxamide
5-(6'-methyl-[2,2'-bipyridin]-3-yl)-N-(oxetan-3-yl)pyrazolo[1,5-a]pyrimidine-3-carboxamide ethyl 5-(5'-fluoro-6'-methyl-[2,2'-bipyridin]-3-yl)pyrazolo[1,5-a]pyrimidine-3-carboxylate
5-(5'-fluoro-6'-methyl-[2,2'-bipyridin]-3-yl)pyrazolo[1,5-a]pyrimidine-3-carboxylic acid
N-cyclopropyl-5-(5'-fluoro-6'-methyl-[2,2'-bipyridin]-3-yl)pyrazolo[1,5-a]pyrimidine-3-carboxamide
5-(5'-fluoro-6'-methyl-[2,2'-bipyridin]-3-yl)-N-(oxetan-3-yl)pyrazolo[1,5-a]pyrimidine-3-carboxamide ethyl 5-(6'-(difluoromethyl)-[2,2'-bipyridin]-3-yl)pyrazolo[1,5-a]pyrimidine-3-carboxylate 5-(6'-(difluoromethyl)-[2,2'-bipyridin]-3-yl)pyrazolo[1,5-a]pyrimidine-3-carboxylic acid 5-(6'-(trifluoromethyl)-[2,2'-bipyridin]-3-yl)pyrazolo[1,5-a]pyrimidine 5-(5'-fluoro-6'-methyl-[2,2'-bipyridin]-3-yl)pyrazolo[1,5-a]pyrimidine 5-(6'-methyl-[2,2'-bipyridin]-3-yl)pyrazolo[1,5-a]pyrimidine or a pharmaceutically acceptable salt, prodrug, or N-oxide thereof, or a solvate or hydrate thereof.

* * * * *